United States Patent
Ewert et al.

(10) Patent No.: US 11,932,681 B2
(45) Date of Patent: Mar. 19, 2024

(54) HEPATITIS B ANTIBODIES

(71) Applicant: Novartis AG, Basel (CH)

(72) Inventors: Stefan Ewert, Geroldswil (CH); Meghan Marie Holdorf, Oakland, CA (US); Elisabetta Traggiai, Basel (CH)

(73) Assignee: Novartis AG, Basel (CH)

( * ) Notice: Subject to any disclaimer, the term of this patent is extended or adjusted under 35 U.S.C. 154(b) by 780 days.

(21) Appl. No.: 17/059,934

(22) PCT Filed: May 30, 2019

(86) PCT No.: PCT/IB2019/054498
§ 371 (c)(1),
(2) Date: Nov. 30, 2020

(87) PCT Pub. No.: WO2019/229699
PCT Pub. Date: Dec. 5, 2019

(65) Prior Publication Data
US 2021/0221871 A1    Jul. 22, 2021

Related U.S. Application Data

(60) Provisional application No. 62/678,756, filed on May 31, 2018.

(51) Int. Cl.
*C07K 16/08* (2006.01)
*A61K 39/00* (2006.01)

(52) U.S. Cl.
CPC ...... *C07K 16/082* (2013.01); *A61K 2039/505* (2013.01); *C07K 2317/21* (2013.01); *C07K 2317/33* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,720,760 A | 3/1973 | Wide et al. |
| 4,522,811 A | 6/1985 | Eppstein et al. |
| 4,526,938 A | 7/1985 | Churchill et al. |
| 4,880,078 A | 11/1989 | Inoue et al. |
| 5,128,326 A | 7/1992 | Balazs et al. |
| 5,290,540 A | 3/1994 | Prince et al. |
| 5,374,548 A | 12/1994 | Caras |

(Continued)

FOREIGN PATENT DOCUMENTS

| | | |
|---|---|---|
| CN | 103588874 A | 2/2014 |
| EP | 1176195 B1 | 5/2013 |

(Continued)

OTHER PUBLICATIONS

Langer, "Controlled release of macromolecules," Chem. Tech. 12:98-105, 1982.

(Continued)

*Primary Examiner* — Agnieszka Boesen
(74) *Attorney, Agent, or Firm* — K&L Gates LLP; Louis C. Cullman; Michelle Glasky Bergman

(57) ABSTRACT

The present invention relates to anti-HBsAg antibodies, antibody fragments, and their uses for the prevention and treatment of hepatitis B virus infection and associated diseases.

19 Claims, 67 Drawing Sheets
Specification includes a Sequence Listing.

(56) References Cited

U.S. PATENT DOCUMENTS

| | | | |
|---|---|---|---|
| 5,399,331 | A | 3/1995 | Loughrey et al. |
| 5,416,016 | A | 5/1995 | Low et al. |
| 5,624,821 | A | 4/1997 | Winter et al. |
| 5,641,870 | A | 6/1997 | Rinderknecht et al. |
| 5,648,260 | A | 7/1997 | Winter et al. |
| 5,667,425 | A | 9/1997 | Pineau et al. |
| 5,679,377 | A | 10/1997 | Bernstein et al. |
| 5,714,350 | A | 2/1998 | Co et al. |
| 5,855,913 | A | 1/1999 | Hanes et al. |
| 5,869,046 | A | 2/1999 | Presta et al. |
| 5,874,064 | A | 2/1999 | Edwards et al. |
| 5,912,015 | A | 6/1999 | Bernstein et al. |
| 5,916,597 | A | 6/1999 | Lee et al. |
| 5,934,272 | A | 8/1999 | Lloyd et al. |
| 5,985,309 | A | 11/1999 | Edwards et al. |
| 5,985,320 | A | 11/1999 | Edwards et al. |
| 5,989,463 | A | 11/1999 | Tracy et al. |
| 6,019,968 | A | 2/2000 | Platz et al. |
| 6,121,022 | A | 9/2000 | Presta et al. |
| 6,165,745 | A | 12/2000 | Ward et al. |
| 6,194,551 | B1 | 2/2001 | Idusogie et al. |
| 6,277,375 | B1 | 8/2001 | Ward |
| 6,316,024 | B1 | 11/2001 | Allen et al. |
| 6,350,466 | B1 | 2/2002 | Li et al. |
| 6,350,861 | B1 | 2/2002 | Co et al. |
| 6,703,199 | B1 | 3/2004 | Koide |
| 6,737,056 | B1 | 5/2004 | Presta |
| 7,786,268 | B2 * | 8/2010 | Fischer .............. A61P 5/14 424/130.1 |
| 8,008,449 | B2 | 8/2011 | Korman et al. |
| 8,354,509 | B2 | 1/2013 | Carven et al. |
| 9,284,378 | B2 * | 3/2016 | Hu ..................... A61P 3/00 |
| 2003/0153043 | A1 | 8/2003 | Carr et al. |
| 2010/0028330 | A1 | 2/2010 | Collins et al. |
| 2010/0150918 | A1 * | 6/2010 | Kufer .............. C07K 16/28 536/23.53 |
| 2012/0114649 | A1 | 5/2012 | Langermann et al. |
| 2016/0326233 | A1 | 11/2016 | Mondelli |
| 2019/0389939 | A1 | 12/2019 | Luo et al. |

FOREIGN PATENT DOCUMENTS

| | | |
|---|---|---|
| JP | 2002-502222 | 1/2002 |
| JP | 2016-504015 | 2/2016 |
| WO | 91/05548 A1 | 5/1991 |
| WO | 92/19244 A2 | 11/1992 |
| WO | 94/29351 A2 | 12/1994 |
| WO | 96/20698 A2 | 7/1996 |
| WO | 97/32572 A2 | 9/1997 |
| WO | 97/44013 A1 | 11/1997 |
| WO | 97/47653 A1 | 12/1997 |
| WO | 98/31346 A1 | 7/1998 |
| WO | 99/15154 A1 | 4/1999 |
| WO | 99/20253 A1 | 4/1999 |
| WO | 99/54342 A1 | 10/1999 |
| WO | 99/66903 A2 | 12/1999 |
| WO | 00/42072 A2 | 7/2000 |
| WO | 03/035835 A2 | 5/2003 |
| WO | 2003/105894 A1 | 12/2003 |
| WO | 2006/121168 A1 | 11/2006 |
| WO | 2007/005874 A2 | 1/2007 |
| WO | 2009/101611 A1 | 8/2009 |
| WO | 2009/114335 A2 | 9/2009 |
| WO | 2010/027423 A2 | 3/2010 |
| WO | 2010/027827 A2 | 3/2010 |
| WO | 2010/077634 A1 | 7/2010 |
| WO | 2011/066342 A2 | 6/2011 |
| WO | 2011066389 A1 | 6/2011 |
| WO | 2012065950 A1 | 5/2012 |
| WO | 2014/048910 A1 | 4/2014 |
| WO | 2015/026684 A1 | 2/2015 |
| WO | 2016/057846 A1 | 4/2016 |
| WO | 2016/061142 A1 | 4/2016 |
| WO | 2017/059813 | 4/2017 |
| WO | 2017/060504 | 4/2017 |

OTHER PUBLICATIONS

Langer, "New methods of drug delivery," Science 249:1527-1533, 1990).

Langer, et al., "Chemical and Physical Structure of Polymers as Carriers for Controlled Release of Bioactive Agents: A Review," J. Macromol. Sci. Rev. Macromol. Chem. 23:61, 1983.

Lefranc, M.P., "IMGT, the international ImMunoGeneTics database," Nucleic Acids Res., 29:207-209 (2001).

Levy et al., "Inhibition of calcification of bioprosthetic heart valves by local controlled-release diphosphonate," Science 228:190, 1985.

Lipsky et al., "Infliximab and Methotrexate in the Treatment of Rheumatoid Arthritis," New Engl. J. Med. 343:1594-1602, 2000.

MacCallum et al., "Antibody-antigen Interactions: Contact Analysis and Binding Site Topography," J. Mol. Biol., 262:732-745 (1996).

Martin et al., "Modeling antibody hypervariable loops: A combined algorithm," Proc. Natl. Acad. Sci. USA, 86:9268-9272 (1989).

Martin et al., "Molecular modeling of antibody combining sites,," Methods Enzymol., 203:121-153 (1991).

Mattila et al., "Fidelity of DNA synthesis by the Thermococcus litoralis DNA polymerase—an extremely heat stable enzyme with proofreading activity," Nucleic Acids Res. 19:4967, 1991.

Meier et al., "Hepatitis B virus covalently closed circular DNA homeostasis is independent of the lymphotoxin pathway during chronic HBV infection," J. Virol Hepat. 2017; 24: 662-671.

Milgrom et al., "Treatment of Allergic Asthma with Monoclonal Anti-IgE Antibody," New Engl. J. Med. 341:1966-1973, 1999.

Narang et al., "Improved phosphotriester method for the synthesis of gene fragments," Meth. Enzymol. 68:90, 1979.

Needleman and Wunsch, "A general method applicable to the search for similarities in the amino acid sequence of two proteins," J. Mol. Biol. 48:443 (1970).

Ning et al., "Intratumoral radioimmunotherapy of a human colon cancer xenograft using a sustained-release gel," Radiotherapy & Oncology 39:179-189, 1996.

O'Shannessy et al., "Determination of rate and equilibrium binding constants for macromolecular interactions using surface plasmon resonance: use of nonlinear least squares analysis methods," Anal. Biochem 1993 212: 457-468.

Ohtsuka et al., "An alternative approach to deoxyoligonucleotides as hybridization probes by insertion of deoxyinosine at ambiguous codon positions," (1985) J. Biol. Chem. 260:2605-2608.

Owais et al., "Chloroquine encapsulated in malaria-infected erythrocyte-specific antibody-bearing liposomes effectively controls chloroquine-resistant Plasmodium berghei infections in mice," (1995) Antimicrob. Agents Chemother. 39:180.

Pearson, et al., "Improved tools for biological sequence comparison.," Proc. Natl. Acad. Sci. USA 85:2444 (1988).

Queen et al., "Cell-type specific regulation of a kappa immunoglobulin gene by promoter and enhancer elements," Immunol. Rev. 89:49-68, 1986.

Ranade, "Drug Delivery Systems. 1. Site-Specific Drug Delivery Using Liposomes as Carriers," (1989) J. Clin. Pharmacol. 29:685.

Rees et al., "Antibody combining sites: structure and prediction," Oxford University Press, Oxford, 141-172 (1996).

Rosenfeld et al., "In vivo transfer of the human cystic fibrosis transmembrane conductance regulator gene to the airway epithelium," Cell 68:143, 1992.

Rossolini et al., "Use of deoxyinosine-containing primers vs degenerate primers for polymerase chain reaction based on ambiguous sequence information," (1994) Mol. Cell. Probes 8:91-98).

Ruiz et al., "IMGT, the international ImMunoGeneTics database," Nucleic Acids Res., 28:219-221 (2000).

Saudek et al., "A preliminary trial of the programmable implantable medication system for insulin delivery," N. Engl. J. Med. 321:574, 1989.

Scharf et al., "Heat Stress Promoters and Transcription Factors," Results Probl. Cell Differ. 20:125, 1994.

(56) References Cited

OTHER PUBLICATIONS

Schreier et al, "Targeting of Liposomes to Cells Expressing CD4 Using Glycosylphosphatidylinositol-anchored gp120," (1994) J. Biol. Chem. 269:9090-9098.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276:6591-6604, 2001.
Shields et al., "Lack of fucose on human IgG1 N-linked oligosaccharide improves binding to human Fcgamma RIII and antibody-dependent cellular toxicity," (2002) J. Biol. Chem. 277:26733-26740.
Sidman et al., "Controlled release of macromolecules and pharmaceuticals from synthetic polypeptides based on glutamic acid," Biopolymers 22:547-556, 1983.
Slamon et al., "Use of Chemotherapy plus a Monoclonal Antibody against HER2 for Metastatic Breast Cancer That Overexpresses HER2," New Engl. J. Med. 344:783-792, 2001.
Smith and Waterman, "Comparison of biosequences," Adv. Appl. Math. 2:482c (1981).
Smith, A.E., "Viral vectors in gene therapy," Annu. Rev. Microbiol. 49:807, 1995.
Song et al.. "Antibody Mediated Lung Targeting of Long Circulating Emulsions," PDA Journal of Pharmaceutical Science & Technology 50:372, 1996.
Strohl, W., "Optimization of Fc-mediated effector functions of monoclonal antibodies," 2009, Curr. Opin. Biotechnol. vol. 20(6):685-691.
Thimme et al., "CD8(+) T cells mediate viral clearance and disease pathogenesis during acute hepatitis B virus infection," J Virol. 2003; 77(1):68-76.
Tropberger et al., "Mapping of histone modifications in episomal HBV cccDNA uncovers an unusual chromatin organization amenable to epigenetic manipulation," Proc. Natl. Acad. Sci. U. S. A. 2015; 112: E5715-E5724.
Umana et al., "Engineered glycoforms of an antineuroblastoma IgG1 with optimized antibody-dependent cellular cytotoxic activity," Nat. Biotech. 17:176-180, 1999.
Umezawa et al., "Liposome targeting to mouse brain: Mannose as a recognition marker," (1988) Biochem. Biophys. Res. Commun. 153:1038.
Ward et al., "Binding activities of a repertoire of single immunoglobulin variable domains secreted from *Escherichia coli*," Nature 341:544-546, 1989.
Wieland et al., "Genomic analysis of the host response to hepatitis B virus infection," Proc Natl Acad Sci U S A. 2004;101(17):6669-74.
Zapata et al., "Engineering linear F(ab')2 fragments for efficient production in *Escherichia coli* and enhanced antiproliferative activity," Protein Eng. 8:1057-1062, 1995.
Al-Lazikani et al., "Standard Conformations for the Canonical Structures of Immunoglobulins," J.Mol.Biol., 273:927-748 (1997).
Zhang et. al., "Prolonged suppression of HBV in mice by a novel antibody that targets a unique epitope on hepatitis B surface antigen," Gut, 2016; (4) 65: 658-671.
Altschul et al., "Basic local alignment search tool," J. Mol. Biol. 215:403-410, 1990.
Altschul et al., "Gapped BLAST and PSI-BLAST: a new generation of protein database search programs," Nuc. Acids Res. 25:3389-3402, 1977.
Asabe, et al., "The size of the viral inoculum contributes to the outcome of hepatitis B virus infection," J Virol. 2009; 83(19):9652-62.
Baert et al., "Influence of immunogenicity on the long-term efficacy of infliximab in Crohn's disease," New Engl. J. Med. 348:601-608, 2003.
Batzer et al., "Enhanced evolutionary PCR using oligonucleotides with inosine at the 3'-terminus," Nucleic Acid Res. 19:5081 (1991).

Baudino et al., "Crucial role of aspartic acid at position 265 in the CH2 domain for murine IgG2a and IgG2b Fc-associated effector functions," J. Immunol. 181 : 6664-69 (2008).
Beaucage et al., "Deoxynucleoside phosphoramidites—A new class of key intermediates for deoxypolynucleotide synthesis," Tetra. Lett., 22:1859, 1981.
Beniaminovitz et al., "Prevention of rejection in cardiac transplantation by blockade of the interleukin-2 receptor with a monoclonal antibody," New Engl. J. Med. 342:613-619, 2000.
Bird et al., "Single-chain antigen-binding proteins," Science 242:423-426, 1988.
Biswas et al., "Shift in the hepatitis B virus genotype distribution in the last decade among the HBV carriers from eastern India: possible effects on the disease status and HBV epidemiology," Med. Virol. 2013; 85:1340-1347.
Bitter et al., "Expression and secretion vectors for yeast," Meth. Enzymol., 153:516, 1987.
Bloeman et al., "Adhesion molecules: a new target for immunoliposome-mediated drug delivery," (1995) FEBS Lett. 357-140.
Boni et al., "Lamivudine treatment can overcome cytotoxic T-cell hyporesponsiveness in chronic hepatitis B: new perspectives for immune therapy," Hepatology. 2001; 33(4):963-71.
Briscoe et al., "Delivery of superoxide dismutase to pulmonary epithelium via pH-sensitive liposomes," (1995) Am. J. Physiol., vol. 12(3), p. L374-L380).
Brown et al., "Chemical synthesis and cloning of a tyrosine tRNA gene," Meth. Enzymol. 68:109, 1979.
Buchwald et al., "Long-term, continuous intravenous heparin administration by an implantable infusion pump in ambulatory patients with recurrent venous thrombosis," Surgery 88:507, 1980.
Chisari, et al., "Hepatitis B virus immunopathogenesis," Annu Rev Immunol. 1995; 13:29-60.
Chothia et al., "Conformations of immunoglobulin hypervariable regions," Nature, 342:877-883 (1989).
Chothia et al., "Structural repertoire of the human VH segments," J. Mol. Biol., 227:799-817 (1992).
Chothia, et al., "Canonical structures for the hypervariable regions of immunoglobulins," J. Mol. Biol., 196:901-917 (1987).
Cleek et al., "Biodegradable Polymeric Carriers for a bFGF Antibody for Cardiovascular Application, " Pro. Int'l. Symp. Control. Rel. Bioact. Mater. 24:853-854, 1997.
Dagan, et al., "Therapeutic antibodies against viral hepatitis," Current Opinion in Molecular Therapeutics, 2003, 5(2):148-155.
DeRienzo et al., "Evaluation of the half-life of intravenous human cytomegalovirus immune globulin in patients receiving partially mismatched related donor bone marrow transplantation," Pharmacotherapy 2000; 20:1175-8.
During et al., "Controlled release of dopamine from a polymeric brain implant: In vivo characterization," Ann. Neurol. 25:351, 1989.
Meyers, et al., "Optimal alignments in linear space," Bioinformatics, vol. 4, Issue 1, Mar. 1988, pp. 11-17.
Eckert et al., "DNA polymerase fidelity and the polymerase chain reaction.," PCR Methods and Applications 1:17, 1991.
Ehrlich, et al., "Characterization of human monoclonal antibodies directed against hepatitis B surface antigen," Hum. Antibod. Hybridomas, 1992, vol. 3, 6 pages.
Elliot and O'Hare, "Intercellular Trafficking and Protein Delivery by a Herpesvirus Structural Protein," Cell 88:223, 1997.
Eppstein et al., "Biological activity of liposome-encapsulated murine interferon y is mediated by a cell membrane receptor," Proc. Natl. Acad. Sci. USA 82:3688-3692, 1985.
Ghosh et al., "Natalizumab for Active Crohn's Disease," New Engl. J. Med. 348:24-32, 2003.
Goodson, in Medical Applications of Controlled Release, vol. 2, pp. 115-138, 1984.
Guidotti et al., "Immunobiology and Pathogenesis of Viral Hepatitis," Annu Rev Pathol. 2006; 1:23-61.
Hamid, O. et al., "Safety and Tumor Responses with Lambrolizumab (Anti-PD-1) in Melanoma," (2013) New England Journal of Medicine 369 (2): 134-44,.
Harrington et al., "Formation of de novo centromeres and construction of first-generation human artificial microchromosomes," Nature Genetics, 15:345-355, 1997.

(56) References Cited

OTHER PUBLICATIONS

Henikoff and Henikoff, "Amino acid substitution matrices from protein blocks," Proc. Natl. Acad. Sci. USA 89:10915-10919, 1992.
Hollinger and Hudson, "Engineered antibody fragments and the rise of single domains," Nature Biotechnology 23:1126-1136, 2005.
Howard et al., "Acute subdural hematomas: an age-dependent clinical entity," J. Neurosurg. 7 1:105, 1989.
Huston et al., "Protein engineering of antibody binding sites: Recovery of specific activity in an anti-digoxin single-chain Fv analogue produced in *Escherichia coli*," Proc. Natl. Acad. Sci. 85:5879-5883, 1988.
Hwang et al., "Hepatic uptake and degradation of unilamellar sphingomyelin/cholesterol liposomes: A kinetic study," Proc. Natl. Acad. Sci. USA 77:4030-4034, 1980.
Jefferis et al., "Human immunoglobulin allotypes," MAbs. 1:332-338 (2009).
Johnson et al., "Kabat Database and its applications: future directions," Nucleic Acids Res., 29:205-206 (2001).
Karlin et al., "Applications and statistics for multiple high-scoring segments in molecular sequences," Proc. Natl. Acad. Sci. USA 90:5873-5787, 1993.
Karlsson, et al., "Experimental design for kinetic analysis of protein-protein interactions with surface plasmon resonance biosensors," J. Immunol. Methods. 1997; 200: 121-133.
Keinanen et al., "Biosynthetic lipid-tagging of antibodies," (1994) FEBS Lett. 346:123.
Killion et al., "Systemic Targeting of Liposome-Encapsulated Immunomodulators to Macrophages for Treatment of Cancer Metastasis," (1994) Immunomethods 4:273.
Knappik et al., "Fully synthetic human combinatorial antibody libraries (HuCAL) based on modular consensus frameworks and CDRs randomized with trinucleotides," J. Mol. Biol. 296:57-86, 2000.
Lam et al., "Microencapsulation of recombinant humanized monoclonal antibody for local delivery," Proc. Int'l. Symp. Control Rel. Bioact. Mater. 24:759-760, 1997.
Langer et al., "Biocompatibility of polymeric delivery systems for macromolecules," J. Biomed. Mater. Res. 15:267-277, 1981.

\* cited by examiner

NOV3842

A.) AD

B.) AY

HEPATITIS B ANTIBODIES

CROSS REFERENCE TO RELATED APPLICATIONS

This application is the U.S. National Stage of International Application No. PCT/IB2019/054498, filed May 30, 2019, which claims the benefit of priority to U.S. Ser. No. 62/678,756, filed May 31, 2018, the contents of which is incorporated herein by reference.

FIELD OF THE INVENTION

The present disclosure is directed to anti-hepatitis B surface antigen antibodies, antibody fragments, and their uses for the reducing the likelihood or treatment of hepatitis B viral infection.

BACKGROUND OF THE INVENTION

Hepatitis B virus (HBV) is an enveloped, hepatotropic virus that infects the liver and may result Chronic hepatitis B (CHB), liver cirrhosis and hepatocellular carcinoma (HCC). While there is a safe vaccine against HBV, at least 600,000 people worldwide die annually of HBV related disorders. Disease progression is affected by viral load, genotype and specific viral mutations (Biswas et al., Med. Virol. 2013; 85:1340-1347). HBV is classified into ten genotypes or classified into four serotypes (asw, adr, ayw and ayr) based on the antigenic determinants found in HBV surface antigen (HBsAg).

HBV is a member of the Hepadnaviridae family and can only infect humans and primates. The virion is constituted by a small 3.2 kb partially double-stranded circular DNA, surrounded by the envelope that interact with hepatocytes. HBV first binds with low-affinity to heparin sulfate proteoglycans on hepatocytes. Subsequently, the pre-S1 lipopeptide of the large envelope protein binds to its higher affinity receptor on the hepatocyte, the bile acid transporter NCTP (sodium taurocholate cotransporting polypeptide). Then, the virus enters the cytoplasm by endocytosis.

HBV clearance and pathogenesis are largely mediated by the adaptive immune response in HBV infection (Guidotti et al., Annu Rev Pathol. 2006; 1:23-61). For HBV to persist it must either not induce a response or it must evade or overwhelm it. Interestingly, HBV "evades" the innate immune response by simply not inducing it (Wieland et al., Proc Natl Acad Sci USA. 2004; 101(17):6669-74). On the other hand, viral persistence is characterized by a state of relative hyporesponsiveness of HBV-specific T cells (Chisari Annu Rev Immunol. 1995; 13:29-60). Several viral proteins have been shown to regulate the adaptive immune response to HBV, suggesting that HBV may employ active evasion strategies that target the adaptive immune response (Thimme et al., J Virol. 2003; 77(1):68-76). It has previously reported that antiviral treatment can overcome CD8+ T cell hyporesponsiveness in chronic HBV infection, suggesting that the T cells are present in these subjects but exhausted (Boni et al., Hepatology. 2001; 33(4):963-71). Induction of an effective HBV specific CD8+ T cell response may be dependent on early CD4+ T cell priming which is regulated by the size of the viral inoculum (Asabe J Virol. 2009; 83(19):9652-62).

The currently approved antiviral therapeutics are two formulations of alpha-interferon (IFN-α) and five nucleoside analogues. While the nucleosides inhibit HBV DNA polymerase activity with varying potencies and barriers to resistance, the therapy does not eliminate the virus and the patient is on this therapy for life. Therefore, better therapeutics to inhibit Hepatitis B infection are needed.

SUMMARY OF THE INVENTION

The present disclosure is directed to neutralizing antibodies to hepatitis B and/or fragments thereof, and antibodies that reduce the amounts of hepatitis B surface antigen (HBsAg).

An antibody, wherein said antibody or antigen binding fragment thereof specifically binds HBsAg.

The antibody wherein said antibody or antigen binding fragment thereof specifically binds HBsAg. In one embodiment, the antibody or antigen binding fragment thereof binds to HBsAg and mutations thereof.

The antibody wherein said antibody or antigen binding fragment specifically binds to and neutralizes hepatitis B. In one embodiment, the antibody or antigen binding fragment thereof neutralizes hepatitis B and hepatitis B containing mutations in HBsAg. In another embodiment, the antibody or antigen binding fragment thereof reduces the amount of HBsAg. In another embodiment, the antibody or antigen binding fragment thereof reduces the amount of circulating HBsAg in the blood.

An isolated antibody, wherein said antibody or antigen binding fragment thereof comprises:
  (i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;
  (ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;
  (iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91;
  (iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO:121, (e) a LCDR2 of SEQ ID NO:122, and (f) a LCDR3 of SEQ ID NO:123;
  (v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO:154, and (f) a LCDR3 of SEQ ID NO:155;
  (vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO:185, (e) a LCDR2 of SEQ ID NO:186, and (f) a LCDR3 of SEQ ID NO:187;
  (vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;

(viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251;

(ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283;

(x) a heavy chain variable region that comprises: (a) a HCDR1 of SEQ ID NO:297, (b) a HCDR2 of SEQ ID NO: 298, (c) a HCDR3 of SEQ ID NO:299; and a light chain variable region that comprises: (d) a LCDR1 of SEQ ID NO:313, (e) a LCDR2 of SEQ ID NO:314, and (f) a LCDR3 of SEQ ID NO: 315;

(xi) a heavy chain variable region that comprises: (a) a HCDR1 of SEQ ID NO:329, (b) a HCDR2 of SEQ ID NO:330, (c) a HCDR3 of SEQ ID NO:331; and a light chain variable region that comprises: (d) a LCDR1 of SEQ ID NO:345, (e) a LCDR2 of SEQ ID NO:346, and (f) a LCDR3 of SEQ ID NO: 347;

(xii) a heavy chain variable region that comprises: (a) a HCDR1 of SEQ ID NO:361, (b) a HCDR2 of SEQ ID NO:362, (c) a HCDR3 of SEQ ID NO:363; and a light chain variable region that comprises: (d) a LCDR1 of SEQ ID NO:377, (e) a LCDR2 of SEQ ID NO:378, and (f) a LCDR3 of SEQ ID NO: 379;

(xiii) a heavy chain variable region that comprises: (a) a HCDR1 of SEQ ID NO:393, (b) a HCDR2 of SEQ ID NO:394, (c) a HCDR3 of SEQ ID NO:395; and a light chain variable region that comprises: (d) a LCDR1 of SEQ ID NO:409, (e) a LCDR2 of SEQ ID NO:410, and (f) a LCDR3 of SEQ ID NO:411;

(xiv) a heavy chain variable region that comprises: (a) a HCDR1 of SEQ ID NO:425, (b) a HCDR2 of SEQ ID NO:426, (c) a HCDR3 of SEQ ID NO:427; and a light chain variable region that comprises: (d) a LCDR1 of SEQ ID NO:441, (e) a LCDR2 of SEQ ID NO:442, and (f) a LCDR3 of SEQ ID NO: 443;

(xv) a heavy chain variable region that comprises: (a) a HCDR1 of SEQ ID NO:457, (b) a HCDR2 of SEQ ID NO:458, (c) a HCDR3 of SEQ ID NO:459; and a light chain variable region that comprises: (d) a LCDR1 of SEQ ID NO:473, (e) a LCDR2 of SEQ ID NO:474, and (f) a LCDR3 of SEQ ID NO:475; or (xvi) a heavy chain variable region that comprises: (a) a HCDR1 of SEQ ID NO:489, (b) a HCDR2 of SEQ ID NO:490, (c) a HCDR3 of SEQ ID NO:491; and a light chain variable region that comprises: (d) a LCDR1 of SEQ ID NO:505, (e) a LCDR2 of SEQ ID NO:506, and (f) a LCDR3 of SEQ ID NO: 507.

The antibody wherein one or two amino acids within a CDR have been modified, deleted or substituted.

The antibody that retains at least 90, 91, 92, 93, 94, 95, 96, 97, 98 or 99% identity over either the variable heavy chain region or the variable light chain region.

The antibody wherein the antibody is a monoclonal antibody, a chimeric antibody, a humanized antibody, a human engineered antibody, a human antibody, a single chain antibody (scFv) or an antibody fragment.

An isolated antibody or antigen binding fragment thereof, wherein said antibody or antigen binding fragment thereof comprises:

(i) a heavy chain variable region (vH) that comprises SEQ ID NO:18, and a light chain variable region (vL) that comprises SEQ ID NO: 34;

(ii) a heavy chain variable region (vH) that comprises SEQ ID NO: 50, and a light chain variable region (vL) that comprises SEQ ID NO: 66;

(iii) a heavy chain variable region (vH) that comprises SEQ ID NO: 82, and a light chain variable region (vL) that comprises SEQ ID NO:98;

(iv) a heavy chain variable region (vH) that comprises SEQ ID NO:114, and a light chain variable region (vL) that comprises SEQ ID NO:130;

(v) a heavy chain variable region (vH) that comprises SEQ ID NO:146, and a light chain variable region (vL) that comprises SEQ ID NO:162;

(vi) a heavy chain variable region (vH) that comprises SEQ ID NO:178, and a light chain variable region (vL) that comprises SEQ ID NO:194;

(vii) a heavy chain variable region (vH) that comprises SEQ ID NO:210, and a light chain variable region (vL) that comprises SEQ ID NO:226;

(viii) a heavy chain variable region (vH) that comprises SEQ ID NO:242, and a light chain variable region (vL) that comprises SEQ ID NO:258;

(ix) a heavy chain variable region (vH) that comprises SEQ ID NO:274, and a light chain variable region (vL) that comprises SEQ ID NO:290;

(x) a heavy chain variable region (vH) that comprises SEQ ID NO:306, and a light chain variable region (vL) that comprises SEQ ID NO:322;

(xi) a heavy chain variable region (vH) that comprises SEQ ID NO:338, and a light chain variable region (vL) that comprises SEQ ID NO:354;

(xii) a heavy chain variable region (vH) that comprises SEQ ID NO:370, and a light chain variable region (vL) that comprises SEQ ID NO:386;

(xiii) a heavy chain variable region (vH) that comprises SEQ ID NO:402, and a light chain variable region (vL) that comprises SEQ ID NO:418;

(xiv) a heavy chain variable region (vH) that comprises SEQ ID NO:434, and a light chain variable region (vL) that comprises SEQ ID NO:450;

(xv) a heavy chain variable region (vH) that comprises SEQ ID NO:466, and a light chain variable region (vL) that comprises SEQ ID NO:482; or (xvi) a heavy chain variable region (vH) that comprises SEQ ID NO:498, and a light chain variable region (vL) that comprises SEQ ID NO:514.

The antibody or fragment thereof, that retains at least 90, 91, 92, 93, 94, 95, 96, 97, 98 or 99% identity over either the variable light or variable heavy region.

The antibody wherein one, two, three, four or five, but less than 10 amino acids within the variable light or variable heavy region have been modified, deleted or substituted.

The antibody wherein the antibody is a monoclonal antibody, a chimeric antibody, a humanized antibody, a human engineered antibody, a human antibody, a single chain antibody (scFv) or an antibody fragment.

The antibody wherein the antibody or fragment thereof has reduced glycosylation or no glycosylation or is hypofucosylated.

A pharmaceutical composition comprising the antibody or fragment thereof, further comprising a pharmaceutically acceptable carrier.

The pharmaceutical composition wherein the pharmaceutically acceptable carrier contains histidine or a sugar.

The pharmaceutical composition wherein the sugar is sucrose.

A pharmaceutical composition comprising a plurality of an antibody or antigen binding fragment wherein at least 0.05%, 0.1%, 0.5%, 1%, 2%, 3%, 5% or more or more of the antibodies in the composition have an α2,3-linked sialic acid residue.

A pharmaceutical composition comprising a plurality of an antibody or antigen binding fragment, wherein none of the antibodies comprise a bisecting GlcNAc.

The pharmaceutical composition comprising the antibody or fragment thereof, wherein the composition is prepared as a lyophilisate.

A method of neutralizing a hepatitis B virus infection comprising administering via injection or infusion to a patient in need an effective amount of the antibody.

The method wherein the patient in need is diagnosed with hepatitis B viruria or hepatitis B viremia.

The method wherein the patient in need is diagnosed with hepatitis B surface antigen (HBsAg) in the blood or serum.

A method of treating or reducing the likelihood of hepatitis B virus associated disorder, comprising administering via injection or infusion to a patient in need an effective amount of the antibody and wherein the disorder is: liver failure, cirrhosis, or hepatocellular carcinoma.

The method wherein the antibody or composition is reconstituted prior to injection or infusion.

The method wherein the antibody or the pharmaceutical composition is administered in combination with another therapeutic agent.

The method wherein the therapeutic agent is an anti-viral agent.

The method wherein the anti-viral agent is: lamivudine, entecavir and tenofovir or alpha-interferon.

The method wherein the therapeutic agent is an antagonist of immune checkpoint inhibitor.

The method wherein the antagonist of the immune checkpoint inhibitor is selected from the group consisting of: PD-1, PD-L1, PD-L2, TIM3, CTLA-4, LAG-3, CEACAM-1, CEACAM-5, VISTA, BTLA, TIGIT, LAIR1, CD160, 2B4 and TGFR.

The method wherein the antagonist of the immune checkpoint inhibitor is an anti-PD-L1 antibody.

The method wherein the therapeutic agent is an additional anti-HBsAg antibody.

The antibody or fragment thereof for use as a medicament.

The antibody or fragment thereof, for use in the neutralization hepatitis B virus infection.

The antibody or fragment thereof, for use in the treatment or reducing the likelihood of: liver failure, cirrhosis, and/or hepatocellular carcinoma.

The use according to any of the above, administered in combination with another therapeutic agent.

The use according to any of the above, wherein the therapeutic agent is an anti-viral agent.

The use according to any of the above, wherein the anti-viral agent is: lamivudine, entecavir and tenofovir or alpha-interferon.

The use according to any of the above, wherein the therapeutic agent is an antagonist of immune checkpoint inhibitor.

The use according to any of the above, wherein the antagonist of the immune checkpoint inhibitor is selected from the group consisting of: PD-1, PD-L1, PD-L2, TIM3, CTLA-4, LAG-3, CEACAM-1, CEACAM-5, VISTA, BTLA, TIGIT, LAIR1, CD160, 2B4 and TGFR.

The use according to the above, wherein the antagonist of the immune checkpoint inhibitor is an anti-PD-L1 antibody.

The use according to any of the above, wherein the therapeutic agent is an additional anti-HBsAg antibody.

A nucleic acid that encodes the antibody or antigen binding fragment.

A vector comprising the nucleic acid.

A host cell comprising the vector.

A diagnostic reagent comprising the antibody or antigen binding fragment thereof, which is labeled.

The diagnostic reagent, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementarity-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting in total about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, IMGT, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Lefranc, M. P., Nucleic Acids Res., 29:207-209 (2001); Al-Lazikani et al., J. Mol. Biol., 273: 927-748 (1997)). Definitions of antigen combining sites are also described in the following: Ruiz et al., Nucleic Acids Res., 28:219-221 (2000); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/Domain Gap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2, or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment," as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR, and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody," as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)), or electron microscopy. A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known or inferred variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91% 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically, a specific or selective binding reaction will produce a signal at least twice over the background signal and, more typically, at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an anti-HBsAg antibody of the present disclosure. In some aspects, the phrase "consisting essentially of" expressly excludes the inclusion of one or more additional active agents other than an anti-HBsAg antibody of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For example, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as a basis for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, (J. Mol. Biol. 48:444-453, 1970), algorithm which has been incorporated into the GAP program in the GCG software package (available from University of South Florida), using either a BLOSUM 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "hepatitis B," "hepatitis B virus" or "HBV" refer to a member of the family Hepadnaviridae, genus *Orthohepadnavirus*. HBV is a double stranded DNA virus. The virus is divided into four major serotypes (adr, adw, ayr, ayw) based on HBsAg.

The term "Hepatitis B surface antigen," "HBsAg" or "HBVsAg" refers to a protein produced by Hepatitis B virus.

TABLE 1

| SEQ ID NO: | Name/accession number | SEQUENCE |
| --- | --- | --- |
| SEQ ID NO: 1 | HBsAg consensus | MENITSGFLGPLLVLQAGFFLLTRILTIPQSLDSWWTSLNFLGGAPTCPG QNSQSPTSNHSPTSCPPTCPGYRWMCLRRFIIFLFILLLCLIFLLVLLDY QGMLPVCPLLPGSSTTSTGPCKTCTIPAQGTSMFPSCCCTKPSDGNCTCI PIPSSWAFAKFLWEWASARFSWLSLLVPFVQWFVGLSPTVWLSVIWMMWY WGPSLYNILSPFLPLLPIFFCLWVYI |

TABLE 1-continued

| SEQ ID NO: | Name/accession number | SEQUENCE |
|---|---|---|
| SEQ ID NO: 2 | HBsAg Serotype ayr X04615.1 | MESTTSGFLGPLLVLQAGFFLLTRILTIPQSLDSWWTSLNFLGGAPTCPGQN SQSPTSNHSPTSCPPTCPGYRWMCLRRFIIFLFILLLCLIFLLVLLDYQGML PVCPLLPGTSTTSTGPCRTCTIPAQGTSMFPSCCCTKPSDGNCTCIPIPSSW AFARFLWEWASVRFSWLSLLVPFVQWFVGLSPTVWLSAIWMMWYWGPSLYNI LSPFLPLLPIFFCLWVYI |
| SEQ ID NO: 3 | HBsAg Serotype adr AF068756.1 | MESTTSGFLGPLLVLQAGFFLLTRILTIPQSLDSWWTSLNFLGGAPTCPGQN LQSPTSNHSPTSCPPICPGYRWMCLRRFIIFLFILLLCLIFLLVLLDYQGML PVCPLLPGTSTTSTGPCKTCTIPAQGTSMFPSCCCTKPSDGNCTCIPIPSSW AFARFLWEWASVRFSWLSLLVPFVQWFVGLSPTVWLSVIWMMWYWGPSLYNI LSPFLPLLPIFFCLWVYI |
| SEQ ID NO: 4 | HBsAg Serotype ayw AY661792.1 | MENITSGFLGPLLVLQAGFFLLTRILTIPQSLDSWWTSLNFLGGTTVCLGQN SQSPTSNHSPTSCPPTCPGYRWMCLRRFIIFLFILLLCLIFLLVLLDYQGML PVCPLIPGSSTTSTGPCRTCTTPAQGTSMYPSCCCTKPSDGNCTCIPIPSSW AFGKFLWEWASARFSWLSLLVPFVQWFVGLSPTVWLSVIWMMWYWGPSLYSI LSPFLPLLPIFFCLWVYI |
| SEQ ID NO: 5 | HBsAg Serotype adw HM066946.2 | MENITSGLLGPLLVLQAVCFLLTKILTIPKSLDSWWTSLNFLGVPPGCPGQN SQSPISNHLPTSCPPTCPGYRWMCLRRFIIFLFILLLCLIFLLVLLDYQGML PVCPLLPGSTTTSTGPCKTCTTLAQGTSMFPSCCCTKPSDGNCTCIPIPSSW AFGKYLWEWASARFSWLSLLVQFVQWCVGLSPTVWLLVIWMIWYWGPNLCSI LSPFIPLLPIFCYLWASI |

"IC50" (half-maximal inhibitory concentration) refers to the concentration of a particular antibody which induces a signal halfway (50%) between the baseline control and the maximum possible signal.

"EC50" (half-maximal effective concentration) refers to the concentration of a particular antibody which induces a response halfway (50%) between the baseline control and the maximum possible effect after a specific exposure or treatment time. For example, the EC50 is the concentration of antibody at which virus infection is neutralized by 50%.

"EC90" refers to the concentration of a particular antibody which induces a response corresponding to 90% of the maximum possible effect after a specific exposure or treatment time. For example, the EC90 is the concentration of antibody at which virus infection is neutralized by 90%.

"Neutralization" refers to the inhibition of viral infection of a host cell, as demonstrated by the absence of viral gene expression. Without being held to any one theory, mechanisms of neutralization by a particular antibody could include blocking the interaction of viral capsid proteins with cell surface receptors or disruption of any stage of the entry and trafficking process prior to delivery of the viral genome to the nucleus of the host cell.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both.

The phrase "reducing the likelihood" refers to delaying the onset or development or progression of the disease, infection or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated polyoma viral infection.

The term "co-administer" refers to the simultaneous presence of two active agents in the blood of an individual. Active agents that are co-administered can be concurrently or sequentially delivered.

DETAILED DESCRIPTION

Figure 1:
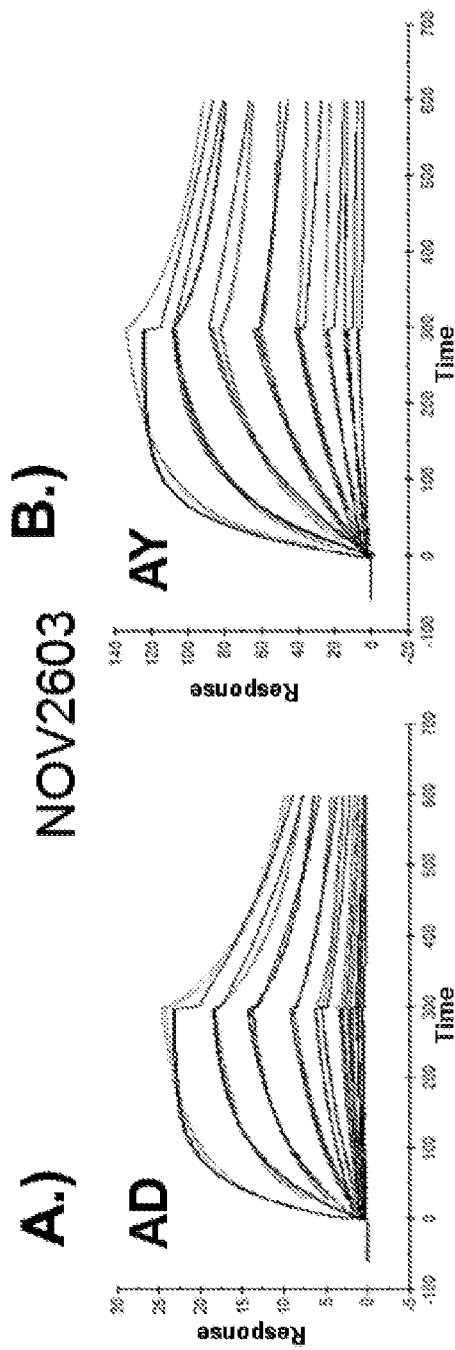
FIGS. 1A/B-16A/B are surface plasmon resonance (SPR/Biacore) measurements of the antibodies, showing the Kd for the AD and AY HBV serotypes.
Figure 2:
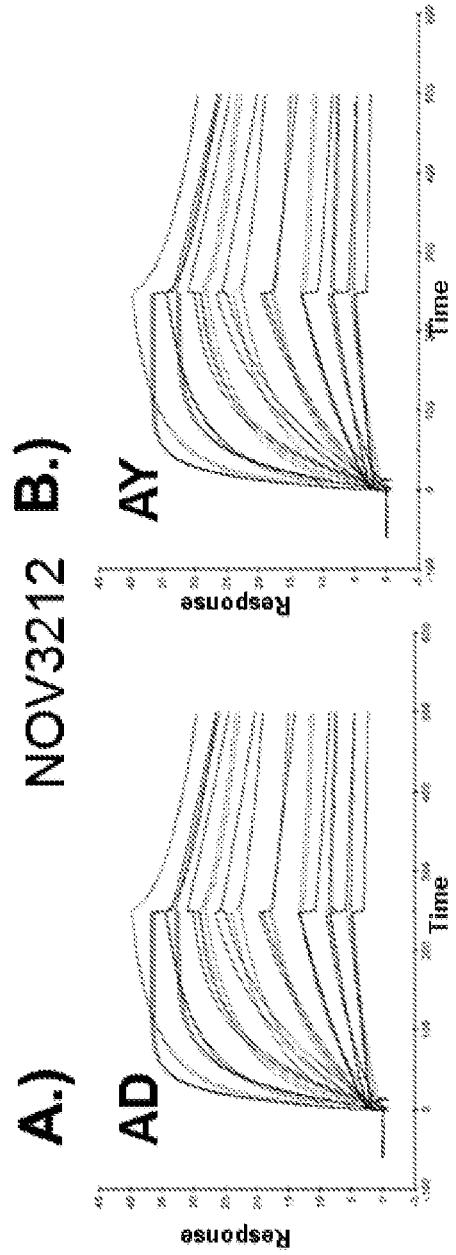
Figure 3:
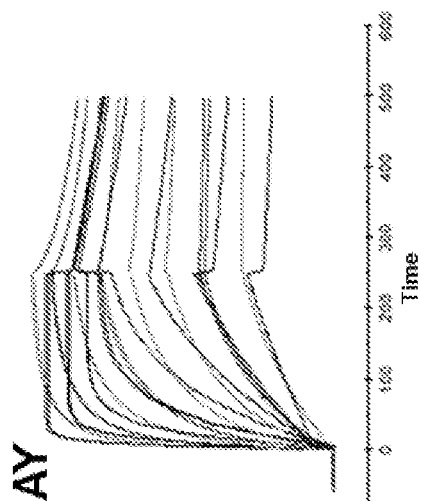
Figure 3:
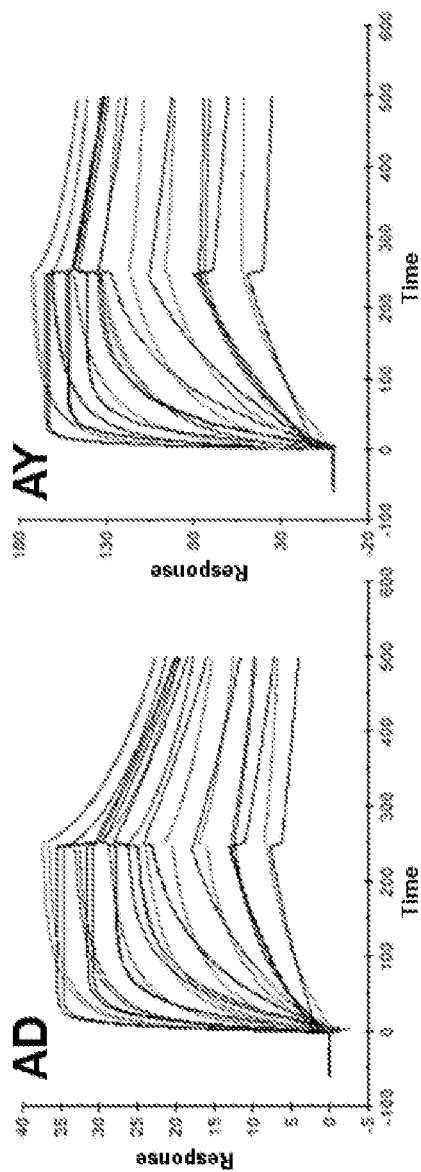
Figure 4:
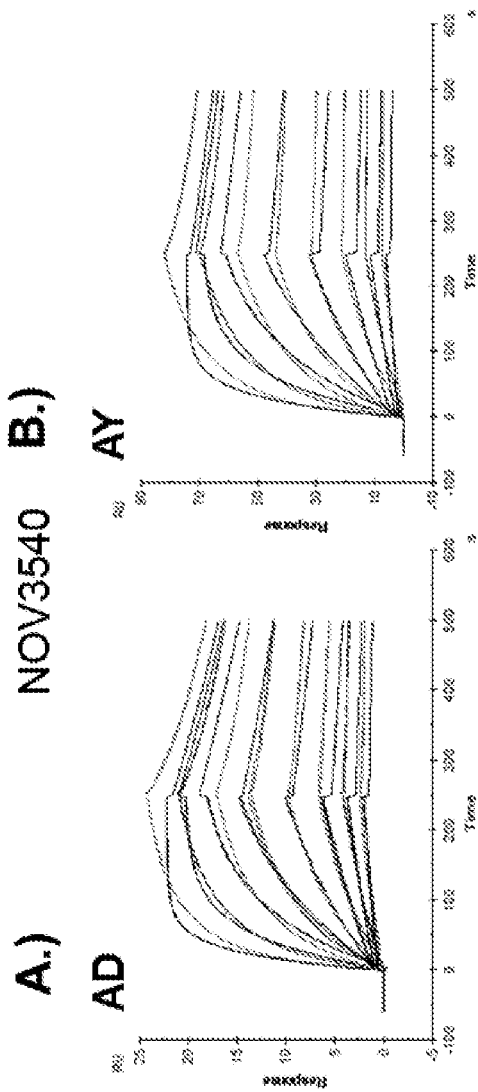
Figure 5:
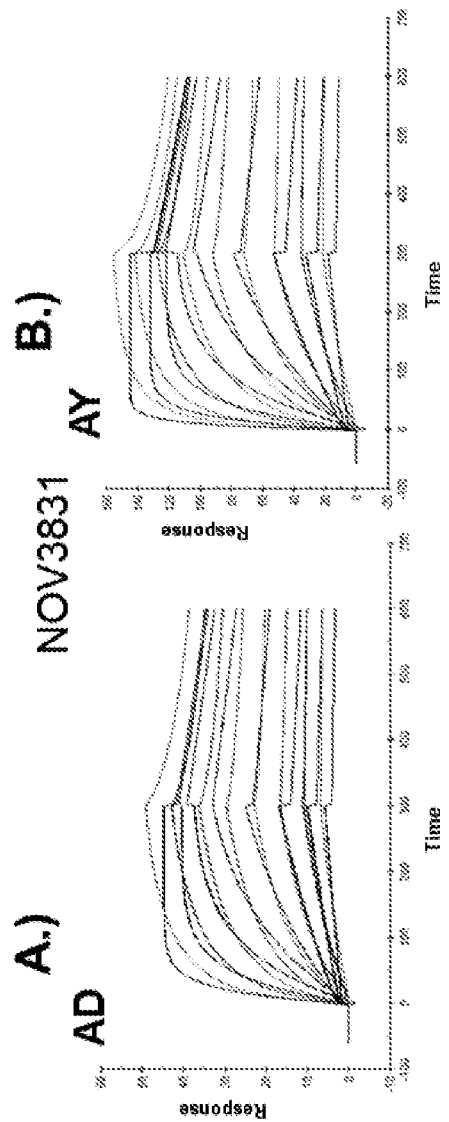
Figure 6:
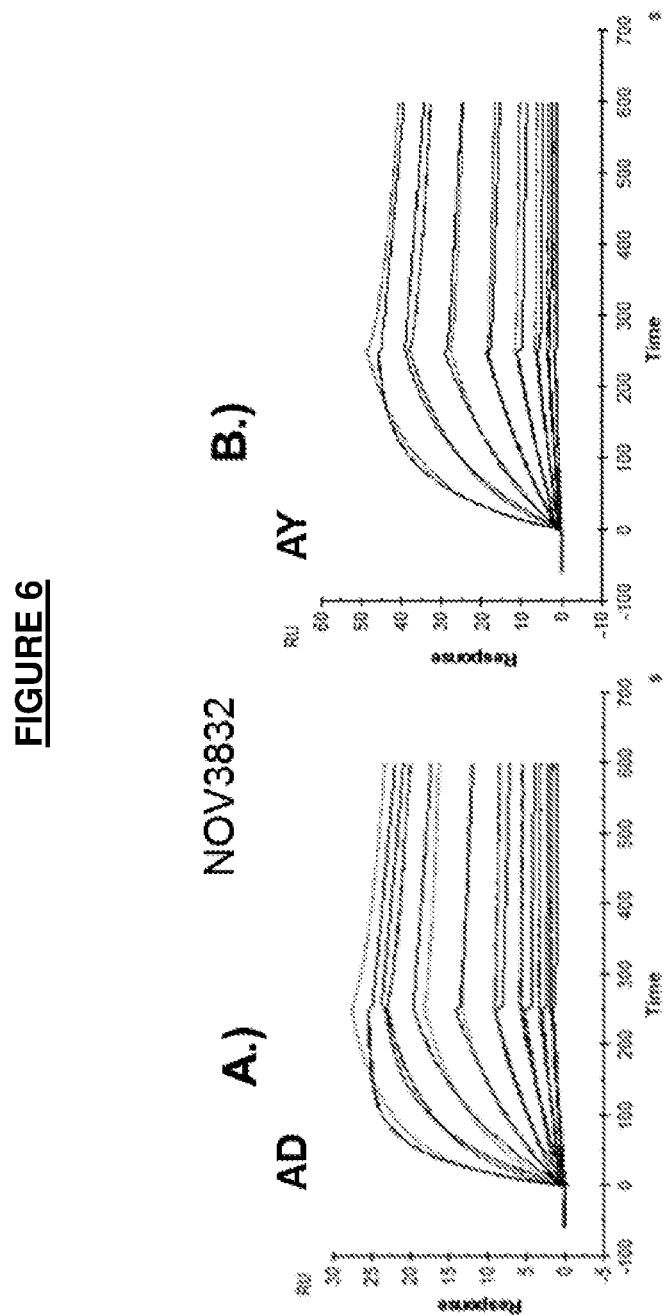
Figure 7:
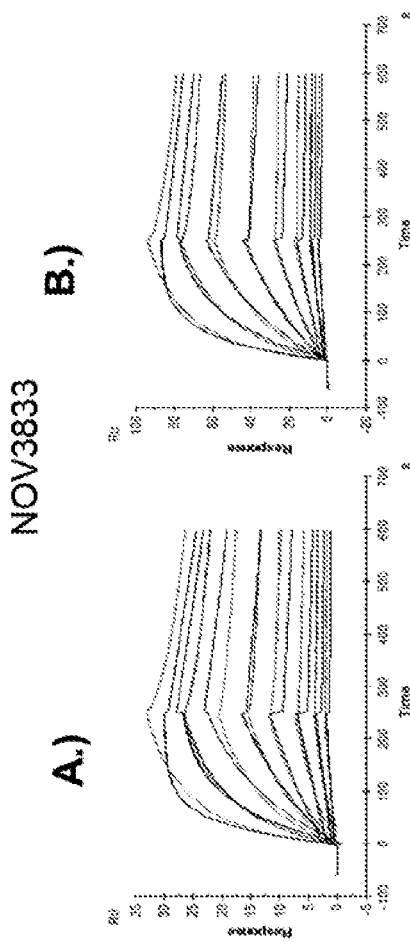
Figure 8:
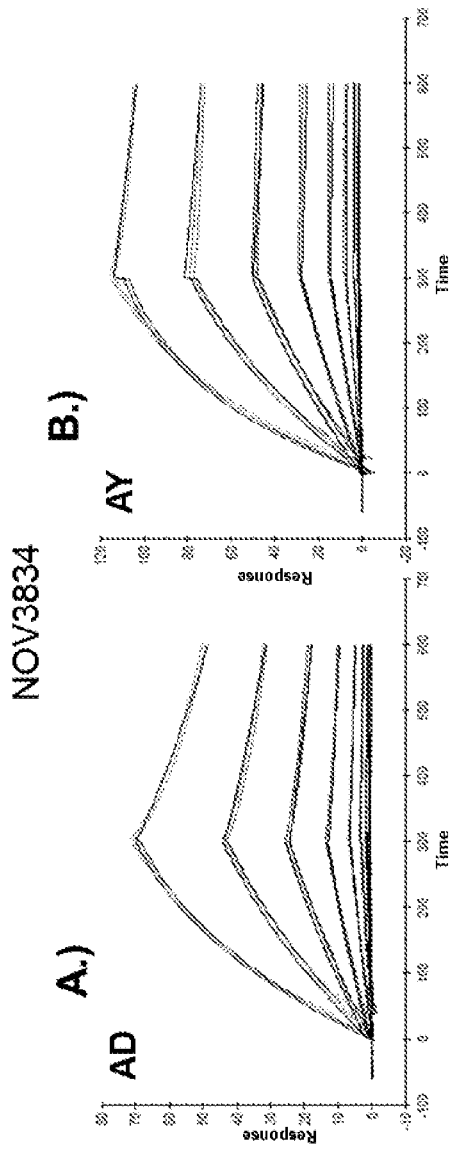
Figure 9:
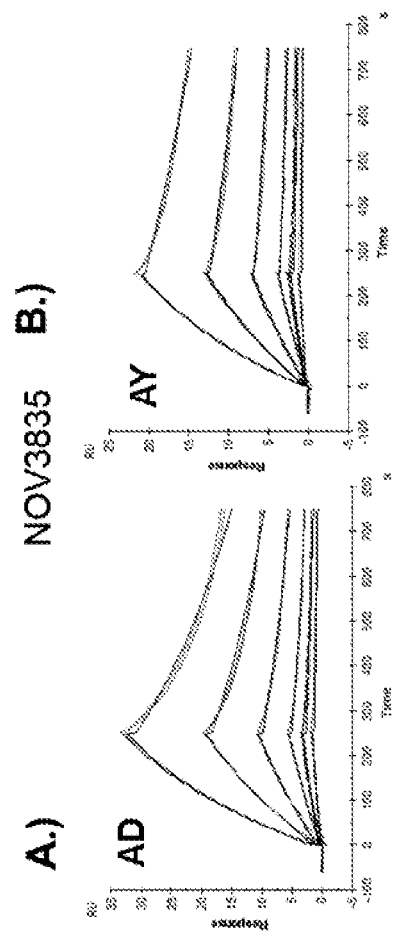
Figure 10:
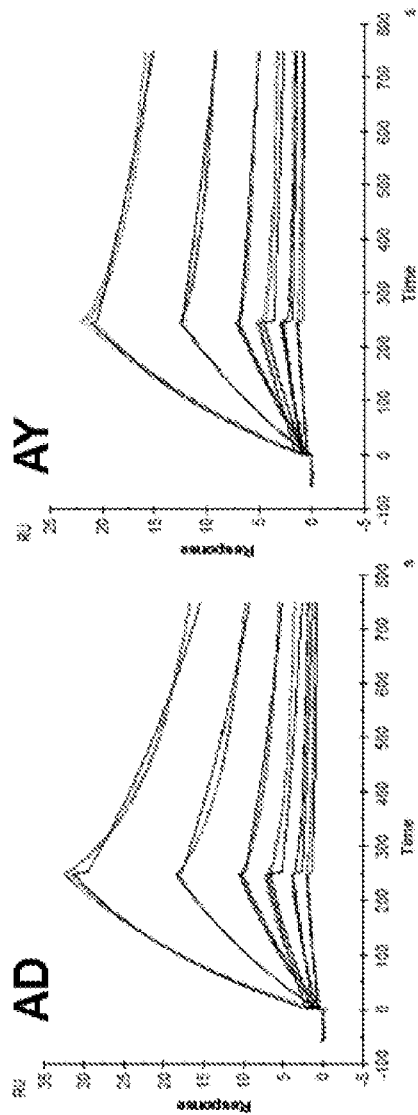
Figure 11:
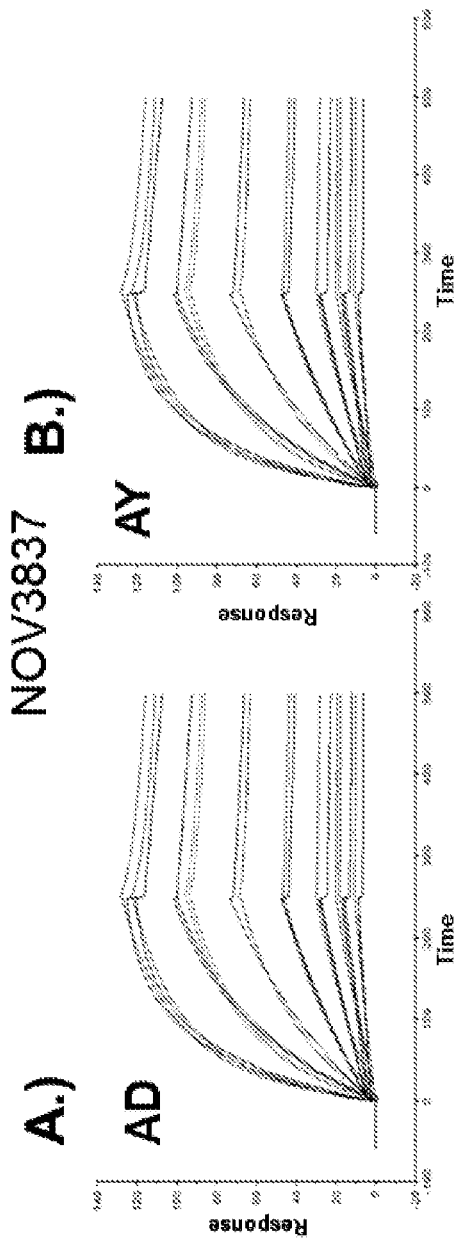
Figure 12:
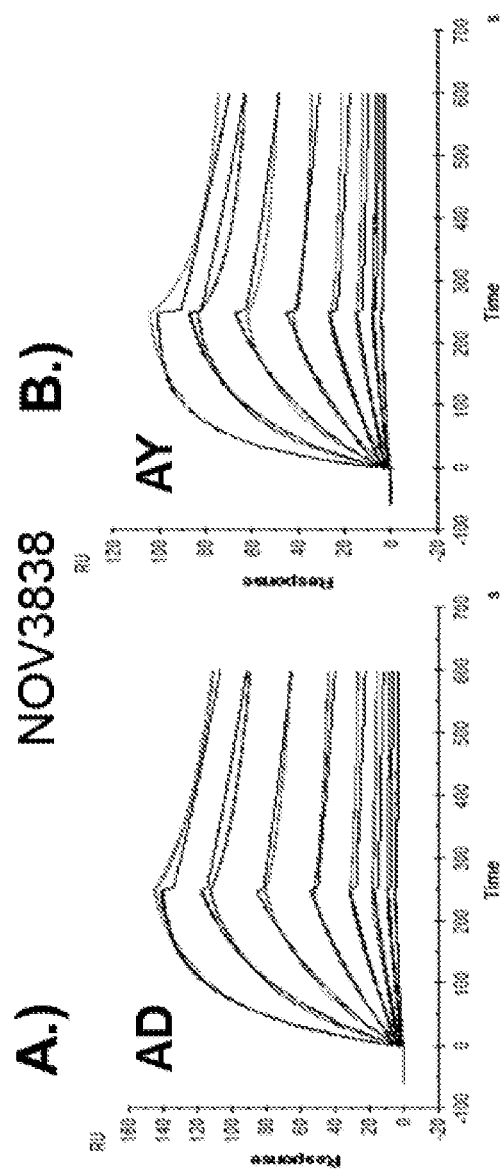
Figure 13:
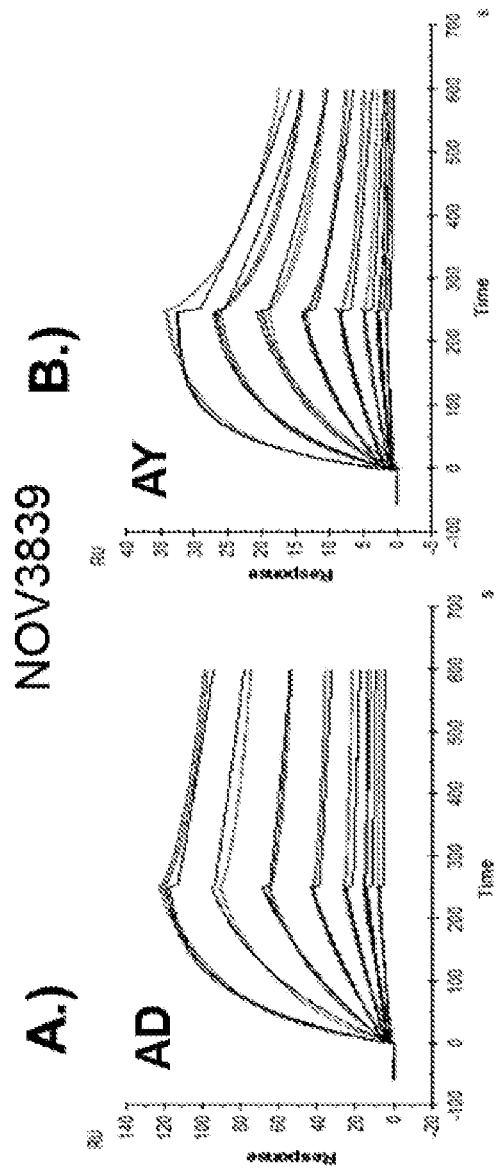
Figure 14:
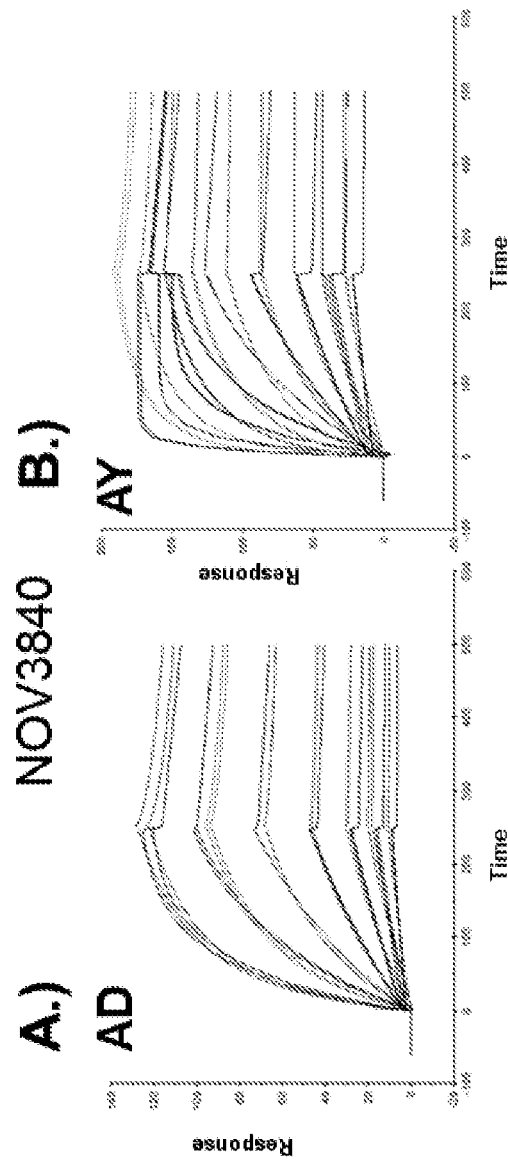
Figure 15:
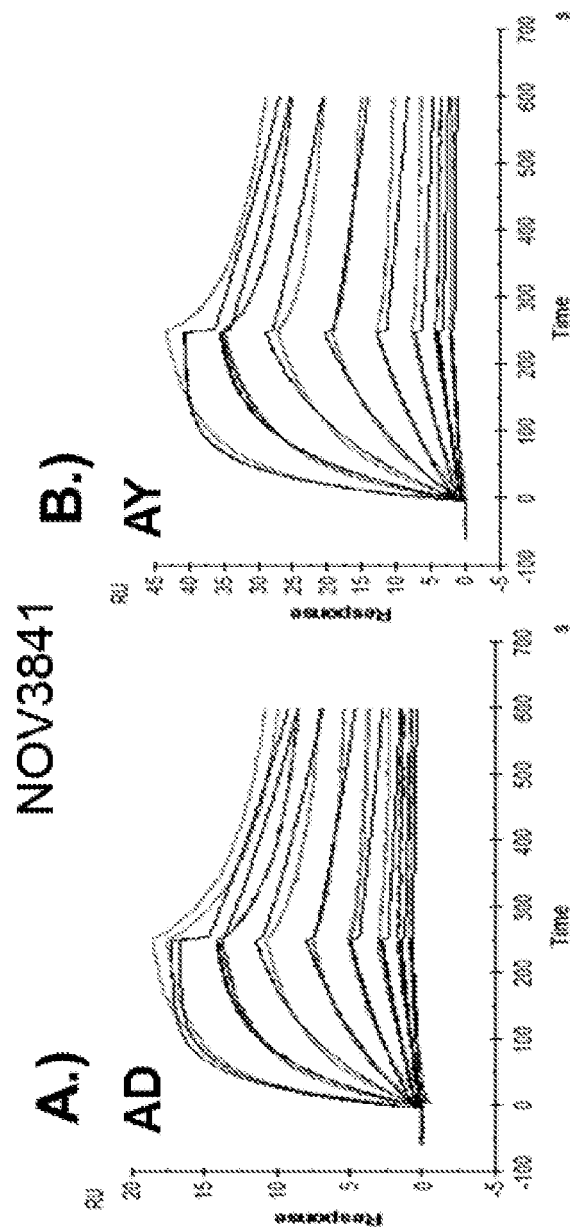
Figure 16:
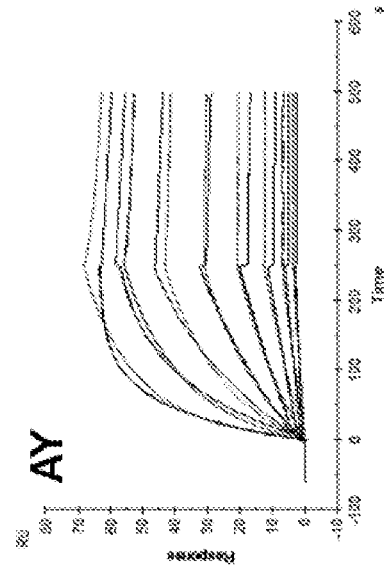
Figure 16:
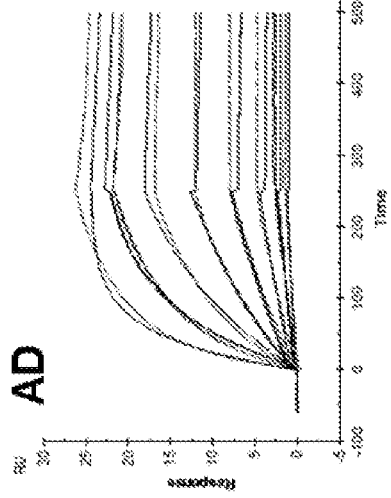
Figure 17:
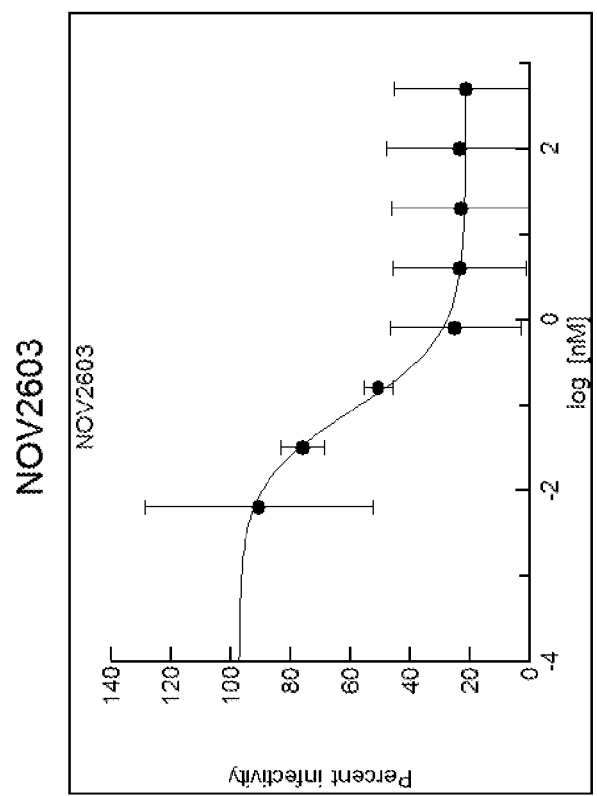
FIGS. 17-33 demonstrates that the antibodies neutralize HBV infection.
Figure 18:
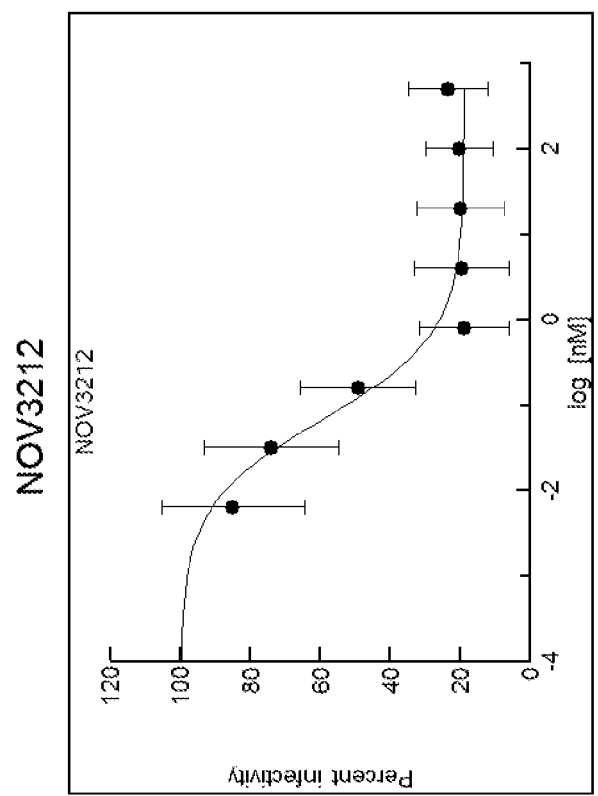
Figure 19:
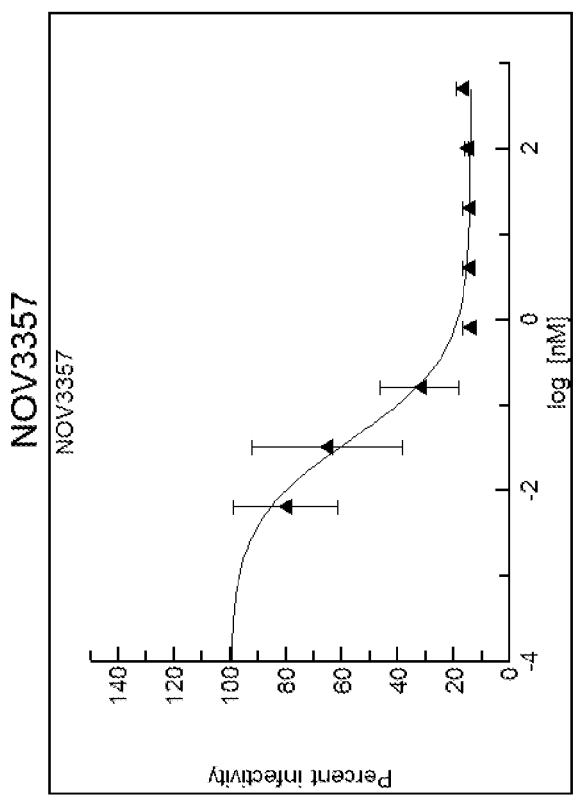
Figure 20:
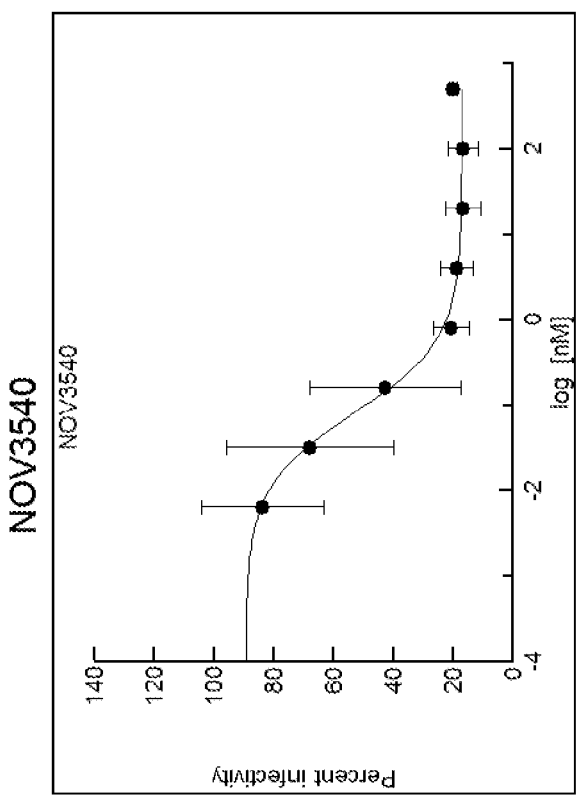
Figure 21:
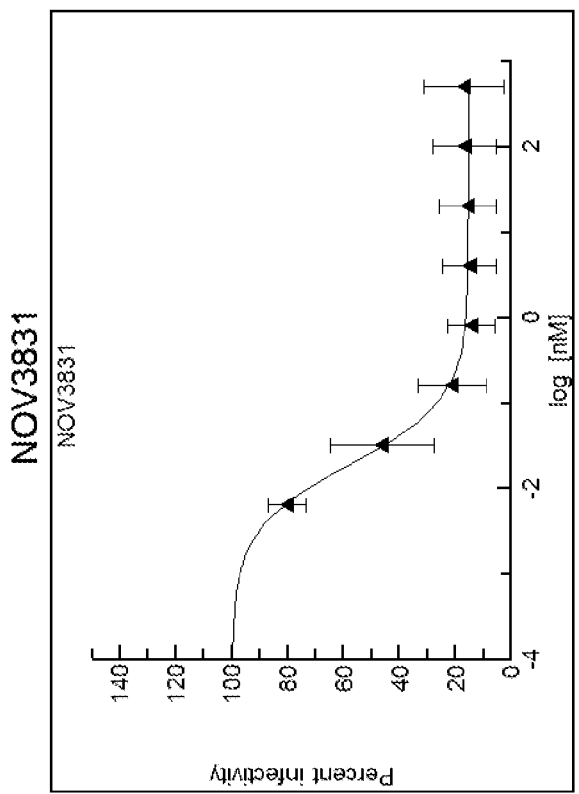
Figure 22:
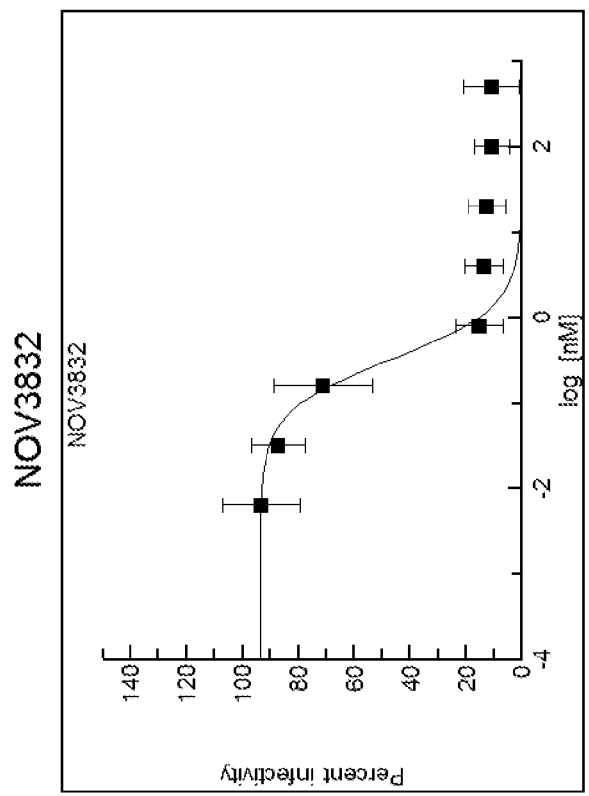
Figure 23:
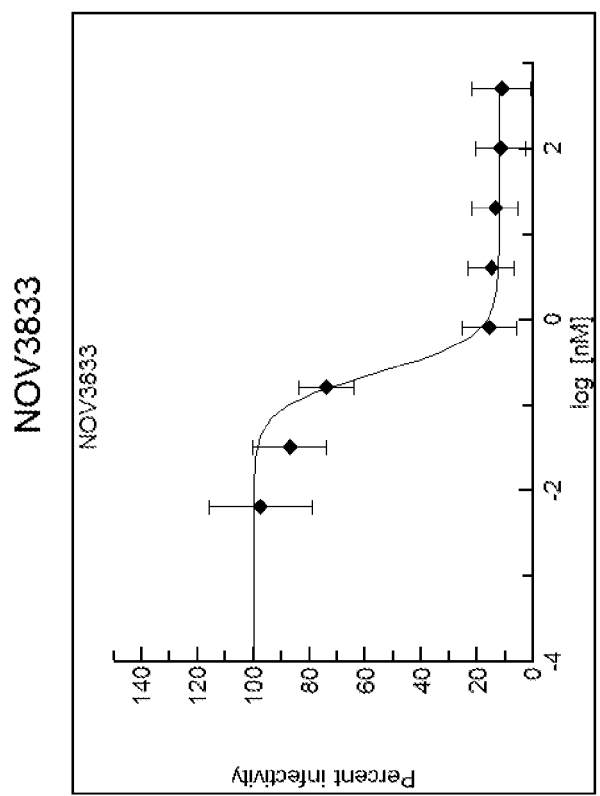
Figure 24:
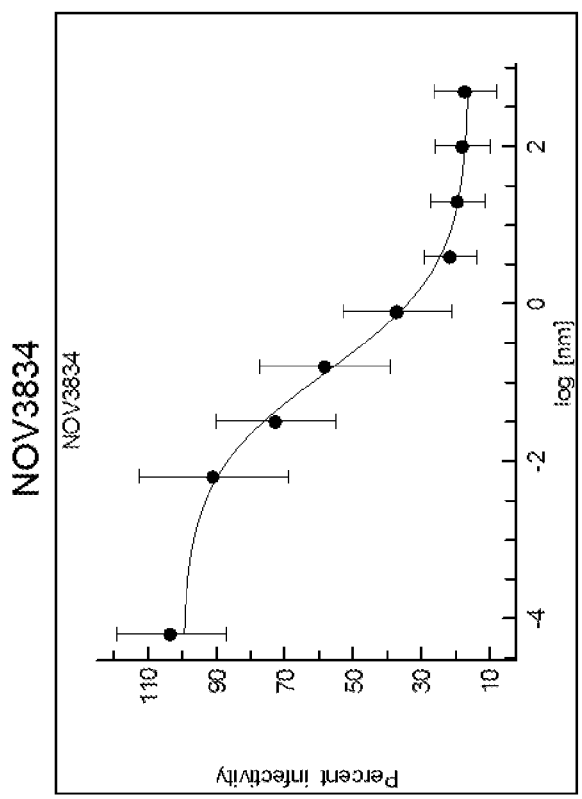
Figure 25:
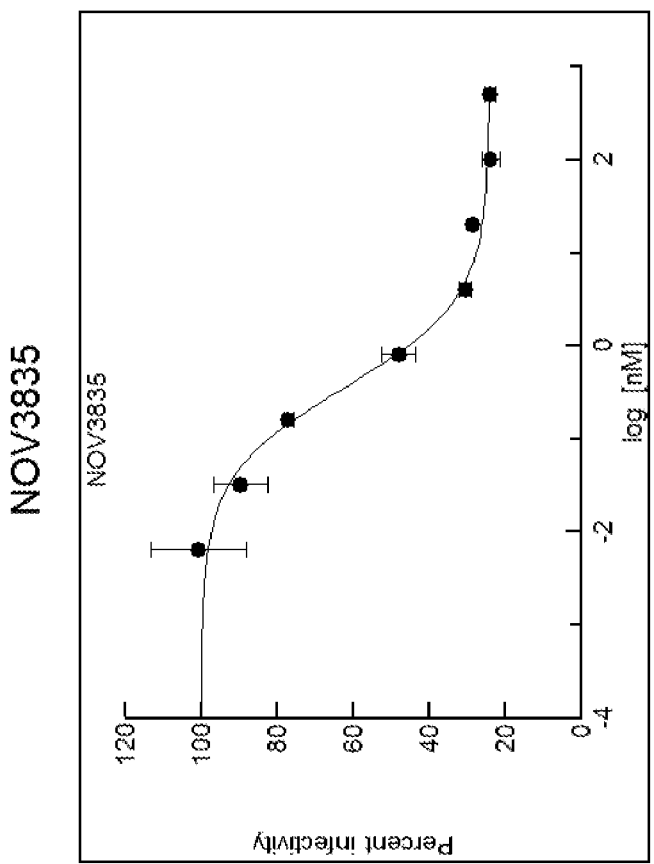
Figure 26:
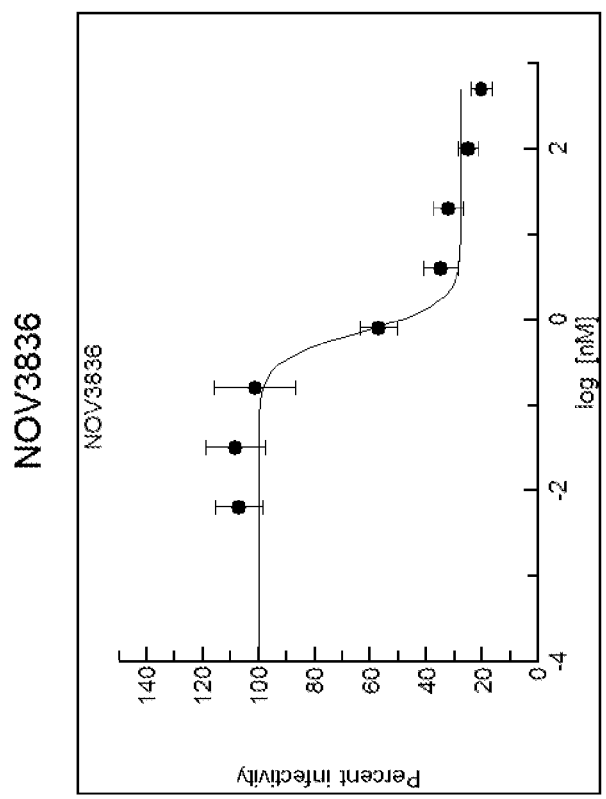
Figure 27:
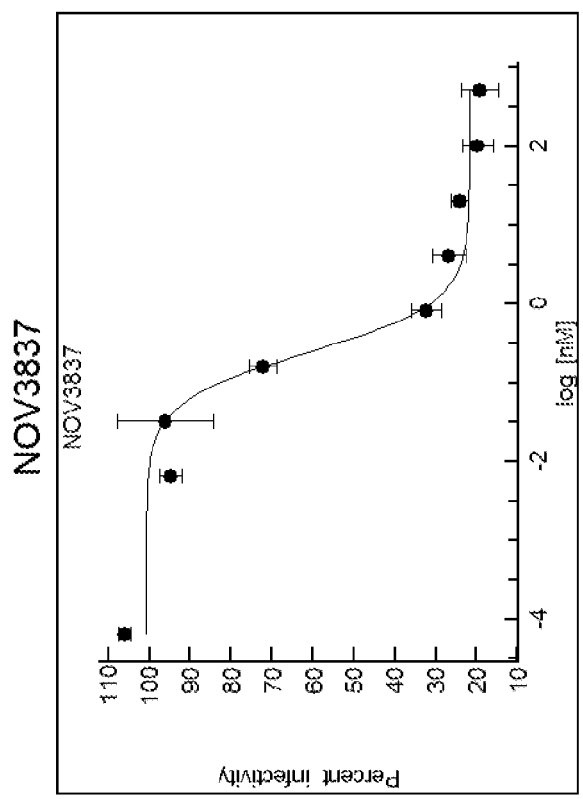
Figure 28:
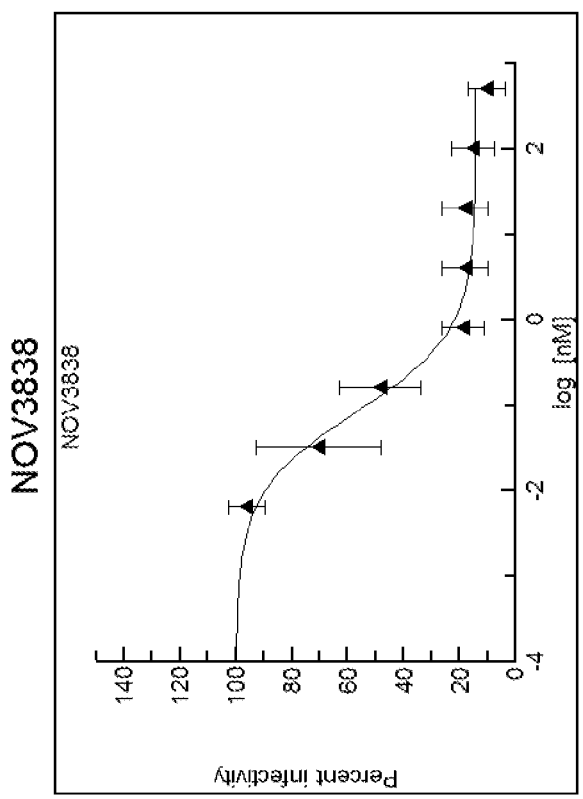
Figure 29:
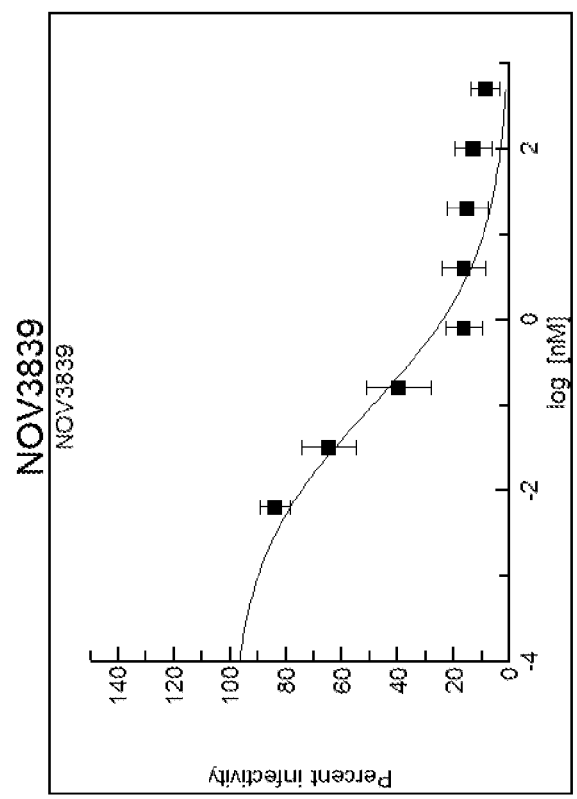
Figure 30:
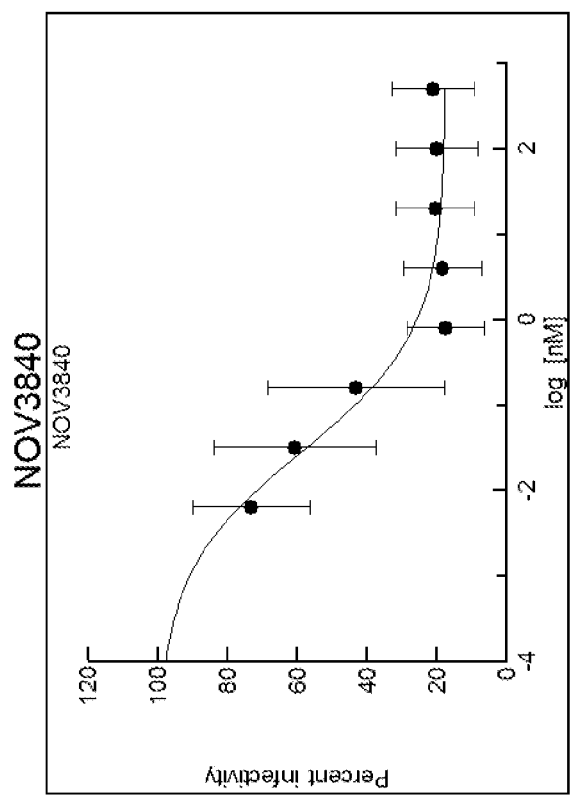
Figure 31:
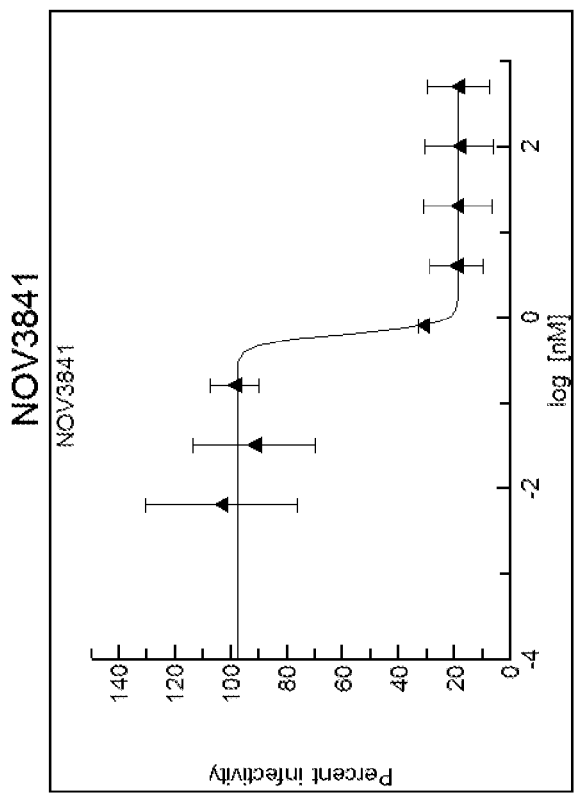
Figure 32:
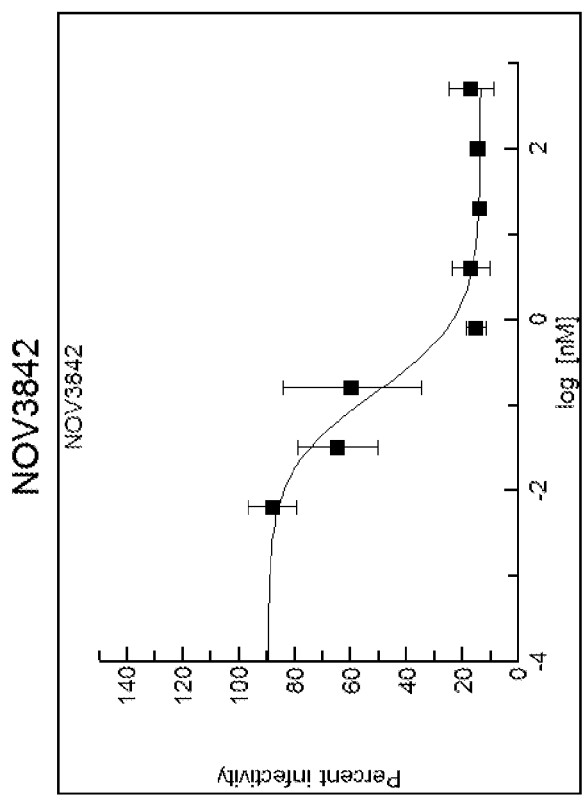
Figure 33:
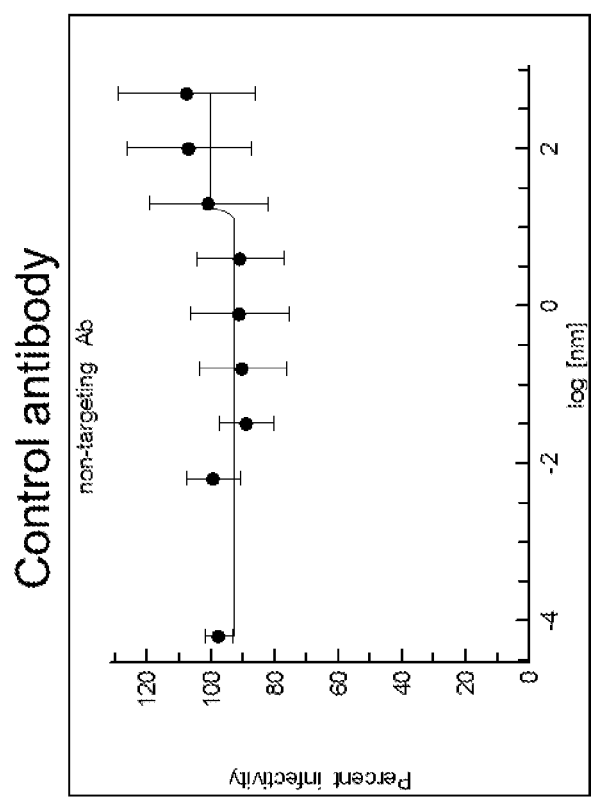
Figure 34:
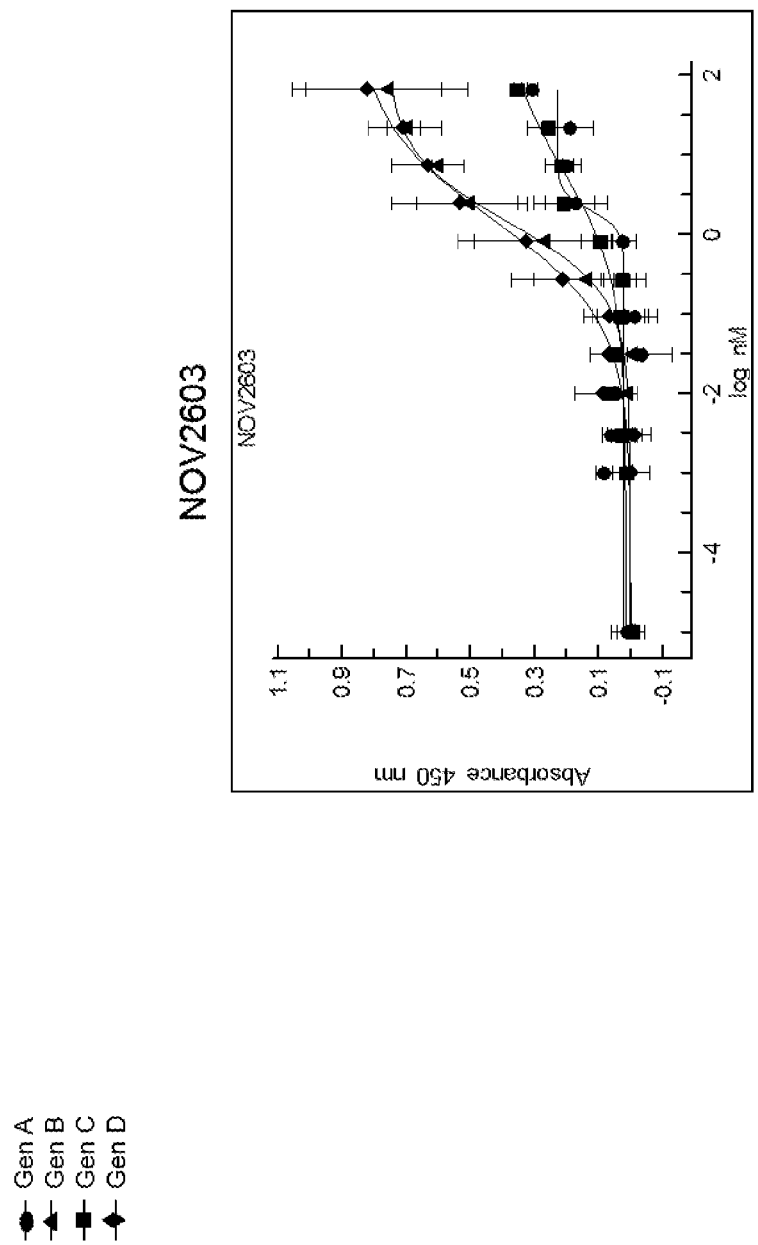
FIGS. 34-50 shows the $IC_{50}$ of the antibodies to four genotypes (A-D).
Figure 35:
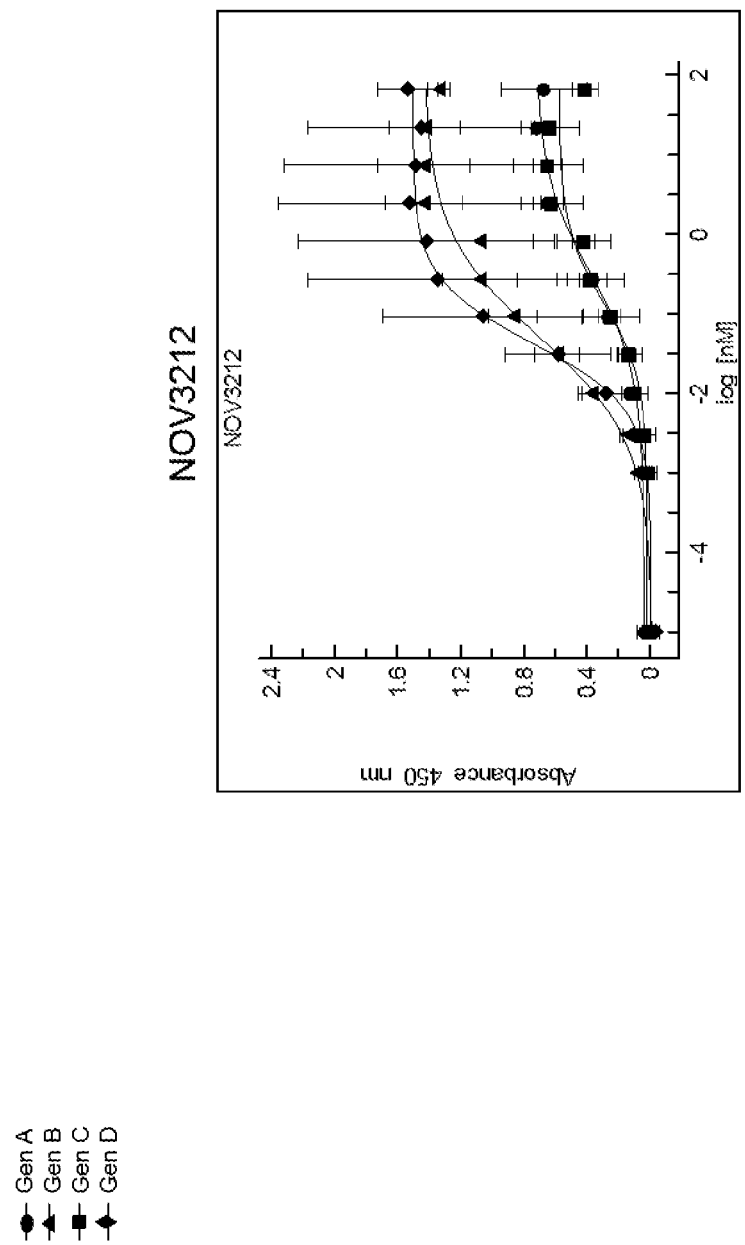
Figure 36:
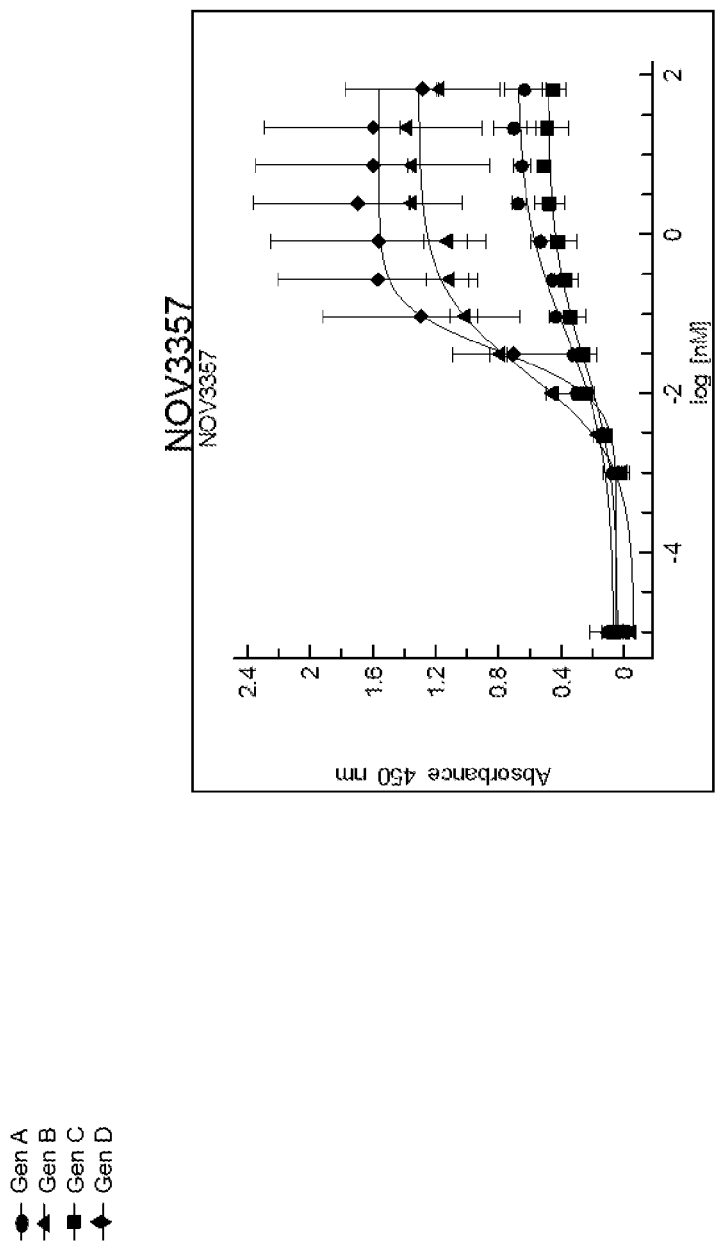
Figure 37:
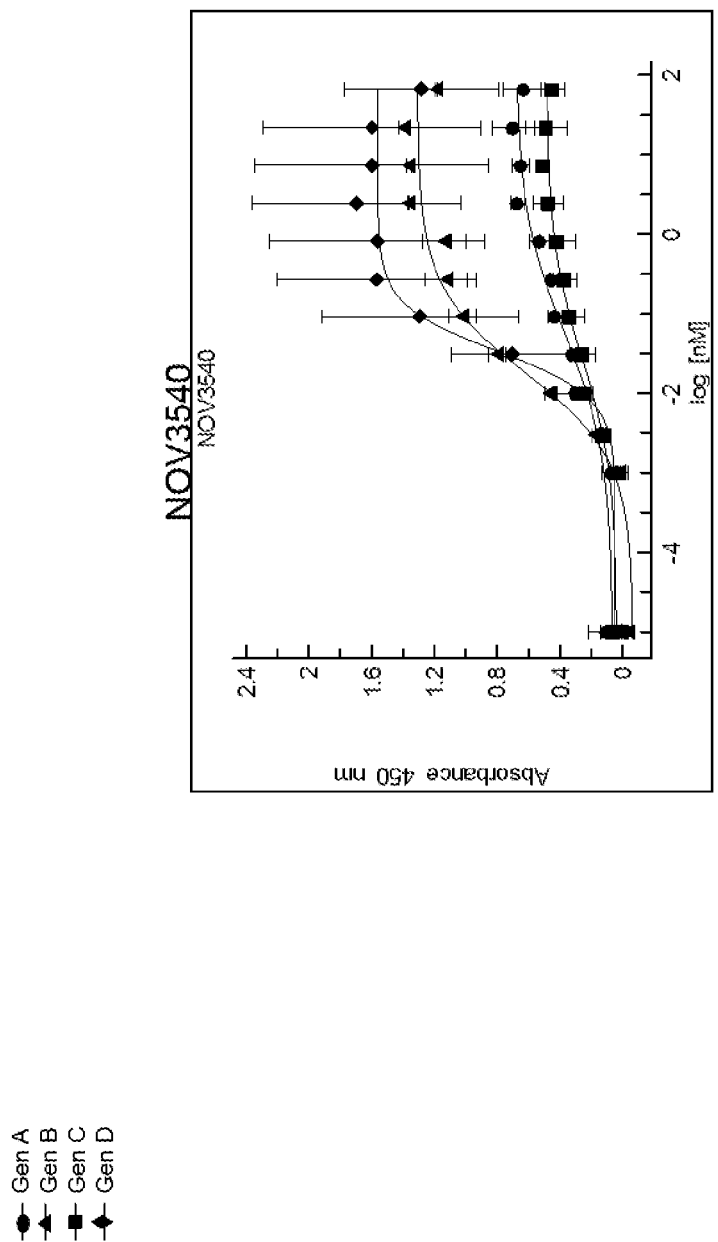
Figure 38:
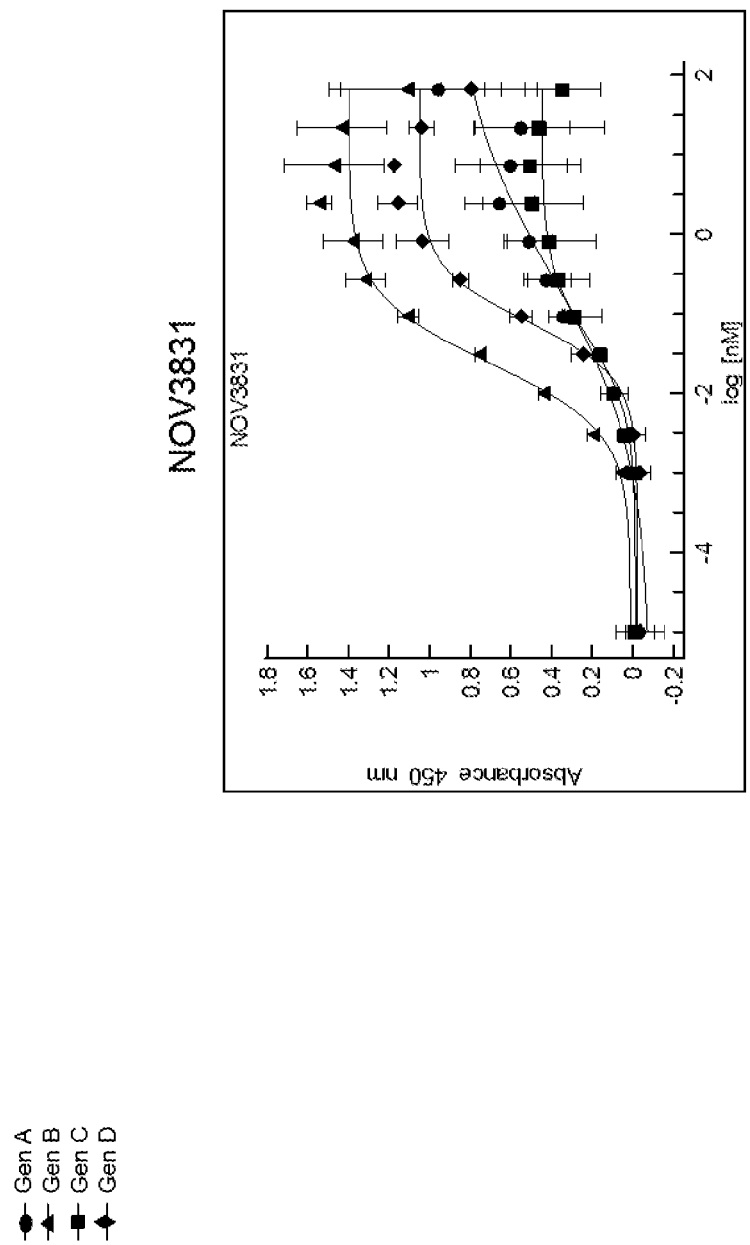
Figure 39:
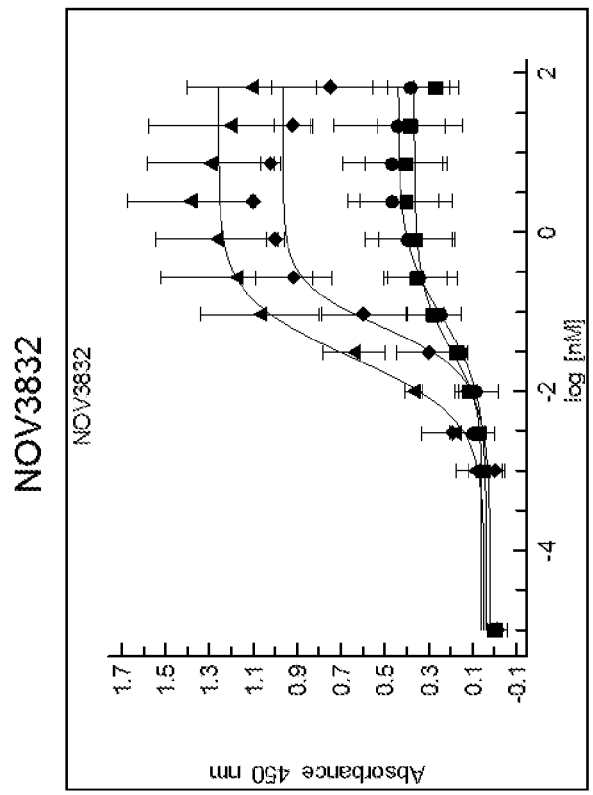
Figure 40:
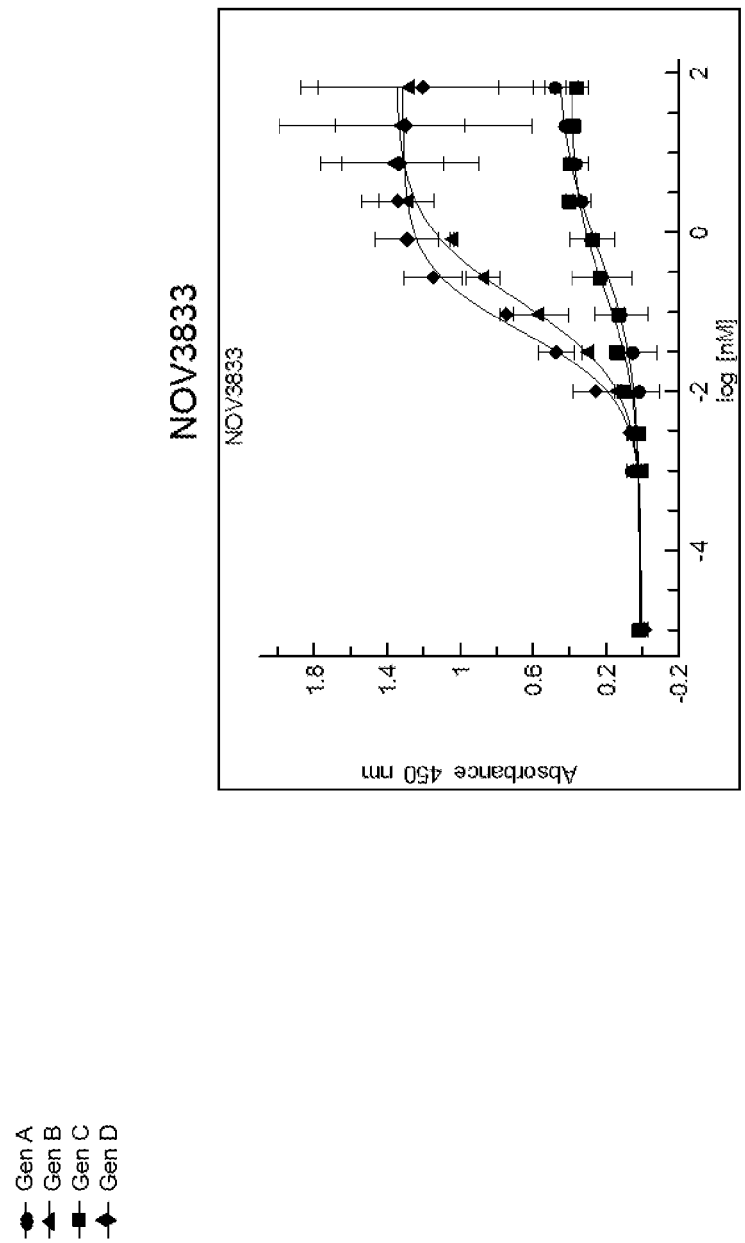
Figure 41:
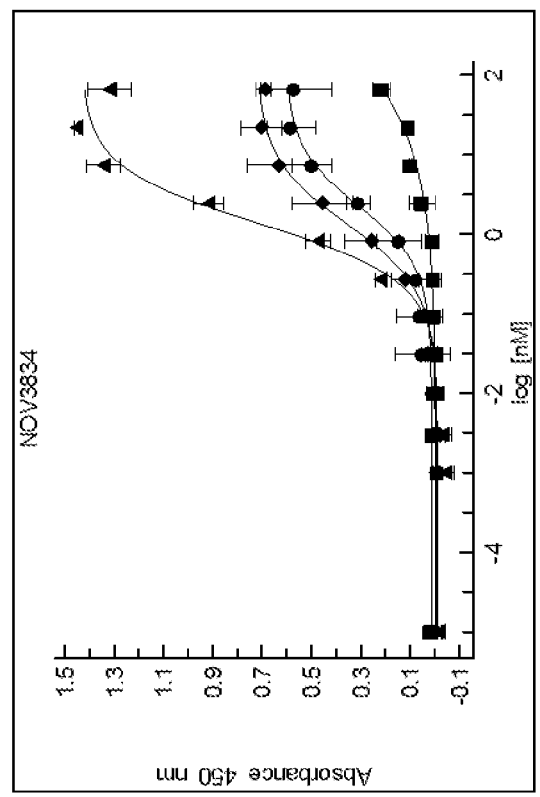
Figure 42:
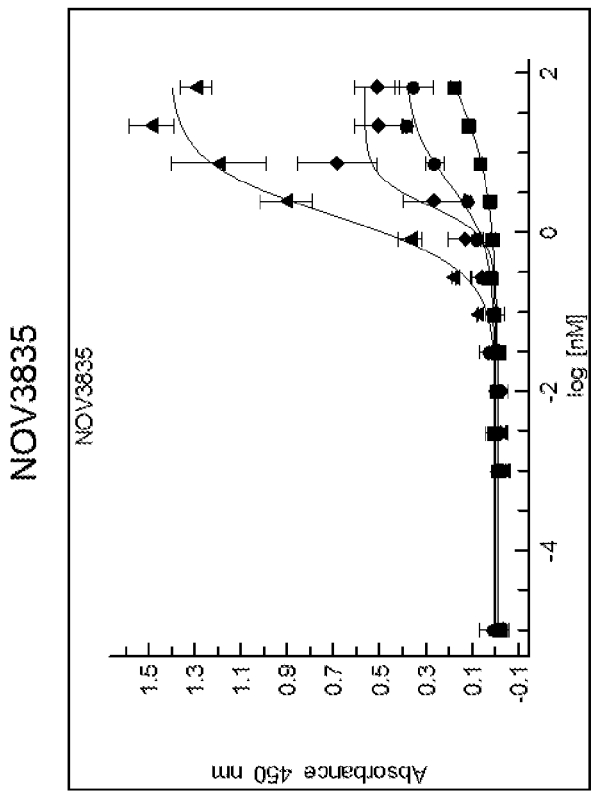
Figure 43:
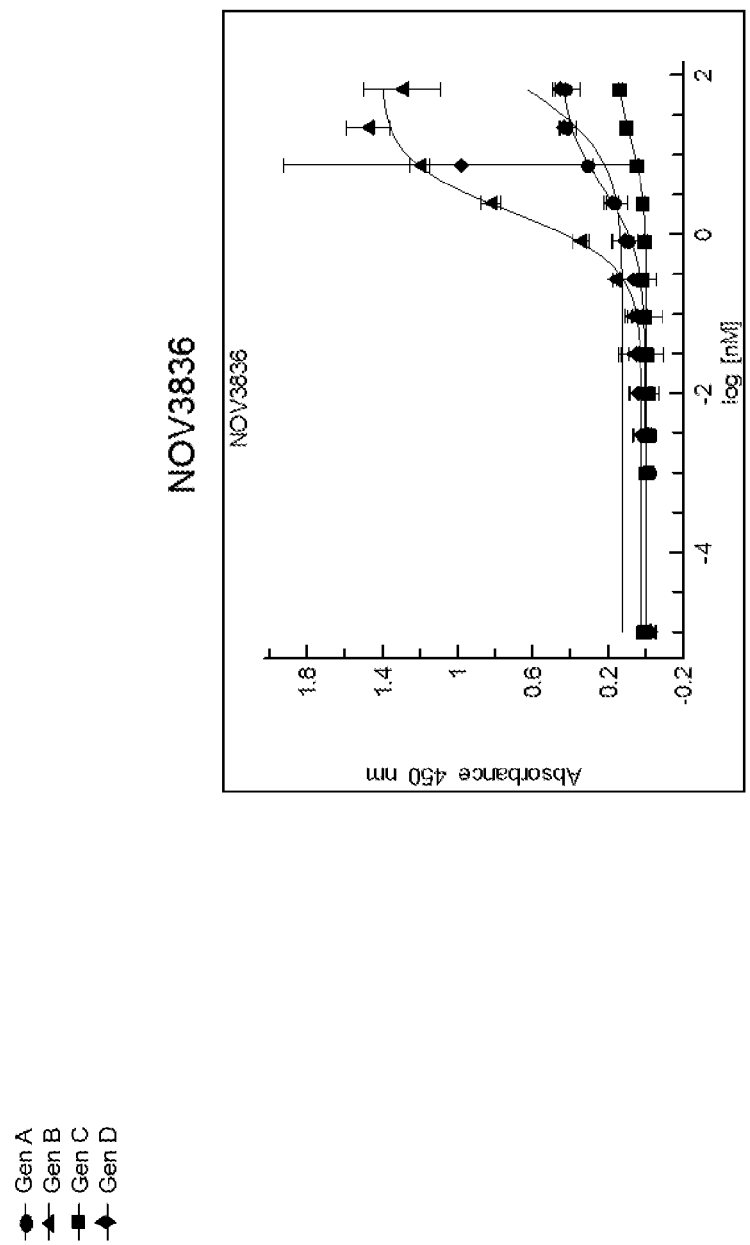
Figure 44:
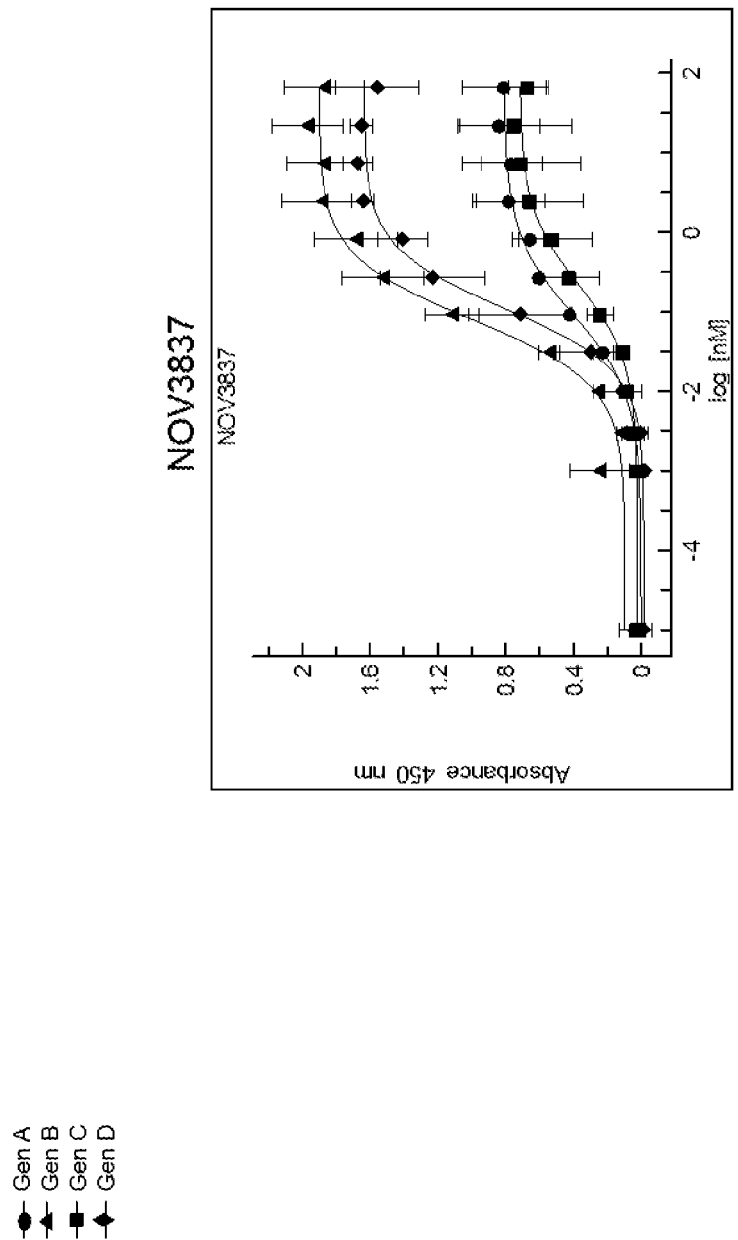
Figure 45:
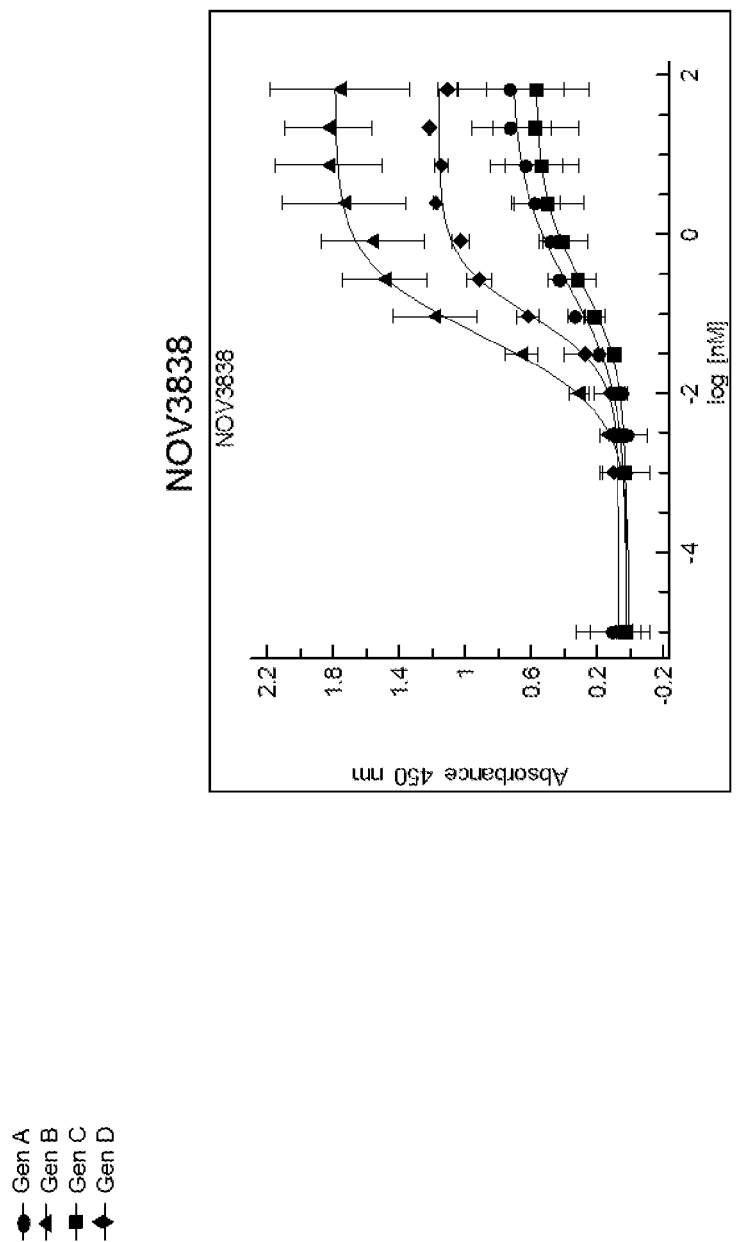
Figure 46:
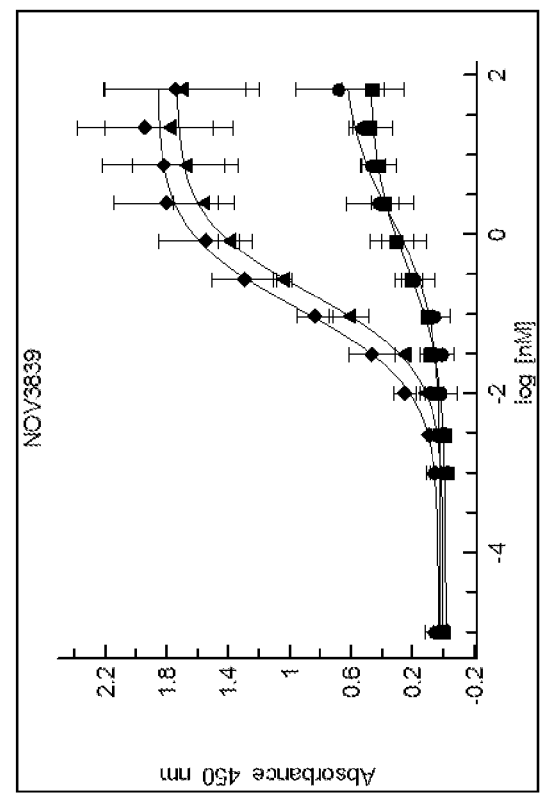
Figure 47:
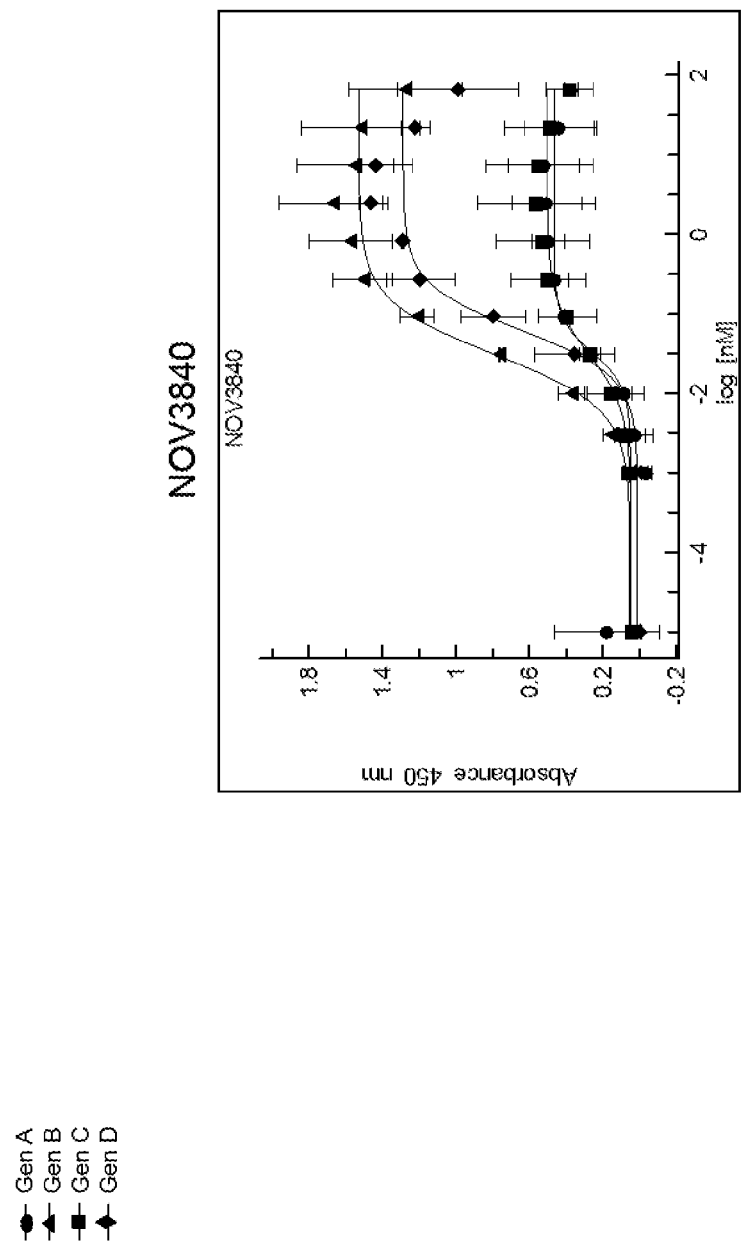
Figure 48:
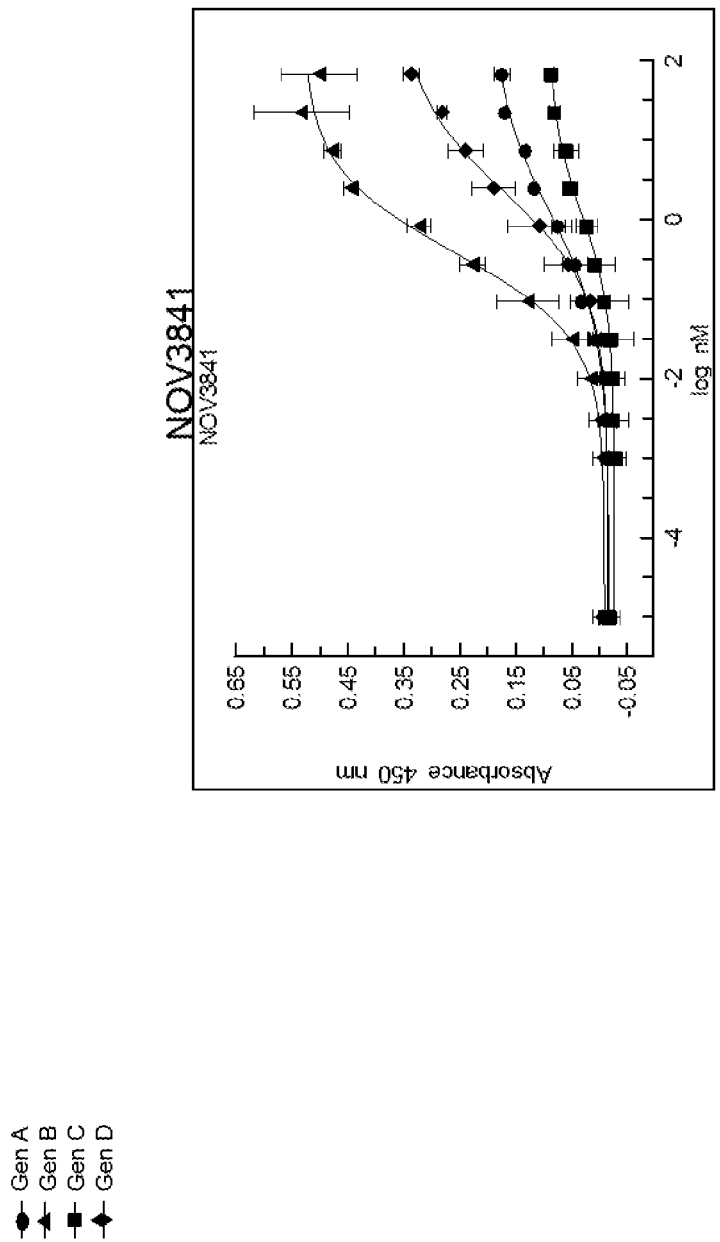
Figure 49:
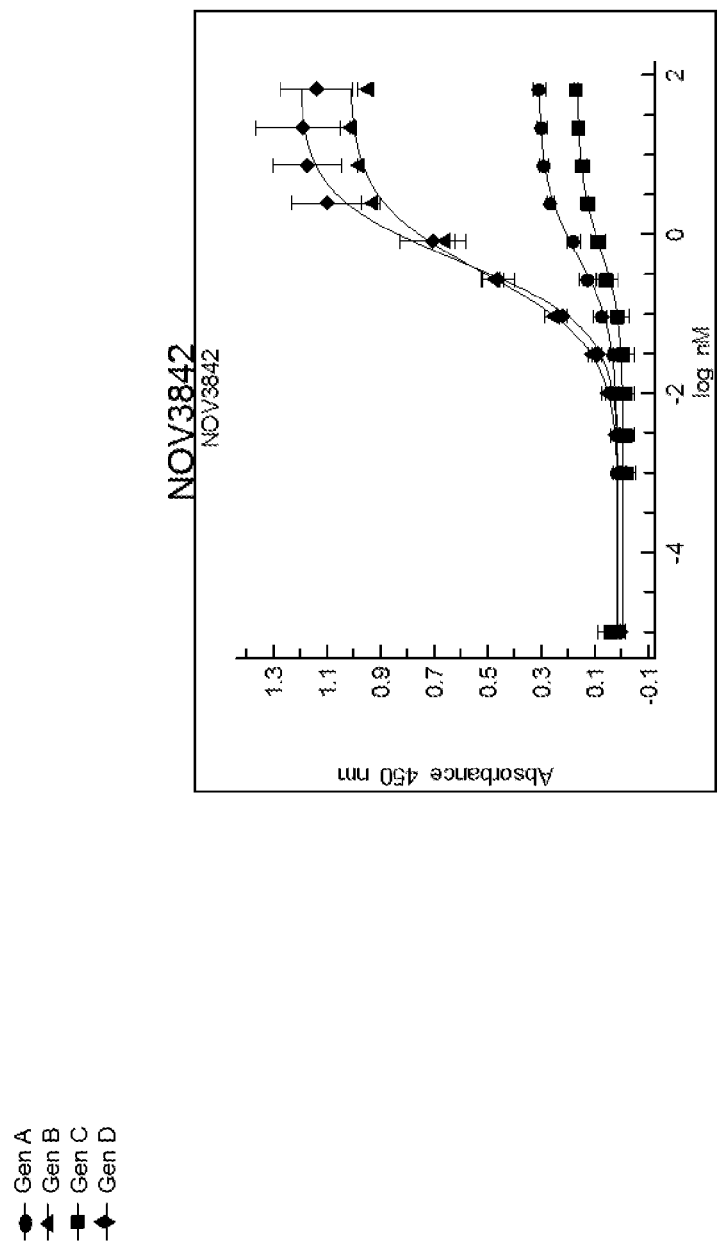
Figure 50:
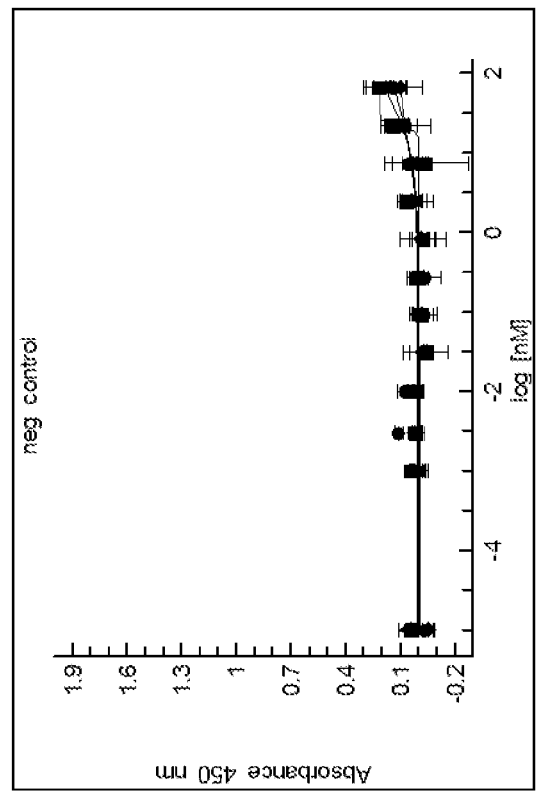
Figure 51:
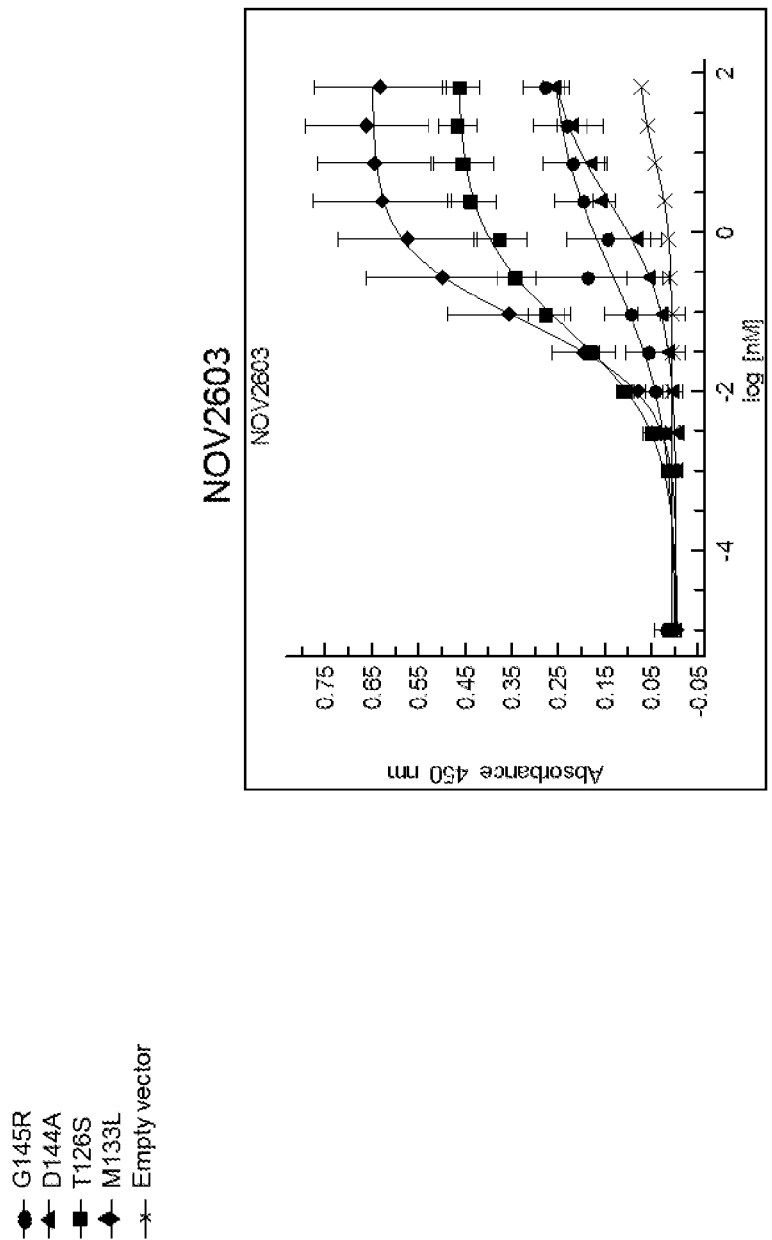
FIGS. 51-66 shows the $IC_{50}$ of the antibodies to four different clinical mutations.
Figure 52:
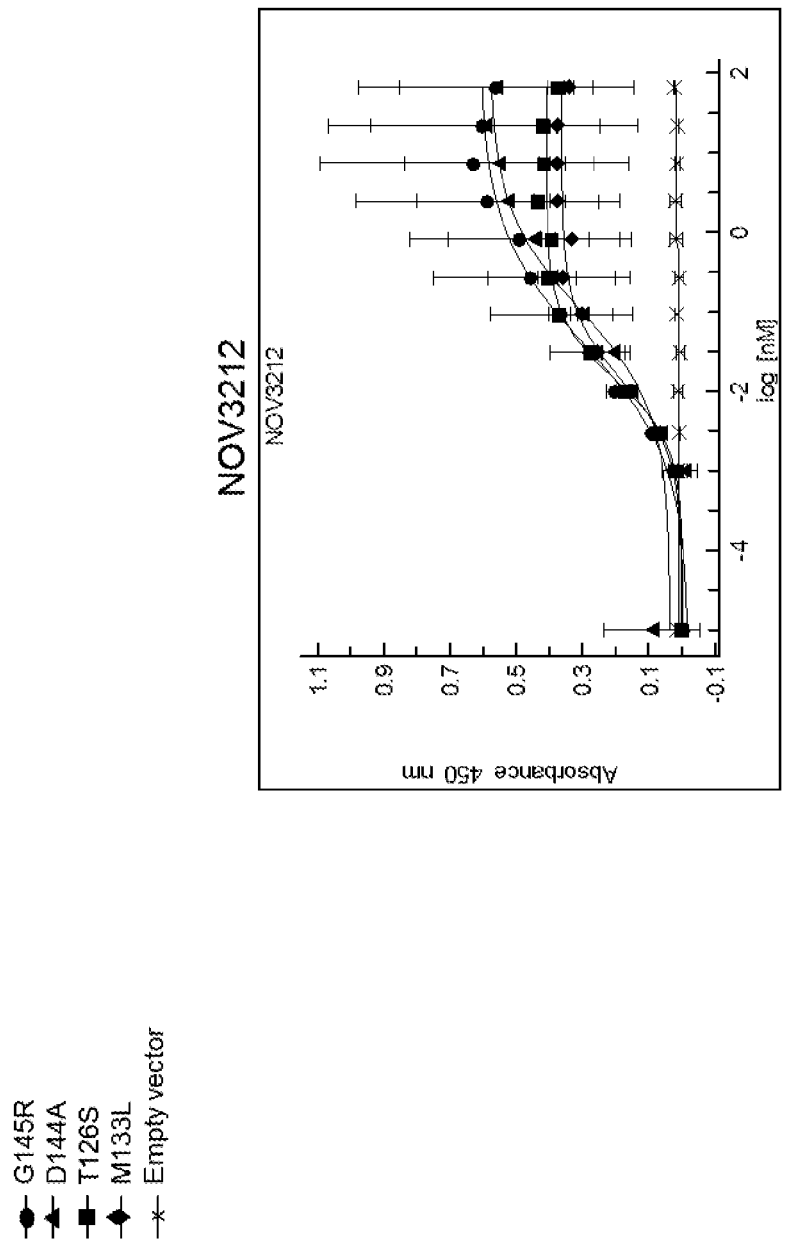
Figure 53:
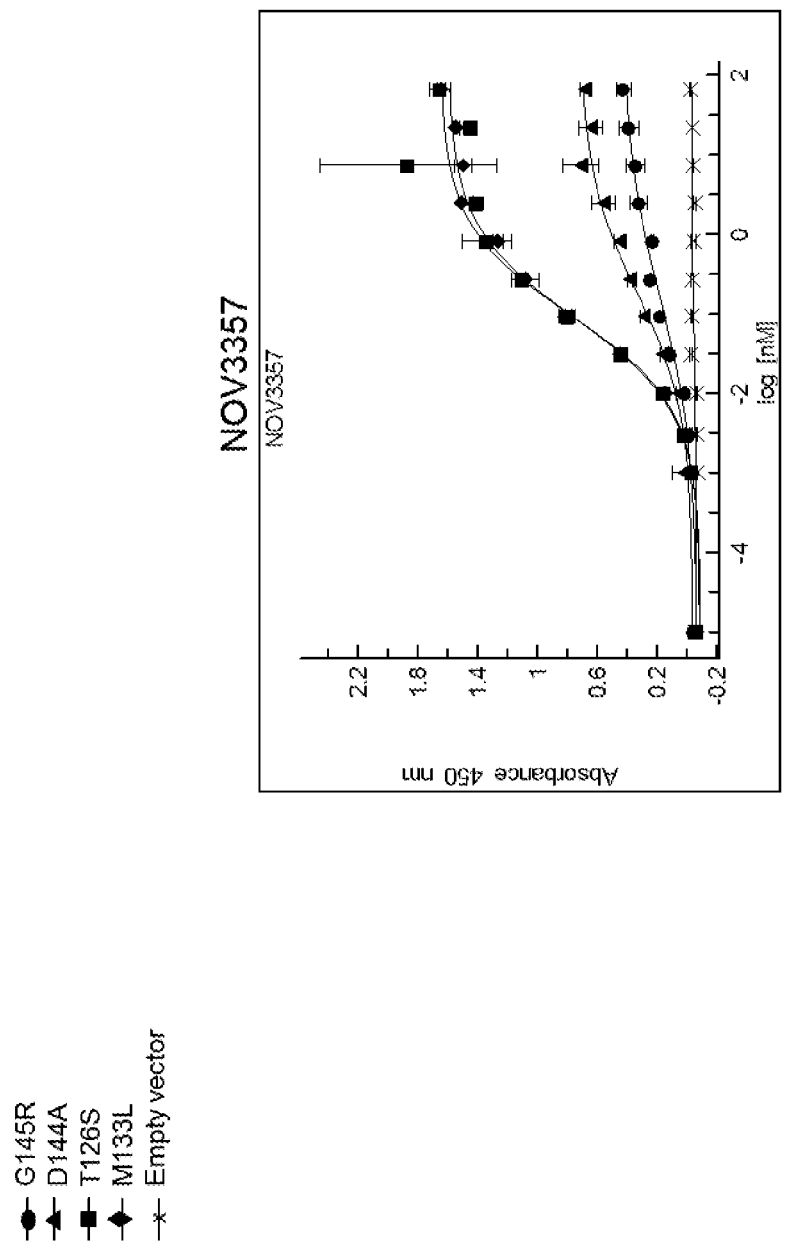
Figure 54:
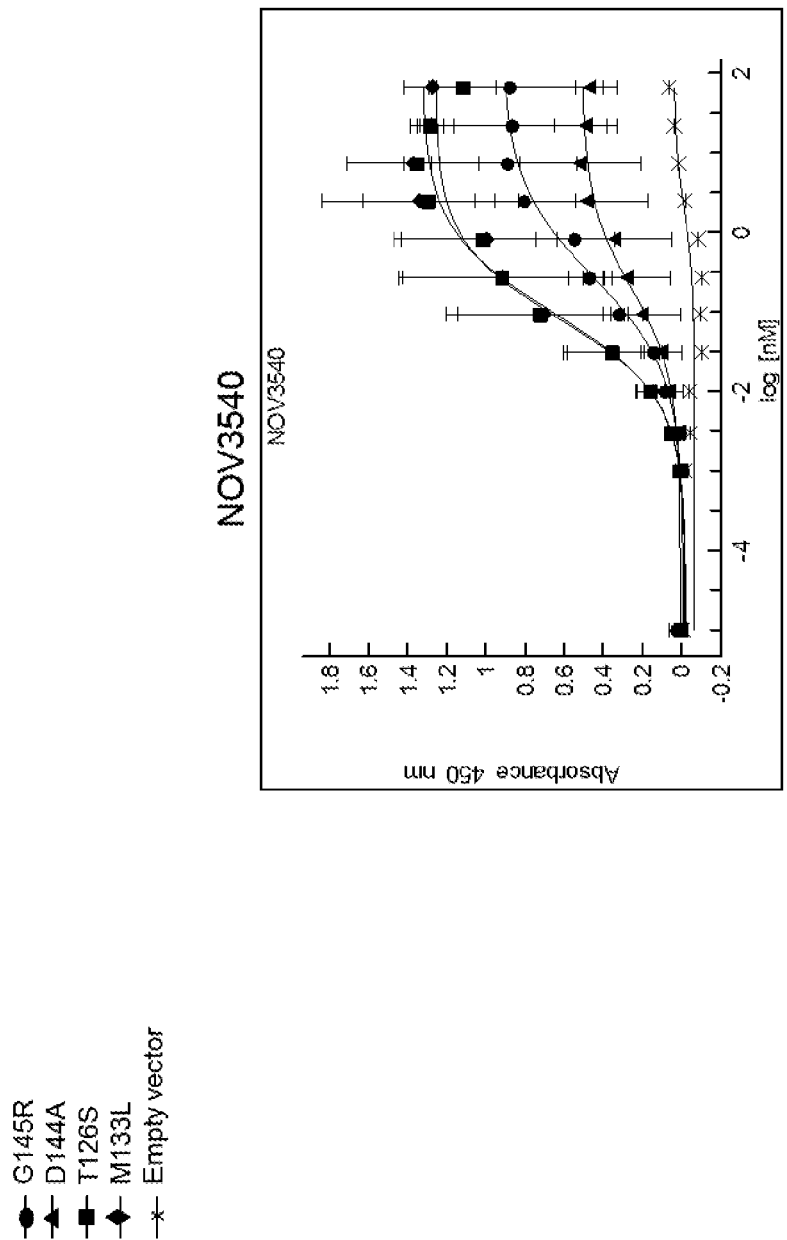
Figure 55:
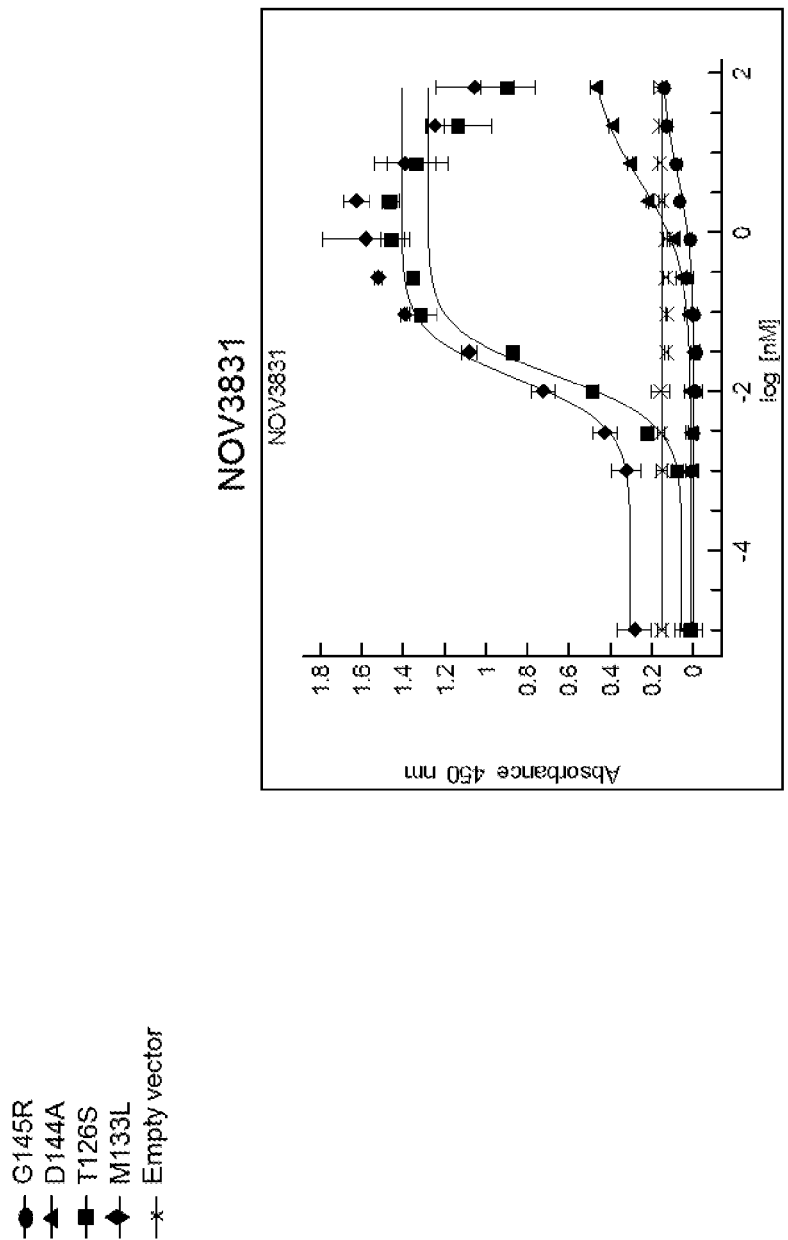
Figure 56:
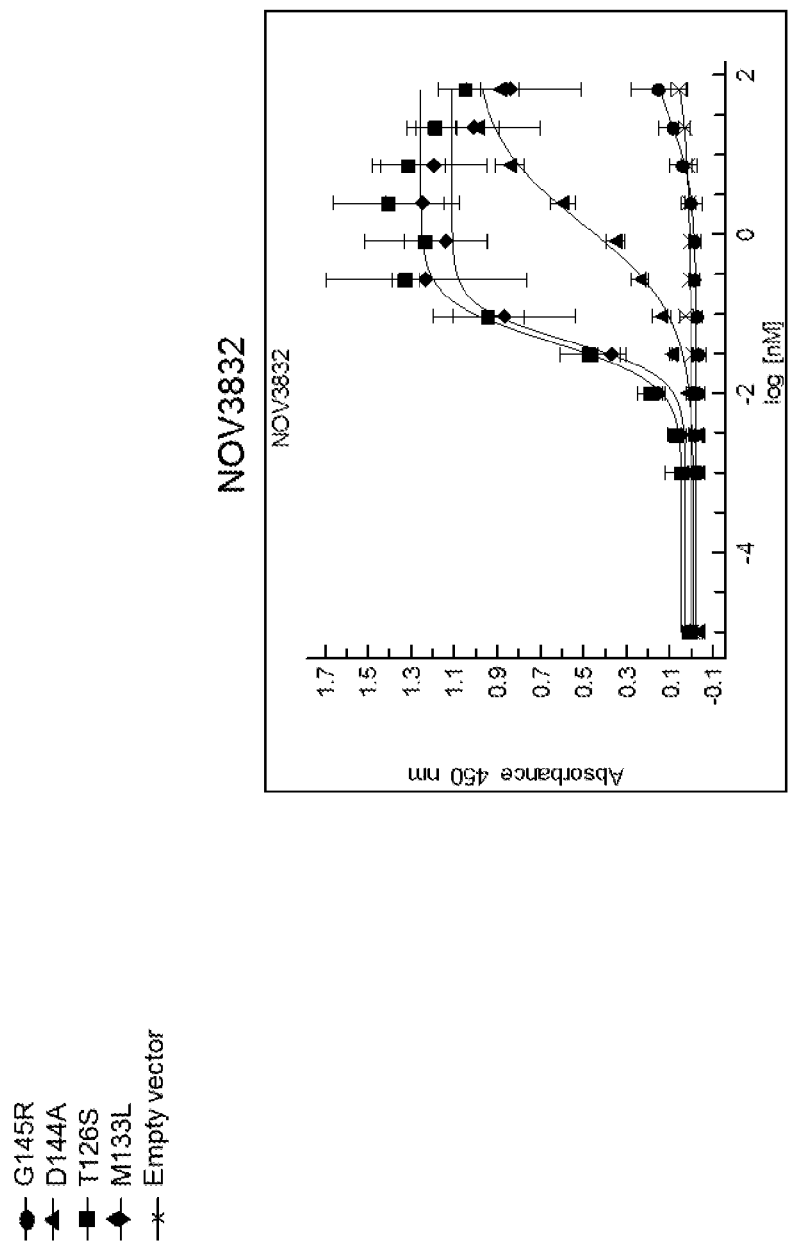
Figure 57:
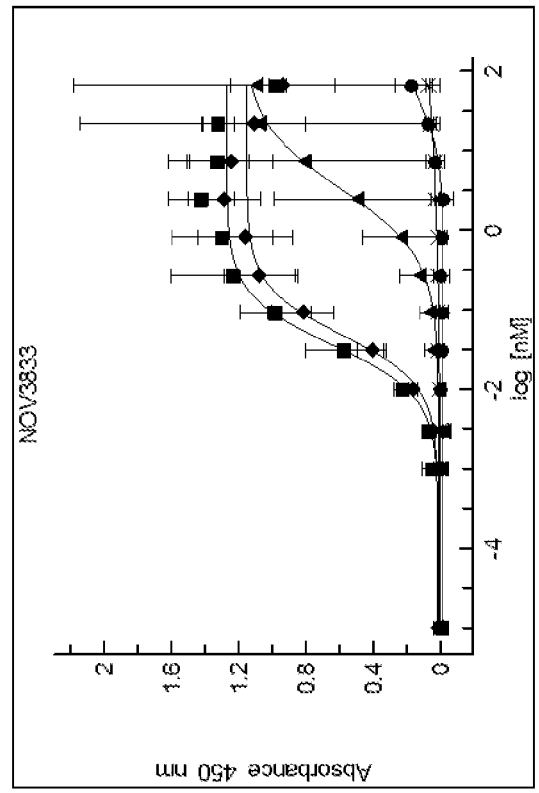
Figure 58:
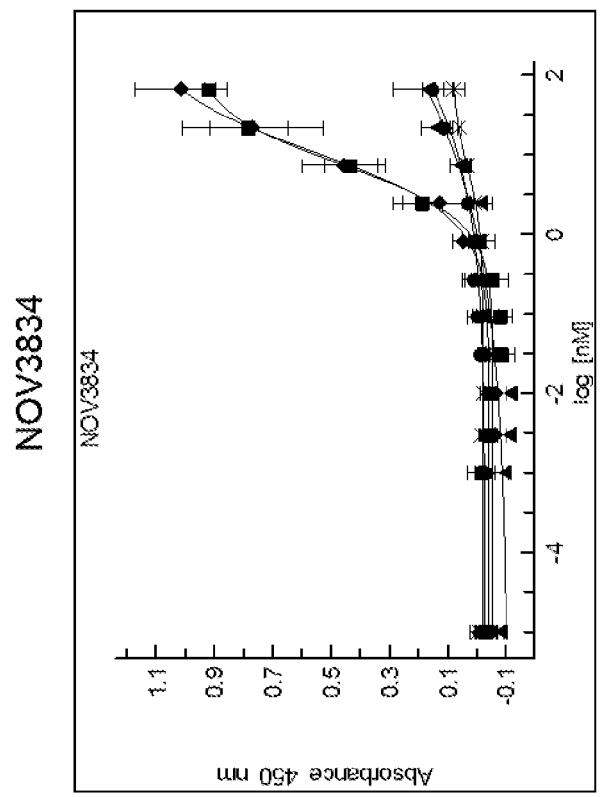
Figure 59:
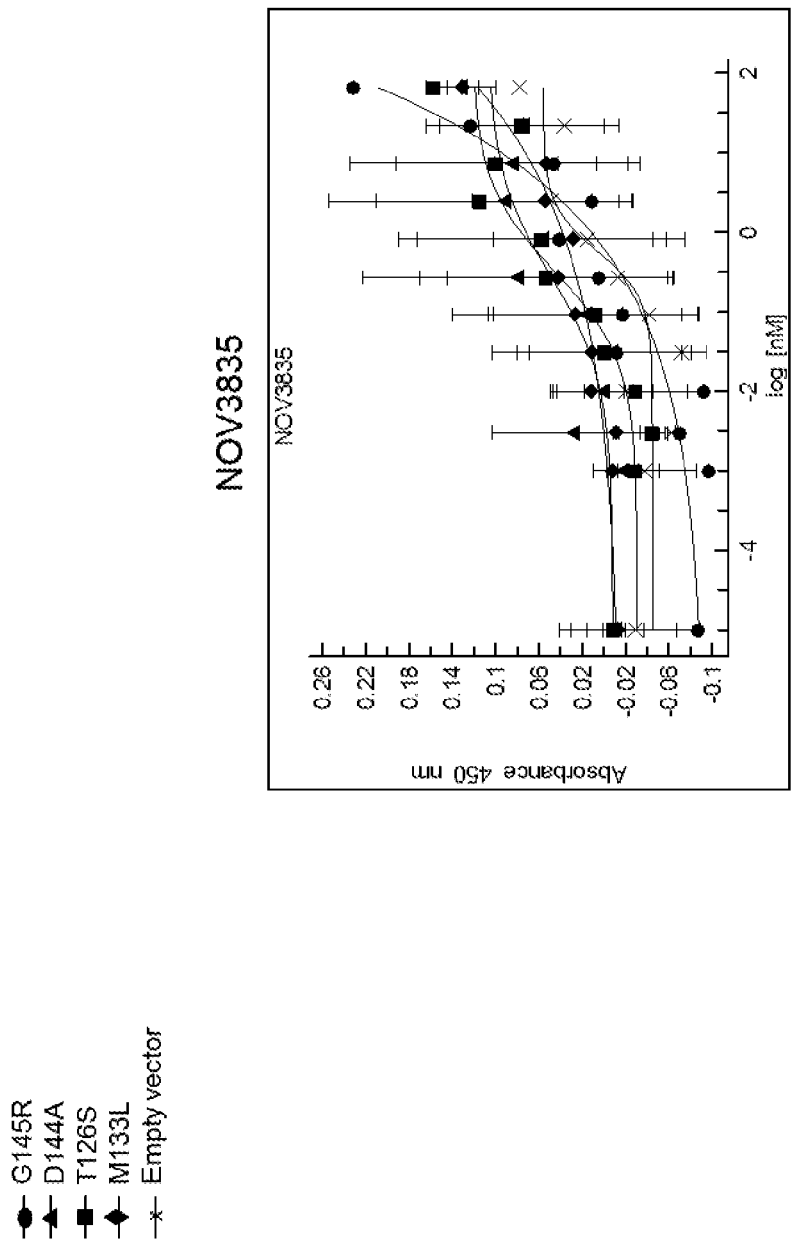
Figure 60:
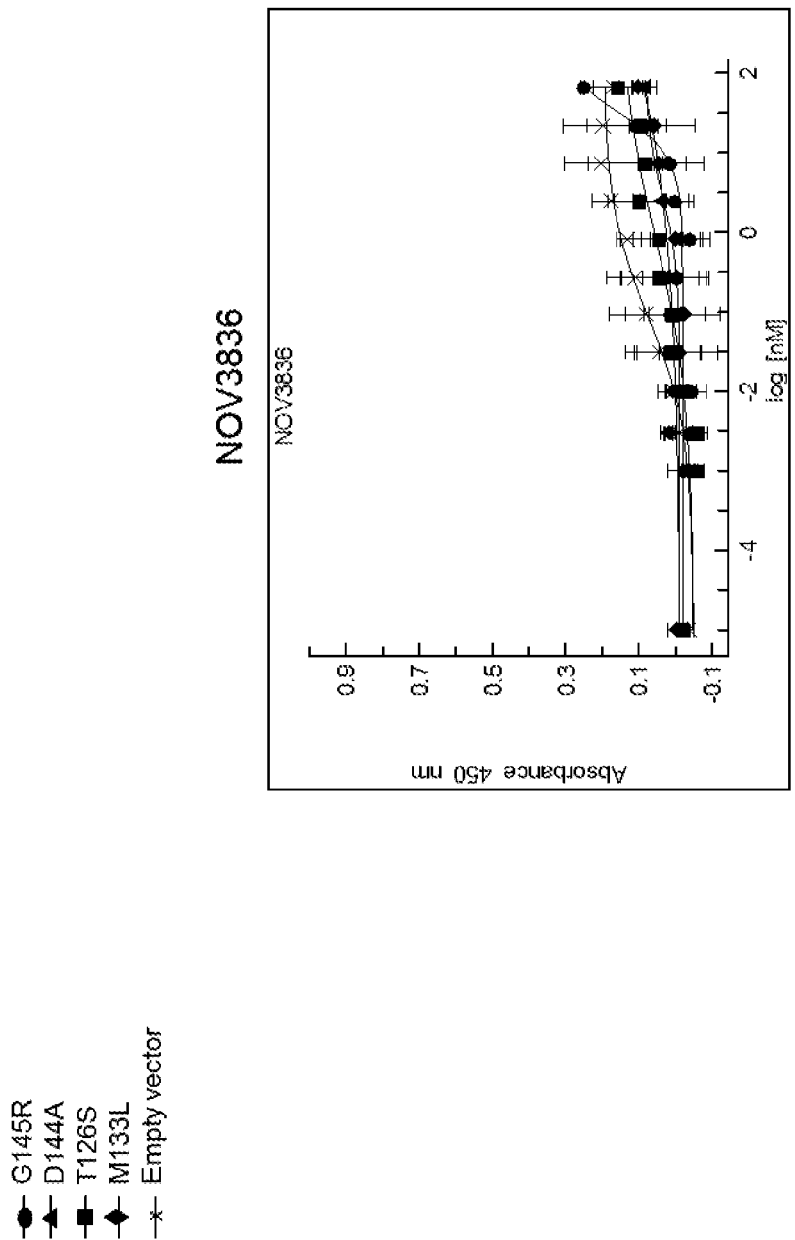
Figure 61:
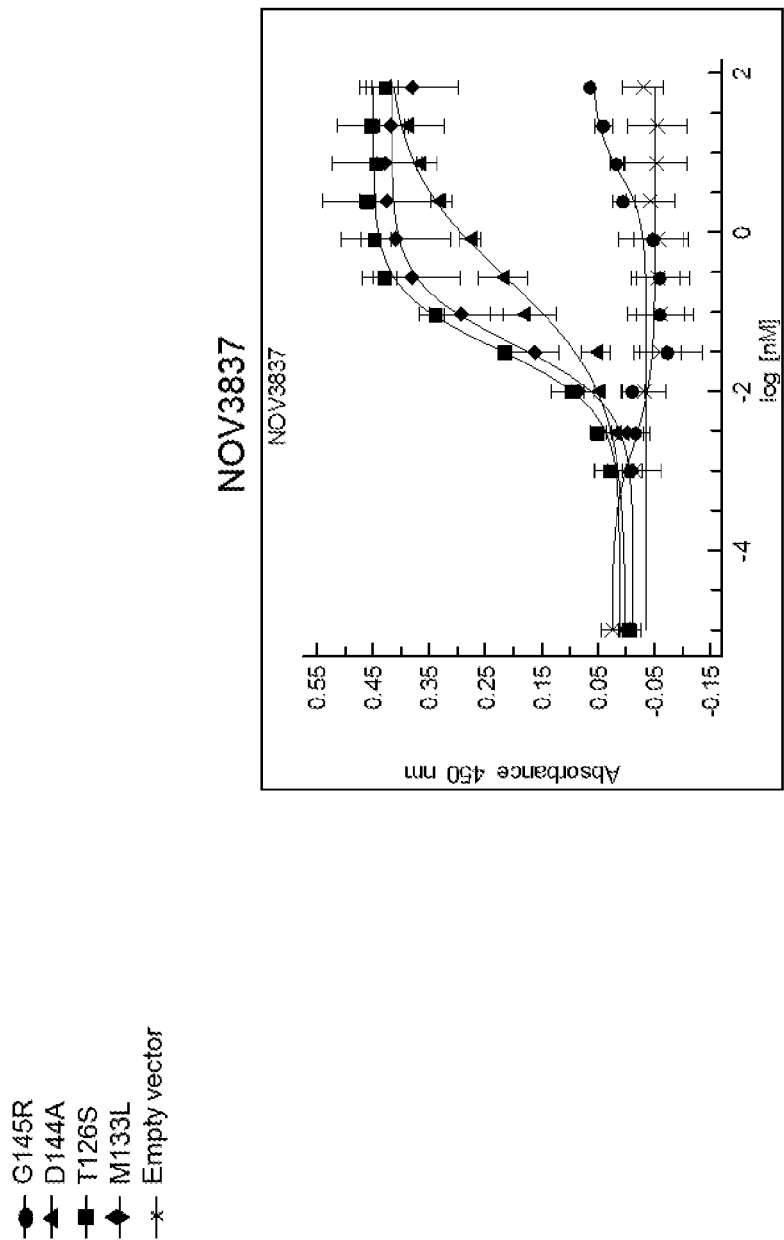
Figure 62:
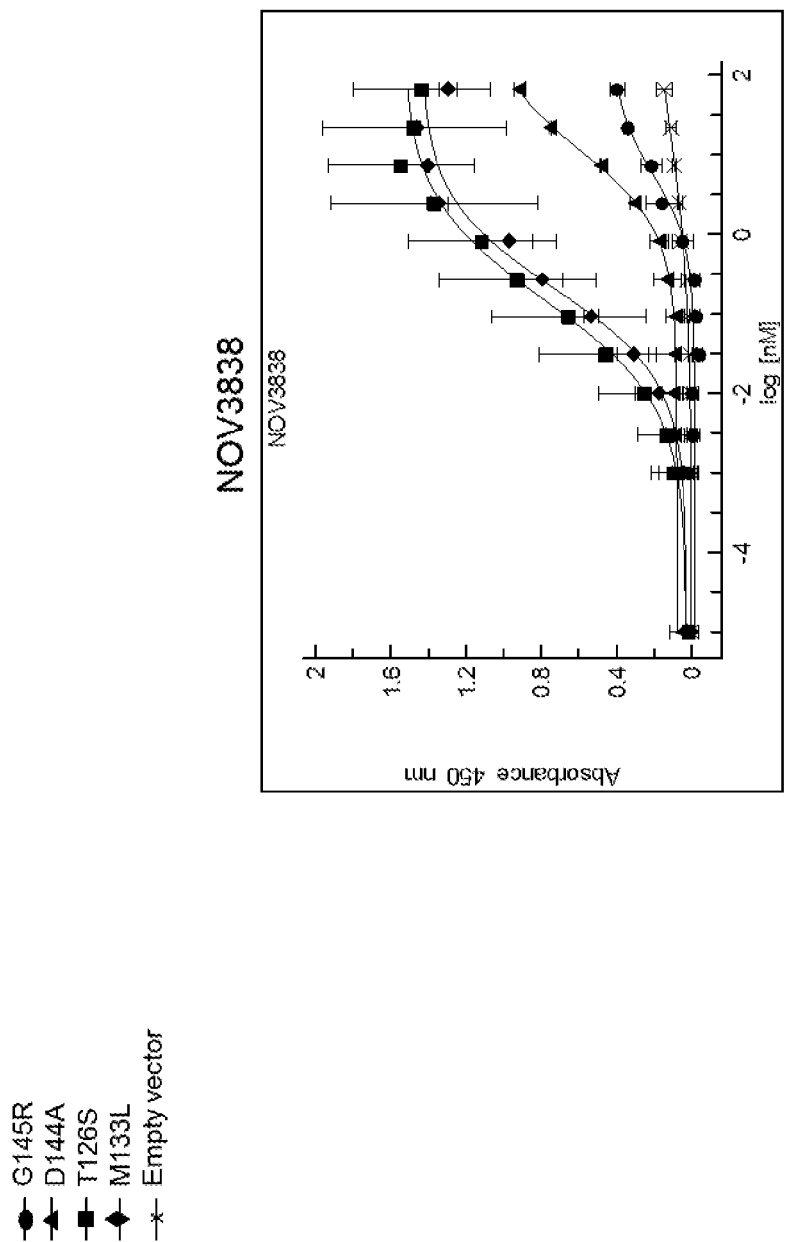
Figure 63:
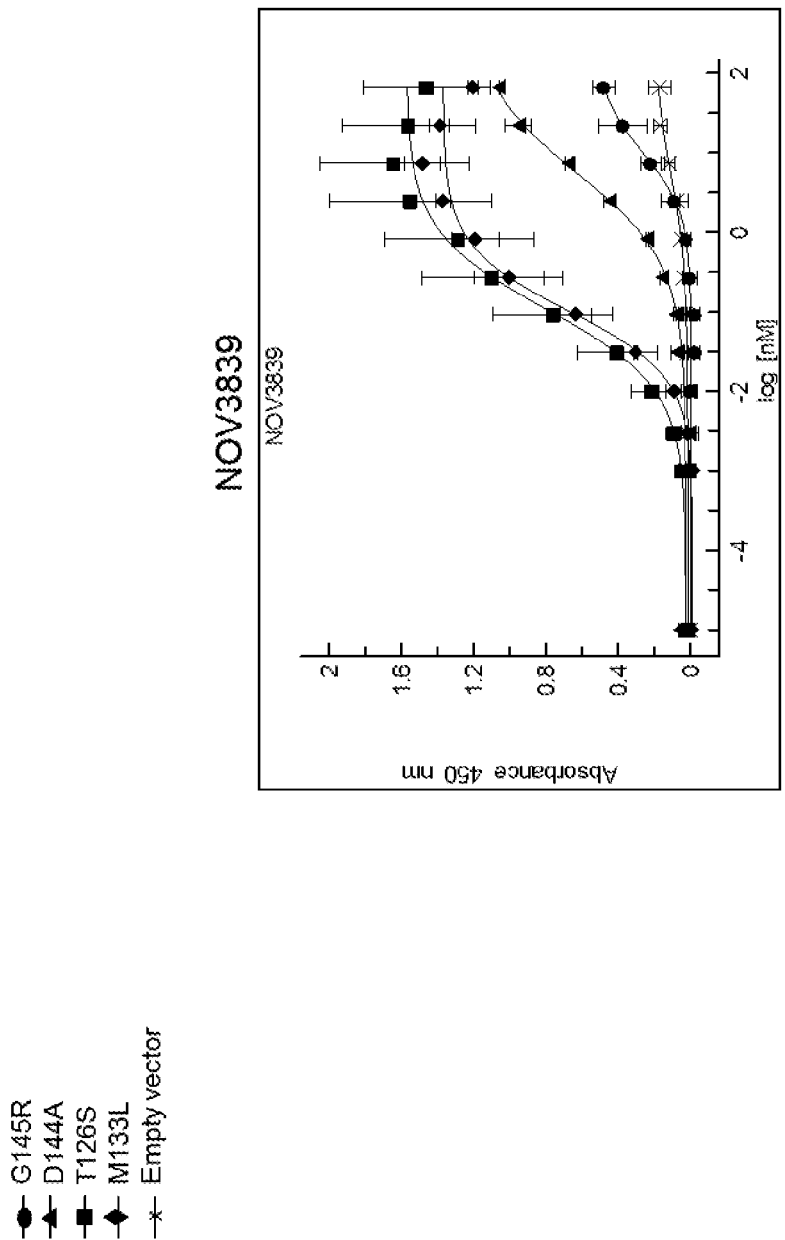
Figure 64:
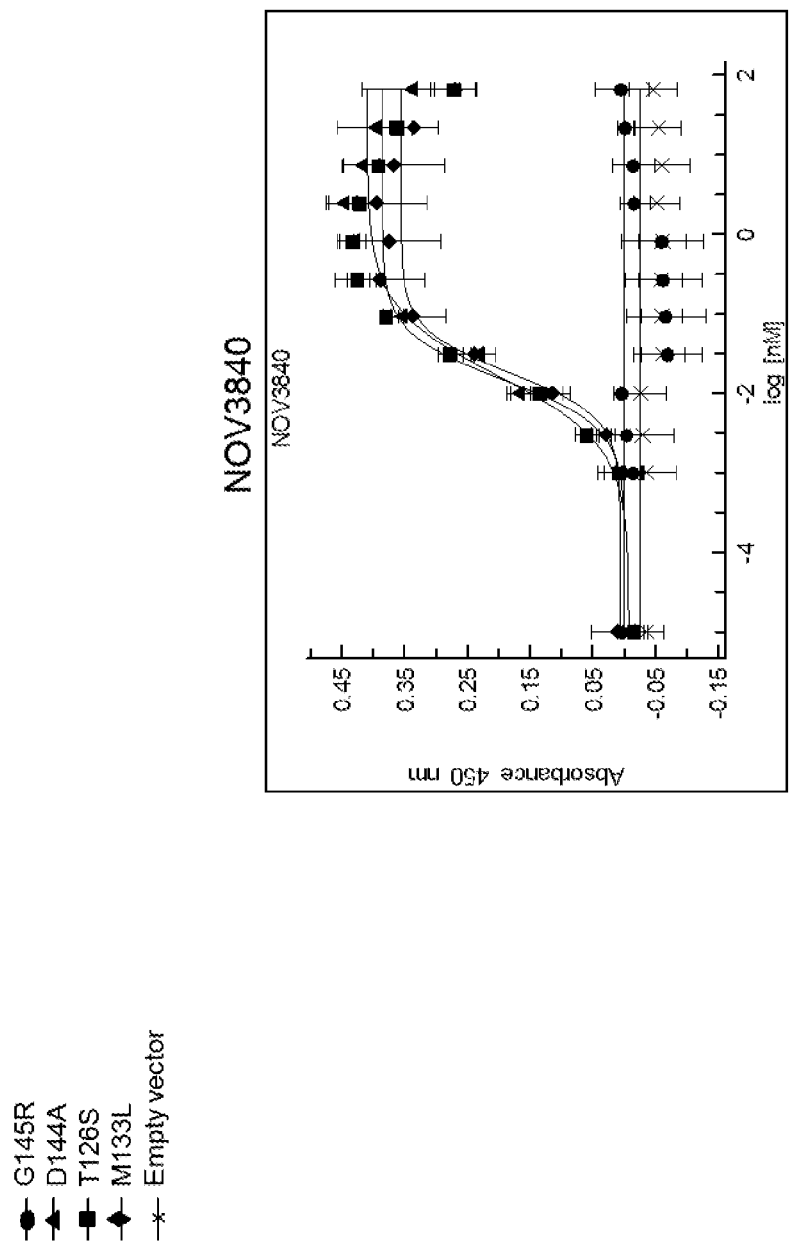
Figure 65:
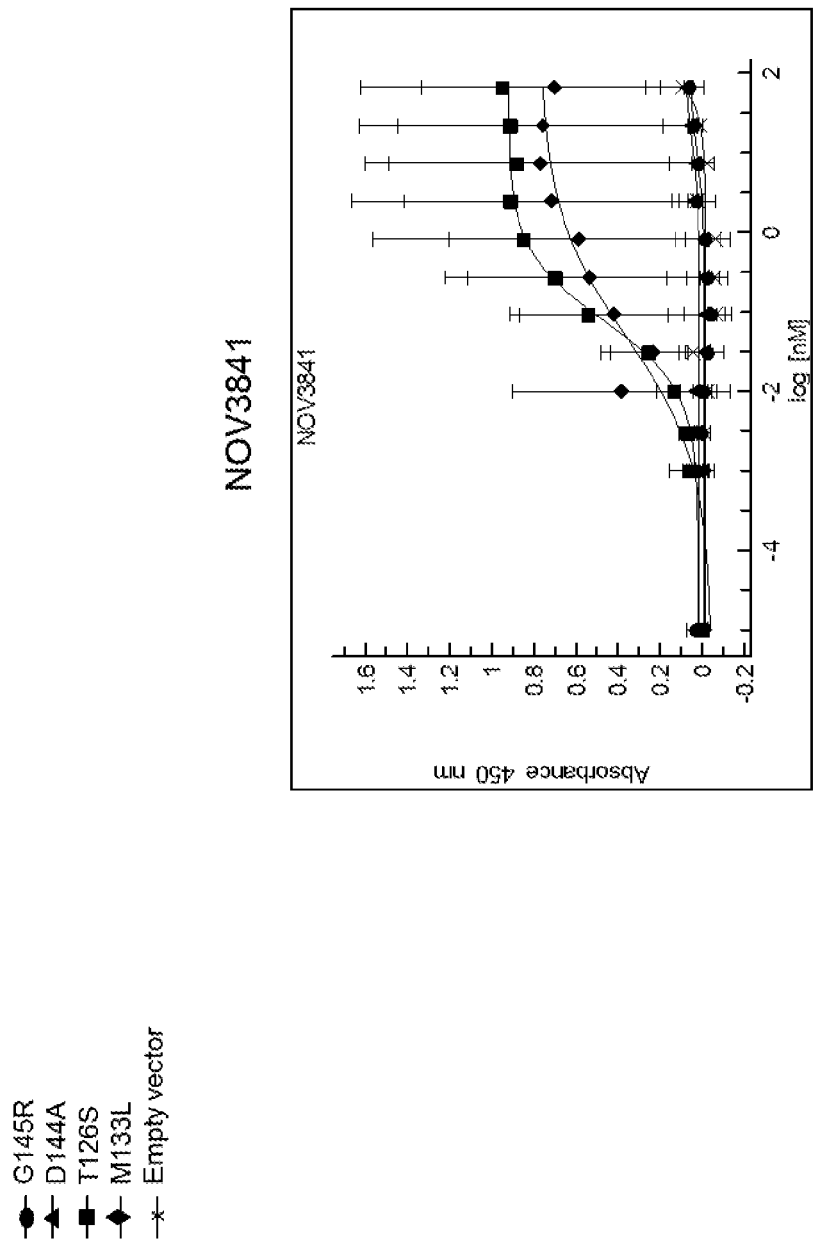
Figure 66:
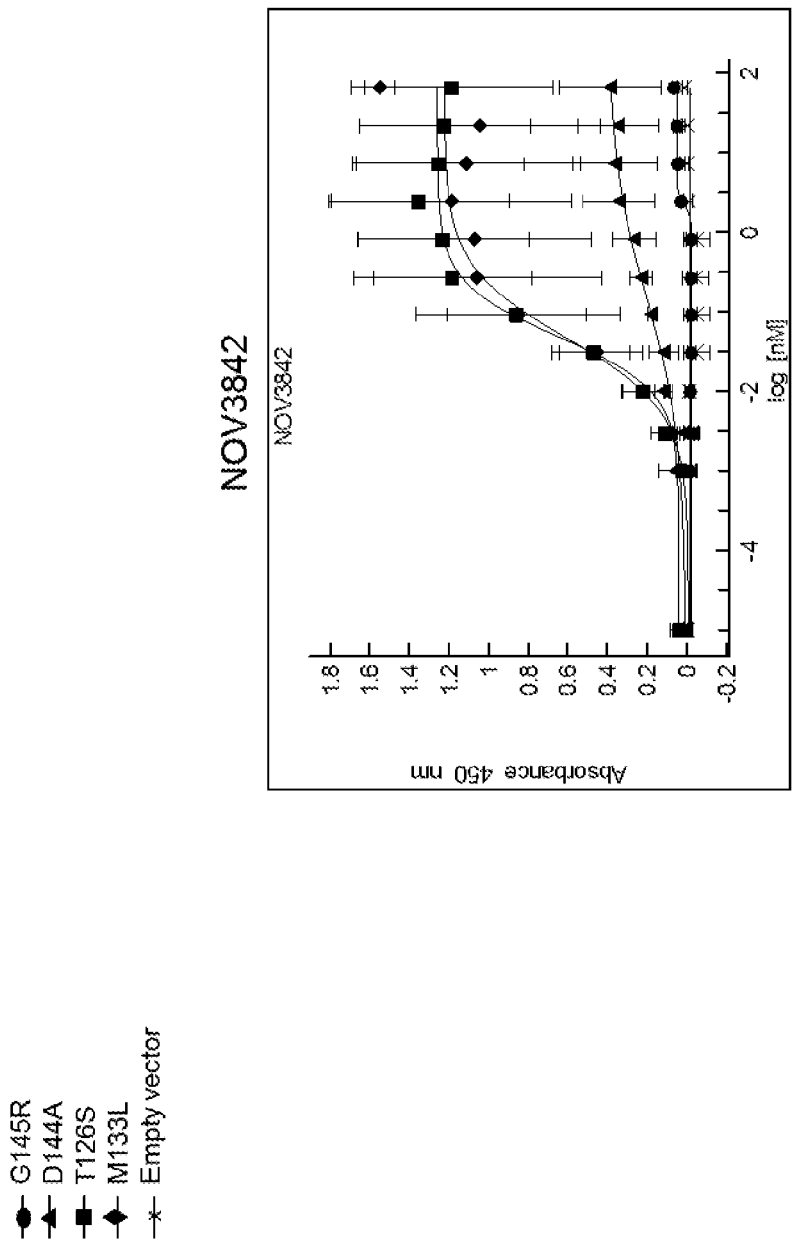

The present disclosure provides for antibodies, antibody fragments (e.g., antigen binding fragments), that bind and neutralize hepatitis B. Furthermore, the present disclosure provides antibodies that have desirable pharmacokinetic characteristics and other desirable attributes, and thus can be used for reducing the likelihood of or treating hepatitis B associate liver failure, liver cirrhosis or hepatocellular cancer. The present disclosure further provides pharmaceutical compositions comprising the antibodies and methods of making and using such pharmaceutical compositions for the prevention and treatment of hepatitis B infection and associated disorders.

Anti-HBsAg Antibodies

The present disclosure provides for antibodies or antibody fragments (e.g., antigen binding fragments) that specifically bind to HBsAg. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind to HBsAg, said antibodies or antibody fragments (e.g., antigen binding fragments) comprise a VH domain having an amino acid sequence of SEQ ID NO: 18, 50, 82, 114, 146, 178, 210, 242, 274, 306, 338, 370, 402, 434, 466, or 498 (Table 2). The present disclosure also provides antibodies or antibody fragments (e.g., antigen binding fragments) that specifically bind to HBsAg, said antibodies or antibody fragments (e.g., antigen binding fragments) comprise a VH CDR having an amino acid sequence of any one of the VH CDRs listed in Table 2. In particular aspects, the present disclosure provides antibodies or antibody fragments (e.g., antigen binding fragments) that specifically bind to HBsAg, said antibodies comprising (or alternatively, consist of) one, two, three, or more VH CDRs having an amino acid sequence of any of the VH CDRs listed in Table 2.

The present disclosure provides antibodies or antibody fragments (e.g., antigen binding fragments) that specifically bind to HBsAg, said antibodies or antibody fragments (e.g., antigen binding fragments) comprise a VL domain having an amino acid sequence of SEQ ID NO: 34, 66, 98, 130, 162, 194, 226, 258, 290, 322, 354, 386, 418, 450, 482 or 514 (Table 2). The present disclosure also provides antibodies or antibody fragments (e.g., antigen binding fragments) that specifically bind to HBsAg, said antibodies or antibody fragments (e.g., antigen binding fragments) comprise a VL CDR having an amino acid sequence of any one of the VL CDRs listed in Table 2. In particular, the disclosure provides antibodies or antibody fragments (e.g., antigen binding fragments) that specifically bind to HBsAg, said antibodies or antibody fragments (e.g., antigen binding fragments) comprise (or alternatively, consist of) one, two, three or more VL CDRs having an amino acid sequence of any of the VL CDRs listed in Table 2.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 2. In some aspects, it includes mutant amino acid sequences wherein no more than 1, 2, 3, 4 or 5 amino acids have been mutated in the CDR regions when compared with the CDR regions depicted in the sequence described in Table 2.

The present disclosure also provides nucleic acid sequences that encode VH, VL, the full length heavy chain, and the full length light chain of the antibodies that specifically bind to HBsAg. Such nucleic acid sequences can be optimized for expression in mammalian cells.

TABLE 2 anti-HBV Antibodies

| NOV3832HC | | | |
|---|---|---|---|
| SEQ ID NO: 6 (Combined) | | HCDR1 | GFTFDNYAMS |
| SEQ ID NO: 7 (Combined) | | HCDR2 | SISGSGGSTYYADSVKG |
| SEQ ID NO: 8 (Combined) | | HCDR3 | SSILSGGHARVYGIDV |
| SEQ ID NO: 9 | (Kabat) | HCDR1 | NYAMS |
| SEQ ID NO: 10 | (Kabat) | HCDR2 | SISGSGGSTYYADSVKG |
| SEQ ID NO: 11 | (Kabat) | HCDR3 | SSILSGGHARVYGIDV |
| SEQ ID NO: 12 (Chothia) | | HCDR1 | GFTFDNY |
| SEQ ID NO: 13 (Chothia) | | HCDR2 | SGSGGS |
| SEQ ID NO: 14 (Chothia) | | HCDR3 | SSILSGGHARVYGIDV |
| SEQ ID NO: 15 | (IMGT) | HCDR1 | GFTFDNYA |
| SEQ ID NO: 16 | (IMGT) | HCDR2 | ISGSGGST |
| SEQ ID NO: 17 | (IMGT) | HCDR3 | AKSSILSGGHARVYGIDV |
| SEQ ID NO: 18 | | VH | EMQVLESGGGLVQPGGSLRLSCAASGFTFDNYAMSW VRQVPGKGLEWVSSISGSGGSTYYADSVKGQFTISRD NSKNTLYLQMNSLRAEDTAVYYCAKSSILSGGHARV YGIDVWGQGTTVTVSS |
| SEQ ID NO: 19 | | DNA VH | GAGATGCAGGTCTTGGAATCTGGCGGAGGACTGGT TCAACCTGGCGGCTCTCTGAGACTGTCTTGTGCCGC CAGCGGCTTCACCTTCGATAACTACGCCATGTCCTG GGTCCGACAGGTGCCAGGCAAAGGACTGGAATGG GTGTCCTCTATCAGCGGCTCTGGCGGCAGCACATAT TACGCCGATAGCGTGAAGGGCCAGTTCACCATCAG CCGGGACAACAGCAAGAACACCCTGTACCTCCAGA TGAACAGCCTGAGAGCCGAGGATACCGCCGTGTAC TACTGTGCCAAGAGCAGCATTCTGTCTGGCGGCCA CGCCAGAGTGTATGGCATTGATGTTTGGGGCCAGG GAACCACCGTGACCGTTAGTTCT |

TABLE 2-continued anti-HBV Antibodies

| | | |
|---|---|---|
| SEQ ID NO: 20 | Heavy Chain | EMQVLESGGGLVQPGGSLRLSCAASGFTFDNYAMSW<br>VRQVPGKGLEWVSSISGSGGSTYYADSVKGQFTISRD<br>NSKNTLYLQMNSLRAEDTAVYYCAKSSILSGGHARV<br>YGIDVWGQGTTVTVSSASTKGPSVFPLAPSSKSTSGG<br>TAALGCLVKDYFPEPVTVSWNSGALTSGVHTFPAVL<br>QSSGLYSLSSVVTVPSSSLGTQTYICNVNHKPSNTKVD<br>KRVEPKSCDKTHTCPPCPAPELLGGPSVFLFPPKPKDT<br>LMISRTPEVTCVVVDVSHEDPEVKFNWYVDGVEVHN<br>AKTKPREEQYNSTYRVVSVLTVLHQDWLNGKEYKC<br>KVSNKALPAPIEKTISKAKGQPREPQVYTLPPSREEMT<br>KNQVSLTCLVKGFYPSDIAVEWESNGQPENNYKTTPP<br>VLDSDGSFFLYSKLTVDKSRWQQGNVFSCSVMHEAL<br>HNHYTQKSLSLSPGK |
| SEQ ID NO: 21 | DNA Heavy Chain | GAGATGCAGGTCTTGGAATCTGGCGGAGGACTGGT<br>TCAACCTGGCGGCTCTCTGAGACTGTCTTGTGCCGC<br>CAGCGGCTTCACCTTCGATAACTACGCCATGTCCTG<br>GGTCCGACAGGTGCCAGGCAAAGGACTGGAATGG<br>GTGTCCTCTATCAGCGGCTCTGGCGGCAGCACATAT<br>TACGCCGATAGCGTGAAGGGCCAGTTCACCATCAG<br>CCGGGACAACAGCAAGAACACCCTGTACCTCCAGA<br>TGAACAGCCTGAGAGCCGAGGATACCGCCGTGTAC<br>TACTGTGCCAAGAGCAGCATTCTGTCTGGCGGCCA<br>CGCCAGAGTGTATGGCATTGATGTTTGGGGCCAGG<br>GAACCACCGTGACCGTTAGTTCTGCTAGCACCAAG<br>GGCCCCAGCGTGTTCCCCCTGGCCCCCAGCAGCAA<br>GAGCACCAGCGGCGGCACAGCCGCCCTGGGCTGCC<br>TGGTGAAGGACTACTTCCCCGAGCCCGTGACCGTG<br>TCCTGGAACAGCGGAGCCCTGACCTCCGGCGTGCA<br>CACCTTCCCCGCCGTGCTGCAGAGCAGCGGCCTGT<br>ACAGCCTGTCCAGCGTGGTGACAGTGCCCAGCAGC<br>AGCCTGGGCACCCAGACCTACATCTGCAACGTGAA<br>CCACAAGCCCAGCAACACCAAGGTGGACAAGAGA<br>GTGGAGCCCAAGAGCTGCGACAAGACCCACACATG<br>CCCCCCCTGCCCGGCGCCAGAGCTGCTGGGCGGAC<br>CCTCCGTGTTCCTGTTCCCCCCCAAGCCCAAGGACA<br>CCCTGATGATCAGCAGGACCCCCGAGGTGACCTGC<br>GTGGTGGTGGACGTGAGCCACGAGGACCCAGAGGT<br>GAAGTTCAACTGGTACGTGGACGGCGTGGAGGTGC<br>ACAACGCCAAGACCAAGCCCAGAGAGGAGCAGTA<br>CAACAGCACCTACAGGGTGGTGTCCGTGCTGACCG<br>TGCTGCACCAGGACTGGCTGAACGGCAAGGAATAC<br>AAGTGCAAGGTCTCCAACAAGGCCCTGCCAGCCCC<br>CATCGAAAAGACCATCAGCAAGGCCAAGGGCCAG<br>CCACGGGAGCCCCAGGTGTACACCCTGCCCCCCTC<br>CCGGGAGGAGATGACCAAGAACCAGGTGTCCCTGA<br>CCTGTCTGGTGAAGGGCTTCTACCCCAGCGACATC<br>GCCGTGGAGTGGGAGAGCAACGGCCAGCCCGAGA<br>ACAACTACAAGACCACCCCCCCAGTGCTGGACAGC<br>GACGGCAGCTTCTTCCTGTACAGCAAGCTGACCGT<br>GGACAAGTCCAGGTGGCAGCAGGGCAACGTGTTCA<br>GCTGCAGCGTGATGCACGAGGCCCTGCACAACCAC<br>TACACCCAGAAGAGCCTGAGCTTAAGCCCCGGCAA<br>G |

NOV3832 LC

| | | |
|---|---|---|
| SEQ ID NO: 22 (Combined) | LCDR1 | GGNNIGSQSVH |
| SEQ ID NO: 23 (Combined) | LCDR2 | DDTDRPS |
| SEQ ID NO: 24 (Combined) | LCDR3 | QVWDSSSDHVV |
| SEQ ID NO: 25 (Kabat) | LCDR1 | GGNNIGSQSVH |
| SEQ ID NO: 26 (Kabat) | LCDR2 | DDTDRPS |
| SEQ ID NO: 27 (Kabat) | LCDR3 | QVWDSSSDHVV |
| SEQ ID NO: 28 (Chothia) | LCDR1 | NNIGSQS |
| SEQ ID NO: 29 (Chothia) | LCDR2 | DDT |
| SEQ ID NO: 30 (Chothia) | LCDR3 | WDSSSDHV |
| SEQ ID NO: 31 (IMGT) | LCDR1 | NIGSQS |
| SEQ ID NO: 32 (IMGT) | LCDR2 | DDT |
| SEQ ID NO: 33 (IMGT) | LCDR3 | QVWDSSSDHVV |
| SEQ ID NO: 34 | VL | QSALTQPPSVSVAPGQTARITCGGNNIGSQSVHWYQQ<br>KPGQAPILVVYDDTDRPSGIPARFSGSSSGSTATLTIGR<br>VEAGDEADYYCQVWDSSSDHVVFGGGTKLTVL |

TABLE 2-continued anti-HBV Antibodies

| | | |
|---|---|---|
| SEQ ID NO: 35 | DNA VL | CAGTCTGCCCTGACTCAGCCACCCTCGGTGTCAGTG<br>GCCCCAGGACAGACGGCCAGGATTACCTGTGGGGG<br>AAACAACATTGGAAGTCAAAGTGTGCACTGGTACC<br>AGCAGAAGCCAGGCCAGGCCCCTATACTGGTCGTC<br>TATGATGATACCGACCGGCCCTCAGGGATCCCTGC<br>GCGATTCTCTGGCTCCAGCTCTGGGAGCACGGCCA<br>CCCTGACCATCGGCAGGGTCGAAGCCGGGGATGAG<br>GCCGACTATTACTGTCAGGTGTGGGATAGTAGTAG<br>TGATCATGTGGTATTCGGCGGAGGGACCAAGCTGA<br>CCGTCTTA |
| SEQ ID NO: 36 | Light Chain | QSALTQPPSVSVAPGQTARITCGGNNIGSQSVHWYQQ<br>KPGQAPILVVYDDTDRPSGIPARFSGSSSGSTATLTIGR<br>VEAGDEADYYCQVWDSSSDHVVFGGGTKLTVLSQP<br>KAAPSVTLFPPSSEELQANKATLVCLISDFYPGAVTVA<br>WKADSSPVKAGVETTTPSKQSNNKYAASSYLSLTPEQ<br>WKSHRSYSCQVTHEGSTVEKTVAPTECS |
| SEQ ID NO: 37 | DNA Light Chain | CAGTCTGCCCTGACTCAGCCACCCTCGGTGTCAGTG<br>GCCCCAGGACAGACGGCCAGGATTACCTGTGGGGG<br>AAACAACATTGGAAGTCAAAGTGTGCACTGGTACC<br>AGCAGAAGCCAGGCCAGGCCCCTATACTGGTCGTC<br>TATGATGATACCGACCGGCCCTCAGGGATCCCTGC<br>GCGATTCTCTGGCTCCAGCTCTGGGAGCACGGCCA<br>CCCTGACCATCGGCAGGGTCGAAGCCGGGGATGAG<br>GCCGACTATTACTGTCAGGTGTGGGATAGTAGTAG<br>TGATCATGTGGTATTCGGCGGAGGGACCAAGCTGA<br>CCGTCTTAAGTCAGCCCAAGGCTGCCCCCTCGGTCA<br>CTCTGTTCCCGCCCTCCTCTGAGGAGCTTCAAGCCA<br>ACAAGGCCACACTGGTGTGTCTCATAAGTGACTTCT<br>ACCCGGGAGCCGTGACAGTGGCCTGGAAGGCAGAT<br>AGCAGCCCCGTCAAGGCGGGAGTGGAGACCACCAC<br>ACCCTCCAAACAAAGCAACAACAAGTACGCCGCCA<br>GCAGCTACCTGAGCCTGACCCCCGAGCAGTGGAAG<br>AGCCACAGAAGCTACAGCTGCCAGGTCACCCACGA<br>GGGCAGCACCGTGGAGAAAACCGTGGCCCCCACCG<br>AGTGCAGC |
| NOV3833 HC | | |
| SEQ ID NO: 38 (Combined) | HCDR1 | GFTFHNYAMS |
| SEQ ID NO: 39 (Combined) | HCDR2 | SISGSGGSTYYADSVKG |
| SEQ ID NO: 40 (Combined) | HCDR3 | SSILSGGHARVYGIDV |
| SEQ ID NO: 41 (Kabat) | HCDR1 | NYAMS |
| SEQ ID NO: 42 (Kabat) | HCDR2 | SISGSGGSTYYADSVKG |
| SEQ ID NO: 43 (Kabat) | HCDR3 | SSILSGGHARVYGIDV |
| SEQ ID NO: 44 (Chothia) | HCDR1 | GFTFHNY |
| SEQ ID NO: 45 (Chothia) | HCDR2 | SGSGGS |
| SEQ ID NO: 46 (Chothia) | HCDR3 | SSILSGGHARVYGIDV |
| SEQ ID NO: 47 (IMGT) | HCDR1 | GFTFHNYA |
| SEQ ID NO: 48 (IMGT) | HCDR2 | ISGSGGST |
| SEQ ID NO: 49 (IMGT) | HCDR3 | AKSSILSGGHARVYGIDV |
| SEQ ID NO: 50 | VH | EMQVLESGGGLVQPGGSLRLSCAASGFTFHNYAMSW<br>VRQVPGKGLEWVSSISGSGGSTYYADSVKGQFTISRD<br>NSKNTLYLQMNSLRAEDTAVYYCAKSSILSGGHARV<br>YGIDVWGQGTTVTVSS |
| SEQ ID NO: 51 | DNA VH | GAGATGCAGGTCTTGGAATCTGGCGGAGGACTGGT<br>TCAACCTGGCGGCTCTCTGAGACTGTCTTGTGCCGC<br>CAGCGGCTTCACCTTCCATAACTACGCCATGTCCTG<br>GGTCCGACAGGTGCCAGGCAAAGGACTGGAATGG<br>GTGTCCTCTATCAGCGGCTCTGGCGGCAGCACATAT<br>TACGCCGATAGCGTGAAGGGCCAGTTCACCATCAG<br>CCGGGACAACAGCAAGAACACCCTGTACCTCCAGA<br>TGAACAGCCTGAGAGCCGAGGATACCGCCGTGTAC<br>TACTGTGCCAAGAGCAGCATTCTGTCTGGCGGCCA<br>CGCCAGAGTGTATGGCATTGATGTTTGGGGCCAGG<br>GAACCACCGTGACCGTTAGTTCT |
| SEQ ID NO: 52 | Heavy Chain | EMQVLESGGGLVQPGGSLRLSCAASGFTFHNYAMSW<br>VRQVPGKGLEWVSSISGSGGSTYYADSVKGQFTISRD<br>NSKNTLYLQMNSLRAEDTAVYYCAKSSILSGGHARV<br>YGIDVWGQGTTVTVSSASTKGPSVFPLAPSSKSTSGG<br>TAALGCLVKDYFPEPVTVSWNSGALTSGVHTFPAVL<br>QSSGLYSLSSVVTVPSSSLGTQTYICNVNHKPSNTKVD<br>KRVEPKSCDKTHTCPPCPAPELLGGPSVFLFPPKPKDT |

TABLE 2-continued anti-HBV Antibodies

|  |  |  |
|---|---|---|
|  |  | LMISRTPEVTCVVVDVSHEDPEVKFNWYVDGVEVHN<br>AKTKPREEQYNSTYRVVSVLTVLHQDWLNGKEYKC<br>KVSNKALPAPIEKTISKAKGQPREPQVYTLPPSREEMT<br>KNQVSLTCLVKGFYPSDIAVEWESNGQPENNYKTTPP<br>VLDSDGSFFLYSKLTVDKSRWQQGNVFSCSVMHEAL<br>HNHYTQKSLSLSPGK |
| SEQ ID NO: 53 | DNA Heavy<br>Chain | GAGATGCAGGTCTTGGAATCTGGCGGAGGACTGGT<br>TCAACCTGGCGGCTCTCTGAGACTGTCTTGTGCCGC<br>CAGCGGCTTCACCTTCCATAACTACGCCATGTCCTG<br>GGTCCGACAGGTGCCAGGCAAAGGACTGGAATGG<br>GTGTCCTCTATCAGCGGCTCTGGCGGCAGCACATAT<br>TACGCCGATAGCGTGAAGGGCCAGTTCACCATCAG<br>CCGGGACAACAGCAAGAACACCCTGTACCTCCAGA<br>TGAACAGCCTGAGAGCCGAGGATACCGCCGTGTAC<br>TACTGTGCCAAGAGCAGCATTCTGTCTGGCGGCCA<br>CGCCAGAGTGTATGGCATTGATGTTTGGGGCCAGG<br>GAACCACCGTGACCGTTAGTTCTGCTAGCACCAAG<br>GGCCCCAGCGTGTTCCCCCTGGCCCCCAGCAGCAA<br>GAGCACCAGCGGCGGCACAGCCGCCCTGGGCTGCC<br>TGGTGAAGGACTACTTCCCCGAGCCCGTGACCGTG<br>TCCTGGAACAGCGGAGCCCTGACCTCCGGCGTGCA<br>CACCTTCCCCGCCGTGCTGCAGAGCAGCGGCCTGT<br>ACAGCCTGTCCAGCGTGGTGACAGTGCCCAGCAGC<br>AGCCTGGGCACCCAGACCTACATCTGCAACGTGAA<br>CCACAAGCCCAGCAACACCAAGGTGGACAAGAGA<br>GTGGAGCCCAAGAGCTGCGACAAGACCCACACATG<br>CCCCCCCTGCCCGGCGCCAGAGCTGCTGGGCGGAC<br>CCTCCGTGTTCCTGTTCCCCCCCAAGCCCAAGGACA<br>CCCTGATGATCAGCAGGACCCCCGAGGTGACCTGC<br>GTGGTGGTGGACGTGAGCCACGAGGACCCAGAGGT<br>GAAGTTCAACTGGTACGTGGACGGCGTGGAGGTGC<br>ACAACGCCAAGACCAAGCCCAGAGAGGAGCAGTA<br>CAACAGCACCTACAGGGTGGTGTCCGTGCTGACCG<br>TGCTGCACCAGGACTGGCTGAACGGCAAGGAATAC<br>AAGTGCAAGGTCTCCAACAAGGCCCTGCCAGCCCC<br>CATCGAAAAGACCATCAGCAAGGCCAAGGGCCAG<br>CCACGGGAGCCCCAGGTGTACACCCTGCCCCCCTC<br>CCGGGAGGAGATGACCAAGAACCAGGTGTCCCTGA<br>CCTGTCTGGTGAAGGGCTTCTACCCCAGCGACATC<br>GCCGTGGAGTGGGAGAGCAACGGCCAGCCCGAGA<br>CAAACTACAAGACCACCCCCCCAGTGCTGGACAGC<br>GACGGCAGCTTCTTCCTGTACAGCAAGCTGACCGT<br>GGACAAGTCCAGGTGGCAGCAGGGCAACGTGTTCA<br>GCTGCAGCGTGATGCACGAGGCCCTGCACAACCAC<br>TACACCCAGAAGAGCCTGAGCTTAAGCCCCGGCAA<br>G |

NOV3833 LC

| SEQ ID NO: 54<br>(Combined) | LCDR1 | GGNNIGSQSVH |
|---|---|---|
| SEQ ID NO: 55<br>(Combined) | LCDR2 | DDTDRPS |
| SEQ ID NO: 56<br>(Combined) | LCDR3 | QVWDSSSDHVV |
| SEQ ID NO: 57 (Kabat) | LCDR1 | GGNNIGSQSVH |
| SEQ ID NO: 58 (Kabat) | LCDR2 | DDTDRPS |
| SEQ ID NO: 59 (Kabat) | LCDR3 | QVWDSSSDHVV |
| SEQ ID NO: 60<br>(Chothia) | LCDR1 | NNIGSQS |
| SEQ ID NO: 61<br>(Chothia) | LCDR2 | DDT |
| SEQ ID NO: 62<br>(Chothia) | LCDR3 | WDSSSDHV |
| SEQ ID NO: 63 (IMGT) | LCDR1 | NIGSQS |
| SEQ ID NO: 64 (IMGT) | LCDR2 | DDT |
| SEQ ID NO: 65 (IMGT) | LCDR3 | QVWDSSSDHVV |
| SEQ ID NO: 66 | VL | QSALTQPPSVSVAPGQTARITCGGNNIGSQSVHWYQQ<br>KPGQAPILVVYDDTDRPSGIPARFSGSSSGSTATLTIGR<br>VEAGDEADYYCQVWDSSSDHVVFGGGTKLTVL |
| SEQ ID NO: 67 | DNA VL | CAGTCTGCCCTGACTCAGCCACCCTCGGTGTCAGTG<br>GCCCCAGGACAGACGGCCAGGATTACCTGTGGGGG<br>AAACAACATTGGAAGTCAAAGTGTGCACTGGTACC<br>AGCAGAAGCCAGGCCAGGCCCCTATACTGGTCGTC<br>TATGATGATACCGACCGGCCCTCAGGGATCCCTGC<br>GCGATTCTCTGGCTCCAGCTCTGGGAGCACGGCCA |

TABLE 2-continued anti-HBV Antibodies

| | | |
|---|---|---|
| | | CCCTGACCATCGGCAGGGTCGAAGCCGGGGATGAG |
| | | GCCGACTATTACTGTCAGGTGTGGGATAGTAGTAG |
| | | TGATCATGTGGTATTCGGCGGAGGGACCAAGCTGA |
| | | CCGTCTTA |
| SEQ ID NO: 68 | Light Chain | QSALTQPPSVSVAPGQTARITCGGNNIGSQSVHWYQQ |
| | | KPGQAPILVVYDDTDRPSGIPARFSGSSSGSTATLTIGR |
| | | VEAGDEADYYCQVWDSSSDHVVFGGGTKLTVLSQP |
| | | KAAPSVTLFPPSSEELQANKATLVCLISDFYPGAVTVA |
| | | WKADSSPVKAGVETTTPSKQSNNKYAASSYLSLTPEQ |
| | | WKSHRSYSCQVTHEGSTVEKTVAPTECS |
| SEQ ID NO: 69 | DNA Light Chain | CAGTCTGCCCTGACTCAGCCACCCTCGGTGTCAGTG |
| | | GCCCCAGGACAGACGGCCAGGATTACCTGTGGGGG |
| | | AAACAACATTGGAAGTCAAAGTGTGCACTGGTACC |
| | | AGCAGAAGCCAGGCCAGGCCCCTATACTGGTCGTC |
| | | TATGATGATACCGACCGGCCCTCAGGGATCCCTGC |
| | | GCGATTCTCTGGCTCCAGCTCTGGGAGCACGGCCA |
| | | CCCTGACCATCGGCAGGGTCGAAGCCGGGGATGAG |
| | | GCCGACTATTACTGTCAGGTGTGGGATAGTAGTAG |
| | | TGATCATGTGGTATTCGGCGGAGGGACCAAGCTGA |
| | | CCGTCTTAAGTCAGCCCAAGGCTGCCCCCTCGGTCA |
| | | CTCTGTTCCCGCCCTCCTCTGAGGAGCTTCAAGCCA |
| | | ACAAGGCCACACTGGTGTGTCTCATAAGTGACTTCT |
| | | ACCCGGGAGCCGTGACAGTGGCCTGGAAGGCAGAT |
| | | AGCAGCCCCGTCAAGGCGGGAGTGGAGACCACCAC |
| | | ACCCTCCAAACAAAGCAACAACAAGTACGCCGCCA |
| | | GCAGCTACCTGAGCCTGACCCCCGAGCAGTGGAAG |
| | | AGCCACAGAAGCTACAGCTGCCAGGTCACCCACGA |
| | | GGGCAGCACCGTGGAGAAAACCGTGGCCCCCACCG |
| | | AGTGCAGC |

NOV3831 HC

| | | |
|---|---|---|
| SEQ ID NO: 70 (Combined) | HCDR1 | GFTFNNYAMS |
| SEQ ID NO: 71 (Combined) | HCDR2 | SISGSGGSTYYADSVKG |
| SEQ ID NO: 72 (Combined) | HCDR3 | SSILSGGHARVYGIDV |
| SEQ ID NO: 73 (Kabat) | HCDR1 | NYAMS |
| SEQ ID NO: 74 (Kabat) | HCDR2 | SISGSGGSTYYADSVKG |
| SEQ ID NO: 75 (Kabat) | HCDR3 | SSILSGGHARVYGIDV |
| SEQ ID NO: 76 (Chothia) | HCDR1 | GFTFNNY |
| SEQ ID NO: 77 (Chothia) | HCDR2 | SGSGGS |
| SEQ ID NO: 78 (Chothia) | HCDR3 | SSILSGGHARVYGIDV |
| SEQ ID NO: 79 (IMGT) | HCDR1 | GFTFNNYA |
| SEQ ID NO: 80 (IMGT) | HCDR2 | ISGSGGST |
| SEQ ID NO: 81 (IMGT) | HCDR3 | AKSSILSGGHARVYGIDV |
| SEQ ID NO: 82 | VH | EMQVLESGGGLVQPGGSLRLSCAASGFTFNNYAMSW |
| | | VRQVPGKGLEWVSSISGSGGSTYYADSVKGQFTISRD |
| | | NSKNTLYLQMNSLRAEDTAVYYCAKSSILSGGHARV |
| | | YGIDVWGQGTTVTVSS |
| SEQ ID NO: 83 | DNA VH | GAAATGCAGGTGTTGGAGTCTGGGGGAGGCCTGGT |
| | | ACAGCCTGGGGGGTCCCTGAGACTCTCCTGTGCAG |
| | | CCTCTGGATTCACCTTTAACAACTATGCCATGAGCT |
| | | GGGTCCGCCAGGTTCCAGGGAAGGGGCTGGAGTGG |
| | | GTCTCAAGTATTAGTGGTAGTGGAGGTAGCACGTA |
| | | CTACGCAGACTCCGTGAAGGGCCAGTTCACCATCT |
| | | CCAGAGACAATTCCAAGAATACGCTGTATCTGCAA |
| | | ATGAACAGCCTGAGAGCCGAGGACACGGCCGTATA |
| | | TTACTGTGCGAAATCCTCTATCTTGAGTGGTGGTCA |
| | | CGCGCGGGTCTACGGCATAGACGTCTGGGGCCAAG |
| | | GGACCACGGTCACCGTCTCCTCA |
| SEQ ID NO: 84 | Heavy Chain | EMQVLESGGGLVQPGGSLRLSCAASGFTFNNYAMSW |
| | | VRQVPGKGLEWVSSISGSGGSTYYADSVKGQFTISRD |
| | | NSKNTLYLQMNSLRAEDTAVYYCAKSSILSGGHARV |
| | | YGIDVWGQGTTVTVSSASTKGPSVFPLAPSSKSTSGG |
| | | TAALGCLVKDYFPEPVTVSWNSGALTSGVHTFPAVL |
| | | QSSGLYSLSSVVTVPSSSLGTQTYICNVNHKPSNTKVD |
| | | KRVEPKSCDKTHTCPPCPAPELLGGPSVFLFPPKPKDT |
| | | LMISRTPEVTCVVVDVSHEDPEVKFNWYVDGVEVHN |
| | | AKTKPREEQYNSTYRVVSVLTVLHQDWLNGKEYKC |
| | | KVSNKALPAPIEKTISKAKGQPREPQVYTLPPSREEMT |
| | | KNQVSLTCLVKGFYPSDIAVEWESNGQPENNYKTTPP |
| | | VLDSDGSFFLYSKLTVDKSRWQQGNVFSCSVMHEAL |
| | | HNHYTQKSLSLSPGK |

TABLE 2-continued anti-HBV Antibodies

| SEQ ID NO: 85 | DNA Heavy Chain | GAAATGCAGGTGTTGGAGTCTGGGGGAGGCCTGGT
ACAGCCTGGGGGGTCCCTGAGACTCTCCTGTGCAG
CCTCTGGATTCACCTTTAACAACTATGCCATGAGCT
GGGTCCGCCAGGTTCCAGGGAAGGGGCTGGAGTGG
GTCTCAAGTATTAGTGGTAGTGGAGGTAGCACGTA
CTACGCAGACTCCGTGAAGGGCCAGTTCACCATCT
CCAGAGACAATTCCAAGAATACGCTGTATCTGCAA
ATGAACAGCCTGAGAGCCGAGGACACGGCCGTATA
TTACTGTGCGAAATCCTCTATCTTGAGTGGTGGTCA
CGCGCGGGTCTACGGCATAGACGTCTGGGGCCAAG
GGACCACGGTCACCGTCTCCTCAGCCTCCACCAAG
GGCCCATCGGTCTTCCCCCTGGCACCCTCCTCCAAG
AGCACCTCTGGGGGCACAGCGGCCCTGGGCTGCCT
GGTCAAGGACTACTTCCCCGAACCGGTGACGGTGT
CATGGAACTCAGGCGCCCTGACCAGCGGCGTGCAC
ACCTTCCCGGCTGTCCTACAGTCCTCAGGACTCTAC
TCCCTCAGCAGCGTGGTGACCGTGCCCTCCAGCAG
CTTGGGCACCCAGACCTACATCTGCAACGTGAACC
ACAAGCCCAGCAACACCAAGGTGGACAAGAGAGT
GGAGCCCAAGAGCTGCGACAAGACCCACACCTGCC
CCCCCTGCCCAGCCCCAGAGCTGCTGGGCGGACCC
TCCGTGTTCCTGTTCCCCCCCAAGCCCAAGGACACC
CTGATGATCAGCAGGACCCCCGAGGTGACCTGCGT
GGTGGTGGACGTGAGCCACGAGGACCCAGAGGTG
AAGTTCAACTGGTACGTGGACGGCGTGGAGGTGCA
CAACGCCAAGACCAAGCCCAGAGAGGAGCAGTAC
AACAGCACCTACAGGGTGGTGTCCGTGCTGACCGT
GCTGCACCAGGACTGGCTGAACGGCAAGGAATACA
AGTGCAAGGTCTCCAACAAGGCCCTGCCAGCCCCC
ATCGAAAAGACCATCAGCAAGGCCAAGGGCCAGC
CACGGGAGCCCCAGGTGTACACCCTGCCCCCCTCC
CGGGAGGAGATGACCAAGAACCAGGTGTCCCTGAC
CTGTCTGGTGAAGGGCTTCTACCCCAGCGACATCG
CCGTGGAGTGGGAGAGCAACGGCCAGCCCGAGAA
CAACTACAAGACCACCCCCCCAGTGCTGGACAGCG
ACGGCAGCTTCTTCCTGTACAGCAAGCTGACCGTG
GACAAGTCCAGGTGGCAGCAGGGCAACGTGTTCAG
CTGCAGCGTGATGCACGAGGCCCTGCACAACCACT
ACACCCAGAAGAGCCTGAGCCTGTCCCCCGGCAAG |

NOV3831 LC

| SEQ ID NO: 86 (Combined) | LCDR1 | GGNNIGSQSVH |
| SEQ ID NO: 87 (Combined) | LCDR2 | DDTDRPS |
| SEQ ID NO: 88 (Combined) | LCDR3 | QVWDSSSDHVV |
| SEQ ID NO: 89 (Kabat) | LCDR1 | GGNNIGSQSVH |
| SEQ ID NO: 90 (Kabat) | LCDR2 | DDTDRPS |
| SEQ ID NO: 91 (Kabat) | LCDR3 | QVWDSSSDHVV |
| SEQ ID NO: 92 (Chothia) | LCDR1 | NNIGSQS |
| SEQ ID NO: 93 (Chothia) | LCDR2 | DDT |
| SEQ ID NO: 94 (Chothia) | LCDR3 | WDSSSDHV |
| SEQ ID NO: 95 (IMGT) | LCDR1 | NIGSQS |
| SEQ ID NO: 96 (IMGT) | LCDR2 | DDT |
| SEQ ID NO: 97 (IMGT) | LCDR3 | QVWDSSSDHVV |
| SEQ ID NO: 98 | VL | QSALTQPPSVSVAPGQTARITCGGNNIGSQSVHWYQQ
KPGQAPILVVYDDTDRPSGIPARFSGSSSGSTATLTIGR
VEAGDEADYYCQVWDSSSDHVVFGGGTKLTVL |
| SEQ ID NO: 99 | DNA VL | CAGTCTGCCCTGACTCAGCCACCCTCGGTGTCAGTG
GCCCCAGGACAGACGGCCAGGATTACCTGTGGGGG
AAACAACATTGGAAGTCAAAGTGTGCACTGGTACC
AGCAGAAGCCAGGCCAGGCCCCTATACTGGTCGTC
TATGATGATACCGACCGGCCCTCAGGGATCCCTGC
GCGATTCTCTGGCTCCAGCTCTGGGAGCACGGCCA
CCCTGACCATCGGCAGGGTCGAAGCGGGGATGAG
GCCGACTATTACTGTCAGGTGTGGGATAGTAGTAG
TGATCATGTGGTATTCGGCGGAGGGACCAAGCTGA
CCGTCTTA |
| SEQ ID NO: 100 | Light Chain | QSALTQPPSVSVAPGQTARITCGGNNIGSQSVHWYQQ
KPGQAPILVVYDDTDRPSGIPARFSGSSSGSTATLTIGR
VEAGDEADYYCQVWDSSSDHVVFGGGTKLTVLSQP
KAAPSVTLFPPSSEELQANKATLVCLISDFYPGAVTVA
WKADSSPVKAGVETTTPSKQSNNKYAASSYLSLTPEQ
WKSHRSYSCQVTHEGSTVEKTVAPTECS |

TABLE 2-continued anti-HBV Antibodies

| SEQ ID NO: 101 | DNA Light Chain | CAGTCTGCCCTGACTCAGCCACCCTCGGTGTCAGTG<br>GCCCCAGGACAGACGGCCAGGATTACCTGTGGGGG<br>AAACAACATTGGAAGTCAAAGTGTGCACTGGTACC<br>AGCAGAAGCCAGGCCAGGCCCCTATACTGGTCGTC<br>TATGATGATACCGACCGGCCCTCAGGGATCCCTGC<br>GCGATTCTCTGGCTCCAGCTCTGGGAGCACGGCCA<br>CCCTGACCATCGGCAGGGTCGAAGCCGGGGATGAG<br>GCCGACTATTACTGTCAGGTGTGGGATAGTAGTAG<br>TGATCATGTGGTATTCGGCGGAGGGACCAAGCTGA<br>CCGTCTTAAGTCAGCCCAAGGCTGCCCCCTCGGTCA<br>CTCTGTTCCCGCCCTCCTCTGAGGAGCTTCAAGCCA<br>ACAAGGCCACACTGGTGTGTCTCATAAGTGACTTCT<br>ACCCGGGAGCCGTGACAGTGGCCTGGAAGGCAGAT<br>AGCAGCCCCGTCAAGGCGGGAGTGGAGACCACCAC<br>ACCCTCCAAACAAAGCAACAACAAGTACGCCGCCA<br>GCAGCTACCTGAGCCTGACCCCCGAGCAGTGGAAG<br>AGCCACAGAAGCTACAGCTGCCAGGTCACCCACGA<br>GGGCAGCACCGTGGAGAAAACCGTGGCCCCCACCG<br>AGTGCAGC |
| --- | --- | --- |
| NOV3540 HC | | |
| SEQ ID NO: 102 (Combined) | HCDR1 | GFTFSPHAMS |
| SEQ ID NO: 103 (Combined) | HCDR2 | AISDSGGSTHYADSVKG |
| SEQ ID NO: 104 (Combined) | HCDR3 | DDDAWSGYDYWFDY |
| SEQ ID NO: 105 (Kabat) | HCDR1 | PHAMS |
| SEQ ID NO: 106 (Kabat) | HCDR2 | AISDSGGSTHYADSVKG |
| SEQ ID NO: 107 (Kabat) | HCDR3 | DDDAWSGYDYWFDY |
| SEQ ID NO: 108 (Chothia) | HCDR1 | GFTFSPH |
| SEQ ID NO: 109 (Chothia) | HCDR2 | SDSGGS |
| SEQ ID NO: 110 (Chothia) | HCDR3 | DDDAWSGYDYWFDY |
| SEQ ID NO: 111 (IMGT) | HCDR1 | GFTFSPHA |
| SEQ ID NO: 112 (IMGT) | HCDR2 | ISDSGGST |
| SEQ ID NO: 113 (IMGT) | HCDR3 | ARDDDAWSGYDYWFDY |
| SEQ ID NO: 114 | VH | EVQLLESGGGLVQPGGSLRLSCAASGFTFSPHAMSW<br>VRQAPGKGLEWVSAISDSGGSTHYADSVKGRFTISRD<br>NSKNTLYLQMNSLRAEDTAVYYCARDDDAWSGYDY<br>WFDYWGQGTLVTVSS |
| SEQ ID NO: 115 | DNA VH | GAGGTCCAATTGCTGGAATCTGGCGGAGGACTGGT<br>TCAGCCTGGTGGCTCTCTGAGACTGTCTTGTGCCGC<br>CAGCGGCTTCACCTTTAGCCCTCATGCCATGTCCTG<br>GGTCCGACAGGCTCCTGGAAAAGGACTCGAGTGGG<br>TGTCCGCCATTTCTGATTCTGGCGGCAGCACACACT<br>ACGCCGATAGCGTGAAGGGCAGATTCACCATCAGC<br>CGGGACAACAGCAAGAACACCCTGTACCTGCAGAT<br>GAACAGCCTGAGAGCCGAGGACACAGCCGTGTACT<br>ATTGCGCGCGTGACGATGATGCTTGGTCCGGCTAC<br>GACTATTGGTTCGATTACTGGGGCCAGGGCACCCT<br>GGTCACAGTTAGCTCA |
| SEQ ID NO: 116 | Heavy Chain | EVQLLESGGGLVQPGGSLRLSCAASGFTFSPHAMSW<br>VRQAPGKGLEWVSAISDSGGSTHYADSVKGRFTISRD<br>NSKNTLYLQMNSLRAEDTAVYYCARDDDAWSGYDY<br>WFDYWGQGTLVTVSSASTKGPSVFPLAPSSKSTSGGT<br>AALGCLVKDYFPEPVTVSWNSGALTSGVHTFPAVLQ<br>SSGLYSLSSVVTVPSSSLGTQTYICNVNHKPSNTKVDK<br>RVEPKSCDKTHTCPPCPAPELLGGPSVFLFPPKPKDTL<br>MISRTPEVTCVVVDVSHEDPEVKFNWYVDGVEVHNA<br>KTKPREEQYNSTYRVVSVLTVLHQDWLNGKEYKCK<br>VSNKALPAPIEKTISKAKGQPREPQVYTLPPSREEMTK<br>NQVSLTCLVKGFYPSDIAVEWESNGQPENNYKTTPPV<br>LDSDGSFFLYSKLTVDKSRWQQGNVFSCSVMHEALH<br>NHYTQKSLSLSPGK |
| SEQ ID NO: 117 | DNA Heavy Chain | GAGGTCCAATTGCTGGAATCTGGCGGAGGACTGGT<br>TCAGCCTGGTGGCTCTCTGAGACTGTCTTGTGCCGC<br>CAGCGGCTTCACCTTTAGCCCTCATGCCATGTCCTG<br>GGTCCGACAGGCTCCTGGAAAAGGACTCGAGTGGG<br>TGTCCGCCATTTCTGATTCTGGCGGCAGCACACACT<br>ACGCCGATAGCGTGAAGGGCAGATTCACCATCAGC<br>CGGGACAACAGCAAGAACACCCTGTACCTGCAGAT |

TABLE 2-continued anti-HBV Antibodies

|  |  |  |
|---|---|---|
|  |  | GAACAGCCTGAGAGCCGAGGACACAGCCGTGTACT |
|  |  | ATTGCGCGCGTGACGATGATGCTTGGTCCGGCTAC |
|  |  | GACTATTGGTTCGATTACTGGGGCCAGGGCACCCT |
|  |  | GGTCACAGTTAGCTCAGCTAGCACCAAGGGCCCCA |
|  |  | GCGTGTTCCCCCTGGCCCCCAGCAGCAAGAGCACC |
|  |  | AGCGGCGGCACAGCCGCCCTGGGCTGCCTGGTGAA |
|  |  | GGACTACTTCCCCGAGCCCGTGACCGTGTCCTGGA |
|  |  | ACAGCGGAGCCCTGACCTCCGGCGTGCACACCTTC |
|  |  | CCCGCCGTGCTGCAGAGCAGCGGCCTGTACAGCCT |
|  |  | GTCCAGCGTGGTGACAGTGCCCAGCAGCAGCCTGG |
|  |  | GCACCCAGACCTACATCTGCAACGTGAACCACAAG |
|  |  | CCCAGCAACACCAAGGTGGACAAGAGAGTGGAGC |
|  |  | CCAAGAGCTGCGACAAGACCCACACATGCCCCCCC |
|  |  | TGCCCGGCGCCAGAGCTGCTGGGCGGACCCTCCGT |
|  |  | GTTCCTGTTCCCCCCCAAGCCCAAGGACACCCTGAT |
|  |  | GATCAGCAGGACCCCCGAGGTGACCTGCGTGGTGG |
|  |  | TGGACGTGAGCCACGAGGACCCAGAGGTGAAGTTC |
|  |  | AACTGGTACGTGGACGGCGTGGAGGTGCACAACGC |
|  |  | CAAGACCAAGCCCAGAGAGGAGCAGTACAACAGC |
|  |  | ACCTACAGGGTGGTGTCCGTGCTGACCGTGCTGCA |
|  |  | CCAGGACTGGCTGAACGGCAAGGAATACAAGTGCA |
|  |  | AGGTCTCCAACAAGGCCCTGCCAGCCCCCATCGAA |
|  |  | AAGACCATCAGCAAGGCCAAGGGCCAGCCACGGG |
|  |  | AGCCCCAGGTGTACACCCTGCCCCCCTCCCGGGAG |
|  |  | GAGATGACCAAGAACCAGGTGTCCCTGACCTGTCT |
|  |  | GGTGAAGGGCTTCTACCCCAGCGACATCGCCGTGG |
|  |  | AGTGGGAGAGCAACGGCCAGCCCGAGAACAACTA |
|  |  | CAAGACCACCCCCCCAGTGCTGGACAGCGACGGCA |
|  |  | GCTTCTTCCTGTACAGCAAGCTGACCGTGGACAAG |
|  |  | TCCAGGTGGCAGCAGGGCAACGTGTTCAGCTGCAG |
|  |  | CGTGATGCACGAGGCCCTGCACAACCACTACACCC |
|  |  | AGAAGAGCCTGAGCTTAAGCCCCGGCAAG |
| NOV3540 LC |  |  |
| SEQ ID NO: 118 (Combined) | LCDR1 | RASQSISPYLN |
| SEQ ID NO: 119 (Combined) | LCDR2 | AADSLQS |
| SEQ ID NO: 120 (Combined) | LCDR3 | QQSYKIPLT |
| SEQ ID NO: 121 (Kabat) | LCDR1 | RASQSISPYLN |
| SEQ ID NO: 122 (Kabat) | LCDR2 | AADSLQS |
| SEQ ID NO: 123 (Kabat) | LCDR3 | QQSYKIPLT |
| SEQ ID NO: 124 (Chothia) | LCDR1 | SQSISPY |
| SEQ ID NO: 125 (Chothia) | LCDR2 | AAD |
| SEQ ID NO: 126 (Chothia) | LCDR3 | SYKIPL |
| SEQ ID NO: 127 (IMGT) | LCDR1 | QSISPY |
| SEQ ID NO: 128 (IMGT) | LCDR2 | AAD |
| SEQ ID NO: 129 (IMGT) | LCDR3 | QQSYKIPLT |
| SEQ ID NO: 130 | VL | DIQMTQSPSSLSASVGDRVTITCRASQSISPYLNWYQQ KPGKAPKLLIYAADSLQSGVPSRFSGSGSGTDFTLTISS LQPEDFATYYCQQSYKIPLTFGQGTKVEIK |
| SEQ ID NO: 131 | DNA VL | GATATCCAGATGACACAGAGCCCTAGCAGCCTGTC TGCCTCTGTGGGCGATAGAGTGACCATCACCTGTA GAGCCAGCCAGAGCATCAGCCCCTACCTGAATTGG TACCAGCAGAAGCCTGGCAAGGCCCCTAAGCTGCT GATCTATGCTGCCGACTCTCTGCAGTCTGGCGTGCC AAGCAGATTTTCTGGCAGCGGCTCTGGCACCGACT TCACCCTGACAATTAGCTCCCTGCAGCCTGAAGACT TCGCCACCTACTACTGCCAGCAGAGCTACAAGATC CCTCTGACCTTTGGCCAGGGCACCAAGGTGGAAAT CAAG |
| SEQ ID NO: 132 | Light Chain | DIQMTQSPSSLSASVGDRVTITCRASQSISPYLNWYQQ KPGKAPKLLIYAADSLQSGVPSRFSGSGSGTDFTLTISS LQPEDFATYYCQQSYKIPLTFGQGTKVEIKRTVAAPS VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| SEQ ID NO: 133 | DNA Light Chain | GATATCCAGATGACACAGAGCCCTAGCAGCCTGTC TGCCTCTGTGGGCGATAGAGTGACCATCACCTGTA GAGCCAGCCAGAGCATCAGCCCCTACCTGAATTGG |

US 11,932,681 B2

TABLE 2-continued anti-HBV Antibodies

|  |  |  |
|---|---|---|
|  |  | TACCAGCAGAAGCCTGGCAAGGCCCCTAAGCTGCT<br>GATCTATGCTGCCGACTCTCTGCAGTCTGGCGTGCC<br>AAGCAGATTTTCTGGCAGCGGCTCTGGCACCGACT<br>TCACCCTGACAATTAGCTCCCTGCAGCCTGAAGACT<br>TCGCCACCTACTACTGCCAGCAGAGCTACAAGATC<br>CCTCTGACCTTTGGCCAGGGCACCAAGGTGGAAAT<br>CAAGCGTACGGTGGCCGCTCCCAGCGTGTTCATCTT<br>CCCCCCCAGCGACGAGCAGCTGAAGAGCGGCACCG<br>CCAGCGTGGTGTGCCTGCTGAACAACTTCTACCCCC<br>GGGAGGCCAAGGTGCAGTGGAAGGTGGACAACGC<br>CCTGCAGAGCGGCAACAGCCAGGAGAGCGTCACCG<br>AGCAGGACAGCAAGGACTCCACCTACAGCCTGAGC<br>AGCACCCTGACCCTGAGCAAGGCCGACTACGAGAA<br>GCATAAGGTGTACGCCTGCGAGGTGACCCACCAGG<br>GCCTGTCCAGCCCCGTGACCAAGAGCTTCAACAGG<br>GGCGAGTGC |
| NOV3357 HC |  |  |
| SEQ ID NO: 134<br>(Combined) | HCDR1 | GFTFSPHAMS |
| SEQ ID NO: 135<br>(Combined) | HCDR2 | AISDSGGSTHYADSVKG |
| SEQ ID NO: 136<br>(Combined) | HCDR3 | DDDGWSGYDYWFDY |
| SEQ ID NO: 137 (Kabat) | HCDR1 | PHAMS |
| SEQ ID NO: 138 (Kabat) | HCDR2 | AISDSGGSTHYADSVKG |
| SEQ ID NO: 139 (Kabat) | HCDR3 | DDDGWSGYDYWFDY |
| SEQ ID NO: 140<br>(Chothia) | HCDR1 | GFTFSPH |
| SEQ ID NO: 141<br>(Chothia) | HCDR2 | SDSGGS |
| SEQ ID NO: 142<br>(Chothia) | HCDR3 | DDDGWSGYDYWFDY |
| SEQ ID NO: 143<br>(IMGT) | HCDR1 | GFTFSPHA |
| SEQ ID NO: 144<br>(IMGT) | HCDR2 | ISDSGGST |
| SEQ ID NO: 145<br>(IMGT) | HCDR3 | ARDDDGWSGYDYWFDY |
| SEQ ID NO: 146 | VH | EVQLLESGGGLVQPGGSLRLSCAASGFTFSPHAMSW<br>VRQAPGKGLEWVSAISDSGGSTHYADSVKGRFTISRD<br>NSKNTLYLQMNSLRAEDTAVYYCARDDDGWSGYDY<br>WFDYWGQGTLVTVSS |
| SEQ ID NO: 147 | DNA VH | GAGGTCCAATTGCTGGAATCTGGCGGAGGACTGGT<br>TCAGCCTGGTGGCTCTCTGAGACTGTCTTGTGCCGC<br>CAGCGGCTTCACATTCAGCCCTCATGCCATGTCCTG<br>GGTCCGACAGGCTCCTGGAAAAGGACTCGAGTGGG<br>TGTCCGCCATTTCTGATTCTGGCGGCAGCACACACT<br>ACGCCGATAGCGTGAAGGGCAGATTCACCATCAGC<br>CGGGACAACAGCAAGAACACCCTGTACCTGCAGAT<br>GAACAGCCTGAGAGCCGAGGACACAGCCGTGTACT<br>ATTGCGCGCGTGACGATGATGGATGGTCCGGCTAC<br>GACTATTGGTTCGATTACTGGGGCCAGGGCACCCT<br>GGTCACAGTTAGCTCA |
| SEQ ID NO: 148 | Heavy Chain | EVQLLESGGGLVQPGGSLRLSCAASGFTFSPHAMSW<br>VRQAPGKGLEWVSAISDSGGSTHYADSVKGRFTISRD<br>NSKNTLYLQMNSLRAEDTAVYYCARDDDGWSGYDY<br>WFDYWGQGTLVTVSSASTKGPSVFPLAPSSKSTSGGT<br>AALGCLVKDYFPEPVTVSWNSGALTSGVHTFPAVLQ<br>SSGLYSLSSVVTVPSSSLGTQTYICNVNHKPSNTKVDK<br>RVEPKSCDKTHTCPPCPAPELLGGPSVFLFPPKPKDTL<br>MISRTPEVTCVVVDVSHEDPEVKFNWYVDGVEVHNA<br>KTKPREEQYNSTYRVVSVLTVLHQDWLNGKEYKCK<br>VSNKALPAPIEKTISKAKGQPREPQVYTLPPSREEMTK<br>NQVSLTCLVKGFYPSDIAVEWESNGQPENNYKTTPPV<br>LDSDGSFFLYSKLTVDKSRWQQGNVFSCSVMHEALH<br>NHYTQKSLSLSPGK |
| SEQ ID NO: 149 | DNA Heavy<br>Chain | GAGGTCCAATTGCTGGAATCTGGCGGAGGACTGGT<br>TCAGCCTGGTGGCTCTCTGAGACTGTCTTGTGCCGC<br>CAGCGGCTTCACATTCAGCCCTCATGCCATGTCCTG<br>GGTCCGACAGGCTCCTGGAAAAGGACTCGAGTGGG<br>TGTCCGCCATTTCTGATTCTGGCGGCAGCACACACT<br>ACGCCGATAGCGTGAAGGGCAGATTCACCATCAGC<br>CGGGACAACAGCAAGAACACCCTGTACCTGCAGAT<br>GAACAGCCTGAGAGCCGAGGACACAGCCGTGTACT<br>ATTGCGCGCGTGACGATGATGGATGGTCCGGCTAC<br>GACTATTGGTTCGATTACTGGGGCCAGGGCACCCT |

TABLE 2-continued anti-HBV Antibodies

```
                              GGTCACAGTTAGCTCAGCTAGCACCAAGGGCCCCA
                              GCGTGTTCCCCCTGGCCCCCAGCAGCAAGAGCACC
                              AGCGGCGGCACAGCCGCCCTGGGCTGCCTGGTGAA
                              GGACTACTTCCCCGAGCCCGTGACCGTGTCCTGGA
                              ACAGCGGAGCCCTGACCTCCGGCGTGCACACCTTC
                              CCCGCCGTGCTGCAGAGCAGCGGCCTGTACAGCCT
                              GTCCAGCGTGGTGACAGTGCCCAGCAGCAGCCTGG
                              GCACCCAGACCTACATCTGCAACGTGAACCACAAG
                              CCCAGCAACACCAAGGTGGACAAGAGAGTGGAGC
                              CCAAGAGCTGCGACAAGACCCACACATGCCCCCCC
                              TGCCCGGCGCCAGAGCTGCTGGGCGGACCCTCCGT
                              GTTCCTGTTCCCCCCCAAGCCCAAGGACACCCTGAT
                              GATCAGCAGGACCCCCGAGGTGACCTGCGTGGTGG
                              TGGACGTGAGCCACGAGGACCCAGAGGTGAAGTTC
                              AACTGGTACGTGGACGGCGTGGAGGTGCACAACGC
                              CAAGACCAAGCCCAGAGAGGAGCAGTACAACAGC
                              ACCTACAGGGTGGTGTCCGTGCTGACCGTGCTGCA
                              CCAGGACTGGCTGAACGGCAAGGAATACAAGTGCA
                              AGGTCTCCAACAAGGCCCTGCCAGCCCCCATCGAA
                              AAGACCATCAGCAAGGCCAAGGGCCAGCCACGGG
                              AGCCCCAGGTGTACACCCTGCCCCCCTCCCGGGAG
                              GAGATGACCAAGAACCAGGTGTCCCTGACCTGTCT
                              GGTGAAGGGCTTCTACCCCAGCGACATCGCCGTGG
                              AGTGGGAGAGCAACGGCCAGCCCGAGAACAACTA
                              CAAGACCACCCCCCCAGTGCTGGACAGCGACGGCA
                              GCTTCTTCCTGTACAGCAAGCTGACCGTGGACAAG
                              TCCAGGTGGCAGCAGGGCAACGTGTTCAGCTGCAG
                              CGTGATGCACGAGGCCCTGCACAACCACTACACCC
                              AGAAGAGCCTGAGCTTAAGCCCCGGCAAG
```

NOV3357LC

| | | |
|---|---|---|
| SEQ ID NO: 150 (Combined) | LCDR1 | RASQSISPYLN |
| SEQ ID NO: 151 (Combined) | LCDR2 | AADSLQS |
| SEQ ID NO: 152 (Combined) | LCDR3 | QQSYKIPLT |
| SEQ ID NO: 153 (Kabat) | LCDR1 | RASQSISPYLN |
| SEQ ID NO: 154 (Kabat) | LCDR2 | AADSLQS |
| SEQ ID NO: 155 (Kabat) | LCDR3 | QQSYKIPLT |
| SEQ ID NO: 156 (Chothia) | LCDR1 | SQSISPY |
| SEQ ID NO: 157 (Chothia) | LCDR2 | AAD |
| SEQ ID NO: 158 (Chothia) | LCDR3 | SYKIPL |
| SEQ ID NO: 159 (IMGT) | LCDR1 | QSISPY |
| SEQ ID NO: 160 (IMGT) | LCDR2 | AAD |
| SEQ ID NO: 161 (IMGT) | LCDR3 | QQSYKIPLT |
| SEQ ID NO: 162 | VL | DIQMTQSPSSLSASVGDRVTITCRASQSISPYLNWYQQ KPGKAPKLLIYAADSLQSGVPSRFSGSGSGTDFTLTISS LQPEDFATYYCQQSYKIPLTFGQGTKVEIK |
| SEQ ID NO: 163 | DNA VL | GATATCCAGATGACACAGAGCCCTAGCAGCCTGTC TGCCTCTGTGGGCGATAGAGTGACCATCACCTGTA GAGCCAGCCAGAGCATCAGCCCCTACCTGAATTGG TACCAGCAGAAGCCTGGCAAGGCCCCTAAGCTGCT GATCTATGCTGCCGACTCTCTGCAGTCTGGCGTGCC AAGCAGATTTTCTGGCAGCGGCTCTGGCACCGACT TCACCCTGACAATTAGCTCCCTGCAGCCTGAAGACT TCGCCACCTACTACTGCCAGCAGAGCTACAAGATC CCTCTGACCTTTGGCCAGGGCACCAAGGTGGAAAT CAAG |
| SEQ ID NO: 164 | Light Chain | DIQMTQSPSSLSASVGDRVTITCRASQSISPYLNWYQQ KPGKAPKLLIYAADSLQSGVPSRFSGSGSGTDFTLTISS LQPEDFATYYCQQSYKIPLTFGQGTKVEIKRTVAAPS VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| SEQ ID NO: 165 | DNA Light Chain | GATATCCAGATGACACAGAGCCCTAGCAGCCTGTC TGCCTCTGTGGGCGATAGAGTGACCATCACCTGTA GAGCCAGCCAGAGCATCAGCCCCTACCTGAATTGG TACCAGCAGAAGCCTGGCAAGGCCCCTAAGCTGCT GATCTATGCTGCCGACTCTCTGCAGTCTGGCGTGCC AAGCAGATTTTCTGGCAGCGGCTCTGGCACCGACT |

TABLE 2-continued anti-HBV Antibodies

```
TCACCCTGACAATTAGCTCCCTGCAGCCTGAAGACT
TCGCCACCTACTACTGCCAGCAGAGCTACAAGATC
CCTCTGACCTTTGGCCAGGGCACCAAGGTGGAAAT
CAAGCGTACGGTGGCCGCTCCCAGCGTGTTCATCTT
CCCCCCCAGCGACGAGCAGCTGAAGAGCGGCACCG
CCAGCGTGGTGTGCCTGCTGAACAACTTCTACCCCC
GGGAGGCCAAGGTGCAGTGGAAGGTGGACAACGC
CCTGCAGAGCGGCAACAGCCAGGAGAGCGTCACCG
AGCAGGACAGCAAGGACTCCACCTACAGCCTGAGC
AGCACCCTGACCCTGAGCAAGGCCGACTACGAGAA
GCATAAGGTGTACGCCTGCGAGGTGACCCACCAGG
GCCTGTCCAGCCCCGTGACCAAGAGCTTCAACAGG
GGCGAGTGC
```

NOV3834HC

| SEQ ID NO: 166 (Combined) | HCDR1 | GFTFNRYGMH |
| --- | --- | --- |
| SEQ ID NO: 167 (Combined) | HCDR2 | GIWHDGSHKYYADSLRG |
| SEQ ID NO: 168 (Combined) | HCDR3 | QTNRGRLDDAFDI |
| SEQ ID NO: 169 (Kabat) | HCDR1 | RYGMH |
| SEQ ID NO: 170 (Kabat) | HCDR2 | GIWHDGSHKYYADSLRG |
| SEQ ID NO: 171 (Kabat) | HCDR3 | QTNRGRLDDAFDI |
| SEQ ID NO: 172 (Chothia) | HCDR1 | GFTFNRY |
| SEQ ID NO: 173 (Chothia) | HCDR2 | WHDGSH |
| SEQ ID NO: 174 (Chothia) | HCDR3 | QTNRGRLDDAFDI |
| SEQ ID NO: 175 (IMGT) | HCDR1 | GFTFNRYG |
| SEQ ID NO: 176 (IMGT) | HCDR2 | IWHDGSHK |
| SEQ ID NO: 177 (IMGT) | HCDR3 | VRQTNRGRLDDAFDI |
| SEQ ID NO: 178 | VH | QVQLVESGGGVVQPGRSLRLSCAASGFTFNRYGMH WVRQAPGKGLEWVAGIWHDGSHKYYADSLRGRFTI SRDNAKNTLDLQLNRLRAEDTSVYYCVRQTNRGRLD DAFDIWGQGTMVTVSS |
| SEQ ID NO: 179 | DNA VH | CAGGTGCAGCTGGTGGAGTCTGGGGGAGGCGTGGT CCAGCCTGGGAGGTCCCTGAGACTCTCCTGTGCAG CGTCAGGATTCACATTCAATAGATATGGCATGCAC TGGGTCCGCCAGGCTCCAGGCAAGGGGTTGGAGTG GGTGGCTGGTATATGGCATGATGGAAGTCATAAAT ACTATGCAGACTCTCTGAGGGGCCGATTCACCATCT CCAGAGACAATGCCAAGAACACGCTGGATCTGCAA TTGAACAGGCTGAGAGCCGAAGACACGTCTGTGTA TTATTGTGTGAGGCAAACCAACAGGGGACGTCTCG ATGATGCTTTTGACATCTGGGGCCAAGGGACAATG GTCACCGTTAGCTCA |
| SEQ ID NO: 180 | Heavy Chain | QVQLVESGGGVVQPGRSLRLSCAASGFTFNRYGMH WVRQAPGKGLEWVAGIWHDGSHKYYADSLRGRFTI SRDNAKNTLDLQLNRLRAEDTSVYYCVRQTNRGRLD DAFDIWGQGTMVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKVD KRVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |
| SEQ ID NO: 181 | DNA Heavy Chain | CAGGTGCAGCTGGTGGAGTCTGGGGGAGGCGTGGT CCAGCCTGGGAGGTCCCTGAGACTCTCCTGTGCAG CGTCAGGATTCACATTCAATAGATATGGCATGCAC TGGGTCCGCCAGGCTCCAGGCAAGGGGTTGGAGTG GGTGGCTGGTATATGGCATGATGGAAGTCATAAAT ACTATGCAGACTCTCTGAGGGGCCGATTCACCATCT CCAGAGACAATGCCAAGAACACGCTGGATCTGCAA TTGAACAGGCTGAGAGCCGAAGACACGTCTGTGTA TTATTGTGTGAGGCAAACCAACAGGGGACGTCTCG ATGATGCTTTTGACATCTGGGGCCAAGGGACAATG GTCACCGTTAGCTCAGCTAGCACCAAGGGCCCCAG CGTGTTCCCCCTGGCCCCCAGCAGCAAGAGCACCA GCGGCGGCACAGCCGCCCTGGGCTGCCTGGTGAAG |

TABLE 2-continued anti-HBV Antibodies

```
GACTACTTCCCCGAGCCCGTGACCGTGTCCTGGAA
CAGCGGAGCCCTGACCTCCGGCGTGCACACCTTCC
CCGCCGTGCTGCAGAGCAGCGGCCTGTACAGCCTG
TCCAGCGTGGTGACAGTGCCCAGCAGCAGCCTGGG
CACCCAGACCTACATCTGCAACGTGAACCACAAGC
CCAGCAACACCAAGGTGGACAAGAGAGTGGAGCC
CAAGAGCTGCGACAAGACCCACACCTGCCCCCCCT
GCCCAGCCCCAGAGCTGCTGGGCGGACCCTCCGTG
TTCCTGTTCCCCCCCAAGCCCAAGGACACCCTGATG
ATCAGCAGGACCCCCGAGGTGACCTGCGTGGTGGT
GGACGTGAGCCACGAGGACCCAGAGGTGAAGTTCA
ACTGGTACGTGGACGGCGTGGAGGTGCACAACGCC
AAGACCAAGCCCAGAGAGGAGCAGTACAACAGCA
CCTACAGGGTGGTGTCCGTGCTGACCGTGCTGCAC
CAGGACTGGCTGAACGGCAAGGAATACAAGTGCA
AGGTCTCCAACAAGGCCCTGCCAGCCCCCATCGAA
AAGACCATCAGCAAGGCCAAGGGCCAGCCACGGG
AGCCCCAGGTGTACACCCTGCCCCCCTCCCGGGAG
GAGATGACCAAGAACCAGGTGTCCCTGACCTGTCT
GGTGAAGGGCTTCTACCCCAGCGACATCGCCGTGG
AGTGGGAGAGCAACGGCCAGCCCGAGAACAACTA
CAAGACCACCCCCCCAGTGCTGGACAGCGACGGCA
GCTTCTTCCTGTACAGCAAGCTGACCGTGGACAAG
TCCAGGTGGCAGCAGGGCAACGTGTTCAGCTGCAG
CGTGATGCACGAGGCCCTGCACAACCACTACACCC
AGAAGAGCCTGAGCCTGTCCCCCGGCAAG
```

NOV3834LC

| SEQ ID NO: 182 (Combined) | LCDR1 | RASQTISSYLN |
|---|---|---|
| SEQ ID NO: 183 (Combined) | LCDR2 | AASTLQS |
| SEQ ID NO: 184 (Combined) | LCDR3 | QQNYDTLWT |
| SEQ ID NO: 185 (Kabat) | LCDR1 | RASQTISSYLN |
| SEQ ID NO: 186 (Kabat) | LCDR2 | AASTLQS |
| SEQ ID NO: 187 (Kabat) | LCDR3 | QQNYDTLWT |
| SEQ ID NO: 188 (Chothia) | LCDR1 | SQTISSY |
| SEQ ID NO: 189 (Chothia) | LCDR2 | AAS |
| SEQ ID NO: 190 (Chothia) | LCDR3 | NYDTLW |
| SEQ ID NO: 191 (IMGT) | LCDR1 | QTISSY |
| SEQ ID NO: 192 (IMGT) | LCDR2 | AAS |
| SEQ ID NO: 193 (IMGT) | LCDR3 | QQNYDTLWT |
| SEQ ID NO: 194 | VL | DIQMTQSPSSLSAAVGDRVTISCRASQTISSYLNWYQ QKPGEAPKLLIYAASTLQSGVPSRFGGSGSGTDFTLTI SSLQPEDSATYYCQQNYDTLWTFGQGTKVEIK |
| SEQ ID NO: 195 | DNA VL | GATATCCAGATGACCCAGTCTCCATCCTCCCTGTCT GCAGCTGTAGGAGACAGAGTCACCATCTCTTGCCG GGCAAGTCAGACCATTAGTAGTTATTTAAATTGGT ATCAGCAGAAACCAGGGGAAGCCCCTAAGCTCCTG ATCTATGCTGCCTCCACCTTGCAAAGTGGGGTCCCT TCAAGGTTCGGTGGCAGTGGATCTGGGACAGATTT CACTCTCACCATCAGCAGTCTGCAACCTGAAGATTC TGCAACTTACTACTGTCAACAGAATTACGATACTTT GTGGACGTTCGGCCAAGGGACCAAGGTGGAAATCA AA |
| SEQ ID NO: 196 | Light Chain | DIQMTQSPSSLSAAVGDRVTISCRASQTISSYLNWYQ QKPGEAPKLLIYAASTLQSGVPSRFGGSGSGTDFTLTI SSLQPEDSATYYCQQNYDTLWTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID NO: 197 | DNA Light Chain | GATATCCAGATGACCCAGTCTCCATCCTCCCTGTCT GCAGCTGTAGGAGACAGAGTCACCATCTCTTGCCG GGCAAGTCAGACCATTAGTAGTTATTTAAATTGGT ATCAGCAGAAACCAGGGGAAGCCCCTAAGCTCCTG ATCTATGCTGCCTCCACCTTGCAAAGTGGGGTCCCT TCAAGGTTCGGTGGCAGTGGATCTGGGACAGATTT CACTCTCACCATCAGCAGTCTGCAACCTGAAGATTC TGCAACTTACTACTGTCAACAGAATTACGATACTTT GTGGACGTTCGGCCAAGGGACCAAGGTGGAAATCA |

TABLE 2-continued anti-HBV Antibodies

AACGTACGGTGGCCGCTCCCAGCGTGTTCATCTTCC
CCCCCAGCGACGAGCAGCTGAAGAGCGGCACCGCC
AGCGTGGTGTGCCTGCTGAACAACTTCTACCCCCG
GGAGGCCAAGGTGCAGTGGAAGGTGGACAACGCC
CTGCAGAGCGGCAACAGCCAGGAGAGCGTCACCG
AGCAGGACAGCAAGGACTCCACCTACAGCCTGAGC
AGCACCCTGACCCTGAGCAAGGCCGACTACGAGAA
GCATAAGGTGTACGCCTGCGAGGTGACCCACCAGG
GCCTGTCCAGCCCCGTGACCAAGAGCTTCAACAGG
GGCGAGTGC

NOV3835 HC

| | | | |
|---|---|---|---|
| SEQ ID NO: 198 (Combined) | | HCDR1 | GFTFDRYGMH |
| SEQ ID NO: 199 (Combined) | | HCDR2 | GIWHEGSHKYYADSLRG |
| SEQ ID NO: 200 (Combined) | | HCDR3 | QTNRGRLDDAFDI |
| SEQ ID NO: 201 | (Kabat) | HCDR1 | RYGMH |
| SEQ ID NO: 202 | (Kabat) | HCDR2 | GIWHEGSHKYYADSLRG |
| SEQ ID NO: 203 | (Kabat) | HCDR3 | QTNRGRLDDAFDI |
| SEQ ID NO: 204 (Chothia) | | HCDR1 | GFTFDRY |
| SEQ ID NO: 205 (Chothia) | | HCDR2 | WHEGSH |
| SEQ ID NO: 206 (Chothia) | | HCDR3 | QTNRGRLDDAFDI |
| SEQ ID NO: 207 (IMGT) | | HCDR1 | GFTFDRYG |
| SEQ ID NO: 208 (IMGT) | | HCDR2 | IWHEGSHK |
| SEQ ID NO: 209 (IMGT) | | HCDR3 | VRQTNRGRLDDAFDI |
| SEQ ID NO: 210 | | VH | QVQLVESGGGVVQPGRSLRLSCAASGFTFDRYGMH WVRQAPGKGLEWVAGIWHEGSHKYYADSLRGRFTIS RDNAKNTLDLQLNRLRAEDTSVYYCVRQTNRGRLD DAFDIWGQGTMVTVSS |
| SEQ ID NO: 211 | | DNA VH | CAGGTGCAGCTGGTTGAATCTGGTGGCGGAGTGGT GCAGCCTGGCAGATCTCTGAGACTGTCTTGTGCCGC CAGCGGCTTCACCTTCGACAGATATGGCATGCACT GGGTCCGACAGGCCCCTGGAAAAGGACTTGAATGG GTGGCCGGAATCTGGCACGAAGGCAGCCACAAGTA CTACGCCGATAGCCTGAGAGGCCGGTTCACCATCA GCAGAGACAACGCCAAGAACACCCTGGACCTCCAG CTGAACAGACTGAGAGCCGAGGATACCAGCGTGTA CTACTGCGTGCGGCAGACCAACAGAGGCAGACTGG ACGATGCCTTCGATATCTGGGGCCAAGGGACAATG GTCACCGTTAGCTCA |
| SEQ ID NO: 212 | | Heavy Chain | QVQLVESGGGVVQPGRSLRLSCAASGFTFDRYGMH WVRQAPGKGLEWVAGIWHEGSHKYYADSLRGRFTIS RDNAKNTLDLQLNRLRAEDTSVYYCVRQTNRGRLD DAFDIWGQGTMVTVSSASTKGPSVFPLAPSSKSTSGG TAALGCLVKDYFPEPVTVSWNSGALTSGVHTFPAVL QSSGLYSLSSVVTVPSSSLGTQTYICNVNHKPSNTKVD KRVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |
| SEQ ID NO: 213 | | DNA Heavy Chain | CAGGTGCAGCTGGTTGAATCTGGTGGCGGAGTGGT GCAGCCTGGCAGATCTCTGAGACTGTCTTGTGCCGC CAGCGGCTTCACCTTCGACAGATATGGCATGCACT GGGTCCGACAGGCCCCTGGAAAAGGACTTGAATGG GTGGCCGGAATCTGGCACGAAGGCAGCCACAAGTA CTACGCCGATAGCCTGAGAGGCCGGTTCACCATCA GCAGAGACAACGCCAAGAACACCCTGGACCTCCAG CTGAACAGACTGAGAGCCGAGGATACCAGCGTGTA CTACTGCGTGCGGCAGACCAACAGAGGCAGACTGG ACGATGCCTTCGATATCTGGGGCCAAGGGACAATG GTCACCGTTAGCTCAGCTAGCACCAAGGGCCCCAG CGTGTTCCCCCTGGCCCCCAGCAGCAAGAGCACCA GCGGCGGCACAGCCGCCCTGGGCTGCCTGGTGAAG GACTACTTCCCCGAGCCCGTGACCGTGTCCTGGAA CAGCGGAGCCCTGACCTCCGGCGTGCACACCTTCC CCGCCGTGCTGCAGAGCAGCGGCCTGTACAGCCTG |

TABLE 2-continued anti-HBV Antibodies

|  |  |  |
|---|---|---|
|  |  | TCCAGCGTGGTGACAGTGCCCAGCAGCAGCCTGGG<br>CACCCAGACCTACATCTGCAACGTGAACCACAAGC<br>CCAGCAACACCAAGGTGGACAAGAGAGTGGAGCC<br>CAAGAGCTGCGACAAGACCCACACCTGCCCCCCCT<br>GCCCAGCCCCAGAGCTGCTGGGCGGACCCTCCGTG<br>TTCCTGTTCCCCCCCAAGCCCAAGGACACCCTGATG<br>ATCAGCAGGACCCCCGAGGTGACCTGCGTGGTGGT<br>GGACGTGAGCCACGAGGACCCAGAGGTGAAGTTCA<br>ACTGGTACGTGGACGGCGTGGAGGTGCACAACGCC<br>AAGACCAAGCCCAGAGAGGAGCAGTACAACAGCA<br>CCTACAGGGTGGTGTCCGTGCTGACCGTGCTGCAC<br>CAGGACTGGCTGAACGGCAAGGAATACAAGTGCA<br>AGGTCTCCAACAAGGCCCTGCCAGCCCCCATCGAA<br>AAGACCATCAGCAAGGCCAAGGGCCAGCCACGGG<br>AGCCCCAGGTGTACACCCTGCCCCCCTCCCGGGAG<br>GAGATGACCAAGAACCAGGTGTCCCTGACCTGTCT<br>GGTGAAGGGCTTCTACCCCAGCGACATCGCCGTGG<br>AGTGGGAGAGCAACGGCCAGCCCGAGAACAACTA<br>CAAGACCACCCCCCCAGTGCTGGACAGCGACGGCA<br>GCTTCTTCCTGTACAGCAAGCTGACCGTGGACAAG<br>TCCAGGTGGCAGCAGGGCAACGTGTTCAGCTGCAG<br>CGTGATGCACGAGGCCCTGCACAACCACTACACCC<br>AGAAGAGCCTGAGCCTGTCCCCGGCAAG |
| NOV3835LC |  |  |
| SEQ ID NO: 214<br>(Combined) | LCDR1 | RASQTISSYLN |
| SEQ ID NO: 215<br>(Combined) | LCDR2 | AASTLQS |
| SEQ ID NO: 216<br>(Combined) | LCDR3 | QQNYDTLWT |
| SEQ ID NO: 217 (Kabat) | LCDR1 | RASQTISSYLN |
| SEQ ID NO: 218 (Kabat) | LCDR2 | AASTLQS |
| SEQ ID NO: 219 (Kabat) | LCDR3 | QQNYDTLWT |
| SEQ ID NO: 220<br>(Chothia) | LCDR1 | SQTISSY |
| SEQ ID NO: 221<br>(Chothia) | LCDR2 | AAS |
| SEQ ID NO: 222<br>(Chothia) | LCDR3 | NYDTLW |
| SEQ ID NO: 223<br>(IMGT) | LCDR1 | QTISSY |
| SEQ ID NO: 224<br>(IMGT) | LCDR2 | AAS |
| SEQ ID NO: 225<br>(IMGT) | LCDR3 | QQNYDTLWT |
| SEQ ID NO: 226 | VL | DIQMTQSPSSLSAAVGDRVTISCRASQTISSYLNWYQ<br>QKPGEAPKLLIYAASTLQSGVPSRFGGSGSGTDFTLTI<br>SSLQPEDSATYYCQQNYDTLWTFGQGTKVEIK |
| SEQ ID NO: 227 | DNA VL | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AA |
| SEQ ID NO: 228 | Light Chain | DIQMTQSPSSLSAAVGDRVTISCRASQTISSYLNWYQ<br>QKPGEAPKLLIYAASTLQSGVPSRFGGSGSGTDFTLTI<br>SSLQPEDSATYYCQQNYDTLWTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 229 | DNA Light<br>Chain | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AACGTACGGTGGCCGCTCCCAGCGTGTTCATCTTCC<br>CCCCAGCGACGAGCAGCTGAAGAGCGGCACCGCC<br>AGCGTGGTGTGCCTGCTGAACAACTTCTACCCCCG |

TABLE 2-continued anti-HBV Antibodies

|  |  |  | GGAGGCCAAGGTGCAGTGGAAGGTGGACAACGCC<br>CTGCAGAGCGGCAACAGCCAGGAGAGCGTCACCG<br>AGCAGGACAGCAAGGACTCCACCTACAGCCTGAGC<br>AGCACCCTGACCCTGAGCAAGGCCGACTACGAGAA<br>GCATAAGGTGTACGCCTGCGAGGTGACCCACCAGG<br>GCCTGTCCAGCCCCGTGACCAAGAGCTTCAACAGG<br>GGCGAGTGC |
|---|---|---|---|
| NOV3836HC |  |  |  |
| SEQ ID NO: 230 (Combined) |  | HCDR1 | GFTFERYGMH |
| SEQ ID NO: 231 (Combined) |  | HCDR2 | GIWHEGSHKYYADSLRG |
| SEQ ID NO: 232 (Combined) |  | HCDR3 | QTNRGRLDDAFDI |
| SEQ ID NO: 233 | (Kabat) | HCDR1 | RYGMH |
| SEQ ID NO: 234 | (Kabat) | HCDR2 | GIWHEGSHKYYADSLRG |
| SEQ ID NO: 235 | (Kabat) | HCDR3 | QTNRGRLDDAFDI |
| SEQ ID NO: 236 (Chothia) |  | HCDR1 | GFTFERY |
| SEQ ID NO: 237 (Chothia) |  | HCDR2 | WHEGSH |
| SEQ ID NO: 238 (Chothia) |  | HCDR3 | QTNRGRLDDAFDI |
| SEQ ID NO: 239 (IMGT) |  | HCDR1 | GFTFERYG |
| SEQ ID NO: 240 (IMGT) |  | HCDR2 | IWHEGSHK |
| SEQ ID NO: 241 (IMGT) |  | HCDR3 | VRQTNRGRLDDAFDI |
| SEQ ID NO: 242 |  | VH | QVQLVESGGGVVQPGRSLRLSCAASGFTFERYGMHW<br>VRQAPGKGLEWVAGIWHEGSHKYYADSLRGRFTISR<br>DNAKNTLDLQLNRLRAEDTSVYYCVRQTNRGRLDD<br>AFDIWGQGTMVTVSS |
| SEQ ID NO: 243 |  | DNA VH | CAGGTGCAGCTGGTTGAATCTGGTGGCGGAGTGGT<br>GCAGCCTGGCAGATCTCTGAGACTGTCTTGTGCCGC<br>CAGCGGCTTCACCTTCGAGAGATATGGCATGCACT<br>GGGTCCGACAGGCCCCTGGAAAAGGACTTGAATGG<br>GTGGCCGGAATCTGGCACGAAGGCAGCCACAAGTA<br>CTACGCCGATAGCCTGAGAGGCCGGTTCACCATCA<br>GCAGAGACAACGCCAAGAACACCCTGGACCTCCAG<br>CTGAACAGACTGAGAGCCGAGGATACCAGCGTGTA<br>CTACTGCGTGCGGCAGACCAACAGAGGCAGACTGG<br>ACGATGCCTTCGATATCTGGGGCCAAGGGACAATG<br>GTCACCGTTAGCTCA |
| SEQ ID NO: 244 |  | Heavy Chain | QVQLVESGGGVVQPGRSLRLSCAASGFTFERYGMHW<br>VRQAPGKGLEWVAGIWHEGSHKYYADSLRGRFTISR<br>DNAKNTLDLQLNRLRAEDTSVYYCVRQTNRGRLDD<br>AFDIWGQGTMVTVSSASTKGPSVFPLAPSSKSTSGGT<br>AALGCLVKDYFPEPVTVSWNSGALTSGVHTFPAVLQ<br>SSGLYSLSSVVTVPSSSLGTQTYICNVNHKPSNTKVDK<br>RVEPKSCDKTHTCPPCPAPELLGGPSVFLFPPKPKDTL<br>MISRTPEVTCVVVDVSHEDPEVKFNWYVDGVEVHNA<br>KTKPREEQYNSTYRVVSVLTVLHQDWLNGKEYKCK<br>VSNKALPAPIEKTISKAKGQPREPQVYTLPPSREEMTK<br>NQVSLTCLVKGFYPSDIAVEWESNGQPENNYKTTPPV<br>LDSDGSFFLYSKLTVDKSRWQQGNVFSCSVMHEALH<br>NHYTQKSLSLSPGK |
| SEQ ID NO: 245 |  | DNA Heavy Chain | CAGGTGCAGCTGGTTGAATCTGGTGGCGGAGTGGT<br>GCAGCCTGGCAGATCTCTGAGACTGTCTTGTGCCGC<br>CAGCGGCTTCACCTTCGAGAGATATGGCATGCACT<br>GGGTCCGACAGGCCCCTGGAAAAGGACTTGAATGG<br>GTGGCCGGAATCTGGCACGAAGGCAGCCACAAGTA<br>CTACGCCGATAGCCTGAGAGGCCGGTTCACCATCA<br>GCAGAGACAACGCCAAGAACACCCTGGACCTCCAG<br>CTGAACAGACTGAGAGCCGAGGATACCAGCGTGTA<br>CTACTGCGTGCGGCAGACCAACAGAGGCAGACTGG<br>ACGATGCCTTCGATATCTGGGGCCAAGGGACAATG<br>GTCACCGTTAGCTCAGCTAGCACCAAGGGCCCCAG<br>CGTGTTCCCCCTGGCCCCCAGCAGCAAGAGCACCA<br>GCGGCGGCACAGCCGCCCTGGGCTGCCTGGTGAAG<br>GACTACTTCCCCGAGCCCGTGACCGTGTCCTGGAA<br>CAGCGGAGCCCTGACCTCCGGCGTGCACACCTTCC<br>CCGCCGTGCTGCAGAGCAGCGGCCTGTACAGCCTG<br>TCCAGCGTGGTGACAGTGCCCAGCAGCAGCCTGGG<br>CACCCAGACCTACATCTGCAACGTGAACCACAAGC<br>CCAGCAACACCAAGGTGGACAAGAGAGTGGAGCC |

TABLE 2-continued anti-HBV Antibodies

| | | |
|---|---|---|
| | | CAAGAGCTGCGACAAGACCCACACCTGCCCCCCCT<br>GCCCAGCCCCAGAGCTGCTGGGCGGACCCTCCGTG<br>TTCCTGTTCCCCCCCAAGCCCAAGGACACCCTGATG<br>ATCAGCAGGACCCCCGAGGTGACCTGCGTGGTGGT<br>GGACGTGAGCCACGAGGACCCAGAGGTGAAGTTCA<br>ACTGGTACGTGGACGGCGTGGAGGTGCACAACGCC<br>AAGACCAAGCCCAGAGAGGAGCAGTACAACAGCA<br>CCTACAGGGTGGTGTCCGTGCTGACCGTGCTGCAC<br>CAGGACTGGCTGAACGGCAAGGAATACAAGTGCA<br>AGGTCTCCAACAAGGCCCTGCCAGCCCCCATCGAA<br>AAGACCATCAGCAAGGCCAAGGGCCAGCCACGGG<br>AGCCCCAGGTGTACACCCTGCCCCCCTCCCGGGAG<br>GAGATGACCAAGAACCAGGTGTCCCTGACCTGTCT<br>GGTGAAGGGCTTCTACCCCAGCGACATCGCCGTGG<br>AGTGGGAGAGCAACGGCCAGCCCGAGAACAACTA<br>CAAGACCACCCCCCCAGTGCTGGACAGCGACGGCA<br>GCTTCTTCCTGTACAGCAAGCTGACCGTGGACAAG<br>TCCAGGTGGCAGCAGGGCAACGTGTTCAGCTGCAG<br>CGTGATGCACGAGGCCCTGCACAACCACTACACCC<br>AGAAGAGCCTGAGCCTGTCCCCGGCAAG |
| NOV3836LC | | |
| SEQ ID NO: 246<br>(Combined) | LCDR1 | RASQTISSYLN |
| SEQ ID NO: 247<br>(Combined) | LCDR2 | AASTLQS |
| SEQ ID NO: 248<br>(Combined) | LCDR3 | QQNYDTLWT |
| SEQ ID NO: 249 (Kabat) | LCDR1 | RASQTISSYLN |
| SEQ ID NO: 250 (Kabat) | LCDR2 | AASTLQS |
| SEQ ID NO: 251 (Kabat) | LCDR3 | QQNYDTLWT |
| SEQ ID NO: 252<br>(Chothia) | LCDR1 | SQTISSY |
| SEQ ID NO: 253<br>(Chothia) | LCDR2 | AAS |
| SEQ ID NO: 254<br>(Chothia) | LCDR3 | NYDTLW |
| SEQ ID NO: 255<br>(IMGT) | LCDR1 | QTISSY |
| SEQ ID NO: 256<br>(IMGT) | LCDR2 | AAS |
| SEQ ID NO: 257<br>(IMGT) | LCDR3 | QQNYDTLWT |
| SEQ ID NO: 258 | VL | DIQMTQSPSSLSAAVGDRVTISCRASQTISSYLNWYQ<br>QKPGEAPKLLIYAASTLQSGVPSRFGGSGSGTDFTLTI<br>SSLQPEDSATYYCQQNYDTLWTFGQGTKVEIK |
| SEQ ID NO: 259 | DNA VL | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AA |
| SEQ ID NO: 260 | Light Chain | DIQMTQSPSSLSAAVGDRVTISCRASQTISSYLNWYQ<br>QKPGEAPKLLIYAASTLQSGVPSRFGGSGSGTDFTLTI<br>SSLQPEDSATYYCQQNYDTLWTFGQGTKVEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC |
| SEQ ID NO: 261 | DNA Light<br>Chain | GATATCCAGATGACCCAGTCTCCATCCTCCCTGTCT<br>GCAGCTGTAGGAGACAGAGTCACCATCTCTTGCCG<br>GGCAAGTCAGACCATTAGTAGTTATTTAAATTGGT<br>ATCAGCAGAAACCAGGGGAAGCCCCTAAGCTCCTG<br>ATCTATGCTGCCTCCACCTTGCAAAGTGGGGTCCCT<br>TCAAGGTTCGGTGGCAGTGGATCTGGGACAGATTT<br>CACTCTCACCATCAGCAGTCTGCAACCTGAAGATTC<br>TGCAACTTACTACTGTCAACAGAATTACGATACTTT<br>GTGGACGTTCGGCCAAGGGACCAAGGTGGAAATCA<br>AACGTACGGTGGCCGCTCCCAGCTGTCTTCATCTTCC<br>CCCCCAGCGACGAGCAGCTGAAGAGCGGCACCGCC<br>AGCGTGGTGTGCCTGCTGAACAACTTCTACCCCCG<br>GGAGGCCAAGGTGCAGTGGAAGGTGGACAACGCC<br>CTGCAGAGCGGCAACAGCCAGGAGAGCGTCACCG<br>AGCAGGACAGCAAGGACTCCACCTACAGCCTGAGC |

TABLE 2-continued anti-HBV Antibodies

AGCACCCTGACCCTGAGCAAGGCCGACTACGAGAA
GCATAAGGTGTACGCCTGCGAGGTGACCCACCAGG
GCCTGTCCAGCCCCGTGACCAAGAGCTTCAACAGG
GGCGAGTGC

NOV3837HC

| | | |
|---|---|---|
| SEQ ID NO: 262 (Combined) | HCDR1 | GFIFTDYYMT |
| SEQ ID NO: 263 (Combined) | HCDR2 | FITSGGETTYYADSVKG |
| SEQ ID NO: 264 (Combined) | HCDR3 | AHFDGYQYDTRGDFTYYFDN |
| SEQ ID NO: 265 (Kabat) | HCDR1 | DYYMT |
| SEQ ID NO: 266 (Kabat) | HCDR2 | FITSGGETTYYADSVKG |
| SEQ ID NO: 267 (Kabat) | HCDR3 | AHFDGYQYDTRGDFTYYFDN |
| SEQ ID NO: 268 (Chothia) | HCDR1 | GFIFTDY |
| SEQ ID NO: 269 (Chothia) | HCDR2 | TSGGET |
| SEQ ID NO: 270 (Chothia) | HCDR3 | AHFDGYQYDTRGDFTYYFDN |
| SEQ ID NO: 271 (IMGT) | HCDR1 | GFIFTDYY |
| SEQ ID NO: 272 (IMGT) | HCDR2 | ITSGGETT |
| SEQ ID NO: 273 (IMGT) | HCDR3 | VRAHFDGYQYDTRGDFTYYFDN |
| SEQ ID NO: 274 | VH | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDGYQYDTR GDFTYYFDNWGLGTLVSVSS |
| SEQ ID NO: 275 | DNA VH | CAGGTGCAGCTGCAGGAGTCGGGGGGACGCTTGGT CAGGCCTGGAGGGTCCCTGAGACTCTCCTGTGCAG CCTCCGGATTCATCTTCACTGACTACTACATGACCT GGATCCGCCAGGCTCCAGGGAAGGGGCCGGAGTG GATTGCATTTATCACAAGTGGGGGCGAGACCACAT ACTACGCAGACTCTGTGAAGGGCCGCTTCACCATTT CCAGGGACAACGCCAAGAAGTCACTCTTTCTGCAA ATGTACAGCCTGAGAGCCGACGACACGGCCGTGTA TTATTGTGTGAGAGCCCACTTTGATGGTTATCAGTA TGATACTCGTGGTGACTTCACTTATTACTTTGACAA CTGGGGCCTGGGAACCCTGGTCAGCGTCTCCTCA |
| SEQ ID NO: 276 | Heavy Chain | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDGYQYDTR GDFTYYFDNWGLGTLVSVSSASTKGPSVFPLAPSSKS TSGGTAALGCLVKDYFPEPVTVSWNSGALTSGVHTFP AVLQSSGLYSLSSVVTVPSSSLGTQTYICNVNHKPSNT KVDKRVEPKSCDKTHTCPPCPAPELLGGPSVFLFPPKP KDTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSRE EMTKNQVSLTCLVKGFYPSDIAVEWESNGQPENNYK TTPPVLDSDGSFFLYSKLTVDKSRWQQGNVFSCSVM HEALHNHYTQKSLSLSPGK |
| SEQ ID NO: 277 | DNA Heavy Chain | CAGGTGCAGCTGCAGGAGTCGGGGGGACGCTTGGT CAGGCCTGGAGGGTCCCTGAGACTCTCCTGTGCAG CCTCCGGATTCATCTTCACTGACTACTACATGACCT GGATCCGCCAGGCTCCAGGGAAGGGGCCGGAGTG GATTGCATTTATCACAAGTGGGGGCGAGACCACAT ACTACGCAGACTCTGTGAAGGGCCGCTTCACCATTT CCAGGGACAACGCCAAGAAGTCACTCTTTCTGCAA ATGTACAGCCTGAGAGCCGACGACACGGCCGTGTA TTATTGTGTGAGAGCCCACTTTGATGGTTATCAGTA TGATACTCGTGGTGACTTCACTTATTACTTTGACAA CTGGGGCCTGGGAACCCTGGTCAGCGTCTCCTCAG CTAGCACCAAGGGCCCCAGCGTGTTCCCCCTGGCC CCCAGCAGCAAGAGCACCAGCGGCGGCACAGCCG CCCTGGGCTGCCTGGTGAAGGACTACTTCCCCGAG CCCGTGACCGTGTCCTGGAACAGCGGAGCCCTGAC CTCCGGCGTGCACACCTTCCCCGCCGTGCTGCAGA GCAGCGGCCTGTACAGCCTGAGCAGCGTGGTGACA GTGCCCAGCAGCAGCCTGGGCACCCAGACCTACAT CTGCAACGTGAACCACAAGCCCAGCAACACCAAGG TGGACAAGAGAGTGGAGCCCAAGAGCTGCGACAA GACCCACACCTGCCCCCCCTGCCCAGCCCCAGAGC TGCTGGGCGGACCCTCCGTGTTCCTGTTCCCCCCA |

TABLE 2-continued anti-HBV Antibodies

```
AGCCCAAGGACACCCTGATGATCAGCAGGACCCCC
GAGGTGACCTGCGTGGTGGTGGACGTGAGCCACGA
GGACCCAGAGGTGAAGTTCAACTGGTACGTGGACG
GCGTGGAGGTGCACAACGCCAAGACCAAGCCCAG
AGAGGAGCAGTACAACAGCACCTACAGGGTGGTGT
CCGTGCTGACCGTGCTGCACCAGGACTGGCTGAAC
GGCAAGGAATACAAGTGCAAGGTCTCCAACAAGGC
CCTGCCAGCCCCCATCGAAAAGACCATCAGCAAGG
CCAAGGGCCAGCCACGGGAGCCCCAGGTGTACACC
CTGCCCCCCTCCCGGGAGGAGATGACCAAGAACCA
GGTGTCCCTGACCTGTCTGGTGAAGGGCTTCTACCC
CAGCGACATCGCCGTGGAGTGGGAGAGCAACGGCC
AGCCCGAGAACAACTACAAGACCACCCCCCCAGTG
CTGGACAGCGACGGCAGCTTCTTCCTGTACAGCAA
GCTGACCGTGGACAAGTCCAGGTGGCAGCAGGGCA
ACGTGTTCAGCTGCAGCGTGATGCACGAGGCCCTG
CACAACCACTACACCCAGAAGAGCCTGAGCCTGTC
CCCCGGCAAG
```

NOV3837LC

| SEQ ID NO: 278 (Combined) | LCDR1 | RASQSVSSSLA |
|---|---|---|
| SEQ ID NO: 279 (Combined) | LCDR2 | GASTRAT |
| SEQ ID NO: 280 (Combined) | LCDR3 | HQYINWPPGDT |
| SEQ ID NO: 281 (Kabat) | LCDR1 | RASQSVSSSLA |
| SEQ ID NO: 282 (Kabat) | LCDR2 | GASTRAT |
| SEQ ID NO: 283 (Kabat) | LCDR3 | HQYINWPPGDT |
| SEQ ID NO: 284 (Chothia) | LCDR1 | SQSVSSS |
| SEQ ID NO: 285 (Chothia) | LCDR2 | GAS |
| SEQ ID NO: 286 (Chothia) | LCDR3 | YINWPPGD |
| SEQ ID NO: 287 (IMGT) | LCDR1 | QSVSSS |
| SEQ ID NO: 288 (IMGT) | LCDR2 | GAS |
| SEQ ID NO: 289 (IMGT) | LCDR3 | HQYINWPPGDT |
| SEQ ID NO: 290 | VL | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIK |
| SEQ ID NO: 291 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 292 | Light Chain | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| SEQ ID NO: 293 | DNA Light Chain | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAACGTACGGTGGCCGCTCCCAGCGTGTT CATCTTCCCCCCCAGCGACGAGCAGCTGAAGAGCG GCACCGCCAGCGTGGTGTGCCTGCTGAACAACTTC TACCCCCGGGAGGCCAAGGTGCAGTGGAAGGTGGA CAACGCCCTGCAGAGCGGCAACAGCCAGGAGAGC GTCACCGAGCAGGACAGCAAGGACTCCACCTACAG CCTGAGCAGCACCCTGACCCTGAGCAAGGCCGACT |

TABLE 2-continued

| anti-HBV Antibodies | | | |
|---|---|---|---|
| | | | ACGAGAAGCATAAGGTGTACGCCTGCGAGGTGACC CACCAGGGCCTGTCCAGCCCCGTGACCAAGAGCTT CAACAGGGGCGAGTGC |
| NOV3838HC | | | |
| SEQ ID NO: 294 (Combined) | | HCDR1 | GFIFTDYYMT |
| SEQ ID NO: 295 (Combined) | | HCDR2 | FITSGGETTYYADSVKG |
| SEQ ID NO: 296 (Combined) | | HCDR3 | AHFDLYQYDTRGDFTYYFDN |
| SEQ ID NO: 297 | (Kabat) | HCDR1 | DYYMT |
| SEQ ID NO: 298 | (Kabat) | HCDR2 | FITSGGETTYYADSVKG |
| SEQ ID NO: 299 | (Kabat) | HCDR3 | AHFDLYQYDTRGDFTYYFDN |
| SEQ ID NO: 300 (Chothia) | | HCDR1 | GFIFTDY |
| SEQ ID NO: 301 (Chothia) | | HCDR2 | TSGGET |
| SEQ ID NO: 302 (Chothia) | | HCDR3 | AHFDLYQYDTRGDFTYYFDN |
| SEQ ID NO: 303 (IMGT) | | HCDR1 | GFIFTDYY |
| SEQ ID NO: 304 (IMGT) | | HCDR2 | ITSGGETT |
| SEQ ID NO: 305 (IMGT) | | HCDR3 | VRAHFDLYQYDTRGDFTYYFDN |
| SEQ ID NO: 306 | | VH | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDLYQYDTR GDFTYYFDNWGLGTLVSVSS |
| SEQ ID NO: 307 | | DNA VH | CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACCTGTACCAGTAC GATACCAGAGGCGATTTCACCTACTACTTCGACAA CTGGGGCCTGGGAACCCTGGTGTCTGTCTCTTCT |
| SEQ ID NO: 308 | | Heavy Chain | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDLYQYDTR GDFTYYFDNWGLGTLVSVSSASTKGPSVFPLAPSSKS TSGGTAALGCLVKDYFPEPVTVSWNSGALTSGVHTFP AVLQSSGLYSLSSVVTVPSSSLGTQTYICNVNHKPSNT KVDKRVEPKSCDKTHTCPPCPAPELLGGPSVFLFPPKP KDTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSRE EMTKNQVSLTCLVKGFYPSDIAVEWESNGQPENNYK TTPPVLDSDGSFFLYSKLTVDKSRWQQGNVFSCSVM HEALHNHYTQKSLSLSPGK |
| SEQ ID NO: 309 | | DNA Heavy Chain | CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACCTGTACCAGTAC GATACCAGAGGCGATTTCACCTACTACTTCGACAA CTGGGGCCTGGGAACCCTGGTGTCTGTCTCTTCTGC TAGCACCAAGGGCCCCAGCGTGTTCCCCCTGGCCC CCAGCAGCAAGAGCACCAGCGGCGGCACAGCCGC CCTGGGCTGCCTGGTGAAGGACTACTTCCCCGAGC CCGTGACCGTGTCCTGGAACAGCGGAGCCCTGACC TCCGGCGTGCACACCTTCCCCGCCGTGCTGCAGAG CAGCGGCCTGTACAGCCTGTCCAGCGTGGTGACAG TGCCCAGCAGCAGCCTGGGCACCCAGACCTACATC TGCAACGTGAACCACAAGCCCAGCAACACCAAGGT GGACAAGAGAGTGGAGCCCAAGAGCTGCGACAAG ACCCACACATGCCCCCCTGCCCGGCGCCAGAGCT GCTGGGCGGACCCTCCGTGTTCCTGTTCCCCCCCAA GCCCAAGGACACCCTGATGATCAGCAGGACCCCCG |

TABLE 2-continued anti-HBV Antibodies

```
                        AGGTGACCTGCGTGGTGGTGGACGTGAGCCACGAG
                        GACCCAGAGGTGAAGTTCAACTGGTACGTGGACGG
                        CGTGGAGGTGCACAACGCCAAGACCAAGCCCAGA
                        GAGGAGCAGTACAACAGCACCTACAGGGTGGTGTC
                        CGTGCTGACCGTGCTGCACCAGGACTGGCTGAACG
                        GCAAGGAATACAAGTGCAAGGTCTCCAACAAGGCC
                        CTGCCAGCCCCCATCGAAAAGACCATCAGCAAGGC
                        CAAGGGCCAGCCACGGGAGCCCCAGGTGTACACCC
                        TGCCCCCCTCCCGGGAGGAGATGACCAAGAACCAG
                        GTGTCCCTGACCTGTCTGGTGAAGGGCTTCTACCCC
                        AGCGACATCGCCGTGGAGTGGGAGAGCAACGGCC
                        AGCCCGAGAACAACTACAAGACCACCCCCCCAGTG
                        CTGGACAGCGACGGCAGCTTCTTCCTGTACAGCAA
                        GCTGACCGTGGACAAGTCCAGGTGGCAGCAGGGCA
                        ACGTGTTCAGCTGCAGCGTGATGCACGAGGCCCTG
                        CACAACCACTACACCCAGAAGAGCCTGAGCTTAAG
                        CCCCGGCAAG
```

NOV3838LC

| SEQ ID NO: 310 (Combined) | LCDR1 | RASQSVSSSLA |
| --- | --- | --- |
| SEQ ID NO: 311 (Combined) | LCDR2 | GASTRAT |
| SEQ ID NO: 312 (Combined) | LCDR3 | HQYINWPPGDT |
| SEQ ID NO: 313 (Kabat) | LCDR1 | RASQSVSSSLA |
| SEQ ID NO: 314 (Kabat) | LCDR2 | GASTRAT |
| SEQ ID NO: 315 (Kabat) | LCDR3 | HQYINWPPGDT |
| SEQ ID NO: 316 (Chothia) | LCDR1 | SQSVSSS |
| SEQ ID NO: 317 (Chothia) | LCDR2 | GAS |
| SEQ ID NO: 318 (Chothia) | LCDR3 | YINWPPGD |
| SEQ ID NO: 319 (IMGT) | LCDR1 | QSVSSS |
| SEQ ID NO: 320 (IMGT) | LCDR2 | GAS |
| SEQ ID NO: 321 (IMGT) | LCDR3 | HQYINWPPGDT |
| SEQ ID NO: 322 | VL | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIK |
| SEQ ID NO: 323 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 324 | Light Chain | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| SEQ ID NO: 325 | DNA Light Chain | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAACGTACGGTGGCCGCTCCCAGCGTGTT CATCTTCCCCCCCAGCGACGAGCAGCTGAAGAGCG GCACCGCCAGCGTGGTGTGCCTGCTGAACAACTTC TACCCCCGGGAGGCCAAGGTGCAGTGGAAGGTGGA CAACGCCCTGCAGAGCGGCAACAGCCAGGAGAGC GTCACCGAGCAGGACAGCAAGGACTCCACCTACAG CCTGAGCAGCACCCTGACCCTGAGCAAGGCCGACT |

TABLE 2-continued anti-HBV Antibodies

ACGAGAAGCATAAGGTGTACGCCTGCGAGGTGACC
CACCAGGGCCTGTCCAGCCCCGTGACCAAGAGCTT
CAACAGGGGCGAGTGC

NOV3839HC

| SEQ ID NO: 326 (Combined) | HCDR1 | GFIFTDYYMT |
| SEQ ID NO: 327 (Combined) | HCDR2 | FITSGGETTYYADSVKG |
| SEQ ID NO: 328 (Combined) | HCDR3 | AHFDIYQYDTRGDFTYYFDN |
| SEQ ID NO: 329 (Kabat) | HCDR1 | DYYMT |
| SEQ ID NO: 330 (Kabat) | HCDR2 | FITSGGETTYYADSVKG |
| SEQ ID NO: 331 (Kabat) | HCDR3 | AHFDIYQYDTRGDFTYYFDN |
| SEQ ID NO: 332 (Chothia) | HCDR1 | GFIFTDY |
| SEQ ID NO: 333 (Chothia) | HCDR2 | TSGGET |
| SEQ ID NO: 334 (Chothia) | HCDR3 | AHFDIYQYDTRGDFTYYFDN |
| SEQ ID NO: 335 (IMGT) | HCDR1 | GFIFTDYY |
| SEQ ID NO: 336 (IMGT) | HCDR2 | ITSGGETT |
| SEQ ID NO: 337 (IMGT) | HCDR3 | VRAHFDIYQYDTRGDFTYYFDN |
| SEQ ID NO: 338 | VH | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDIYQYDTRG DFTYYFDNWGLGTLVSVSS |
| SEQ ID NO: 339 | DNA VH | CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACATCTACCAGTAC GATACCAGAGGCGATTTCACCTACTACTTCGACAA CTGGGGCCTGGGAACCCTGGTGTCTGTCTCTTCT |
| SEQ ID NO: 340 | Heavy Chain | QVQLQESGGRLVRPGGSLRLSCAASGFIFTDYYMTWI RQAPGKGPEWIAFITSGGETTYYADSVKGRFTISRDN AKKSLFLQMYSLRADDTAVYYCVRAHFDIYQYDTRG DFTYYFDNWGLGTLVSVSSASTKGPSVFPLAPSSKSTS |
| SEQ ID NO: 341 | DNA Heavy Chain | GGTAALGCLVKDYFPEPVTVSWNSGALTSGVHTFPA VLQSSGLYSLSSVVTVPSSSLGTQTYICNVNHKPSNTK VDKRVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSREE MTKNQVSLTCLVKGFYPSDIAVEWESNGQPENNYKT TPPVLDSDGSFFLYSKLTVDKSRWQQGNVFSCSVMH EALHNHYTQKSLSLSPGK CAGGTTCAGCTGCAAGAATCTGGCGGCAGACTCGT TAGACCTGGCGGCTCTCTGAGACTGTCTTGTGCCGC CAGCGGCTTCATCTTCACCGACTACTACATGACCTG GATCAGACAGGCCCCTGGCAAGGGACCTGAGTGGA TCGCCTTTATCACAAGCGGCGAGAGACAACCTAC TACGCCGATAGCGTGAAGGGCAGATTCACCATCAG CCGGGACAACGCCAAGAAGTCCCTGTTCCTCCAGA TGTACAGCCTGAGAGCCGACGATACCGCCGTGTAT TATTGCGTGCGGGCCCACTTTGACATCTACCAGTAC GATACCAGAGGCGATTTCACCTACTACTTCGACAA CTGGGGCCTGGGAACCCTGGTGTCTGTCTCTTCTGC TAGCACCAAGGGCCCCAGCGTGTTCCCCCTGGCCC CCAGCAGCAAGAGCACCAGCGGCGGCACAGCCGC CCTGGGCTGCCTGGTGAAGGACTACTTCCCCGAGC CCGTGACCGTGTCCTGGAACAGCGGAGCCCTGACC TCCGGCGTGCACACCTTCCCCGCCGTGCTGCAGAG CAGCGGCCTGTACAGCCTGTCCAGCGTGGTGACAG TGCCCAGCAGCAGCCTGGGCACCCAGACCTACATC TGCAACGTGAACCACAAGCCCAGCAACACCAAGGT GGACAAGAGAGTGGAGCCCAAGAGCTGCGACAAG ACCCACACATGCCCCCCTGCCCGGCGCCAGAGCT GCTGGGCGGACCCTCCGTGTTCCTGTTCCCCCCCAA GCCCAAGGACACCCTGATGATCAGCAGGACCCCCG |

TABLE 2-continued anti-HBV Antibodies

AGGTGACCTGCGTGGTGGTGGACGTGAGCCACGAG
GACCCAGAGGTGAAGTTCAACTGGTACGTGGACGG
CGTGGAGGTGCACAACGCCAAGACCAAGCCCAGA
GAGGAGCAGTACAACAGCACCTACAGGGTGGTGTC
CGTGCTGACCGTGCTGCACCAGGACTGGCTGAACG
GCAAGGAATACAAGTGCAAGGTCTCCAACAAGGCC
CTGCCAGCCCCCATCGAAAAGACCATCAGCAAGGC
CAAGGGCCAGCCACGGGAGCCCCAGGTGTACACCC
TGCCCCCCTCCCGGGAGGAGATGACCAAGAACCAG
GTGTCCCTGACCTGTCTGGTGAAGGGCTTCTACCCC
AGCGACATCGCCGTGGAGTGGGAGAGCAACGGCC
AGCCCGAGAACAACTACAAGACCACCCCCCCAGTG
CTGGACAGCGACGGCAGCTTCTTCCTGTACAGCAA
GCTGACCGTGGACAAGTCCAGGTGGCAGCAGGGCA
ACGTGTTCAGCTGCAGCGTGATGCACGAGGCCCTG
CACAACCACTACACCCAGAAGAGCCTGAGCTTAAG
CCCCGGCAAG

NOV3839LC

| SEQ ID NO: 342 (Combined) | LCDR1 | RASQSVSSSLA |
| SEQ ID NO: 343 (Combined) | LCDR2 | GASTRAT |
| SEQ ID NO: 344 (Combined) | LCDR3 | HQYINWPPGDT |
| SEQ ID NO: 345 (Kabat) | LCDR1 | RASQSVSSSLA |
| SEQ ID NO: 346 (Kabat) | LCDR2 | GASTRAT |
| SEQ ID NO: 347 (Kabat) | LCDR3 | HQYINWPPGDT |
| SEQ ID NO: 348 (Chothia) | LCDR1 | SQSVSSS |
| SEQ ID NO: 349 (Chothia) | LCDR2 | GAS |
| SEQ ID NO: 350 (Chothia) | LCDR3 | YINWPPGD |
| SEQ ID NO: 351 (IMGT) | LCDR1 | QSVSSS |
| SEQ ID NO: 352 (IMGT) | LCDR2 | GAS |
| SEQ ID NO: 353 (IMGT) | LCDR3 | HQYINWPPGDT |
| SEQ ID NO: 354 | VL | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIK |
| SEQ ID NO: 355 | DNA VL | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAA |
| SEQ ID NO: 356 | Light Chain | EIVMTQSPATLSVSPGERVTLSCRASQSVSSSLAWYQ QKPGRAPRLLIYGASTRATGVPARFSGGGSGTDFTLTI SSLQSEDFAVYYCHQYINWPPGDTFGQGTRLDIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| SEQ ID NO: 357 | DNA Light Chain | GAAATAGTGATGACTCAGTCTCCAGCCACCCTGTCT GTGTCTCCAGGGGAAAGAGTCACCCTCTCCTGCAG GGCCAGTCAGAGTGTTAGTAGCAGCTTAGCCTGGT ACCAGCAGAAACCTGGCCGGGCTCCCAGGCTCCTC ATTTATGGAGCATCCACCAGGGCCACTGGTGTCCC AGCCAGGTTCAGTGGCGGTGGGTCTGGGACAGACT TCACTCTCACCATCAGCAGCCTGCAGTCTGAAGATT TTGCAGTTTATTACTGTCACCAGTATATTAATTGGC CTCCGGGGGACACTTTTGGCCAGGGGACGAGGCTG GATATCAAACGTACGGTGGCCGCTCCCAGCGTGTT CATCTTCCCCCCCAGCGACGAGCAGCTGAAGAGCG GCACCGCCAGCGTGGTGTGCCTGCTGAACAACTTC TACCCCCGGGAGGCCAAGGTGCAGTGGAAGGTGGA CAACGCCCTGCAGAGCGGCAACAGCCAGGAGAGC GTCACCGAGCAGGACAGCAAGGACTCCACCTACAG CCTGAGCAGCACCCTGACCCTGAGCAAGGCCGACT |

TABLE 2-continued anti-HBV Antibodies

ACGAGAAGCATAAGGTGTACGCCTGCGAGGTGACC
CACCAGGGCCTGTCCAGCCCCGTGACCAAGAGCTT
CAACAGGGGCGAGTGC

NOV3840HC

| SEQ ID NO: 358 (Combined) | HCDR1 | GFTFSYYGMN |
|---|---|---|
| SEQ ID NO: 359 (Combined) | HCDR2 | GITNSGSITYYADSVKG |
| SEQ ID NO: 360 (Combined) | HCDR3 | VGVRSSSGMWDLDY |
| SEQ ID NO: 361 (Kabat) | HCDR1 | YYGMN |
| SEQ ID NO: 362 (Kabat) | HCDR2 | GITNSGSITYYADSVKG |
| SEQ ID NO: 363 (Kabat) | HCDR3 | VGVRSSSGMWDLDY |
| SEQ ID NO: 364 (Chothia) | HCDR1 | GFTFSYY |
| SEQ ID NO: 365 (Chothia) | HCDR2 | TNSGSI |
| SEQ ID NO: 366 (Chothia) | HCDR3 | VGVRSSSGMWDLDY |
| SEQ ID NO: 367 (IMGT) | HCDR1 | GFTFSYYG |
| SEQ ID NO: 368 (IMGT) | HCDR2 | ITNSGSIT |
| SEQ ID NO: 369 (IMGT) | HCDR3 | AKVGVRSSSGMWDLDY |
| SEQ ID NO: 370 | VH | EVQLLESGGGLVQPGGSRRLSCAASGFTFSYYGMNW VRQAPGKGLEWVSGITNSGSITYYADSVKGRFSISRD NSKNTLFLQMNSLRAEDTAVYYCAKVGVRSSSGMW DLDYWGQGTLVTVSS |
| SEQ ID NO: 371 | DNA VH | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATAGTGGTAGTATCACATAC TACGCAGACTCCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 372 | Heavy Chain | EVQLLESGGGLVQPGGSRRLSCAASGFTFSYYGMNW VRQAPGKGLEWVSGITNSGSITYYADSVKGRFSISRD NSKNTLFLQMNSLRAEDTAVYYCAKVGVRSSSGMW DLDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVDK RVEPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCK VSNKALPAPIEKTISKAKGQPREPQVYTLPPSREEMTK NQVSLTCLVKGFYPSDIAVEWESNGQPENNYKTTPPV LDSDGSFFLYSKLTVDKSRWQQGNVFSCSVMHEALH NHYTQKSLSLSPGK |
| SEQ ID NO: 373 | DNA Heavy Chain | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATAGTGGTAGTATCACATAC TACGCAGACTCCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCAGCTAGCACCAAGGGCCCC AGCGTGTTCCCCCTGGCCCCCAGCAGCAAGAGCAC CAGCGGCGGCACAGCCGCCCTGGGCTGCCTGGTGA AGGACTACTTCCCCGAGCCCGTGACCGTGTCCTGG AACAGCGGAGCCCTGACCTCCGGCGTGCACACCTT CCCCGCCGTGCTGCAGAGCAGCGGCCTGTACAGCC TGTCCAGCGTGGTGACAGTGCCCAGCAGCAGCCTG GGCACCCAGACCTACATCTGCAACGTGAACCACAA GCCCAGCAACACCAAGGTGGACAAGAGAGTGGAG CCCAAGAGCTGCGACAAGACCCACACCTGCCCCCC CTGCCCAGCCCCAGAGCTGCTGGGCGGACCCTCCG TGTTCCTGTTCCCCCCAAGCCCAAGGACACCCTGA TGATCAGCAGGACCCCCGAGGTGACCTGCGTGGTG |

TABLE 2-continued anti-HBV Antibodies

```
                        GTGGACGTGAGCCACGAGGACCCAGAGGTGAAGTT
                        CAACTGGTACGTGGACGGCGTGGAGGTGCACAACG
                        CCAAGACCAAGCCCAGAGAGGAGCAGTACAACAG
                        CACCTACAGGGTGGTGTCCGTGCTGACCGTGCTGC
                        ACCAGGACTGGCTGAACGGCAAGGAATACAAGTGC
                        AAGGTCTCCAACAAGGCCCTGCCAGCCCCCATCGA
                        AAAGACCATCAGCAAGGCCAAGGGCCAGCCACGG
                        GAGCCCCAGGTGTACACCCTGCCCCCCTCCCGGGA
                        GGAGATGACCAAGAACCAGGTGTCCCTGACCTGTC
                        TGGTGAAGGGCTTCTACCCCAGCGACATCGCCGTG
                        GAGTGGGAGAGCAACGGCCAGCCCGAGAACAACT
                        ACAAGACCACCCCCCCAGTGCTGGACAGCGACGGC
                        AGCTTCTTCCTGTACAGCAAGCTGACCGTGGACAA
                        GTCCAGGTGGCAGCAGGGCAACGTGTTCAGCTGCA
                        GCGTGATGCACGAGGCCCTGCACAACCACTACACC
                        CAGAAGAGCCTGAGCCTGTCCCCCGGCAAG
```

NOV3840LC

| | | |
|---|---|---|
| SEQ ID NO: 374 (Combined) | LCDR1 | GGNNIGSKSLQ |
| SEQ ID NO: 375 (Combined) | LCDR2 | DDSDRPS |
| SEQ ID NO: 376 (Combined) | LCDR3 | QVWDTSSDHVV |
| SEQ ID NO: 377 (Kabat) | LCDR1 | GGNNIGSKSLQ |
| SEQ ID NO: 378 (Kabat) | LCDR2 | DDSDRPS |
| SEQ ID NO: 379 (Kabat) | LCDR3 | QVWDTSSDHVV |
| SEQ ID NO: 380 (Chothia) | LCDR1 | NNIGSKS |
| SEQ ID NO: 381 (Chothia) | LCDR2 | DDS |
| SEQ ID NO: 382 (Chothia) | LCDR3 | WDTSSDHV |
| SEQ ID NO: 383 (IMGT) | LCDR1 | NIGSKS |
| SEQ ID NO: 384 (IMGT) | LCDR2 | DDS |
| SEQ ID NO: 385 (IMGT) | LCDR3 | QVWDTSSDHVV |
| SEQ ID NO: 386 | VL | SYVLTQPPSVSVAPGQTARLSCGGNNIGSKSLQWYQQ KPGQAPVLVVNDDSDRPSGIPERFSGSNSGNTATLTIS RVEAGDEADYYCQVWDTSSDHVVFGGGTKLTVL |
| SEQ ID NO: 387 | DNA VL | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGATAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTA |
| SEQ ID NO: 388 | Light Chain | SYVLTQPPSVSVAPGQTARLSCGGNNIGSKSLQWYQQ KPGQAPVLVVNDDSDRPSGIPERFSGSNSGNTATLTIS RVEAGDEADYYCQVWDTSSDHVVFGGGTKLTVLGQ PKAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 389 | DNA Light Chain | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGATAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTAGGCCAGCCTAAGGCCGCTCCCTCCGTG ACCCTGTTCCCCCCAGCTCCGAGGAACTGCAGGC CAACAAGGCCACCCTGGTGTGCCTGATCAGCGACT TCTACCCTGGCGCCGTGACCGTGGCCTGGAAGGCC GACAGCAGCCCGTGAAGGCCGGCGTGGAGACAA CCACCCCCAGCAAGCAGAGCAACAACAAGTACGCC GCCAGCAGCTACCTGAGCCTGACCCCCGAGCAGTG GAAGAGCCACAGAAGCTACAGCTGCCAGGTCACCC ACGAGGGCAGCACCGTGGAGAAAACCGTGGCCCCC ACCGAGTGCAGC |

TABLE 2-continued anti-HBV Antibodies

NOV3841HC

| SEQ ID NO: 390 (Combined) | HCDR1 | GFTFSYYGMN |
| --- | --- | --- |
| SEQ ID NO: 391 (Combined) | HCDR2 | GITQSGSITYYADTVKG |
| SEQ ID NO: 392 (Combined) | HCDR3 | VGVRSSSGMWDLDY |
| SEQ ID NO: 393 (Kabat) | HCDR1 | YYGMN |
| SEQ ID NO: 394 (Kabat) | HCDR2 | GITQSGSITYYADTVKG |
| SEQ ID NO: 395 (Kabat) | HCDR3 | VGVRSSSGMWDLDY |
| SEQ ID NO: 396 (Chothia) | HCDR1 | GFTFSYY |
| SEQ ID NO: 397 (Chothia) | HCDR2 | TQSGSI |
| SEQ ID NO: 398 (Chothia) | HCDR3 | VGVRSSSGMWDLDY |
| SEQ ID NO: 399 (IMGT) | HCDR1 | GFTFSYYG |
| SEQ ID NO: 400 (IMGT) | HCDR2 | ITQSGSIT |
| SEQ ID NO: 401 (IMGT) | HCDR3 | AKVGVRSSSGMWDLDY |
| SEQ ID NO: 402 | VH | EVQLLESGGGLVQPGGSRRLSCAASGFTFSYYGMNW VRQAPGKGLEWVSGITQSGSITYYADTVKGRFSISRD NSKNTLFLQMNSLRAEDTAVYYCAKVGVRSSSGMW DLDYWGQGTLVTVSS |
| SEQ ID NO: 403 | DNA VH | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTCAGAGTGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 404 | Heavy Chain | EVQLLESGGGLVQPGGSRRLSCAASGFTFSYYGMNW VRQAPGKGLEWVSGITQSGSITYYADTVKGRFSISRD NSKNTLFLQMNSLRAEDTAVYYCAKVGVRSSSGMW DLDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVDK RVEPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCK VSNKALPAPIEKTISKAKGQPREPQVYTLPPSREEMTK NQVSLTCLVKGFYPSDIAVEWESNGQPENNYKTTPPV LDSDGSFFLYSKLTVDKSRWQQGNVFSCSVMHEALH NHYTQKSLSLSPGK |
| SEQ ID NO: 405 | DNA Heavy Chain | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTCAGAGTGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCAGCTAGCACCAAGGGCCCC AGCGTGTTCCCCCTGGCCCCCAGCAGCAAGAGCAC CAGCGGCGGCACAGCCGCCCTGGGCTGCCTGGTGA AGGACTACTTCCCCGAGCCCGTGACCGTGTCCTGG AACAGCGGAGCCCTGACCTCCGGCGTGCACACCTT CCCCGCCGTGCTGCAGAGCAGCGGCCTGTACAGCC TGTCCAGCGTGGTGACAGTGCCCAGCAGCAGCCTG GGCACCCAGACCTACATCTGCAACGTGAACCACAA GCCCAGCAACACCAAGGTGGACAAGAGAGTGGAG CCCAAGAGCTGCGACAAGACCCACACCTGCCCCCC CTGCCCAGCCCCAGAGCTGCTGGGCGGACCCTCCG TGTTCCTGTTCCCCCCCAAGCCCAAGGACACCCTGA TGATCAGCAGGACCCCCGAGGTGACCTGCGTGGTG GTGGACGTGAGCCACGAGGACCCAGAGGTGAAGTT CAACTGGTACGTGGACGGCGTGGAGGTGCACAACG CCAAGACCAAGCCCAGAGAGGAGCAGTACAACAG |

TABLE 2-continued anti-HBV Antibodies

CACCTACAGGGTGGTGTCCGTGCTGACCGTGCTGC
ACCAGGACTGGCTGAACGGCAAGGAATACAAGTGC
AAGGTCTCCAACAAGGCCCTGCCAGCCCCCATCGA
AAAGACCATCAGCAAGGCCAAGGGCCAGCCACGG
GAGCCCCAGGTGTACACCCTGCCCCCCTCCCGGGA
GGAGATGACCAAGAACCAGGTGTCCCTGACCTGTC
TGGTGAAGGGCTTCTACCCCAGCGACATCGCCGTG
GAGTGGGAGAGCAACGGCCAGCCCGAGAACAACT
ACAAGACCACCCCCCCAGTGCTGGACAGCGACGGC
AGCTTCTTCCTGTACAGCAAGCTGACCGTGGACAA
GTCCAGGTGGCAGCAGGGCAACGTGTTCAGCTGCA
GCGTGATGCACGAGGCCCTGCACAACCACTACACC
CAGAAGAGCCTGAGCCTGTCCCCCGGCAAG

NOV3841LC

| SEQ ID NO: 406 (Combined) | LCDR1 | GGNNIGSKSLQ |
|---|---|---|
| SEQ ID NO: 407 (Combined) | LCDR2 | DESDRPS |
| SEQ ID NO: 408 (Combined) | LCDR3 | QVWDTSSDHVV |
| SEQ ID NO: 409 (Kabat) | LCDR1 | GGNNIGSKSLQ |
| SEQ ID NO: 410 (Kabat) | LCDR2 | DESDRPS |
| SEQ ID NO: 411 (Kabat) | LCDR3 | QVWDTSSDHVV |
| SEQ ID NO: 412 (Chothia) | LCDR1 | NNIGSKS |
| SEQ ID NO: 413 (Chothia) | LCDR2 | DES |
| SEQ ID NO: 414 (Chothia) | LCDR3 | WDTSSDHV |
| SEQ ID NO: 415 (IMGT) | LCDR1 | NIGSKS |
| SEQ ID NO: 416 (IMGT) | LCDR2 | DES |
| SEQ ID NO: 417 (IMGT) | LCDR3 | QVWDTSSDHVV |
| SEQ ID NO: 418 | VL | SYVLTQPPSVSVAPGQTARLSCGGNNIGSKSLQWYQQ KPGQAPVLVVNDESDRPSGIPERFSGSNSGNTATLTIS RVEAGDEADYYCQVWDTSSDHVVFGGGTKLTVL |
| SEQ ID NO: 419 | DNA VL | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTA |
| SEQ ID NO: 420 | Light Chain | SYVLTQPPSVSVAPGQTARLSCGGNNIGSKSLQWYQQ KPGQAPVLVVNDESDRPSGIPERFSGSNSGNTATLTIS RVEAGDEADYYCQVWDTSSDHVVFGGGTKLTVLGQ PKAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 421 | DNA Light Chain | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTAGGCCAGCCTAAGGCCGCTCCCTCCGTG ACCCTGTTCCCCCCCAGCTCCGAGGAACTGCAGGC CAACAAGGCCACCCTGGTGTGCCTGATCAGCGACT TCTACCCTGGCGCCGTGACCGTGGCCTGGAAGGCC GACAGCAGCCCCGTGAAGGCCGGCGTGGAGACAA CCACCCCCAGCAAGCAGAGCAACAACAAGTACGCC GCCAGCAGCTACCTGAGCCTGACCCCCGAGCAGTG GAAGAGCCACAGAAGCTACAGCTGCCAGGTCACCC ACGAGGGCAGCACCGTGGAGAAAACCGTGGCCCCC ACCGAGTGCAGC |

TABLE 2-continued anti-HBV Antibodies

NOV3842HC

| SEQ ID NO: 422 (Combined) | HCDR1 | GFTFSYYGMN |
| SEQ ID NO: 423 (Combined) | HCDR2 | GITNVGSITYYADTVKG |
| SEQ ID NO: 424 (Combined) | HCDR3 | VGVRSSSGMWDLDY |
| SEQ ID NO: 425 (Kabat) | HCDR1 | YYGMN |
| SEQ ID NO: 426 (Kabat) | HCDR2 | GITNVGSITYYADTVKG |
| SEQ ID NO: 427 (Kabat) | HCDR3 | VGVRSSSGMWDLDY |
| SEQ ID NO: 428 (Chothia) | HCDR1 | GFTFSYY |
| SEQ ID NO: 429 (Chothia) | HCDR2 | TNVGSI |
| SEQ ID NO: 430 (Chothia) | HCDR3 | VGVRSSSGMWDLDY |
| SEQ ID NO: 431 (IMGT) | HCDR1 | GFTFSYYG |
| SEQ ID NO: 432 (IMGT) | HCDR2 | ITNVGSIT |
| SEQ ID NO: 433 (IMGT) | HCDR3 | AKVGVRSSSGMWDLDY |
| SEQ ID NO: 434 | VH | EVQLLESGGGLVQPGGSRRLSCAASGFTFSYYGMNW VRQAPGKGLEWVSGITNVGSITYYADTVKGRFSISRD NSKNTLFLQMNSLRAEDTAVYYCAKVGVRSSSGMW DLDYWGQGTLVTVSS |
| SEQ ID NO: 435 | DNA VH | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATGTGGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCA |
| SEQ ID NO: 436 | Heavy Chain | EVQLLESGGGLVQPGGSRRLSCAASGFTFSYYGMNW VRQAPGKGLEWVSGITNVGSITYYADTVKGRFSISRD NSKNTLFLQMNSLRAEDTAVYYCAKVGVRSSSGMW DLDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVDK RVEPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCK VSNKALPAPIEKTISKAKGQPREPQVYTLPPSREEMTK NQVSLTCLVKGFYPSDIAVEWESNGQPENNYKTTPPV LDSDGSFFLYSKLTVDKSRWQQGNVFSCSVMHEALH NHYTQKSLSLSPGK |
| SEQ ID NO: 437 | DNA Heavy Chain | GAGGTTCAATTGTTGGAGTCTGGGGGAGGCCTGGT ACAGCCGGGGGGGTCCCGGAGACTGTCCTGTGCAG CCTCTGGATTCACCTTTAGCTACTATGGCATGAACT GGGTCCGCCAGGCTCCAGGGAAGGGACTGGAATGG GTCTCAGGTATTACTAATGTGGGTAGTATCACATAC TACGCAGACACCGTGAAGGGCCGGTTCAGCATCTC CAGAGACAATTCCAAGAACACGTTGTTTCTGCAAA TGAACAGCCTGAGAGCCGAGGACACGGCCGTATAT TACTGTGCGAAGGTGGGAGTGCGCAGTTCGTCCGG GATGTGGGACCTTGACTACTGGGGCCAGGGAACCC TGGTCACCGTCAGCTCAGCTAGCACCAAGGGCCCC AGCGTGTTCCCCCTGGCCCCCAGCAGCAAGAGCAC CAGCGGCGGCACAGCCGCCCTGGGCTGCCTGGTGA AGGACTACTTCCCCGAGCCCGTGACCGTGTCCTGG AACAGCGGAGCCCTGACCTCCGGCGTGCACACCTT CCCCGCCGTGCTGCAGAGCAGCGGCCTGTACAGCC TGTCCAGCGTGGTGACAGTGCCCAGCAGCAGCCTG GGCACCCAGACCTACATCTGCAACGTGAACCACAA GCCCAGCAACACCAAGGTGGACAAGAGAGTGGAG CCCAAGAGCTGCGACAAGACCCACACCTGCCCCCC CTGCCCAGCCCCAGAGCTGCTGGGCGGACCCTCCG TGTTCCTGTTCCCCCCCAAGCCCAAGGACACCCTGA TGATCAGCAGGACCCCCGAGGTGACCTGCGTGGTG GTGGACGTGAGCCACGAGGACCCAGAGGTGAAGTT CAACTGGTACGTGGACGGCGTGGAGGTGCACAACG CCAAGACCAAGCCCAGAGAGGAGCAGTACAACAG |

TABLE 2-continued anti-HBV Antibodies

```
CACCTACAGGGTGGTGTCCGTGCTGACCGTGCTGC
ACCAGGACTGGCTGAACGGCAAGGAATACAAGTGC
AAGGTCTCCAACAAGGCCCTGCCAGCCCCCATCGA
AAAGACCATCAGCAAGGCCAAGGGCCAGCCACGG
GAGCCCCAGGTGTACACCCTGCCCCCCTCCCGGGA
GGAGATGACCAAGAACCAGGTGTCCCTGACCTGTC
TGGTGAAGGGCTTCTACCCCAGCGACATCGCCGTG
GAGTGGGAGAGCAACGGCCAGCCCGAGAACAACT
ACAAGACCACCCCCCCAGTGCTGGACAGCGACGGC
AGCTTCTTCCTGTACAGCAAGCTGACCGTGGACAA
GTCCAGGTGGCAGCAGGGCAACGTGTTCAGCTGCA
GCGTGATGCACGAGGCCCTGCACAACCACTACACC
CAGAAGAGCCTGAGCCTGTCCCCCGGCAAG
```

NOV3842LC

| | | |
|---|---|---|
| SEQ ID NO: 438 (Combined) | LCDR1 | GGNNIGSKSLQ |
| SEQ ID NO: 439 (Combined) | LCDR2 | DESDRPS |
| SEQ ID NO: 440 (Combined) | LCDR3 | QVWDTSSDHVV |
| SEQ ID NO: 441 (Kabat) | LCDR1 | GGNNIGSKSLQ |
| SEQ ID NO: 442 (Kabat) | LCDR2 | DESDRPS |
| SEQ ID NO: 443 (Kabat) | LCDR3 | QVWDTSSDHVV |
| SEQ ID NO: 444 (Chothia) | LCDR1 | NNIGSKS |
| SEQ ID NO: 445 (Chothia) | LCDR2 | DES |
| SEQ ID NO: 446 (Chothia) | LCDR3 | WDTSSDHV |
| SEQ ID NO: 447 (IMGT) | LCDR1 | NIGSKS |
| SEQ ID NO: 448 (IMGT) | LCDR2 | DES |
| SEQ ID NO: 449 (IMGT) | LCDR3 | QVWDTSSDHVV |
| SEQ ID NO: 450 | VL | SYVLTQPPSVSVAPGQTARLSCGGNNIGSKSLQWYQQ KPGQAPVLVVNDESDRPSGIPERFSGSNSGNTATLTIS RVEAGDEADYYCQVWDTSSDHVVFGGGTKLTVL |
| SEQ ID NO: 451 | DNA VL | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTA |
| SEQ ID NO: 452 | Light Chain | SYVLTQPPSVSVAPGQTARLSCGGNNIGSKSLQWYQQ KPGQAPVLVVNDESDRPSGIPERFSGSNSGNTATLTIS RVEAGDEADYYCQVWDTSSDHVVFGGGTKLTVLGQ PKAAPSVTLFPPSSEELQANKATLVCLISDFYPGAVTV AWKADSSPVKAGVETTTPSKQSNNKYAASSYLSLTPE QWKSHRSYSCQVTHEGSTVEKTVAPTECS |
| SEQ ID NO: 453 | DNA Light Chain | TCCTATGTGCTGACTCAGCCACCCTCGGTGTCAGTG GCCCCAGGACAGACGGCCAGACTTTCCTGTGGGGG AAACAACATTGGAAGTAAAAGTCTGCAGTGGTACC AGCAGAAGCCAGGCCAGGCCCCTGTGCTGGTCGTC AATGATGAGAGCGACCGGCCCTCAGGGATCCCTGA GCGATTCTCTGGCTCCAACTCTGGGAACACGGCCA CCCTGACCATCAGCAGGGTCGAAGCCGGGGATGAG GCCGACTATTACTGTCAGGTGTGGGATACTAGTAG TGATCATGTGGTCTTCGGCGGAGGGACCAAGCTGA CCGTCCTAGGCCAGCCTAAGGCCGCTCCCTCCGTG ACCCTGTTCCCCCCCAGCTCCGAGGAACTGCAGGC CAACAAGGCCACCCTGGTGTGCCTGATCAGCGACT TCTACCCTGGCGCCGTGACCGTGGCCTGGAAGGCC GACAGCAGCCCCGTGAAGGCCGGCGTGGAGACAA CCACCCCCAGCAAGCAGAGCAACAACAAGTACGCC GCCAGCAGCTACCTGAGCCTGACCCCCGAGCAGTG GAAGAGCCACAGAAGCTACAGCTGCCAGGTCACCC ACGAGGGCAGCACCGTGGAGAAAACCGTGGCCCCC ACCGAGTGCAGC |

TABLE 2-continued

| anti-HBV Antibodies | | | |
|---|---|---|---|
| NOV2603 HC | | | |
| SEQ ID NO: 454 (Combined) | | HCDR1 | GYTFTSYYMH |
| SEQ ID NO: 455 (Combined) | | HCDR2 | IISPSGGSTSYAQKFQG |
| SEQ ID NO: 456 (Combined) | | HCDR3 | DWEGGDPYGYYYAFDY |
| SEQ ID NO: 457 | (Kabat) | HCDR1 | SYYMH |
| SEQ ID NO: 458 | (Kabat) | HCDR2 | IISPSGGSTSYAQKFQG |
| SEQ ID NO: 459 | (Kabat) | HCDR3 | DWEGGDPYGYYYAFDY |
| SEQ ID NO: 460 (Chothia) | | HCDR1 | GYTFTSY |
| SEQ ID NO: 461 (Chothia) | | HCDR2 | SPSGGS |
| SEQ ID NO: 462 (Chothia) | | HCDR3 | DWEGGDPYGYYYAFDY |
| SEQ ID NO: 463 (IMGT) | | HCDR1 | GYTFTSYY |
| SEQ ID NO: 464 (IMGT) | | HCDR2 | ISPSGGST |
| SEQ ID NO: 465 (IMGT) | | HCDR3 | ARDWEGGDPYGYYYAFDY |
| SEQ ID NO: 466 | | VH | QVQLVQSGAEVKKPGASVKVSCKASGYTFTSYYMH WVRQAPGQGLEWMGIISPSGGSTSYAQKFQGRVTMT RDTSTSTVYMELSSLRSEDTAVYYCARDWEGGDPYG YYYAFDYWGQGTLVTVSS |
| SEQ ID NO: 467 | | DNA VH | CAGGTGCAATTGGTGCAGAGCGGAGCCGAAGTGAA AAAACCTGGGGCCAGCGTGAAAGTGTCCTGCAAAG CCTCCGGATACACCTTCACCAGCTACTACATGCACT GGGTCCGCCAGGCCCCAGGCCAGGGACTCGAGTGG ATGGGCATCATCAGCCCTAGCGGCGGCAGCACCAG CTACGCCCAGAAATTCCAGGGCCGGGTGACCATGA CCCGCGACACCAGCACCAGCACCGTGTACATGGAA CTGAGCAGCCTGCGCAGCGAGGACACCGCCGTGTA TTATTGCGCGCGTGACTGGGAAGGTGGTGACCCGT ACGGTTACTACTACGCTTTCGACTACTGGGGTCAAG GCACCCTGGTTACAGTCAGCTCA |
| SEQ ID NO: 468 | | Heavy Chain | QVQLVQSGAEVKKPGASVKVSCKASGYTFTSYYMH WVRQAPGQGLEWMGIISPSGGSTSYAQKFQGRVTMT RDTSTSTVYMELSSLRSEDTAVYYCARDWEGGDPYG YYYAFDYWGQGTLVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKRVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSREE MTKNQVSLTCLVKGFYPSDIAVEWESNGQPENNYKT TPPVLDSDGSFFLYSKLTVDKSRWQQGNVFSCSVMH EALHNHYTQKSLSLSPGK |
| SEQ ID NO: 469 | | DNA Heavy Chain | CAGGTGCAATTGGTGCAGAGCGGAGCCGAAGTGAA AAAACCTGGGGCCAGCGTGAAAGTGTCCTGCAAAG CCTCCGGATACACCTTCACCAGCTACTACATGCACT GGGTCCGCCAGGCCCCAGGCCAGGGACTCGAGTGG ATGGGCATCATCAGCCCTAGCGGCGGCAGCACCAG CTACGCCCAGAAATTCCAGGGCCGGGTGACCATGA CCCGCGACACCAGCACCAGCACCGTGTACATGGAA CTGAGCAGCCTGCGCAGCGAGGACACCGCCGTGTA TTATTGCGCGCGTGACTGGGAAGGTGGTGACCCGT ACGGTTACTACTACGCTTTCGACTACTGGGGTCAAG GCACCCTGGTTACAGTCAGCTCAGCTAGCACCAAG GGCCCCAGCGTGTTCCCCCTGGCCCCAGCAGCAA GAGCACCAGCGGCGGCACAGCCGCCCTGGGCTGCC TGGTGAAGGACTACTTCCCCGAGCCCGTGACCGTG TCCTGGAACAGCGGAGCCCTGACCTCCGGCGTGCA CACCTTCCCCGCCGTGCTGCAGAGCAGCGGCCTGT ACAGCCTGTCCAGCGTGGTGACAGTGCCCAGCAGC AGCCTGGGCACCCAGACCTACATCTGCAACGTGAA CCACAAGCCCAGCAACACCAAGGTGGACAAGAGA GTGGAGCCCAAGAGCTGCGACAAGACCCACACCTG CCCCCCCTGCCCAGCCCCAGAGCTGCTGGGCGGAC CCTCCGTGTTCCTGTTCCCCCCCAAGCCCAAGGACA CCCTGATGATCAGCAGGACCCCCGAGGTGACCTGC GTGGTGGTGGACGTGAGCCACGAGGACCCAGAGGT GAAGTTCAACTGGTACGTGGACGGCGTGGAGGTGC ACAACGCCAAGACCAAGCCCAGAGAGGAGCAGTA |

TABLE 2-continued anti-HBV Antibodies

```
CAACAGCACCTACAGGGTGGTGTCCGTGCTGACCG
TGCTGCACCAGGACTGGCTGAACGGCAAGGAATAC
AAGTGCAAGGTCTCCAACAAGGCCCTGCCAGCCCC
CATCGAAAAGACCATCAGCAAGGCCAAGGGCCAG
CCACGGGAGCCCCAGGTGTACACCCTGCCCCCCTC
CCGGGAGGAGATGACCAAGAACCAGGTGTCCCTGA
CCTGTCTGGTGAAGGGCTTCTACCCCAGCGACATC
GCCGTGGAGTGGGAGAGCAACGGCCAGCCCGAGA
ACAACTACAAGACCACCCCCCCAGTGCTGGACAGC
GACGGCAGCTTCTTCCTGTACAGCAAGCTGACCGT
GGACAAGTCCAGGTGGCAGCAGGGCAACGTGTTCA
GCTGCAGCGTGATGCACGAGGCCCTGCACAACCAC
TACACCCAGAAGAGCCTGAGCCTGTCCCCCGGCAA
G
```

NOV2603 LC

| SEQ ID NO: 470 (Combined) | LCDR1 | RASQSISSYLN |
|---|---|---|
| SEQ ID NO: 471 (Combined) | LCDR2 | AASSLQS |
| SEQ ID NO: 472 (Combined) | LCDR3 | QQSYSTPLT |
| SEQ ID NO: 473 (Kabat) | LCDR1 | RASQSISSYLN |
| SEQ ID NO: 474 (Kabat) | LCDR2 | AASSLQS |
| SEQ ID NO: 475 (Kabat) | LCDR3 | QQSYSTPLT |
| SEQ ID NO: 476 (Chothia) | LCDR1 | SQSISSY |
| SEQ ID NO: 477 (Chothia) | LCDR2 | AAS |
| SEQ ID NO: 478 (Chothia) | LCDR3 | SYSTPL |
| SEQ ID NO: 479 (IMGT) | LCDR1 | QSISSY |
| SEQ ID NO: 480 (IMGT) | LCDR2 | AAS |
| SEQ ID NO: 481 (IMGT) | LCDR3 | QQSYSTPLT |
| SEQ ID NO: 482 | VL | DIQMTQSPSSLSASVGDRVTITCRASQSISSYLNWYQQ KPGKAPKLLIYAASSLQSGVPSRFSGSGSGTDFTLTISS LQPEDFATYYCQQSYSTPLTFGQGTKVEIK |
| SEQ ID NO: 483 | DNA VL | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAA |
| SEQ ID NO: 484 | Light Chain | DIQMTQSPSSLSASVGDRVTITCRASQSISSYLNWYQQ KPGKAPKLLIYAASSLQSGVPSRFSGSGSGTDFTLTISS LQPEDFATYYCQQSYSTPLTFGQGTKVEIKRTVAAPS VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| SEQ ID NO: 485 | DNA Light Chain | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAACGTACGGTGGCCGCTCCCAGCGTGTTCATCT TCCCCCCCAGCGACGAGCAGCTGAAGAGCGGCACC GCCAGCGTGGTGTGCCTGCTGAACAACTTCTACCCC CGGGAGGCCAAGGTGCAGTGGAAGGTGGACAACG CCCTGCAGAGCGGCAACAGCCAGGAGAGCGTCACC GAGCAGGACAGCAAGGACTCCACCTACAGCCTGAG CAGCACCCTGACCCTGAGCAAGGCCGACTACGAGA AGCATAAGGTGTACGCCTGCGAGGTGACCCACCAG GGCCTGTCCAGCCCCGTGACCAAGAGCTTCAACAG GGGCGAGTGC |

TABLE 2-continued anti-HBV Antibodies

NOV3212 HC

| SEQ ID NO: 486 (Combined) | HCDR1 | GYTFTSLEMH |
| SEQ ID NO: 487 (Combined) | HCDR2 | IIEPSGGSTSYAQKFQG |
| SEQ ID NO: 488 (Combined) | HCDR3 | DWEGGDPYGYYYAFDY |
| SEQ ID NO: 489 (Kabat) | HCDR1 | SLEMH |
| SEQ ID NO: 490 (Kabat) | HCDR2 | IIEPSGGSTSYAQKFQG |
| SEQ ID NO: 491 (Kabat) | HCDR3 | DWEGGDPYGYYYAFDY |
| SEQ ID NO: 492 (Chothia) | HCDR1 | GYTFTSL |
| SEQ ID NO: 493 (Chothia) | HCDR2 | EPSGGS |
| SEQ ID NO: 494 (Chothia) | HCDR3 | DWEGGDPYGYYYAFDY |
| SEQ ID NO: 495 (IMGT) | HCDR1 | GYTFTSLE |
| SEQ ID NO: 496 (IMGT) | HCDR2 | IEPSGGST |
| SEQ ID NO: 497 (IMGT) | HCDR3 | ARDWEGGDPYGYYYAFDY |
| SEQ ID NO: 498 | VH | QVQLVQSGAEVKKPGASVKVSCKASGYTFTSLEMH WVRQAPGQGLEWMGIIEPSGGSTSYAQKFQGRVTMT RDTSTSTVYMELSSLRSEDTAVYYCARDWEGGDPYG YYYAFDYWGQGTLVTVSS |
| SEQ ID NO: 499 | DNA VH | CAGGTCCAATTGGTGCAGTCTGGCGCCGAAGTGAA GAAACCAGGCGCCAGCGTGAAGGTGTCCTGTAAAG CCAGCGGCTACACCTTTACCAGCCTGGAAATGCAT TGGGTCCGACAGGCTCCAGGACAGGGACTCGAGTG GATGGGAATTATCGAGCCTAGCGGCGGCAGCACAA GCTACGCCCAGAAATTCCAGGGCAGAGTGACCATG ACCAGAGACACCAGCACCTCCACCGTGTACATGGA ACTGAGCAGCCTGAGAAGCGAGGACACCGCCGTGT ATTATTGCGCGCGTGATTGGGAAGGCGGCGACCCT TATGGCTACTACTACGCCTTTGATTACTGGGGCCAG GGCACCCTGGTCACAGTTAGCTCA |
| SEQ ID NO: 500 | Heavy Chain | QVQLVQSGAEVKKPGASVKVSCKASGYTFTSLEMH WVRQAPGQGLEWMGIIEPSGGSTSYAQKFQGRVTMT RDTSTSTVYMELSSLRSEDTAVYYCARDWEGGDPYG YYYAFDYWGQGTLVTVSSASTKGPSVFPLAPSSKSTS GGTAALGCLVKDYFPEPVTVSWNSGALTSGVHTFPA VLQSSGLYSLSSVVTVPSSSLGTQTYICNVNHKPSNTK VDKRVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEY KCKVSNKALPAPIEKTISKAKGQPREPQVYTLPPSREE MTKNQVSLTCLVKGFYPSDIAVEWESNGQPENNYKT TPPVLDSDGSFFLYSKLTVDKSRWQQGNVFSCSVMH EALHNHYTQKSLSLSPGK |
| SEQ ID NO: 501 | DNA Heavy Chain | CAGGTCCAATTGGTGCAGTCTGGCGCCGAAGTGAA GAAACCAGGCGCCAGCGTGAAGGTGTCCTGTAAAG CCAGCGGCTACACCTTTACCAGCCTGGAAATGCAT TGGGTCCGACAGGCTCCAGGACAGGGACTCGAGTG GATGGGAATTATCGAGCCTAGCGGCGGCAGCACAA GCTACGCCCAGAAATTCCAGGGCAGAGTGACCATG ACCAGAGACACCAGCACCTCCACCGTGTACATGGA ACTGAGCAGCCTGAGAAGCGAGGACACCGCCGTGT ATTATTGCGCGCGTGATTGGGAAGGCGGCGACCCT TATGGCTACTACTACGCCTTTGATTACTGGGGCCAG GGCACCCTGGTCACAGTTAGCTCAGCTAGCACCAA GGGCCCCAGCGTGTTCCCCCTGGCCCCCAGCAGCA AGAGCACCAGCGGCGGCACAGCCGCCCTGGGCTGC CTGGTGAAGGACTACTTCCCCGAGCCCGTGACCGT GTCCTGGAACAGCGGAGCCCTGACCTCCGGCGTGC ACACCTTCCCGCCGTGCTGCAGAGCAGCGGCCTG TACAGCCTGTCCAGCGTGGTGACAGTGCCCAGCAG CAGCCTGGGCACCCAGACCTACATCTGCAACGTGA ACCACAAGCCCAGCAACACCAAGGTGGACAAGAG AGTGGAGCCCAAGAGCTGCGACAAGACCCACACAT GCCCCCCCTGCCCAGCCCCAGAGCTGCTGGGCGGA CCCTCCGTGTTCCTGTTCCCCCCCAAGCCCAAGGAC ACCCTGATGATCAGCAGGACCCCCGAGGTGACCTG CGTGGTGGTGGACGTGAGCCACGAGGACCCAGAGG TGAAGTTCAACTGGTACGTGGACGGCGTGGAGGTG CACAACGCCAAGACCAAGCCCAGAGAGGAGCAGT |

TABLE 2-continued anti-HBV Antibodies

ACAACAGCACCTACAGGGTGGTGTCCGTGCTGACC
GTGCTGCACCAGGACTGGCTGAACGGCAAGGAATA
CAAGTGCAAGGTCTCCAACAAGGCCCTGCCAGCCC
CCATCGAAAAGACCATCAGCAAGGCCAAGGGCCA
GCCACGGGAGCCCCAGGTGTACACCCTGCCCCCCT
CCCGGGAGGAGATGACCAAGAACCAGGTGTCCCTG
ACCTGTCTGGTGAAGGGCTTCTACCCCAGCGACAT
CGCCGTGGAGTGGGAGAGCAACGGCCAGCCCGAG
AACAACTACAAGACCACCCCCCCAGTGCTGGACAG
CGACGGCAGCTTCTTCCTGTACAGCAAGCTGACCG
TGGACAAGTCCAGGTGGCAGCAGGGCAACGTGTTC
AGCTGCAGCGTGATGCACGAGGCCCTGCACAACCA
CTACACCCAGAAGAGCCTGAGCTTAAGCCCCGGCA
AG

NOV3212 LC

| SEQ ID NO: 502 (Combined) | LCDR1 | RASQSISSYLN |
| SEQ ID NO: 503 (Combined) | LCDR2 | AASSLQS |
| SEQ ID NO: 504 (Combined) | LCDR3 | QQSYSTPLT |
| SEQ ID NO: 505 (Kabat) | LCDR1 | RASQSISSYLN |
| SEQ ID NO: 506 (Kabat) | LCDR2 | AASSLQS |
| SEQ ID NO: 507 (Kabat) | LCDR3 | QQSYSTPLT |
| SEQ ID NO: 508 (Chothia) | LCDR1 | SQSISSY |
| SEQ ID NO: 509 (Chothia) | LCDR2 | AAS |
| SEQ ID NO: 510 (Chothia) | LCDR3 | SYSTPL |
| SEQ ID NO: 511 (IMGT) | LCDR1 | QSISSY |
| SEQ ID NO: 512 (IMGT) | LCDR2 | AAS |
| SEQ ID NO: 513 (IMGT) | LCDR3 | QQSYSTPLT |
| SEQ ID NO: 514 | VL | DIQMTQSPSSLSASVGDRVTITCRASQSISSYLNWYQQ KPGKAPKLLIYAASSLQSGVPSRFSGSGSGTDFTLTISS LQPEDFATYYCQQSYSTPLTFGQGTKVEIK |
| SEQ ID NO: 515 | DNA VL | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAA |
| SEQ ID NO: 516 | Light Chain | DIQMTQSPSSLSASVGDRVTITCRASQSISSYLNWYQQ KPGKAPKLLIYAASSLQSGVPSRFSGSGSGTDFTLTISS LQPEDFATYYCQQSYSTPLTFGQGTKVEIKRTVAAPS VFIFPPSDEQLKSGTASVVCLLNNFYPREAKVQWKVD NALQSGNSQESVTEQDSKDSTYSLSSTLTLSKADYEK HKVYACEVTHQGLSSPVTKSFNRGEC |
| SEQ ID NO: 517 | DNA Light Chain | GATATCCAGATGACCCAGAGCCCTAGCAGCCTGAG CGCCAGCGTGGGCGACCGCGTGACCATTACCTGCA GAGCCAGCCAGAGCATCAGCAGCTACCTGAACTGG TACCAGCAGAAACCTGGCAAGGCGCCCAAACTATT AATCTACGCCGCCAGCAGCCTTCAGAGCGGCGTGC CAAGCCGCTTTAGCGGATCCGGCAGCGGCACCGAC TTCACCCTGACCATCAGCTCCCTTCAGCCTGAAGAC TTCGCCACCTACTACTGCCAGCAGAGCTACAGCAC CCCTCTGACCTTTGGCCAGGGCACCAAAGTGGAAA TCAAACGTACGGTGGCCGCTCCCAGCGTGTTCATCT TCCCCCCCAGCGACGAGCAGCTGAAGAGCGGCACC GCCAGCGTGGTGTGCCTGCTGAACAACTTCTACCCC CGGGAGGCCAAGGTGCAGTGGAAGGTGGACAACG CCCTGCAGAGCGGCAACAGCCAGGAGAGCGTCACC GAGCAGGACAGCAAGGACTCCACCTACAGCCTGAG CAGCACCCTGACCCTGAGCAAGGCCGACTACGAGA AGCATAAGGTGTACGCCTGCGAGGTGACCCACCAG GGCCTGTCCAGCCCCGTGACCAAGAGCTTCAACAG GGGCGAGTGC |

Other antibodies of the present disclosure include those where the amino acids or nucleic acids encoding the amino acids have been mutated; yet have at least 60, 70, 80, 90 or 95 percent identity to the sequences described in Table 2. In some aspects, it includes mutant amino acid sequences wherein no more than 1, 2, 3, 4 or 5 amino acids have been mutated in the variable regions when compared with the variable regions depicted in the sequence described in Table 2, while retaining substantially the same therapeutic activity.

Since these antibodies can bind to HBsAg, the VH, VL, full length light chain, and full length heavy chain sequences (amino acid sequences and the nucleotide sequences encoding the amino acid sequences) can be "mixed and matched" to create other HBsAg-binding antibodies. Such "mixed and matched" HBsAg-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NO: 18, 50, 82, 114, 146, 178, 210, 242, 274, 306, 338, 370, 402, 434, 466, or 498 (Table 2); and a light chain variable region comprising an amino acid sequence selected from the group consisting of SEQ ID NO: 34, 66, 98, 130, 162, 194, 226, 258, 290, 322, 354, 386, 418, 450, 482 or 514 (Table 2); wherein the antibody specifically binds to HBsAg.

In another aspect, the disclosure provides (i) an isolated monoclonal antibody having: a full length heavy chain comprising an amino acid sequence that has been optimized for expression in the cell of a mammalian selected from the group consisting of SEQ ID NOs: 20, 52, 84, 116, 148, 180, 212, 244, 276, 308, 340, 372, 404, 436, 468, or 500 (Table 2) and a full length light chain comprising an amino acid sequence that has been optimized for expression in the cell of a mammalian selected from the group consisting of SEQ ID NOs: 36, 68, 100, 132, 164, 196, 228, 260, 292, 324, 356, 388, 420, 452, 484 or 516 (Table 2) or (ii) a functional protein comprising an antigen binding portion thereof.

In another aspect, the present disclosure provides HBsAg binding antibodies that comprise the heavy chain and light chain CDR1s, CDR2s and CDR3s as described in Table 2, or combinations thereof. The amino acid sequences of the VH CDR1s of the antibodies are shown in SEQ ID NOs 9, 41, 73, 105, 137, 169, 201, 233, 265, 297, 329, 361, 393, 425, 457 or 489. The amino acid sequences of the VH CDR2s of the antibodies and are shown in SEQ ID NOs: 10, 42, 74, 106, 138, 170, 202, 234, 266, 298, 330, 362, 394, 426, 458 or 490. The amino acid sequences of the VH CDR3s of the antibodies are shown in SEQ ID NOs: 11, 43, 75, 107, 139, 171, 203, 235, 267, 299, 331, 363, 395, 427, 459 or 491. The amino acid sequences of the VL CDR1s of the antibodies are shown in SEQ ID NOs: 25, 57, 89, 121, 153, 185, 217, 249, 281, 313, 345, 377, 409, 441, 473 or 505. The amino acid sequences of the VL CDR2s of the antibodies are shown in SEQ ID NOs 26, 58, 90, 122, 154, 186, 218, 250, 282, 314, 346, 378, 410, 442, 474 or 506. The amino acid sequences of the VL CDR3s of the antibodies are shown in SEQ ID NOs: 27, 59, 91, 123, 155, 187, 219, 251, 283, 315, 347, 379, 411, 443, 475 or 507.

Given that each of these antibodies can bind to HBsAg and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody must contain a VH CDR1, 2 and 3 and a VL CDR1, 2 and 3 to create other HBsAg-binding binding molecules. Such "mixed and matched" HBsAg-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 9, 41, 73, 105, 137, 169, 201, 233, 265, 297, 329, 361, 393, 425, 457 or 489; a heavy chain CDR2 comprising an amino acid sequence selected from the group consisting of SEQ ID NOs: 10, 42, 74, 106, 138, 170, 202, 234, 266, 298, 330, 362, 394, 426, 458 or 490; a heavy chain CDR3 comprising an amino acid sequence selected from the group consisting of SEQ ID NOs: 11, 43, 75, 107, 139, 171, 203, 235, 267, 299, 331, 363, 395, 427, 459 or 491; a light chain CDR1 comprising an amino acid sequence selected from the group consisting of SEQ ID NOs: 25, 57, 89, 121, 153, 185, 217, 249, 281, 313, 345, 377, 409, 441, 473 or 505; a light chain CDR2 comprising an amino acid sequence selected from the group consisting of SEQ ID NOs: 26, 58, 90, 122, 154, 186, 218, 250, 282, 314, 346, 378, 410, 442, 474 or 506; and a light chain CDR3 comprising an amino acid sequence selected from the group consisting of SEQ ID NOs: 27, 59, 91, 123, 155, 187, 219, 251, 283, 315, 347, 379, 411, 443, 475 or 507; wherein the antibody specifically binds to HBsAg.

In certain aspects, an antibody that specifically binds to HBsAg is an antibody or antibody fragment (e.g., antigen binding fragment) that is described in Table 2.

1. Identification of Antibodies

The present disclosure provides antibodies and antibody fragments (e.g., antigen binding fragments) that bind to HBsAg. In certain aspects the antibodies and antibody fragments can bind to the same epitope within all four hepatitis B serotypes.

The present disclosure also provides antibodies and antibody fragments (e.g., antigen binding fragments) that bind to the same epitope as do the HBsAg antibodies described in Table 2. Additional antibodies and antibody fragments (e.g., antigen binding fragments) can therefore be identified based on their ability to cross-compete (e.g., to competitively inhibit the binding of, in a statistically significant manner) with other antibodies in binding assays. The ability of a test antibody to inhibit the binding of antibodies and antibody fragments (e.g., antigen binding fragments) of the present disclosure to HBsAg demonstrates that the test antibody can compete with that antibody or antibody fragment (e.g., antigen binding fragments) for binding to HBsAg; such an antibody may, according to non-limiting theory, bind to the same or a related (e.g., a structurally similar or spatially proximal) epitope on HBsAg as the antibody or antibody fragment (e.g., antigen binding fragments) with which it competes. In a certain aspect, the antibody that binds to the same epitope on HBsAg as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure disclosed specific HBsAg antibodies. These antibodies comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγR1, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., 2009, Curr. Opin. Biotechnol. vol. 20(6):685-691); and D265A (Baudino et al., 2008, J. Immunol. 181: 6664-69) see also Heusser et al., WO2012065950. Examples of silent Fc lgG1 antibodies are the LALA mutant comprising L234A and L235A mutation in the lgG1 Fc amino acid sequence. Another example of a silent lgG1 antibody is the DAPA (D265A, P329A) mutation (U.S. Pat. No. 6,737,056). Another silent lgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis (low ADCC activity), or that is below 1% specific cell lysis (no ADCC activity).

3. Production of the Antibodies

Anti-HBsAg antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 19, 51, 83, 115, 147, 179, 211, 243, 275, 307, 339, 371, 403, 435, 467 or 499. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 35, 67, 99, 131, 163, 195, 227, 259, 291, 323, 355, 387, 419, 451, 483 or 515.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 21, 53, 85, 117, 149, 181, 213, 245, 277, 309, 341, 373, 405, 437, 469 or 501. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:37, 69, 101, 133, 165, 197, 229, 261, 293, 325, 357, 389, 421, 453, 485, or 517

The polynucleotides of the present disclosure can encode only the variable region sequence of an anti-HBsAg antibody. They can also encode both a variable region and a constant region of the antibody. Some of the polynucleotide sequences encode a polypeptide that comprises variable regions of both the heavy chain and the light chain of one of an exemplified anti-HBsAg antibody. Some other polynucleotides encode two polypeptide segments that respectively are substantially identical to the variable regions of the heavy chain and the light chain of one of the antibodies.

The polynucleotide sequences can be produced by de novo solid-phase DNA synthesis or by PCR mutagenesis of an existing sequence encoding an anti-HBsAg antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458, 066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the present disclosure are expression vectors and host cells for producing the anti-HBsAg antibodies described above. Various expression vectors can be employed to express the polynucleotides encoding the anti-HBsAg antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-HBsAg polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-HBsAg antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an anti-HBsAg antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-HBsAg antibody sequences. More often, the inserted anti-HBsAg antibody sequences are linked to a signal sequences before inclusion in the vector. Vectors to be used to receive sequences encoding anti-HBsAg antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-HBsAg antibody chains can be either prokaryotic or eukaryotic. E. coli is one prokaryotic host useful for cloning and expressing the polynucleotides of the present disclosure. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-HBsAg antibodies. Insect cells in combination with baculovirus vectors can also be used.

In other aspects, mammalian host cells are used to express and produce the anti-HBsAg antibodies of the present disclosure. For example, they can be either a hybridoma cell line expressing endogenous immunoglobulin genes (e.g., the myeloma hybridoma clones as described in the Examples) or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-HBsAg antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments) of the present disclosure are useful in a variety of applications including, but not limited to, hepatitis B viral infection and disease. In certain aspects, the antibodies, antibody fragments (e.g., antigen binding fragments), and are useful for neutralizing hepatitis B infection and the prevention or treatment of liver cirrhosis or liver cancer). The methods of use can be in vitro, ex vivo, or in vivo methods.

In one aspect, the antibodies, antibody fragments (e.g., antigen binding fragments), are useful for detecting the presence of HBsAg in a biological sample. The term "detecting" as used herein encompasses quantitative or qualitative detection. In certain aspects, a biological sample comprises a cell or tissue. In certain aspects, such tissues include normal and/or cancerous tissues that express HBsAg at higher levels relative to other tissues.

In one aspect, the present disclosure provides a method of detecting the presence of HBsAg or hepatitis B in a biological sample. In certain aspects, the method comprises contacting the biological sample with an anti-HBsAg antibody under conditions permissive for binding of the antibody to the antigen, and detecting whether a complex is formed between the antibody and the antigen. The biological sample can include, without limitation, urine or blood samples.

Also included is a method of diagnosing a disorder associated with expression of HBsAg. In certain aspects, the method comprises contacting a test cell with an anti-HBsAg antibody; determining the level of expression (either quantitatively or qualitatively) of HBsAg in the test cell by detecting binding of the antibody to HBsAg; and comparing the level of infection in the test cell with the level of infection of hepatitis B virus in a control cell (e.g., a normal cell of the same tissue origin as the test cell or a non-virus infected cell), wherein a higher level of presence of HBsAg in the test cell as compared to the control cell indicates the presence of a disorder associated with infection with hepatitis B. In certain aspects, the test cell is obtained from an individual suspected of having a hepatitis B virus infection.

In certain aspects, a method of diagnosis or detection, such as those described above, comprises detecting binding of a HBsAg antibody to a hepatitis B virus infected cell. An exemplary assay for detecting binding of an anti-HBsAg antibody to a hepatitis B infected cell is a "FACS" assay.

Certain other methods can be used to detect binding of anti-HBsAg antibodies. Such methods include, but are not limited to, antigen-binding assays that are well known in the art, such as Western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, the anti-HBsAg antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, the anti-HBsAg antibodies are immobilized on an insoluble matrix. Immobilization entails separating the anti-HBsAg antibody from any hepatitis B proteins that remain free in solution. This conventionally is accomplished by either insolubilizing the anti-HBsAg antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-HBsAg antibody after formation of a complex between the anti-HBsAg antibody and HBsAg protein, e.g., by immunoprecipitation.

Any of the above aspects of diagnosis or detection can be carried out using an anti-HBsAg antibody of the present disclosure in place of or in addition to another anti-HBsAg antibody.

In one aspect, the disclosure provides for a method of treating, reducing the likelihood of or ameliorating a disease comprising administering the antibodies, antibody fragments (e.g., antigen binding fragments), to a patient, thereby treating the disease. In certain aspects, the disease treated with the antibodies, antibody fragments (e.g., antigen binding fragments), is a hepatitis B viral infection. Examples of hepatitis B diseases which can be treated and/or prevented include, but are not limited to; liver failure, cirrhosis, and hepatocellular carcinoma. In certain aspects, the infection is characterized by HBsAg expressing cells to which the anti-HBsAg antibodies, antibody fragments (e.g., antigen binding fragments) can specifically bind.

The present disclosure provides for methods of treating hepatitis B viral infection and liver failure, cirrhosis, and/or hepatocellular carcinoma comprising administering a therapeutically effective amount of the antibodies, antibody fragments (e.g., antigen binding fragments). In certain aspects, the subject is a human.

In certain aspects, the method of reducing hepatitis B viral infection comprises administering to a subject a therapeutically effective amount of antibodies or antibody fragments (e.g., antigen binding fragments). In certain aspects, the subject is a human. In certain aspects, the subject is immunosuppressed, immunocompromised or has reduced immune function. For immunosuppressed subjects, the amount of immunosuppression can be increased or decreased due to the therapeutic effects of the anti-HBsAg antibodies.

For the treatment of hepatitis B viral infection, the appropriate dosage of the HBsAg antibodies, or antibody fragments (e.g., antigen binding fragments), depend on various factors, such as the type of infection to be treated, the severity and course of the infection, the responsiveness of the infection, the generation of viral resistance to therapy, previous therapy, patient's clinical history, and so on. The antibody can be administered one time or over a series of treatments lasting from several days to several months, or until a cure is effected or a diminution of the infection is achieved (e.g., reduction in viruria or viral damage to the liver). Optimal dosing schedules can be calculated from measurements of drug accumulation in the body of the patient and will vary depending on the relative potency of an individual antibody or antibody fragment (e.g., antigen binding fragment). In certain aspects, dosage is from 0.01 mg to 100 mg (e.g., 0.01 mg, 0.05 mg, 0.1 mg, 0.5 mg, 1 mg, 2 mg, 3 mg, 4 mg, 5 mg, 7 mg, 8 mg, 9 mg, 10 mg, 20 mg, 30 mg, 40 mg, 50 mg, 60 mg, 70 mg, 80 mg. 90 mg or 100 mg) per kg of body weight, and can be given once or more daily, weekly, monthly or yearly. In certain aspects, the antibody or antibody fragment (e.g., antigen binding fragment), of the present disclosure is given once every two weeks or once every three weeks. The treating physician can estimate repetition rates for dosing based on measured half-life and concentrations of the antibody in bodily fluids or tissues.

Combination Therapy

In certain instances, the antibody or antibody fragment (e.g., antigen binding fragment), of the present disclosure is combined with other therapeutic agents, such as other antiviral agents, anti-allergic agents, anti-nausea agents (or anti-emetics), pain relievers, cytoprotective agents, immunosuppressants and combinations thereof.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or infection described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the individual components separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the individual components are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating hepatitis B infection by administering to a subject in need thereof anti-HBsAg antibody in together with immunosuppressant therapies. The anti-HBsAg antibodies will reduce the amount of HBsAg in the circulation and allow the immune system to mount a response to the hepatitis B viral infection resulting from the immunosuppressant therapy prior to or post administration. Examples of immunosuppressant therapy include, but are not limited to; a monophosphate dehydrogenase inhibitor, a purine synthesis inhibitor, a calcineurin inhibitor or an mTOR inhibitor. Specific examples of immunosuppressive therapeutics include but are not limited to; mycophenolate mofetil (MMF), mycophenolate sodium, azathioprine, tacrolimus, sirolimus and cyclosporine.

In one embodiment, an anti-HBsAg antibody combination is used with a PD-1 inhibitor, e.g., as described in WO2015/026684 or WO2016/057846. In some embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed therein (or a sequence substantially identical or similar thereto, e.g., a sequence at least 85%, 90%, 95% identical or higher to the sequence specified).

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509 and WO2009/114335.

In one embodiment, the inhibitor of PD-1 is Pembrolizumab, disclosed in, e.g., U.S. Pat. No. 8,354,509 and WO 2009/114335, and having a sequence disclosed therein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgGlk monoclonal antibody that binds to PD1. Pidilizumab and other humanized anti-PD-1 monoclonal antibodies are disclosed in WO2009/101611. Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342), is a PD-L2 Fc fusion soluble receptor that blocks the interaction between PD-1 and B7-H1.

In one embodiment, an anti-HBsAg antibody combination is used with an anti-PD-L1 antibody, e.g., as described in WO2016/061142. In some embodiments, the anti-PD-L1 antibody is Atezolizumab, Avelumab or Durvalumab. In some embodiments, the anti-PD-L1 antibody is Atezolizumab, disclosed in WO2010/077634. In some embodiments, the anti-PD-L1 antibody is Durvalumab, disclosed in WO2011/066389. Other anti-PD-L1 antibodies include BMS-936559 also known as MDX-1105, as disclosed in WO2007/005874 and AMP-224 also known as GSK2661380 disclosed in WO2010/027423.

Pharmaceutical Compositions

To prepare pharmaceutical or sterile compositions including anti-HBsAg antibodies, the antibodies of the present disclosure are mixed with a pharmaceutically acceptable carrier or excipient. The compositions can additionally contain one or more other therapeutic agents that are suitable for neutralizing hepatitis B infection.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In a specific aspect, the anti-HBsAg antibody is a lyophilisate in a vial containing the antibody. The lyophilisate can be reconstituted with water or a pharmaceutical carrier suitable for injection. For subsequent intravenous administration, the obtained solution will usually be further diluted into a carrier solution.

The antibodies disclosed herein are useful in the neutralization of hepatitis B in patients suffering from liver failure, cirrhosis, and/or hepatocellular carcinoma, so a pharmaceutical carrier of sucrose and human albumin as used previously in bone marrow transplant patients receiving CytoGam® can be used (DeRienzo et al. Pharmacotherapy 2000; 20:1175-8). Alternatively, the anti-HBsAg antibodies can be introduced into transplant patients via a pharmaceutical carrier as described for another anti-viral antibody, Synagis®, as described in WO2003/105894. In this publication, the pharmaceutical carrier was comprised of histidine and/or glycine, a saccharide (e.g. sucrose) and a polyol (e.g. polysorbate).

Selecting an administration regimen for a therapeutic depends on several factors, including the severity of the infection, the level of symptoms, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., infusion reactions.

Actual dosage levels of the active ingredients in the pharmaceutical compositions with the anti-HBsAg antibodies can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the neutralizing activity of the antibodies, the route of administration, the time of administration, the half-life of the antibody in the patient, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the antibodies described herein, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the antibodies then can be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the antibodies include intravenous, intramuscular, intradermal, intraperitoneal, subcutaneous, spinal or other parenteral routes of administration, for example by injection or infusion. Parenteral administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the antibodies of the present disclosure are administered by infusion. In another aspect, the antibodies are administered subcutaneously.

If the antibodies of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the antibodies (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253.

Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more antibodies of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rd. Bioact. Mater. 24:853-854, 1997; and Lam et al., Proc. Int'l. Symp. Control Rd. Bioact. Mater. 24:759-760, 1997, each of which is incorporated herein by reference in their entirety.

If the antibodies of the disclosure are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the antibodies are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., an immunosuppressant, a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the anti-HBsAg antibodies may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the anti-HBsAg antibodies of the present disclosure. The two or more therapies may be administered within one same patient visit.

In certain aspects, anti-HBsAg antibodies can be formulated to ensure proper distribution in vivo. For example, the blood-brain barrier (BBB) excludes many highly hydrophilic compounds. To ensure that the anti-HBsAg antibodies cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising antibodies alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the antibodies can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of Anti-HBsAg Virus Antibodies

Human memory B cells from HBV vaccinated donors were in vitro expanded and selected for their capacity to secrete IgG antibodies against HBsAg. Specific B cells were lysed and the VH (heavy) and VL (light) chains were amplified by RT-PCR and subsequently sequenced and analyzed to identify critical post translational modification (PTM) sites. Plasmids of the VH and VL chains were then transfected in a CHO mammalian cell line in an IgG1 backbone vector for expression of the full IgG1 antibodies.

Methods for generation of monoclonal antibodies using phage display technology are known in the art (Antibody Methods and Protocols, Methods in Molecular Biology vol. 901, 2012, Chapter 3: 33). Briefly, a synthetic human germline framework antibody library in Fab format randomized in CDR-H3 was screened for anti-HBsAg antibodies by solution panning with streptavidin-coupled magnetic beads complexed with biotinylated recombinant HBsAg (TRINA Bioreactives AG, Cat #C028-3001994774 (AD serotype), C028-3001994774 (AY serotype) or Biorbyte, Cat #orb82536 (AD isotype)) over 3 rounds of selection with increasing stringency. Isolates were first expressed as Fab and screened for binding to both HBsAg serotype AD and serotype AY by ELISA. Selected isolates were then cloned and expressed as IgG1, reanalyzed for binding to HBsAg (serotype AD and AY) by ELISA and for functional activity in neutralization assays, and finally transfected in a CHO mammalian cell line for expression of the full IgG1, antibodies. Anti-HBsAg antibodies were affinity matured by CDR-directed mutagenesis. Beneficial mutations have been identified by comparing enrichment after two rounds of phage display in relation to the initial mutagenesis library by deep sequencing. Selected beneficial mutations alone and in combination were then cloned and expressed as IgG1, reanalyzed for binding to HBsAg (serotype AD and AY) by ELISA and for functional activity in neutralization assays, and finally transfected in a CHO mammalian cell line for expression of the full IgG1.

Changes to the anti-HBsAg antibodies are provided in Table 3.

TABLE 3

| Antibody | Changes |
| --- | --- |
| NOV2603 | No change |
| NOV3212 | Affinity maturation |
| NOV3357 | Affinity maturation |
| NOV3540 | NOV3357 change to remove post-translational |

TABLE 3-continued

| Antibody | Changes |
|---|---|
|  | modification: DDDGWSGYDYWFDY (SEQ ID NO: 139) to DDDAWSGYDYWFDY in HCDR3 (Kabat) (SEQ ID NO: 107) resulted in no significant change in affinity or activity |
| NOV3831 | No change |
| NOV3832 | NOV3831 change to remove post-translational modification: FNN to FDN resulted in no significant change in affinity or activity |
| NOV3833 | NOV3831 change to remove post-translational modification: FNN to FHN resulted in no significant change in affinity or activity |
| NOV3834 | No change |
| NOV3835 | NOV3834 change to remove post-translational modification: FNR to FDR resulted in no significant change in affinity or activity |
| NOV3836 | NOV3834 change to remove post-translational modification: FNR to FER resulted in no significant change in affinity or activity |
| NOV3837 | No change |
| NOV3838 | NOV3837 change to remove post-translational modification: DGY to DLY resulted in no significant change in affinity or activity |
| NOV3839 | NOV3837 change to remove post-translational modification: DGY to DIY resulted in no significant change in affinity or activity |
| NOV3840 | No change |
| NOV3841 | NOV3840 change to remove post-translational modification: TNS to TQS and DS to DT for VH, and DDS to DES for VI resulted in no significant change in affinity or activity |
| NOV3842 | NOV3840 change to remove post-translational modification: TNS to TNV and DS to DT for VH, and DDS to DES for VI resulted in no significant change in affinity or activity |

Example 2: Binding of Anti-HBsAg Antibodies to HBsAg

Binding affinity interaction ($K_D$) of the anti-HBsAg antibodies with the two major serotypes of HBsAg, AY and AD, was determined utilizing surface plasma resonance (SPR) technology. HBsAg particles were immobilized at about 800 RU onto a Series S CM5 sensor chip and anti-HBsAg antibody flowed over in 2 fold serial dilutions starting at 128 nM to assess binding utilizing the Biacore T200 instrument (GE Heathcare, Cat #28975001, Pittsburgh, Pa.). The $K_D$ was determined by fitting the plot with a 1:1 fit model (O'Shannessy et al. Anal. Biochem 1993; 212: 457-468; Karlsson, Falt J. Immunol. Methods. 1997; 200: 121-133).

Biacore measured $K_D$ values range from 110 pM to 40 nM of the anti-HBsAg antibodies and were comparable across the two major serotypes for each of the antibodies tested (AD and AY). A summary of Biacore affinity data for the anti-HBsAg antibodies is found in Table 4, and the SPR tracings are found in FIGS. 1A/B-16A/B.

TABLE 4

| Antibody | Kd AD (nM) | Kd AY (nM) |
|---|---|---|
| NOV2603 | 15.5 | 3.1 |
| NOV3212 | 1.1 | 0.6 |
| NOV3357 | 0.18 | 0.11 |
| NOV3540 | 0.39 | 0.25 |
| NOV3831 | 0.67 | 0.59 |
| NOV3832 | 0.22 | 0.40 |
| NOV3833 | 0.33 | 0.26 |
| NOV3834 | 40.0 | 5.3 |
| NOV3835 | 33.0 | 11.0 |
| NOV3836 | 29.0 | 10.0 |
| NOV3837 | 0.67 | 0.75 |
| NOV3838 | 0.68 | 0.6 |
| NOV3839 | 0.59 | 2.4 |
| NOV3840 | 0.45 | 0.38 |
| NOV3841 | 0.91 | 0.61 |
| NOV3842 | 0.13 | 0.15 |

Example 3: Neutralization of Hepatitis B Viral Infection by Anti-HBsAg Antibodies Infectious HBV virus was purified from genotype D, serotype ayw cell culture-derived HBV as described (Meier et al., J. Virol Hepat. 2017; 24: 662-671). Anti-HBsAg antibodies were pre-incubated with the virus for 1 hour at 37° C. to allow for binding and neutralization. HepG2-hNTCP1 cells, generated in house as described (Tropberger et al., Proc. Natl. Acad. Sci. U.S.A. 2015; 112: E5715-E5724), were then exposed to the virus-antibody mixture for 24 hrs, replaced with fresh medium, and incubated for 6 additional days to allow for viral entry, cccDNA establishment, and viral protein expression. Supernatant was recovered and HBeAg levels were analyzed by a custom made in-house eAg AlphaScreen assay (Perkin Elmer, Bridgeville Pa.). Data was analyzed using the Envision Plate Reader (Perkin Elmer, Cat #2105-0010, Bridgeville Pa.) and presented as percent of infection relative to untreated control wells.

All antibodies were able to neutralize the infection by HBV with $EC_{50}$ values ranging from 17 pM to 740 pM and this is shown in Table 5 and is show graphically in FIGS. 17-33.

TABLE 5

| Antibody | Virus neutralization $EC_{50}$ (nM) |
|---|---|
| NOV2603 | 0.14 |
| NOV3212 | 0.11 |
| NOV3357 | 0.056 |
| NOV3540 | 0.085 |
| NOV3831 | 0.026 |
| NOV3832 | 0.26 |
| NOV3833 | 0.27 |
| NOV3834 | 0.24 |
| NOV3835 | 0.72 |
| NOV3836 | 0.017 |
| NOV3837 | 0.049 |
| NOV3838 | 0.12 |
| NOV3839 | 0.09 |
| NOV3840 | 0.056 |
| NOV3841 | 0.74 |
| NOV3842 | 0.23 |
| Neg. Control | >500 |

Example 4: Hepatitis B Genotype Binding

The binding of anti-HBsAg antibodies to the 4 major genotypes (A-D) of HBV were analyzed by sandwich ELISA. Briefly, ELISA plates (Thermo Scientific, Cat #15031) were coated with 5 µg/ml horse polyclonal-HBsAg capture antibody (MyBiosource, Cat #MBS315002) for 2 hours at 37° C., then blocked overnight at 4° C. with 5% milk Supernatant collected from HBV cell-culture derived genotypes in pcDNA3.1 backbone (Genotype A: AY934772, Genotype B: AF121245, Genotype C: DQ087960, Genotype D: DQ219811.1) was allowed to bind antibody coated plates for 1 hour. Plates were washed (Alpha diagonostics wash buffer, Cat #80080) and incubated with serial dilutions of anti-HBsAg antibodies in LowCross buffer (Candor, Cat #100500) for 1 hour at room temperature. Following anti-HBsAg antibody incubation plates were washed and incubated with secondary antibody (HRP-conjugated goat anti-human IgG Fab fragment, Jackson ImmunoResearch Inc, Cat #109-035-097) diluted 1:2000 in dilution buffer (LowCross buffer, Candor, Cat #100500) for 1 hour at room temperature. Plates were washed and tetramethylbenzidine (TMB) microwell peroxidase substrate (Alpha Diagnostics, Cat #80091) was used to develop the reactions.

The anti-HBsAg antibodies NOV3834-36 showed similar binding to genotypes A ($IC_{50}$ ranging from 2 to 3.3 nM), genotype B ($IC_{50}$ ranging from 1.2 to 1.7 nM), and genotype D ($IC_{50}$ ranging from 1.3 to 8.2 nM), but showed reduced binding to genotype C ($IC_{50}$ ranging from 12-16 nM). In contrast, the remainder of the anti-HBsAg antibodies showed similar binding across the 4 major genotypes ($IC_{50}$ for genotype A ranging from 0.023 to 2.3 nM, genotype B ranging from 0.017 to 1.5 nM, genotype C ranging from 0.015 to 3.6 nM, and genotype D ranging from 0.026 to 1.3 nM). For example, NOV3832 had $IC_{50}$ of 0.05 nM for genotype A, 0.02 nM for genotype B, 0.015 nM for genotype C and 0.043 nM for genotype D. The $IC_{50}$ for all of the antibodies in Table 6 are shown graphically in FIGS. 34-50.

TABLE 6

| Antibody | $IC_{50}$ nM A | $IC_{50}$ nM B | $IC_{50}$ nM C | $IC_{50}$ nM D |
|---|---|---|---|---|
| NOV2603 | 2.3 | 1.5 | 3.6 | 1.3 |
| NOV3212 | 0.23 | 0.045 | 0.068 | 0.045 |
| NOV3357 | 0.03 | 0.017 | 0.016 | 0.026 |
| NOV3540 | 0.1 | 0.059 | 0.1 | 0.1 |
| NOV3831 | 0.69 | 0.015 | 0.031 | 0.056 |
| NOV3832 | 0.05 | 0.02 | 0.015 | 0.043 |
| NOV3833 | 0.56 | 0.12 | 0.12 | 0.047 |
| NOV3834 | 2 | 1.2 | 16 | 1.3 |
| NOV3835 | 3.3 | 1.4 | 14 | 2 |
| NOV3836 | 3.3 | 1.7 | 12 | 8.2 |
| NOV3837 | 0.093 | 0.069 | 0.17 | 0.1 |
| NOV3838 | 0.2 | 0.05 | 0.21 | 0.081 |
| NOV3839 | 1.6 | 0.17 | 0.37 | 0.097 |
| NOV3840 | 0.023 | 0.022 | 0.016 | 0.045 |
| NOV3841 | 1.1 | 0.35 | 2 | 2.1 |
| NOV3842 | 0.46 | 0.28 | 0.75 | 0.41 |
| Neg. Control | >67 | >67 | >67 | >67 |

Example 5: Anti-HBsAg Recognition of Hepatitis B Clinical Mutations

The binding of anti-HBsAg antibodies to 4 well characterized vaccine and/or HBsAg clinical mutations of HBsAg (G145R, D144A, T126S, M133L) were analyzed by sandwich ELISA. Mutations were generated by Q5 site directed mutagenesis (New England Biolabs, Cat #E0554S) along the HBV Genotype D, (ayw serotype) and the HBsAg sequence cloned into the pCl-neo vector (Promega, Cat #E1841) for generation of stable cell lines. Briefly, ELISA plates (Thermo Scientific, Cat #15031) were coated with 5 μg/ml horse polyclonal-HB sAg capture antibody (MyBioSource, Cat #MBS315002) for 2 hours at 37° C., then blocked overnight at 4° C. with 5% milk Supernatant collected from HBsAg cell-culture derived clinical mutation stables (G145R, D144A, T126S, M133L) was allowed to bind antibody coated plates for 1 hour. Plates were washed (Alpha diagonostics wash buffer, Cat #80080) and incubated with serial dilutions of anti-HBsAg antibodies in LowCross buffer (Candor, Cat #100500) for 1 hour at room temperature. Following anti-HBsAg antibody incubation plates were washed and incubated with secondary antibody (HRP-conjugated goat anti-human IgG Fab fragment, Jackson ImmunoResearch Inc, Cat #109-035-097) diluted 1:2000 in dilution buffer (LowCross buffer, Candor, Cat #100500) for 1 hour at room temperature. Plates were washed and tetramethylbenzidine (TMB) microwell peroxidase substrate (Alpha Diagnostics, Cat #80091) was used to develop the reactions.

As shown in Table 7, the anti-HBsAg antibodies NOV2603, NOV3212, NOV3357, and NOV3540 are able to bind all 4 clinical mutations (G145R $IC_{50}$ values ranging from 0.033 to 5.5 nM, D144A ranging from 0.079 to 2.1 nM, T126S ranging from 0.06 to 0.22 nM, and M133L ranging from 0.012 to 0.67 nM). The antibodies NOV3831, NOV3832, NOV3833, NOV3838, NOV3839, NOV3841 and NOV3842 show loss of binding to the G145R mutation but retain binding to the other 3 clinical mutations (D144A $IC_{50}$ values ranging from 0.012 to 7.8 nM, T126S ranging from 0.01 to 0.11 nM, and M133L ranging from 0.013 to 0.15 nM). In contrast, the anti-HBsAg antibodies NOV3834-36 show either no binding to any of the 4 mutations (NOV3835, NOV3836) or very reduced binding (NOV3835) to just 2 (T126S, M133L) of the clinical mutation panel (T126S $IC_{50}$ value 7.4 nM, M133L IC50 value 9.2 nM). The results shown in Table 7 are also represented graphically in FIGS. 51-66.

TABLE 7

| Antibody | $IC_{50}$ nM Clinical mutation G145R | $IC_{50}$ nM Clinical mutation D144A | $IC_{50}$ nM Clinical mutation T126S | $IC_{50}$ nM Clinical mutation M133L | Control Empty Vector |
|---|---|---|---|---|---|
| NOV2603 | 0.33 | 1.34 | 0.06 | 0.072 | >67 |
| NOV3212 | 0.033 | 0.079 | 0.012 | 0.012 | >67 |
| NOV3357 | 5.5 | 2.1 | 0.22 | 0.67 | >67 |
| NOV3540 | 0.25 | 0.16 | 0.063 | 0.091 | >67 |
| NOV3831 | >67 | 3.6 | 0.0093 | 0.0058 | >67 |
| NOV3832 | >67 | 0.99 | 0.034 | 0.034 | >67 |
| NOV3833 | >67 | 2.8 | 0.025 | 0.036 | >67 |
| NOV3834 | >67 | >67 | 7.4 | 9.2 | >67 |
| NOV3835 | >67 | >67 | >67 | >67 | >67 |
| NOV3836 | >67 | >67 | >67 | >67 | >67 |
| NOV3837 | >67 | 0.27 | 0.03 | 0.035 | >67 |
| NOV3838 | 5.2 | 6.1 | 0.11 | 0.15 | >67 |
| NOV3839 | 8.6 | 3.6 | 0.088 | 0.085 | >67 |
| NOV3840 | >67 | 0.012 | 0.01 | 0.013 | >67 |
| NOV3841 | >67 | 7.8 | 0.079 | 0.044 | >67 |
| NOV3842 | >67 | 0.12 | 0.042 | 0.084 | >67 |

Example 6: Anti-HBsAg Antibodies Show Efficacy in a FRGN Mouse Model

In vivo efficacy for the anti-HBsAg antibodies was determined in a HBV-infected FRGN mouse model by monitoring loss of HBsAg following antibody administration. Human liver populated FRGN mice were purchased from Yecuris (FRGN KO on NOD, Cat #10-0013) and infected with $1.7\times10^7$ copies HBV (Genotype C). Following stable infection, mice were treated with 20 mg/ml anti-HBsAg antibodies (n=2 per group) at day 0 and day 21 with serum collected at timepoints 0, 0.02, 0.3, 1, 3, 7, 14, 21, 24, and 28 days post initial antibody treatment. Free HBsAg levels were monitored through a protocol from Zhang et. al., Gut 2016; (4) 65: 658-671. Briefly, serum was diluted 1:5 in sample diluent (provided in Alpha Diagnostic International, Cat #4110), 0.5 volumes lysis buffer added (15% sodium dodecyl sulphate in 20 mM Tris HCL buffer-pH 8.0) and samples incubated for 1 hour at 37° C. Samples were neutralized with the addition of 5 volumes 4% CHAPS dissolved in 20 mM Tris HCL buffer-pH 8.0 and HBsAg levels monitored utilizing an HBsAg commercial ELISA kit (Alpha Diagnostic International, Cat #4110) following the manufacturers protocol. HBsAg levels graphed as log fold change from prebleed levels collected at timepoint 0. Maxium log fold change for this model was −3.9.

Figure 67:
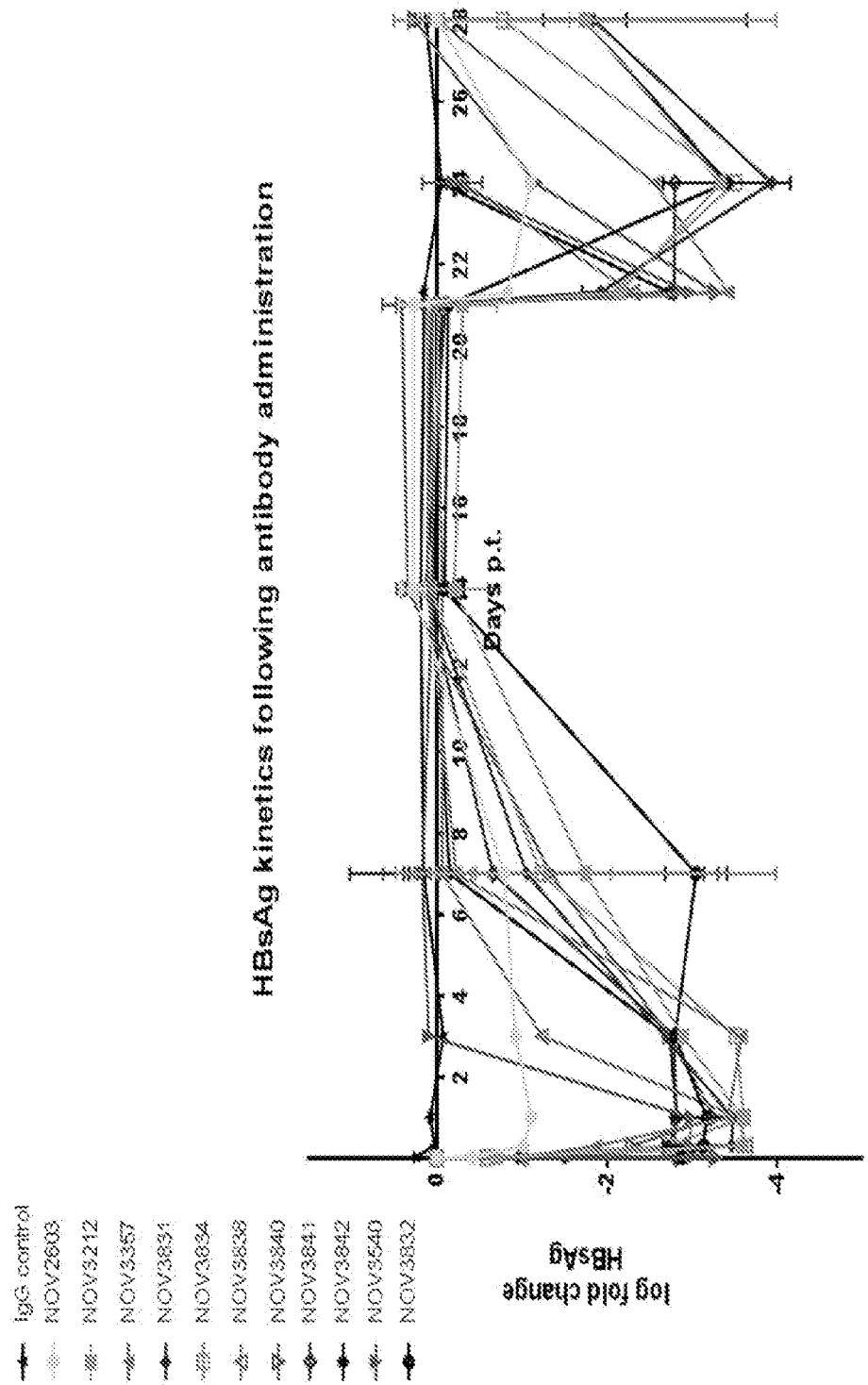
FIG. 67 shows the efficacy of the antibodies, reducing the amount of HBsAg in an FRGN mouse model.

Anti-HBsAg antibodies NOV3212, NOV3357, NOV3540, NOV3831, NOV3832, NOV3834, NOV3838, NOV3841 and NOV3842 all significantly dropped the levels of HBsAg with the max log drop ranging from −3.9 to −2.8, as shown in Table 8. In contrast, NOV2603 showed only a moderate log drop of HBsAg (−1.1). For example, in FIG. 67, NOV3832 greatly reduced HBsAg at the 0.3 day time point and kept the HBsAg level reduced for 7 days, with only a slow increase in HBsAg levels to day 14. After the second administration of NOV3832 at day 21, HBsAg levels were again reduced, and remained reduced until the end of the study on day 28. Thus, this study demonstrated that the anti-HBsAg antibodies of the disclosure can greatly reduce HBsAg in the serum in vivo.

TABLE 8

| Antibody | Max ΔHBsAg log reduction |
| --- | --- |
| NOV2603 | −1.1 |
| NOV3212 | −3.6 |
| NOV3357 | −3.6 |
| NOV3540 | −2.8 |
| NOV3831 | −3.9 |
| NOV3832 | −3.6 |
| NOV3834 | −3.6 |
| NOV3838 | −3.6 |
| NOV3840 | −3.3 |
| NOV3841 | −2.8 |
| NOV3842 | −2.8 |
| Neg. Control | 0 |

Example 7: Anti-HBsAg Cytotoxicity

Cytotoxicity of the anti-HBsAg antibodies on both de novo HBV infected and non-infected HepG2-hNTCP1 cells (Tropberger et al. Proc. Natl. Acad. Sci. U.S.A. 2015; 112: E5715-E5724) was measured utilizing CellTiter-Glo (Promega, Cat #G7570), which monitors metabolic activity of cells through ATP concentration. In brief, HepG2-hNTCP1 cells were infected with either purified virus from genotype D (serotype ayw) cell culture-derived HBV or mock virus as described (Meier et al. J. Virol Hepat. 2017; 24: 662-671). Cells were cultured for 4 days following infection to allow for viral entry, cccDNA establishment, and viral protein expression, media removed and replaced with fresh media containing serial dilutions of anti-HBsAg antibodies starting at 3.3 µM. Cells incubated with antibody mixture for an additional 4 days and then assayed with CellTiter-Glo reagent per manufactor protocol. Luminescence readout was performed using a PHERAstar microplate reader (BMG Labtech, Cary N.C.) and percent viability was presented relative to the negative (no antibody) control.

All of the anti-HBsAg antibodies of the disclosure show no effect on cell viability in the presence or absence of virus. In brief, the anti-HBsAg antibodies of the disclosure show no toxicity. This is in contrast to two published antibodies, CR8097 and HB48-59, which show cytotoxicity (CC50s ranging from 2.24 to 2.86 uM for uninfected HepG2-NTCP1, and 2.09 to 2.11 uM for HBV infected HepG2-NTCP1). As the CR8097 and HB48-59 antibodies show toxicity to uninfected cells at the same level as infected cells, this indicates that these antibodies are binding to off-target, normal cell proteins.

TABLE 9

| Antibody | CC50 (no virus) (µM) | CC50 (HBV infected) (µM) |
| --- | --- | --- |
| NOV2603 | >3.3 | >3.3 |
| NOV3212 | >3.3 | >3.3 |
| NOV3357 | >3.3 | >3.3 |
| NOV3540 | >3.3 | >3.3 |
| NOV3831 | >3.3 | >3.3 |
| NOV3832 | >3.3 | >3.3 |
| NOV3833 | >3.3 | >3.3 |
| NOV3834 | >3.3 | >3.3 |
| NOV3835 | >3.3 | >3.3 |
| NOV3836 | >3.3 | >3.3 |
| NOV3837 | >3.3 | >3.3 |
| NOV3838 | >3.3 | >3.3 |
| NOV3839 | >3.3 | >3.3 |
| NOV3840 | >3.3 | >3.3 |
| NOV3841 | >3.3 | >3.3 |
| NOV3842 | >3.3 | >3.3 |
| Pos Control (puromycin) | 0.0003 nM | 0.0006 nM |
| Published antibodies | | |
| HBC34 | >3.3 | >3.3 |
| CR8097 | 2.86 | 2.11 |
| Green27 | >3.3 | >3.3 |
| HB48-33 | >3.3 | >3.3 |
| HB48-35 | >3.3 | >3.3 |
| HB48-59 | 2.24 | 2.09 |

Example 8: Eptiope Binning by SPR for Anti-HBsAg Antibodies

Epitope binning of anti-HBsAg antibodies with the two major serotypes of HBsAg, AY and AD, was performed utilizing surface plasmon resonance (SPR) technology. Antigens HBsAg AD and AY (TRINA Bioreactives AG, Cat #0824 [AD serotype], #0823 [AY serotype], Naenikon, Switzerland) were immobilized at about 800 RU in separate cells on the surface of a CM5 chip by amine coupling. Each pair of antibodies was tested for blocking one another's binding to their epitope on the antigen by subsequently applying one antibody as first (saturating) followed by the other as second (competing) antibody and vice versa. Saturating antibodies were applied at 500 nM for 120s. Competing antibodies utilized the same conditions but were supplemented with the first antibody at 500 nM to maintain saturation. Binding signals were corrected by subtracting the reference cell signal. Specific binding of the competing antibody in presence of the saturating antibody was calculated by subtracting a saturating antibody plus buffer reference signal. All signals were normalized to 100 RU of immobilized ligand. The specific binding signal obtained from the application as competing antibody was expressed as percentage of the binding signal obtained from the application of the same antibody as saturating (first) antibody, the signal of which was regarded 100% binding. Binding values less than 40% indicate that the first and second antibody cover the same region, and values greater than 60% represent different epitopes. The results indicate that the antibodies NOV3540, NOV3832, NOV3841 and NOV3842 do not compete with either CR8087 or HBC34 antibodies. Thus NOV3540, NOV3832, NOV3841 and NOV3842 bind different epitopes than CR8087 or HBC34. Results are show below in Table 10.

TABLE 10

| | HBsAg AD serotype | | | | | | |
|---|---|---|---|---|---|---|---|
| | CR8087 | | | | HBC34 | | |
| 2nd Ab | 1st Ab | 2nd Ab | 1st Ab | 2nd Ab | 1st Ab | 2nd Ab | 1st Ab |
| NOV3540 | 254 | 105 | NOV3540 | NOV3540 | 111 | 121 | NOV3540 |
| NOV3832 | 223 | 103 | NOV3832 | NOV3832 | 176 | 126 | NOV3832 |
| NOV3841 | 282 | 104 | NOV3841 | NOV3841 | 145 | 124 | NOV3841 |
| NOV3842 | 216 | 106 | NOV3842 | NOV3842 | 115 | 121 | NOV3842 |
| HBC34 | 146 | 98 | HBC34 | HBC34 | 0 | 0 | HBC34 |
| CR8087 | 0 | 0 | CR8087 | CR8087 | 98 | 146 | CR8087 |
| | HBsAg AY serotype | | | | | | |
| | CR8087 | | | | HBC34 | | |
| 2nd Ab | 1st Ab | 2nd Ab | 1st Ab | 2nd Ab | 1st Ab | 2nd Ab | 1st Ab |
| NOV3540 | 118 | 107 | NOV3540 | NOV3540 | 102 | 131 | NOV3540 |
| NOV3832 | 117 | 113 | NOV3832 | NOV3832 | 113 | 257 | NOV3832 |
| NOV3841 | 129 | 105 | NOV3841 | NOV3841 | 107 | 151 | NOV3841 |
| NOV3842 | 118 | 109 | NOV3842 | NOV3842 | 103 | 134 | NOV3842 |
| HBC34 | 166 | 107 | HBC34 | HBC34 | 0 | 0 | HBC34 |
| CR8087 | 0 | 0 | CR8087 | CR8087 | 107 | 166 | CR8087 |

Binding of second antibody <40: First and second antibody cover the same region
Binding of second antibody >60: First and second antibody have different epitopes Example 9: Formulation The anti-HBsAg virus antibodies described herein are monoclonal antibodies, IgG1 isotype with kappa or lambda light chains, and can be lyophilized. For subsequent intravenous administration, the obtained solution will usually be further diluted into a carrier solution to the ready-to-use antibody solution for infusion. Important stability-indicating analytical methods to select the most stable formulation encompassed, amongst others, size-exclusion chromatography to determine aggregation levels, subvisible particulate matter testing, and potency testing.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. An isolated antibody, wherein said antibody or antigen binding fragment thereof comprises:
 (i) a heavy chain variable region that comprises (a) a HCDR1 (CDR-Complementarity Determining Region) of SEQ ID NO: 9, (b) a HCDR2 of SEQ ID NO:10, (c) a HCDR3 of SEQ ID NO:11 and a light chain variable region that comprises: (d) a LCDR1 of SEQ ID NO:25, (e) a LCDR2 of SEQ ID NO:26, and (f) a LCDR3 of SEQ ID NO:27;
 (ii) a heavy chain variable region that comprises (a) a HCDR1 of SEQ ID NO:41, (b) a HCDR2 of SEQ ID NO:42, (c) a HCDR3 of SEQ ID NO:43; and a light chain variable region that comprises: (d) a LCDR1 of SEQ ID NO:57, (e) a LCDR2 of SEQ ID NO:58, and (f) a LCDR3 of SEQ ID NO:59;
 (iii) a heavy chain variable region that comprises (a) a HCDR1 of SEQ ID NO:73, (b) a HCDR2 of SEQ ID NO:74, (c) a HCDR3 of SEQ ID NO:75; and a light chain variable region that comprises: (d) a LCDR1 of SEQ ID NO:89, (e) a LCDR2 of SEQ ID NO:90, and (f) a LCDR3 of SEQ ID NO:91;
 (iv) a heavy chain variable region that comprises: (a) a HCDR1 of SEQ ID NO:105, (b) a HCDR2 of SEQ ID NO:106, (c) a HCDR3 of SEQ ID NO:107; and a light chain variable region that comprises: (d) a LCDR1 of SEQ ID NO:121, (e) a LCDR2 of SEQ ID NO:122, and (f) a LCDR3 of SEQ ID NO:123;
 (v) a heavy chain variable region that comprises: (a) a HCDR1 of SEQ ID NO:137, (b) a HCDR2 of SEQ ID NO:138, (c) a HCDR3 of SEQ ID NO:139; and a light chain variable region that comprises: (d) a LCDR1 of SEQ ID NO:153, (e) a LCDR2 of SEQ ID NO:154, and (f) a LCDR3 of SEQ ID NO:155;
 (vi) a heavy chain variable region that comprises: (a) a HCDR1 of SEQ ID NO:169, (b) a HCDR2 of SEQ ID NO:170, (c) a HCDR3 of SEQ ID NO:171; and a light chain variable region that comprises: (d) a LCDR1 of SEQ ID NO:185, (e) a LCDR2 of SEQ ID NO:186, and (f) a LCDR3 of SEQ ID NO:187;
 (vii) a heavy chain variable region that comprises: (a) a HCDR1 of SEQ ID NO:201, (b) a HCDR2 of SEQ ID NO: 202, (c) a HCDR3 of SEQ ID NO:203; and a light chain variable region that comprises: (d) a LCDR1 of SEQ ID NO:217, (e) a LCDR2 of SEQ ID NO:218, and (f) a LCDR3 of SEQ ID NO:219;
 (viii) a heavy chain variable region that comprises: (a) a HCDR1 of SEQ ID NO:233, (b) a HCDR2 of SEQ ID NO:234, (c) a HCDR3 of SEQ ID NO:235; and a light chain variable region that comprises: (d) a LCDR1 of SEQ ID NO:249, (e) a LCDR2 of SEQ ID NO:250, and (f) a LCDR3 of SEQ ID NO:251;
 (ix) a heavy chain variable region that comprises: (a) a HCDR1 of SEQ ID NO:265, (b) a HCDR2 of SEQ ID NO: 266, (c) a HCDR3 of SEQ ID NO:267; and a light chain variable region that comprises: (d) a LCDR1 of SEQ ID NO:281, (e) a LCDR2 of SEQ ID NO:282, and (f) a LCDR3 of SEQ ID NO: 283;
 (x) a heavy chain variable region that comprises: (a) a HCDR1 of SEQ ID NO:297, (b) a HCDR2 of SEQ ID NO: 298, (c) a HCDR3 of SEQ ID NO:299; and a light chain variable region that comprises: (d) a LCDR1 of SEQ ID NO:313, (e) a LCDR2 of SEQ ID NO:314, and (f) a LCDR3 of SEQ ID NO: 315;
 (xi) a heavy chain variable region that comprises: (a) a HCDR1 of SEQ ID NO:329, (b) a HCDR2 of SEQ ID NO:330, (c) a HCDR3 of SEQ ID NO:331; and a light chain variable region that comprises: (d) a LCDR1 of SEQ ID NO:345, (e) a LCDR2 of SEQ ID NO:346, and (f) a LCDR3 of SEQ ID NO: 347;
 (xii) a heavy chain variable region that comprises: (a) a HCDR1 of SEQ ID NO:361, (b) a HCDR2 of SEQ ID NO:362, (c) a HCDR3 of SEQ ID NO:363; and a light chain variable region that comprises: (d) a LCDR1 of SEQ ID NO:377, (e) a LCDR2 of SEQ ID NO:378, and (f) a LCDR3 of SEQ ID NO: 379;
 (xiii) a heavy chain variable region that comprises: (a) a HCDR1 of SEQ ID NO:393, (b) a HCDR2 of SEQ ID NO:394, (c) a HCDR3 of SEQ ID NO:395; and a light chain variable region that comprises: (d) a LCDR1 of SEQ ID NO:409, (e) a LCDR2 of SEQ ID NO:410, and (f) a LCDR3 of SEQ ID NO:411;
 (xiv) a heavy chain variable region that comprises: (a) a HCDR1 of SEQ ID NO:425, (b) a HCDR2 of SEQ ID NO:426, (c) a HCDR3 of SEQ ID NO:427; and a light chain variable region that comprises: (d) a LCDR1 of SEQ ID NO:441, (e) a LCDR2 of SEQ ID NO:442, and (f) a LCDR3 of SEQ ID NO: 443;
 (xv) a heavy chain variable region that comprises: (a) a HCDR1 of SEQ ID NO:457, (b) a HCDR2 of SEQ ID NO:458, (c) a HCDR3 of SEQ ID NO:459; and a light chain variable region that comprises: (d) a LCDR1 of SEQ ID NO:473, (e) a LCDR2 of SEQ ID NO:474, and (f) a LCDR3 of SEQ ID NO:475; or
 (xvi) a heavy chain variable region that comprises: (a) a HCDR1 of SEQ ID NO:489, (b) a HCDR2 of SEQ ID NO:490, (c) a HCDR3 of SEQ ID NO:491; and a light chain variable region that comprises: (d) a LCDR1 of SEQ ID NO:505, (e) a LCDR2 of SEQ ID NO:506, and (f) a LCDR3 of SEQ ID NO: 507.

2. The antibody of claim 1, wherein one or two amino acids within a CDR have been modified, deleted or substituted.

3. The antibody of claim 1, that retains at least 90, 91, 92, 93, 94, 95, 96, 97, 98 or 99% identity over either the variable heavy chain region or the variable light chain region.

4. The antibody of claim 1, wherein the antibody is a monoclonal antibody, a chimeric antibody, a humanized antibody, a human engineered antibody, a human antibody, a single chain antibody (scFv) or an antibody fragment.

5. An isolated antibody or antigen binding fragment thereof, wherein said antibody or antigen binding fragment thereof comprises:

(i) a heavy chain variable region (vH) that comprises SEQ ID NO:18, and a light chain variable region (vL) that comprises SEQ ID NO: 34;
(ii) a heavy chain variable region (vH) that comprises SEQ ID NO: 50, and a light chain variable region (vL) that comprises SEQ ID NO: 66;
(iii) a heavy chain variable region (vH) that comprises SEQ ID NO: 82, and a light chain variable region (vL) that comprises SEQ ID NO:98;
(iv) a heavy chain variable region (vH) that comprises SEQ ID NO:114, and a light chain variable region (vL) that comprises SEQ ID NO:130;
(v) a heavy chain variable region (vH) that comprises SEQ ID NO:146, and a light chain variable region (vL) that comprises SEQ ID NO:162;
(vi) a heavy chain variable region (vH) that comprises SEQ ID NO:178, and a light chain variable region (vL) that comprises SEQ ID NO:194;
(vii) a heavy chain variable region (vH) that comprises SEQ ID NO:210, and a light chain variable region (vL) that comprises SEQ ID NO:226;
(viii) a heavy chain variable region (vH) that comprises SEQ ID NO:242, and a light chain variable region (vL) that comprises SEQ ID NO:258;
(ix) a heavy chain variable region (vH) that comprises SEQ ID NO:274, and a light chain variable region (vL) that comprises SEQ ID NO:290;
(x) a heavy chain variable region (vH) that comprises SEQ ID NO:306, and a light chain variable region (vL) that comprises SEQ ID NO:322;
(xi) a heavy chain variable region (vH) that comprises SEQ ID NO:338, and a light chain variable region (vL) that comprises SEQ ID NO:354;
(xii) a heavy chain variable region (vH) that comprises SEQ ID NO:370, and a light chain variable region (vL) that comprises SEQ ID NO:386;
(xiii) a heavy chain variable region (vH) that comprises SEQ ID NO:402, and a light chain variable region (vL) that comprises SEQ ID NO:418;
(xiv) a heavy chain variable region (vH) that comprises SEQ ID NO:434, and a light chain variable region (vL) that comprises SEQ ID NO:450;
(xv) a heavy chain variable region (vH) that comprises SEQ ID NO:466, and a light chain variable region (vL) that comprises SEQ ID NO:482; or
(xvi) a heavy chain variable region (vH) that comprises SEQ ID NO:498, and a light chain variable region (vL) that comprises SEQ ID NO:514.

6. The antibody or fragment thereof of claim 5, that retains at least 90, 91, 92, 93, 94, 95, 96, 97, 98 or 99% identity over either the variable light or variable heavy region.

7. The antibody of claim 5, wherein one, two, three, four or five, but less than 10 amino acids within the variable light or variable heavy region have been modified, deleted or substituted.

8. The antibody of claim 5, wherein the antibody is a monoclonal antibody, a chimeric antibody, a humanized antibody, a human engineered antibody, a human antibody, a single chain antibody (scFv) or an antibody fragment.

9. The antibody of claim 1 wherein the antibody or fragment thereof has reduced glycosylation or no glycosylation or is hypofucosylated.

10. A pharmaceutical composition comprising the antibody or fragment thereof, of claim 1, further comprising a pharmaceutically acceptable carrier.

11. A pharmaceutical composition comprising a plurality of an antibody or antigen binding fragment of claim 1, wherein at least 0.05%, 0.1%, 0.5%, 1%, 2%, 3%, 5% or more or more of the antibodies in the composition have an α2,3-linked sialic acid residue.

12. A pharmaceutical composition comprising a plurality of an antibody or antigen binding fragment of claim 1, wherein none of the antibodies comprise a bisecting GlcNAc.

13. The pharmaceutical composition comprising the antibody or fragment thereof of claim 1, wherein the composition is prepared as a lyophilisate.

14. A method of neutralizing a hepatitis B virus infection comprising administering via injection or infusion to a patient in need an effective amount of the antibody of claim 1.

15. A method of treating or reducing the likelihood of hepatitis B virus associated disorder, comprising administering via injection or infusion to a patient in need an effective amount of the antibody of claim 1, and wherein the disorder is: liver failure, cirrhosis, or hepatocellular carcinoma.

16. A nucleic acid that encodes the antibody or antigen binding fragment of claim 1.

17. A vector comprising the nucleic acid of claim 16.

18. A host cell comprising the vector of claim 17.

19. A diagnostic reagent comprising the antibody or antigen binding fragment thereof of claim 1 which is labeled.

* * * * *

```
                         SEQUENCE LISTING

<160> NUMBER OF SEQ ID NOS: 517

<210> SEQ ID NO 1
<211> LENGTH: 226
<212> TYPE: PRT
<213> ORGANISM: Hepatitis B virus

<400> SEQUENCE: 1

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Ser Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
```

```
            130                 135                 140
Gly Asn Cys Thr Cys Ile Pro Ile Pro Ser Ser Trp Ala Phe Ala Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Asn Ile
                195                 200                 205

Leu Ser Pro Phe Leu Pro Leu Leu Pro Ile Phe Phe Cys Leu Trp Val
                210                 215                 220

Tyr Ile
225

<210> SEQ ID NO 2
<211> LENGTH: 226
<212> TYPE: PRT
<213> ORGANISM: Hepatitis B virus

<400> SEQUENCE: 2

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ala Pro Thr Cys
            35                  40                  45

Pro Gly Gln Asn Ser Gln Ser Pro Thr Ser Asn His Ser Pro Thr Ser
50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
                100                 105                 110

Thr Ser Thr Thr Ser Thr Gly Pro Cys Arg Thr Cys Thr Ile Pro Ala
            115                 120                 125

Gln Gly Thr Ser Met Phe Pro Ser Cys Cys Cys Thr Lys Pro Ser Asp
130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Ala Ile Trp Met Met Trp Tyr Trp Gly Pro Ser Leu Tyr Asn Ile
                195                 200                 205

Leu Ser Pro Phe Leu Pro Leu Leu Pro Ile Phe Phe Cys Leu Trp Val
                210                 215                 220

Tyr Ile
225

<210> SEQ ID NO 3
<211> LENGTH: 226
<212> TYPE: PRT
<213> ORGANISM: Hepatitis B virus
```

```
<400> SEQUENCE: 3

Met Glu Ser Thr Thr Ser Gly Phe Leu Gly Pro Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Leu Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
            115                 120                 125

Gln Gly Thr Ser Met Phe Pro Ser Cys Cys Cys Thr Lys Pro Ser Asp
            130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
            195                 200                 205

Leu Ser Pro Phe Leu Pro Leu Leu Pro Ile Phe Phe Cys Leu Trp Val
    210                 215                 220

Tyr Ile
225

<210> SEQ ID NO 4
<211> LENGTH: 226
<212> TYPE: PRT
<213> ORGANISM: Hepatitis B virus

<400> SEQUENCE: 4

Met Glu Asn Ile Thr Ser Gly Phe Leu Gly Pro Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Thr Thr Pro Ala
            115                 120                 125
```

-continued

```
Gln Gly Thr Ser Met Tyr Pro Ser Cys Cys Cys Thr Lys Pro Ser Asp
        130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
210                 215                 220

Tyr Ile
225
```

<210> SEQ ID NO 5
<211> LENGTH: 226
<212> TYPE: PRT
<213> ORGANISM: Hepatitis B virus

<400> SEQUENCE: 5

```
Met Glu Asn Ile Thr Ser Gly Leu Leu Gly Pro Leu Leu Val Leu Gln
1               5                   10                  15

Ala Val Cys Phe Leu Leu Thr Lys Ile Leu Thr Ile Pro Lys Ser Leu
            20                  25                  30

Asp Ser Trp Trp Thr Ser Leu Asn Phe Leu Gly Val Pro Pro Gly Cys
        35                  40                  45

Pro Gly Gln Asn Ser Gln Ser Pro Ile Ser Asn His Leu Pro Thr Ser
50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
                100                 105                 110

Ser Thr Thr Thr Ser Thr Gly Pro Cys Lys Thr Cys Thr Thr Leu Ala
            115                 120                 125

Gln Gly Thr Ser Met Phe Pro Ser Cys Cys Cys Thr Lys Pro Ser Asp
        130                 135                 140

Gly Asn Cys Thr Cys Ile Pro Ile Pro Ser Ser Trp Ala Phe Gly Lys
145                 150                 155                 160

Tyr Leu Trp Glu Trp Ala Ser Ala Arg Phe Ser Trp Leu Ser Leu Leu
                165                 170                 175

Val Gln Phe Val Gln Trp Cys Val Gly Leu Ser Pro Thr Val Trp Leu
            180                 185                 190

Leu Val Ile Trp Met Ile Trp Tyr Trp Gly Pro Asn Leu Cys Ser Ile
        195                 200                 205

Leu Ser Pro Phe Ile Pro Leu Leu Pro Ile Phe Cys Tyr Leu Trp Ala
210                 215                 220

Ser Ile
225
```

<210> SEQ ID NO 6
<211> LENGTH: 10
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 6

Gly Phe Thr Phe Asp Asn Tyr Ala Met Ser
1               5                   10

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser Ile Ser Gly Ser Gly Gly Ser Thr Tyr Tyr Ala Asp Ser Val Lys
1               5                   10                  15

Gly

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Ser Ile Leu Ser Gly Gly His Ala Arg Val Tyr Gly Ile Asp Val
1               5                   10                  15

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Asn Tyr Ala Met Ser
1               5

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Ile Ser Gly Ser Gly Gly Ser Thr Tyr Tyr Ala Asp Ser Val Lys
1               5                   10                  15

Gly

<210> SEQ ID NO 11
<211> LENGTH: 16
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 11

Ser Ser Ile Leu Ser Gly Gly His Ala Arg Val Tyr Gly Ile Asp Val
1               5                   10                  15

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Phe Thr Phe Asp Asn Tyr
1               5

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gly Ser Gly Gly Ser
1               5

<210> SEQ ID NO 14
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Ser Ile Leu Ser Gly Gly His Ala Arg Val Tyr Gly Ile Asp Val
1               5                   10                  15

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Phe Thr Phe Asp Asn Tyr Ala
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 16

Ile Ser Gly Ser Gly Gly Ser Thr
1               5

<210> SEQ ID NO 17
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala Lys Ser Ser Ile Leu Ser Gly Gly His Ala Arg Val Tyr Gly Ile
1               5                   10                  15

Asp Val

<210> SEQ ID NO 18
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Met Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met Ser Trp Val Arg Gln Val Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ile Leu Ser Gly Gly His Ala Arg Val Tyr Gly Ile
            100                 105                 110

Asp Val Trp Gly Gln Gly Thr Thr Val Thr Val Ser Ser
        115                 120                 125

<210> SEQ ID NO 19
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
gagatgcagg tcttggaatc tggcggagga ctggttcaac tggcggctc tctgagactg     60 tcttgtgccg ccagcggctt caccttcgat aactacgcca tgtcctgggt ccgacaggtg    120
ccaggcaaag gactggaatg ggtgtcctct atcagcggct ctggcggcag cacatattac    180
gccgatagcg tgaagggcca gttcaccatc agccgggaca acagcaagaa caccctgtac    240

-continued

```
ctccagatga acagcctgag agccgaggat accgccgtgt actactgtgc caagagcagc    300
attctgtctg gcggccacgc cagagtgtat ggcattgatg tttggggcca gggaaccacc    360
gtgaccgtta gttct                                                     375
```

```
<210> SEQ ID NO 20
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Met Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Ala Met Ser Trp Val Arg Gln Val Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ile Leu Ser Gly His Ala Arg Val Tyr Gly Ile
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
                    325                 330                 335
Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 21
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gagatgcagg tcttggaatc tggcggagga ctggttcaac ctggcggctc tctgagactg      60
tcttgtgccg ccagcggctt caccttcgat aactacgcca tgtcctgggt ccgacaggtg     120
ccaggcaaag gactggaatg ggtgtcctct atcagcggct ctggcggcag cacatattac     180
gccgatagcg tgaagggcca gttcaccatc agccgggaca cagcaagaa caccctgtac     240 ctccagatga acagcctgag agccgaggat accgccgtgt actactgtgc aagagcagc     300 attctgtctg gcggccacgc cagagtgtat ggcattgatg tttggggcca gggaaccacc     360
gtgaccgtta gttctgctag caccaagggc cccagcgtgt tcccctggc ccccagcagc     420 aagagcacca gcggcggcac agccgccctg ggctgcctgg tgaaggacta cttccccgag     480
cccgtgaccg tgtcctggaa cagcggagcc ctgacctccg gcgtgcacac cttccccgcc     540
gtgctgcaga gcagcggcct gtacagcctg tccagcgtgg tgacagtgcc agcagcagc     600 ctgggcaccc agacctacat ctgcaacgtg aaccacaagc ccagcaacac caaggtggac     660
aagagagtgg agcccaagag ctgcgacaag acccacacat gccccccctg cccggcgcca     720
gagctgctgg gcggaccctc cgtgttcctg ttccccccca gcccaagga cacctgatg     780 atcagcagga ccccgaggt gacctgcgtg gtggtggacg tgagccacga ggacccagag     840
gtgaagttca actggtacgt ggacggcgtg gaggtgcaca cgccaagac caagcccaga     900 gaggagcagt acaacagcac ctacagggtg gtgtccgtgc tgaccgtgct gcaccaggac     960
tggctgaacg gcaaggaata caagtgcaag gtctccaaca aggccctgcc agccccatc    1020 gaaaagacca tcagcaaggc caagggccag ccacgggagc ccaggtgta caccctgccc    1080 ccctcccggg aggagatgac caagaaccag gtgtccctga cctgtctggt gaagggcttc    1140
taccccagcg acatcgccgt ggagtgggag agcaacggcc agcccgagaa caactacaag    1200 accaccccccc cagtgctgga cagcgacggc agcttcttcc tgtacagcaa gctgaccgtg    1260
```

```
gacaagtcca ggtggcagca gggcaacgtg ttcagctgca gcgtgatgca cgaggccctg    1320
cacaaccact acacccagaa gagcctgagc ttaagccccg gcaag                    1365
```

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Gly Asn Asn Ile Gly Ser Gln Ser Val His
1               5                   10

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Asp Thr Asp Arg Pro Ser
1               5

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Val Trp Asp Ser Ser Ser Asp His Val Val
1               5                   10

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Asn Asn Ile Gly Ser Gln Ser Val His
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Asp Thr Asp Arg Pro Ser
1               5

```
<210> SEQ ID NO 27
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Val Trp Asp Ser Ser Ser Asp His Val Val
1               5                   10

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asn Asn Ile Gly Ser Gln Ser
1               5

<210> SEQ ID NO 29
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Asp Thr
1

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Trp Asp Ser Ser Ser Asp His Val
1               5

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asn Ile Gly Ser Gln Ser
1               5

<210> SEQ ID NO 32
<211> LENGTH: 3
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asp Asp Thr
1

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gln Val Trp Asp Ser Ser Ser Asp His Val Val
1               5                   10

<210> SEQ ID NO 34
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Ser Ala Leu Thr Gln Pro Pro Ser Val Ser Val Ala Pro Gly Gln
1               5                   10                  15

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
        35                  40                  45

Asp Asp Thr Asp Arg Pro Ser Gly Ile Pro Ala Arg Phe Ser Gly Ser
    50                  55                  60

Ser Ser Gly Ser Thr Ala Thr Leu Thr Ile Gly Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 35
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
cagtctgccc tgactcagcc accctcggtg tcagtggccc caggacagac ggccaggatt      60
acctgtgggg gaaacaacat tggaagtcaa agtgtgcact ggtaccagca gaagccaggc     120
caggccccta tactggtcgt ctatgatgat accgaccggc cctcagggat ccctgcgcga     180
ttctctggct ccagctctgg gagcacggcc accctgacca tcggcagggt cgaagccggg     240
```

```
gatgaggccg actattactg tcaggtgtgg gatagtagta gtgatcatgt ggtattcggc      300
ggagggacca agctgaccgt ctta                                             324
```

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Gln Ser Ala Leu Thr Gln Pro Pro Ser Val Ser Val Ala Pro Gly Gln
1               5                   10                  15

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
        35                  40                  45

Asp Asp Thr Asp Arg Pro Ser Gly Ile Pro Ala Arg Phe Ser Gly Ser
    50                  55                  60

Ser Ser Gly Ser Thr Ala Thr Leu Thr Ile Gly Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 37
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
cagtctgccc tgactcagcc accctcggtg tcagtggccc caggacagac ggccaggatt       60
acctgtgggg gaaacaacat tggaagtcaa agtgtgcact ggtaccagca gaagccaggc      120
caggccccta tactggtcgt ctatgatgat accgaccggc cctcagggat ccctgcgcga      180
ttctctggct ccagctctgg gagcacggcc accctgacca tcggcagggt cgaagccggg      240
```

```
gatgaggccg actattactg tcaggtgtgg gatagtagta gtgatcatgt ggtattcggc    300
ggagggacca agctgaccgt cttaagtcag cccaaggctg cccctcggt cactctgttc     360 ccgcccctcct ctgaggagct tcaagccaac aaggccacac tggtgtgtct cataagtgac   420
ttctacccgg gagccgtgac agtggcctgg aaggcagata gcagcccgt caaggcggga    480 gtggagacca ccacaccctc caaacaaagc aacaacaagt acgccgccag cagctacctg    540
agcctgaccc ccgagcagtg gaagagccac agaagctaca gctgccaggt cacccacgag    600
ggcagcaccg tggagaaaac cgtggccccc accgagtgca gc                      642
```

```
<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Phe Thr Phe His Asn Tyr Ala Met Ser
1               5                   10

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ser Ile Ser Gly Ser Gly Gly Ser Thr Tyr Tyr Ala Asp Ser Val Lys
1               5                   10                  15
Gly

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ser Ser Ile Leu Ser Gly Gly His Ala Arg Val Tyr Gly Ile Asp Val
1               5                   10                  15

<210> SEQ ID NO 41
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Asn Tyr Ala Met Ser
1               5

<210> SEQ ID NO 42
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Ile Ser Gly Ser Gly Gly Ser Thr Tyr Tyr Ala Asp Ser Val Lys
1               5                   10                  15

Gly

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ser Ser Ile Leu Ser Gly Gly His Ala Arg Val Tyr Gly Ile Asp Val
1               5                   10                  15

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Phe Thr Phe His Asn Tyr
1               5

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Gly Ser Gly Gly Ser
1               5

<210> SEQ ID NO 46
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ser Ser Ile Leu Ser Gly Gly His Ala Arg Val Tyr Gly Ile Asp Val
1               5                   10                  15

<210> SEQ ID NO 47
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 47

Gly Phe Thr Phe His Asn Tyr Ala
1               5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ile Ser Gly Ser Gly Gly Ser Thr
1               5

<210> SEQ ID NO 49
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Lys Ser Ser Ile Leu Ser Gly Gly His Ala Arg Val Tyr Gly Ile
1               5                   10                  15

Asp Val

<210> SEQ ID NO 50
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Met Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Tyr
                20                  25                  30

Ala Met Ser Trp Val Arg Gln Val Pro Gly Lys Gly Leu Glu Trp Val
            35                  40                  45

Ser Ser Ile Ser Gly Ser Gly Gly Ser Thr Tyr Tyr Ala Asp Ser Val
        50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ile Leu Ser Gly Gly His Ala Arg Val Tyr Gly Ile
                100                 105                 110

Asp Val Trp Gly Gln Gly Thr Thr Val Thr Val Ser Ser
            115                 120                 125
```

-continued

```
<210> SEQ ID NO 51
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
gagatgcagg tcttggaatc tggcggagga ctggttcaac ctggcggctc tctgagactg     60
tcttgtgccg ccagcggctt caccttccat aactacgcca tgtcctgggt ccgacaggtg    120
ccaggcaaag gactggaatg ggtgtcctct atcagcggct ctggcggcag cacatattac    180
gccgatagcg tgaagggcca gttcaccatc agccgggaca cagcaagaa caccctgtac     240 ctccagatga acagcctgag agccgaggat accgccgtgt actactgtgc aagagcagc    300 attctgtctg gcggccacgc cagagtgtat ggcattgatg tttggggcca gggaaccacc    360
gtgaccgtta gttct                                                    375

<210> SEQ ID NO 52
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Met Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Tyr
            20                  25                  30

Ala Met Ser Trp Val Arg Gln Val Pro Gly Lys Gly Leu Glu Trp Val
        35                  40                  45

Ser Ser Ile Ser Gly Ser Gly Gly Ser Thr Tyr Tyr Ala Asp Ser Val
    50                  55                  60

Lys Gly Gln Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ile Leu Ser Gly Gly His Ala Arg Val Tyr Gly Ile
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220
```

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 53
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
gagatgcagg tcttggaatc tggcggagga ctggttcaac tggcggctc tctgagactg      60 tcttgtgccg ccagcggctt caccttccat aactacgcca tgtcctgggt ccgacaggtg    120
ccaggcaaag gactggaatg ggtgtcctct atcagcggct ctggcggcag cacatattac    180
gccgatagcg tgaagggcca gttcaccatc agccgggaca cagcaagaa caccctgtac    240 ctccagatga acagcctgag agccgaggat accgccgtgt actactgtgc caagagcagc    300
attctgtctg gcggccacgc cagagtgtat ggcattgatg tttggggcca gggaaccacc    360
gtgaccgtta gttctgctag caccaagggc ccagccgtgt tccccctggc ccccagcagc    420
aagagccaca gcggcggcac agccgccctg ggctgcctgg tgaaggacta cttccccgag    480
cccgtgaccg tgtcctggaa cagcggagcc ctgacctccg gcgtgcacac cttccccgcc    540
gtgctgcaga gcagcggcct gtacagcctg tccagcgtgg tgacagtgcc agcagcagc    600 ctgggcaccc agacctacat ctgcaacgtg aaccacaagc ccagcaacac caaggtggac    660

```
aagagagtgg agcccaagag ctgcgacaag acccacacat gcccccctg cccggcgcca    720 gagctgctgg gcggaccctc cgtgttcctg ttcccccca gcccaagga caccctgatg     780 atcagcagga cccccgaggt gacctgcgtg gtggtggacg tgagccacga ggacccagag    840
gtgaagttca actggtacgt ggacggcgtg gaggtgcaca acgccaagac caagcccaga    900
gaggagcagt acaacagcac ctacagggtg gtgtccgtgc tgaccgtgct gcaccaggac    960
tggctgaacg gcaaggaata caagtgcaag gtctccaaca aggccctgcc agcccccatc   1020
gaaaagacca tcagcaaggc caagggccag ccacgggagc cccaggtgta caccctgccc   1080
ccctcccggg aggagatgac caagaaccag gtgtccctga cctgtctggt gaagggcttc   1140
taccccagcg acatcgccgt ggagtgggag agcaacggcc agcccgagaa caactacaag   1200
accacccccc cagtgctgga cagcgacggc agcttcttcc tgtacagcaa gctgaccgtg   1260
gacaagtcca ggtggcagca gggcaacgtg ttcagctgca cgtgatgca cgaggccctg   1320 cacaaccact acacccagaa gagcctgagc ttaagccccg gcaag                   1365
```

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Gly Gly Asn Asn Ile Gly Ser Gln Ser Val His
1               5                   10

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

Asp Asp Thr Asp Arg Pro Ser
1               5

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Gln Val Trp Asp Ser Ser Ser Asp His Val Val
1               5                   10

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 57

Gly Gly Asn Asn Ile Gly Ser Gln Ser Val His
1               5                   10

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asp Asp Thr Asp Arg Pro Ser
1               5

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gln Val Trp Asp Ser Ser Ser Asp His Val Val
1               5                   10

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Asn Asn Ile Gly Ser Gln Ser
1               5

<210> SEQ ID NO 61
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Asp Asp Thr
1

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Trp Asp Ser Ser Ser Asp His Val
1               5
```

```
<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asn Ile Gly Ser Gln Ser
1               5

<210> SEQ ID NO 64
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Asp Asp Thr
1

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gln Val Trp Asp Ser Ser Ser Asp His Val Val
1               5                   10

<210> SEQ ID NO 66
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Ser Ala Leu Thr Gln Pro Pro Ser Val Ser Val Ala Pro Gly Gln
1               5                   10                  15

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
        35                  40                  45

Asp Asp Thr Asp Arg Pro Ser Gly Ile Pro Ala Arg Phe Ser Gly Ser
    50                  55                  60

Ser Ser Gly Ser Thr Ala Thr Leu Thr Ile Gly Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 67
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt ctta                                          324
```

<210> SEQ ID NO 68
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

Gln Ser Ala Leu Thr Gln Pro Pro Ser Val Ser Val Ala Pro Gly Gln
1               5                  10                  15

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
        35                  40                  45

Asp Asp Thr Asp Arg Pro Ser Gly Ile Pro Ala Arg Phe Ser Gly Ser
    50                  55                  60

Ser Ser Gly Ser Thr Ala Thr Leu Thr Ile Gly Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 69
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
cagtctgccc tgactcagcc accctcggtg tcagtggccc caggacagac ggccaggatt      60
acctgtgggg gaaacaacat tggaagtcaa agtgtgcact ggtaccagca gaagccaggc     120
caggccccta tactggtcgt ctatgatgat accgaccggc cctcagggat ccctgcgcga     180
ttctctggct ccagctctgg gagcacggcc accctgacca tcggcagggt cgaagccggg     240
gatgaggccg actattactg tcaggtgtgg gatagtagta gtgatcatgt ggtattcggc     300
ggagggacca agctgaccgt cttaagtcag cccaaggctg ccccctcggt cactctgttc     360
ccgcccttct ctgaggagct tcaagccaac aaggccacac tggtgtgtct cataagtgac     420
ttctacccgg agccgtgac agtggcctgg aaggcagata gcagcccgt caaggcggga     480
gtggagacca ccacaccctc caaacaaagc aacaacaagt acgccgccag cagctacctg     540
agcctgaccc ccgagcagtg gaagagccac agaagctaca gctgccaggt cacccacgag     600
ggcagcaccg tggagaaaac cgtggccccc accgagtgca gc                         642
```

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

Gly Phe Thr Phe Asn Asn Tyr Ala Met Ser
1               5                   10

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 71

Ser Ile Ser Gly Ser Gly Gly Ser Thr Tyr Tyr Ala Asp Ser Val Lys
1               5                   10                  15
Gly

<210> SEQ ID NO 72
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 72

Ser Ser Ile Leu Ser Gly Gly His Ala Arg Val Tyr Gly Ile Asp Val
1               5                   10                  15

<210> SEQ ID NO 73
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Asn Tyr Ala Met Ser
1               5

<210> SEQ ID NO 74
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ser Ile Ser Gly Ser Gly Gly Ser Thr Tyr Tyr Ala Asp Ser Val Lys
1               5                   10                  15

Gly

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ser Ser Ile Leu Ser Gly Gly His Ala Arg Val Tyr Gly Ile Asp Val
1               5                   10                  15

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Phe Thr Phe Asn Asn Tyr
1               5

<210> SEQ ID NO 77
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Ser Gly Ser Gly Gly Ser
1               5

-continued

```
<210> SEQ ID NO 78
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Ser Ser Ile Leu Ser Gly Gly His Ala Arg Val Tyr Gly Ile Asp Val
1               5                   10                  15

<210> SEQ ID NO 79
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gly Phe Thr Phe Asn Asn Tyr Ala
1               5

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Ile Ser Gly Ser Gly Gly Ser Thr
1               5

<210> SEQ ID NO 81
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Ala Lys Ser Ser Ile Leu Ser Gly Gly His Ala Arg Val Tyr Gly Ile
1               5                   10                  15

Asp Val

<210> SEQ ID NO 82
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Glu Met Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
                20                  25                  30
```

Ala Met Ser Trp Val Arg Gln Val Pro Gly Lys Gly Leu Glu Trp Val
            35                  40                  45

Ser Ser Ile Ser Gly Ser Gly Gly Ser Thr Tyr Tyr Ala Asp Ser Val
 50                  55                  60

Lys Gly Gln Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ser Ile Leu Ser Gly Gly His Ala Arg Val Tyr Gly Ile
            100                 105                 110

Asp Val Trp Gly Gln Gly Thr Thr Val Thr Val Ser Ser
            115                 120                 125

<210> SEQ ID NO 83
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83
gaaatgcagg tgttggagtc tgggggaggc ctggtacagc ctgggggtc cctgagactc      60 tcctgtgcag cctctggatt cacctttaac aactatgcca tgagctgggt ccgccaggtt    120
ccagggaagg gctggagtg gtctcaagt attagtggta gtggaggtag cacgtactac      180
gcagactccg tgaagggcca gttcaccatc tccagagaca attccaagaa tacgctgtat    240
ctgcaaatga acagcctgag agccgaggac acggccgtat attactgtgc gaaatcctct    300
atcttgagtg gtggtcacgc gcgggtctac ggcatagacg tctggggcca agggaccacg    360
gtcaccgtct cctca                                                     375

<210> SEQ ID NO 84
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Met Gln Val Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
             20                  25                  30

Ala Met Ser Trp Val Arg Gln Val Pro Gly Lys Gly Leu Glu Trp Val
            35                  40                  45

Ser Ser Ile Ser Gly Ser Gly Gly Ser Thr Tyr Tyr Ala Asp Ser Val
 50                  55                  60

Lys Gly Gln Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ser Ile Leu Ser Gly Gly His Ala Arg Val Tyr Gly Ile
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 85
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
gaaatgcagg tgttggagtc tgggggaggc ctggtacagc ctgggggtc cctgagactc      60 tcctgtgcag cctctggatt caccttaac aactatgcca tgagctgggt ccgccaggtt    120

```
ccagggaagg ggctggagtg ggtctcaagt attagtggta gtggaggtag cacgtactac    180
gcagactccg tgaagggcca gttcaccatc tccagagaca attccaagaa tacgctgtat    240
ctgcaaatga acagcctgag agccgaggac acggccgtat attactgtgc gaaatcctct    300
atcttgagtg gtggtcacgc gcgggtctac ggcatagacg tctggggcca agggaccacg    360
gtcaccgtct cctcagcctc caccaagggc ccatcggtct tccccctggc accctcctcc    420
aagagcacct ctgggggcac agcggccctg ggctgcctgg tcaaggacta cttccccgaa    480
ccggtgacgg tgtcatggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aaccacaagc ccagcaacac caaggtggac    660
aagagagtgg agcccaagag ctgcgacaag acccacacct gcccccctg cccagcccca    720 gagctgctgg gcggaccctc cgtgttcctg ttccccccca gcccaagga caccctgatg    780 atcagcagga ccccgaggt gacctgcgtg gtggtggacg tgagccacga ggacccagag    840
gtgaagttca actggtacgt ggacggcgtg gaggtgcaca acgccaagac caagcccaga    900
gaggagcagt acaacagcac ctacagggtg gtgtccgtgc tgaccgtgct gcaccaggac    960
tggctgaacg gcaaggaata caagtgcaag gtctccaaca aggccctgcc agcccccatc   1020
gaaaagacca tcagcaaggc caagggccag ccacgggagc cccaggtgta caccctgccc   1080
ccctcccggg aggagatgac caagaaccag gtgtccctga cctgtctggt gaagggcttc   1140
taccccagcg acatcgccgt ggagtgggag agcaacggcc agcccgagaa caactacaag   1200
accacccccc cagtgctgga cagcgacggc agcttcttcc tgtacagcaa gctgaccgtg   1260
gacaagtcca ggtggcagca gggcaacgtg ttcagctgca gcgtgatgca cgaggccctg   1320
cacaaccact acacccagaa gagcctgagc ctgtcccccg gcaag                    1365
```

<210> SEQ ID NO 86
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Gly Asn Asn Ile Gly Ser Gln Ser Val His
1               5                   10

<210> SEQ ID NO 87
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Asp Asp Thr Asp Arg Pro Ser
1               5

<210> SEQ ID NO 88
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 88

Gln Val Trp Asp Ser Ser Ser Asp His Val Val
1               5                   10

<210> SEQ ID NO 89
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Gly Asn Asn Ile Gly Ser Gln Ser Val His
1               5                   10

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Asp Asp Thr Asp Arg Pro Ser
1               5

<210> SEQ ID NO 91
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gln Val Trp Asp Ser Ser Ser Asp His Val Val
1               5                   10

<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asn Asn Ile Gly Ser Gln Ser
1               5

<210> SEQ ID NO 93
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 93

Asp Asp Thr
1

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Trp Asp Ser Ser Ser Asp His Val
1               5

<210> SEQ ID NO 95
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Asn Ile Gly Ser Gln Ser
1               5

<210> SEQ ID NO 96
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Asp Asp Thr
1

<210> SEQ ID NO 97
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gln Val Trp Asp Ser Ser Ser Asp His Val Val
1               5                   10

<210> SEQ ID NO 98
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Ser Ala Leu Thr Gln Pro Pro Ser Val Ser Val Ala Pro Gly Gln
1               5                   10                  15
```

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
            35                  40                  45

Asp Asp Thr Asp Arg Pro Ser Gly Ile Pro Ala Arg Phe Ser Gly Ser
 50                  55                  60

Ser Ser Gly Ser Thr Ala Thr Leu Thr Ile Gly Arg Val Glu Ala Gly
 65                  70                  75                  80

Asp Glu Ala Asp Tyr Tyr Cys Gln Val Trp Asp Ser Ser Asp His
                 85                  90                  95

Val Val Phe Gly Gly Gly Thr Lys Leu Thr Val Leu
            100                 105

<210> SEQ ID NO 99
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
cagtctgccc tgactcagcc accctcggtg tcagtggccc caggacagac ggccaggatt    60
acctgtgggg gaaacaacat tggaagtcaa agtgtgcact ggtaccagca gaagccaggc   120
caggccccta tactggtcgt ctatgatgat accgaccggc cctcagggat ccctgcgcga   180
ttctctggct ccagctctgg gagcacggcc accctgacca tcggcagggt cgaagccggg   240
gatgaggccg actattactg tcaggtgtgg gatagtagta gtgatcatgt ggtattcggc   300
ggagggacca agctgaccgt ctta                                          324

<210> SEQ ID NO 100
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Gln Ser Ala Leu Thr Gln Pro Pro Ser Val Ser Val Ala Pro Gly Gln
 1               5                  10                  15

Thr Ala Arg Ile Thr Cys Gly Gly Asn Asn Ile Gly Ser Gln Ser Val
            20                  25                  30

His Trp Tyr Gln Gln Lys Pro Gly Gln Ala Pro Ile Leu Val Val Tyr
            35                  40                  45

Asp Asp Thr Asp Arg Pro Ser Gly Ile Pro Ala Arg Phe Ser Gly Ser
 50                  55                  60

Ser Ser Gly Ser Thr Ala Thr Leu Thr Ile Gly Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Ser Gln Pro Lys
            100                 105                 110

Ala Ala Pro Ser Val Thr Leu Phe Pro Pro Ser Ser Glu Glu Leu Gln
        115                 120                 125

```
Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 101
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 101
cagtctgccc tgactcagcc accctcggtg tcagtggccc aggacagac ggccaggatt      60 acctgtgggg gaaacaacat tggaagtcaa agtgtgcact ggtaccagca gaagccaggc    120
caggccccta tactggtcgt ctatgatgat accgaccggc cctcagggat ccctgcgcga    180
ttctctggct ccagctctgg gagcacggcc accctgacca tcggcagggt cgaagccggg    240
gatgaggccg actattactg tcaggtgtgg gatagtagta gtgatcatgt ggtattcggc    300
ggagggacca gctgaccgt cttaagtcag cccaaggctg ccccctcggt cactctgttc    360
ccgccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacaccctc caaacaaagc aacaacaagt acgccgccag cagctacctg    540
agcctgaccc ccgagcagtg gaagagccac agaagctaca gctgccaggt cacccacgag    600
ggcagcaccg tggagaaaac cgtggccccc accgagtgca gc                       642

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Phe Thr Phe Ser Pro His Ala Met Ser
1               5                   10

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103
```

```
Ala Ile Ser Asp Ser Gly Gly Ser Thr His Tyr Ala Asp Ser Val Lys
1               5                   10                  15

Gly
```

<210> SEQ ID NO 104
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

```
Asp Asp Asp Ala Trp Ser Gly Tyr Asp Tyr Trp Phe Asp Tyr
1               5                   10
```

<210> SEQ ID NO 105
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

```
Pro His Ala Met Ser
1               5
```

<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

```
Ala Ile Ser Asp Ser Gly Gly Ser Thr His Tyr Ala Asp Ser Val Lys
1               5                   10                  15

Gly
```

<210> SEQ ID NO 107
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

```
Asp Asp Asp Ala Trp Ser Gly Tyr Asp Tyr Trp Phe Asp Tyr
1               5                   10
```

<210> SEQ ID NO 108
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

```
Gly Phe Thr Phe Ser Pro His
1               5
```

<210> SEQ ID NO 109
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

```
Ser Asp Ser Gly Gly Ser
1               5
```

<210> SEQ ID NO 110
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

```
Asp Asp Asp Ala Trp Ser Gly Tyr Asp Tyr Trp Phe Asp Tyr
1               5                   10
```

<210> SEQ ID NO 111
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

```
Gly Phe Thr Phe Ser Pro His Ala
1               5
```

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

```
Ile Ser Asp Ser Gly Gly Ser Thr
1               5
```

<210> SEQ ID NO 113
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

```
Ala Arg Asp Asp Asp Ala Trp Ser Gly Tyr Asp Tyr Trp Phe Asp Tyr
1               5                   10                  15
```

-continued

<210> SEQ ID NO 114
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro His
            20                  25                  30

Ala Met Ser Trp Val Arg Gln Ala Pro Gly Lys Gly Leu Glu Trp Val
        35                  40                  45

Ser Ala Ile Ser Asp Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Asp Ala Trp Ser Gly Tyr Asp Tyr Trp Phe Asp Tyr
            100                 105                 110

Trp Gly Gln Gly Thr Leu Val Thr Val Ser Ser
        115                 120

<210> SEQ ID NO 115
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
gaggtccaat tgctggaatc tggcggagga ctggttcagc ctggtggctc tctgagactg      60
tcttgtgccg ccagcggctt cacctttagc cctcatgcca tgtcctgggt ccgacaggct     120
cctggaaaag gactcgagtg ggtgtccgcc atttctgatt ctggcggcag cacacactac     180
gccgatagcg tgaagggcag attcaccatc agccgggaca cagcaagaa caccctgtac      240 ctgcagatga acagcctgag agccgaggac acagccgtgt actattgcgc gcgtgacgat     300
gatgcttggt ccggctacga ctattggttc gattactggg gccagggcac cctggtcaca     360
gttagctca                                                              369

<210> SEQ ID NO 116
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro His
            20                  25                  30

```
Ala Met Ser Trp Val Arg Gln Ala Pro Gly Lys Gly Leu Glu Trp Val
        35                  40                  45
Ser Ala Ile Ser Asp Ser Gly Ser Thr His Tyr Ala Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Asp Asp Ala Trp Ser Gly Tyr Asp Tyr Trp Phe Asp Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
```

<210> SEQ ID NO 117
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117

```
gaggtccaat tgctggaatc tggcggagga ctggttcagc ctggtggctc tctgagactg      60
tcttgtgccg ccagcggctt cacctttagc cctcatgcca tgtcctgggt ccgacaggct     120
cctggaaaag gactcgagtg ggtgtccgcc atttctgatt ctggcggcag cacacactac     180
gccgatagcg tgaagggcag attcaccatc agccgggaca acagcaagaa cacccctgtac    240
ctgcagatga acagcctgag agccgaggac acagccgtgt actattgcgc gcgtgacgat     300
gatgcttggt ccggctacga ctattggttc gattactggg gccagggcac cctggtcaca    360
gttagctcag ctagcaccaa gggcccagc gtgttccccc tggcccccag cagcaagagc      420
accagcggcg gcacagccgc cctgggctgc ctggtgaagg actacttccc cgagcccgtg     480
accgtgtcct ggaacagcgg agccctgacc tccggcgtgc acaccttccc cgccgtgctg     540
cagagcagcg gcctgtacag cctgtccagc gtggtgacag tgcccagcag cagcctgggc     600
acccagacct acatctgcaa cgtgaaccac aagcccagca acaccaaggt ggacaagaga     660
gtggagccca gagctgcga caagacccac acatgccccc cctgcccggc gccagagctg      720
ctgggcggac cctccgtgtt cctgttcccc ccaagcccca aggacaccct gatgatcagc     780
aggacccccg aggtgacctg cgtggtggtg gacgtgagcc acgaggaccc agaggtgaag     840
ttcaactggt acgtggacgg cgtggaggtg cacaacgcca agaccaagcc cagagaggag     900
cagtacaaca gcacctacag ggtggtgtcc gtgctgaccg tgctgcacca ggactggctg     960
aacggcaagg aatacaagtg caaggtctcc aacaaggccc tgccagcccc catcgaaaag    1020
accatcagca aggccaaggg ccagccacgg gagcccagg tgtacaccct gccccctcc      1080
cgggaggaga tgaccaagaa ccaggtgtcc ctgacctgtc tggtgaaggg cttctacccc    1140
agcgacatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagagcct gagcttaagc cccggcaag                            1359
```

<210> SEQ ID NO 118
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 118

Arg Ala Ser Gln Ser Ile Ser Pro Tyr Leu Asn
1               5                   10

<210> SEQ ID NO 119
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ala Ala Asp Ser Leu Gln Ser
1               5

<210> SEQ ID NO 120
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gln Gln Ser Tyr Lys Ile Pro Leu Thr
1               5

<210> SEQ ID NO 121
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Arg Ala Ser Gln Ser Ile Ser Pro Tyr Leu Asn
1               5                   10

<210> SEQ ID NO 122
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Ala Ala Asp Ser Leu Gln Ser
1               5

<210> SEQ ID NO 123
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gln Gln Ser Tyr Lys Ile Pro Leu Thr
1               5

<210> SEQ ID NO 124
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

```
Synthetic peptide"

<400> SEQUENCE: 124

Ser Gln Ser Ile Ser Pro Tyr
1               5

<210> SEQ ID NO 125
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ala Ala Asp
1

<210> SEQ ID NO 126
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Ser Tyr Lys Ile Pro Leu
1               5

<210> SEQ ID NO 127
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Gln Ser Ile Ser Pro Tyr
1               5

<210> SEQ ID NO 128
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Ala Ala Asp
1

<210> SEQ ID NO 129
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129
```

```
Gln Gln Ser Tyr Lys Ile Pro Leu Thr
1               5
```

<210> SEQ ID NO 130
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
        35                  40                  45

Tyr Ala Ala Asp Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Ile Pro Leu
                85                  90                  95

Thr Phe Gly Gln Gly Thr Lys Val Glu Ile Lys
            100                 105
```

<210> SEQ ID NO 131
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 131

```
gatatccaga tgacacagag ccctagcagc ctgtctgcct ctgtgggcga tagagtgacc      60
atcacctgta gagccagcca gagcatcagc ccctacctga attggtacca gcagaagcct    120
ggcaaggccc ctaagctgct gatctatgct gccgactctc tgcagtctgg cgtgccaagc    180
agattttctg gcagcggctc tggcaccgac ttcaccctga caattagctc cctgcagcct    240
gaagacttcg ccacctacta ctgccagcag agctacaaga tccctctgac ctttggccag    300
ggcaccaagg tggaaatcaa g                                              321
```

<210> SEQ ID NO 132
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
```

```
                35                  40                  45
Tyr Ala Ala Asp Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Lys Ile Pro Leu
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210
```

<210> SEQ ID NO 133
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133

```
gatatccaga tgacacagag ccctagcagc ctgtctgcct ctgtgggcga tagagtgacc      60
atcacctgta gagccagcca gagcatcagc ccctacctga attggtacca gcagaagcct    120
ggcaaggccc ctaagctgct gatctatgct gccgactctc tgcagtctgg cgtgccaagc    180
agattttctg gcagcggctc tggcaccgac ttcaccctga caattagctc cctgcagcct    240
gaagacttcg ccacctacta ctgccagcag agctacaaga tccctctgac ctttggccag    300
ggcaccaagg tggaaatcaa gcgtacggtg gccgctccca gcgtgttcat cttcccccc     360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac agggggcgagt gc                      642
```

<210> SEQ ID NO 134
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 134

Gly Phe Thr Phe Ser Pro His Ala Met Ser
1               5                   10

<210> SEQ ID NO 135
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Ala Ile Ser Asp Ser Gly Gly Ser Thr His Tyr Ala Asp Ser Val Lys
1               5                   10                  15

Gly

<210> SEQ ID NO 136
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Asp Asp Asp Gly Trp Ser Gly Tyr Asp Tyr Trp Phe Asp Tyr
1               5                   10

<210> SEQ ID NO 137
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Pro His Ala Met Ser
1               5

<210> SEQ ID NO 138
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ala Ile Ser Asp Ser Gly Gly Ser Thr His Tyr Ala Asp Ser Val Lys
1               5                   10                  15

Gly

<210> SEQ ID NO 139
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 139

Asp Asp Asp Gly Trp Ser Gly Tyr Asp Tyr Trp Phe Asp Tyr
1               5                   10

<210> SEQ ID NO 140
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Phe Thr Phe Ser Pro His
1               5

<210> SEQ ID NO 141
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Ser Asp Ser Gly Gly Ser
1               5

<210> SEQ ID NO 142
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Asp Asp Asp Gly Trp Ser Gly Tyr Asp Tyr Trp Phe Asp Tyr
1               5                   10

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Gly Phe Thr Phe Ser Pro His Ala
1               5

<210> SEQ ID NO 144
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Ile Ser Asp Ser Gly Gly Ser Thr
1               5
```

<210> SEQ ID NO 145
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ala Arg Asp Asp Asp Gly Trp Ser Gly Tyr Asp Tyr Trp Phe Asp Tyr
1               5                   10                  15

<210> SEQ ID NO 146
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro His
            20                  25                  30

Ala Met Ser Trp Val Arg Gln Ala Pro Gly Lys Gly Leu Glu Trp Val
        35                  40                  45

Ser Ala Ile Ser Asp Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Asp Gly Trp Ser Gly Tyr Asp Tyr Trp Phe Asp Tyr
            100                 105                 110

Trp Gly Gln Gly Thr Leu Val Thr Val Ser Ser
        115                 120

<210> SEQ ID NO 147
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 147
gaggtccaat tgctggaatc tggcggagga ctggttcagc ctggtggctc tctgagactg      60
tcttgtgccg ccagcggctt cacattcagc cctcatgcca tgtcctgggt ccgacaggct    120
cctggaaaag gactcgagtg ggtgtccgcc atttctgatt ctggcggcag cacacactac    180
gccgatagcg tgaagggcag attcaccatc agccgggaca acagcaagaa cacccctgtac    240 ctgcagatga acagcctgag agccgaggac acagccgtgt actattgcgc gcgtgacgat    300
gatggatggt ccggctacga ctattggttc gattactggg gccagggcac cctggtcaca    360
gttagctca                                                             369

```
<210> SEQ ID NO 148
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro His
            20                  25                  30

Ala Met Ser Trp Val Arg Gln Ala Pro Gly Lys Gly Leu Glu Trp Val
        35                  40                  45

Ser Ala Ile Ser Asp Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Asp Gly Trp Ser Gly Tyr Asp Tyr Trp Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 149
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 149
gaggtccaat tgctggaatc tggcggagga ctggttcagc ctggtggctc tctgagactg      60
tcttgtgccg ccagcggctt cacattcagc cctcatgcca tgtcctgggt ccgacaggct     120
cctggaaaag gactcgagtg ggtgtccgcc atttctgatt ctggcggcag cacacactac     180
gccgatagcg tgaagggcag attcaccatc agccgggaca cagcaagaa caccctgtac     240 ctgcagatga acagcctgag agccgaggac acagccgtgt actattgcgc cgtgacgat     300 gatggatggt ccggctacga ctattggttc gattactggg gccagggcac cctggtcaca     360
gttagctcag ctagcaccaa gggcccccagc gtgttccccc tggccccag cagcaagagc     420 accagcggcg gcacagccgc cctgggctgc ctggtgaagg actacttccc cgagccgtg     480 accgtgtcct ggaacagcgg agccctgacc tccggcgtgc acaccttccc cgccgtgctg     540
cagagcagcg gcctgtacag cctgtccagc gtggtgacag tgcccagcag cagcctgggc     600
acccagacct acatctgcaa cgtgaaccac aagcccagca caccaaggt ggacaagaga     660 gtggagccca gagctgcga caagacccac acatgccccc cctgcccggc gccagagctg     720
ctgggcggac cctccgtgtt cctgttcccc ccaagcccca aggacaccct gatgatcagc     780
aggacccccg aggtgacctg cgtggtggtg gacgtgagcc acgaggaccc agaggtgaag     840
ttcaactggt acgtggacgg cgtggaggtg cacaacgcca agaccaagcc cagagaggag     900
cagtacaaca gcacctacag ggtggtgtcc gtgctgaccg tgctgcacca ggactggctg     960
aacggcaagg aatacaagtg caaggtctcc aacaaggccc tgccagcccc catcgaaaag    1020
accatcagca aggccaaggg ccagccacgg gagcccagg tgtacacct gcccccctcc    1080 cgggaggaga tgaccaagaa ccaggtgtcc ctgacctgtc tggtgaaggg cttctacccc    1140
agcgacatcg ccgtggagtg ggagagcaac ggccagcccg agaacaacta caagaccacc    1200 ccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagagcct gagcttaagc cccggcaag                           1359

<210> SEQ ID NO 150

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Arg Ala Ser Gln Ser Ile Ser Pro Tyr Leu Asn
1               5                   10

<210> SEQ ID NO 151
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ala Ala Asp Ser Leu Gln Ser
1               5

<210> SEQ ID NO 152
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Gln Gln Ser Tyr Lys Ile Pro Leu Thr
1               5

<210> SEQ ID NO 153
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Arg Ala Ser Gln Ser Ile Ser Pro Tyr Leu Asn
1               5                   10

<210> SEQ ID NO 154
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Ala Ala Asp Ser Leu Gln Ser
1               5

<210> SEQ ID NO 155
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 155

Gln Gln Ser Tyr Lys Ile Pro Leu Thr
1               5

<210> SEQ ID NO 156
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Ser Gln Ser Ile Ser Pro Tyr
1               5

<210> SEQ ID NO 157
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Ala Ala Asp
1

<210> SEQ ID NO 158
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ser Tyr Lys Ile Pro Leu
1               5

<210> SEQ ID NO 159
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Gln Ser Ile Ser Pro Tyr
1               5

<210> SEQ ID NO 160
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 160

Ala Ala Asp
1

<210> SEQ ID NO 161
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Gln Gln Ser Tyr Lys Ile Pro Leu Thr
1               5

<210> SEQ ID NO 162
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
        35                  40                  45

Tyr Ala Ala Asp Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Ile Pro Leu
                85                  90                  95

Thr Phe Gly Gln Gly Thr Lys Val Glu Ile Lys
            100                 105

<210> SEQ ID NO 163
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163
gatatccaga tgacacagag ccctagcagc ctgtctgcct ctgtgggcga tagagtgacc      60
atcacctgta gagccagcca gagcatcagc ccctacctga attggtacca gcagaagcct     120
ggcaaggccc ctaagctgct gatctatgct gccgactctc tgcagtctgg cgtgccaagc     180
agattttctg gcagcggctc tggcaccgac ttcaccctga caattagctc cctgcagcct     240
gaagacttcg ccacctacta ctgccagcag agctacaaga tccctctgac ctttggccag     300
ggcaccaagg tggaaatcaa g                                               321

<210> SEQ ID NO 164

<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Tyr
            20                  25                  30

Leu Asn Trp Tyr Gln Gln Lys Pro Gly Lys Ala Pro Lys Leu Leu Ile
        35                  40                  45

Tyr Ala Ala Asp Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Lys Ile Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 165
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 165
gatatccaga tgacacagag ccctagcagc ctgtctgcct ctgtgggcga tagagtgacc      60
atcacctgta gagccagcca gagcatcagc ccctacctga ttggtacca gcagaagcct     120
ggcaaggccc ctaagctgct gatctatgct gccgactctc tgcagtctgg cgtgccaagc     180
agattttctg gcagcggctc tggcaccgac ttcaccctga caattagctc cctgcagcct     240
gaagacttcg ccacctacta ctgccagcag agctacaaga tccctctgac ctttggccag     300
ggcaccaagg tggaaatcaa gcgtacggtg gccgctccca gcgtgttcat cttcccccc      360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480

```
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642
```

```
<210> SEQ ID NO 166
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Gly Phe Thr Phe Asn Arg Tyr Gly Met His
1               5                   10

<210> SEQ ID NO 167
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Gly Ile Trp His Asp Gly Ser His Lys Tyr Tyr Ala Asp Ser Leu Arg
1               5                   10                  15

Gly

<210> SEQ ID NO 168
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Gln Thr Asn Arg Gly Arg Leu Asp Asp Ala Phe Asp Ile
1               5                   10

<210> SEQ ID NO 169
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Arg Tyr Gly Met His
1               5

<210> SEQ ID NO 170
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 170

Gly Ile Trp His Asp Gly Ser His Lys Tyr Tyr Ala Asp Ser Leu Arg
1               5                   10                  15
Gly

<210> SEQ ID NO 171
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gln Thr Asn Arg Gly Arg Leu Asp Asp Ala Phe Asp Ile
1               5                   10

<210> SEQ ID NO 172
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Gly Phe Thr Phe Asn Arg Tyr
1               5

<210> SEQ ID NO 173
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Trp His Asp Gly Ser His
1               5

<210> SEQ ID NO 174
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Gln Thr Asn Arg Gly Arg Leu Asp Asp Ala Phe Asp Ile
1               5                   10

<210> SEQ ID NO 175
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175
```

```
Gly Phe Thr Phe Asn Arg Tyr Gly
1               5
```

<210> SEQ ID NO 176
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

```
Ile Trp His Asp Gly Ser His Lys
1               5
```

<210> SEQ ID NO 177
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

```
Val Arg Gln Thr Asn Arg Gly Arg Leu Asp Asp Ala Phe Asp Ile
1               5                   10                  15
```

<210> SEQ ID NO 178
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Arg Tyr
            20                  25                  30

Gly Met His Trp Val Arg Gln Ala Pro Gly Lys Gly Leu Glu Trp Val
        35                  40                  45

Ala Gly Ile Trp His Asp Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95

Val Arg Gln Thr Asn Arg Gly Arg Leu Asp Asp Ala Phe Asp Ile Trp
            100                 105                 110

Gly Gln Gly Thr Met Val Thr Val Ser Ser
        115                 120
```

<210> SEQ ID NO 179
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 179

```
caggtgcagc tggtggagtc tgggggaggc gtggtccagc ctggagggtc cctgagactc      60
tcctgtgcag cgtcaggatt cacattcaat agatatggca tgcactgggt ccgccaggct     120
ccaggcaagg ggttggagtg ggtggctggt atatggcatg atggaagtca taaatactat     180
gcagactctc tgaggggccg attcaccatc tccagagaca atgccaagaa cacgctggat     240
ctgcaattga acaggctgag agccgaagac acgtctgtgt attattgtgt gaggcaaacc     300
aacaggggac gtctcgatga tgcttttgac atctggggcc aagggacaat ggtcaccgtt     360
agctca                                                                366
```

<210> SEQ ID NO 180
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Arg Tyr
            20                  25                  30

Gly Met His Trp Val Arg Gln Ala Pro Gly Lys Gly Leu Glu Trp Val
        35                  40                  45

Ala Gly Ile Trp His Asp Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95

Val Arg Gln Thr Asn Arg Gly Arg Leu Asp Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 181
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 181
caggtgcagc tggtggagtc tgggggaggc gtggtccagc ctggggaggtc cctgagactc      60 tcctgtgcag cgtcaggatt cacattcaat agatatggca tgcactgggt ccgccaggct     120
ccaggcaagg ggttggagtg ggtggctggt atatggcatg atggaagtca taaatactat     180
gcagactctc tgaggggccg attcaccatc tccagagaca atgccaagaa cacgctggat     240
ctgcaattga acaggctgag agccgaagac acgtctgtgt attattgtgt gaggcaaacc     300
aacaggggac gtctcgatga tgcttttgac atctggggcc aagggacaat ggtcaccgtt     360
agctcagcta gcaccaaggg cccatcgctg ttccccctgg cccccagcag caagagcacc     420
agcggcggca cagccgccct gggctgcctg gtgaaggact acttccccga gcccgtgacc     480
gtgtcctgga acagcggagc cctgacctcc ggcgtgcaca ccttcccgc cgtgctgcag     540 agcagcggcc tgtacagcct gtccagcgtg gtgacagtgc ccagcagcag cctgggcacc     600
cagacctaca tctgcaacgt gaaccacaag cccagcaaca ccaaggtgga caagagagtg     660
gagcccaaga gctgcgacaa gacccacacc tgccccccct gcccagcccc agagctgctg     720
ggcggaccct ccgtgttcct gttcccccc aagcccaagg acaccctgat gatcagcagg     780 accccccgagg tgacctgcgt ggtggtggac gtgagccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
```

```
ggcaaggaat acaagtgcaa ggtctccaac aaggccctgc cagcccccat cgaaaagacc    1020
atcagcaagg ccaagggcca gccacgggag ccccaggtgt acaccctgcc cccctcccgg    1080
gaggagatga ccaagaacca ggtgtccctg acctgtctgg tgaagggctt ctaccccagc    1140
gacatcgccg tggagtggga gagcaacggc cagcccgaga caactacaa gaccaccccc     1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gagcctgag cctgtccccc ggcaag                               1356
```

<210> SEQ ID NO 182
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Arg Ala Ser Gln Thr Ile Ser Ser Tyr Leu Asn
1               5                   10

<210> SEQ ID NO 183
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Ala Ala Ser Thr Leu Gln Ser
1               5

<210> SEQ ID NO 184
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Gln Gln Asn Tyr Asp Thr Leu Trp Thr
1               5

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 185

Arg Ala Ser Gln Thr Ile Ser Ser Tyr Leu Asn
1               5                   10

<210> SEQ ID NO 186
<211> LENGTH: 7
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Ala Ala Ser Thr Leu Gln Ser
1               5

<210> SEQ ID NO 187
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gln Gln Asn Tyr Asp Thr Leu Trp Thr
1               5

<210> SEQ ID NO 188
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Ser Gln Thr Ile Ser Ser Tyr
1               5

<210> SEQ ID NO 189
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ala Ala Ser
1

<210> SEQ ID NO 190
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Asn Tyr Asp Thr Leu Trp
1               5

<210> SEQ ID NO 191
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 191

Gln Thr Ile Ser Ser Tyr
1               5

<210> SEQ ID NO 192
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Ala Ala Ser
1

<210> SEQ ID NO 193
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Gln Gln Asn Tyr Asp Thr Leu Trp Thr
1               5

<210> SEQ ID NO 194
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Asn Tyr Asp Thr Leu Trp
                85                  90                  95

Thr Phe Gly Gln Gly Thr Lys Val Glu Ile Lys
            100                 105

<210> SEQ ID NO 195
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195

```
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa a                                             321
```

<210> SEQ ID NO 196
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 196

```
Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Asn Tyr Asp Thr Leu Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 197
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 197

```
gatatccaga tgacccagtc tccatcctcc ctgtctgcag ctgtaggaga cagagtcacc    60
atctcttgcc gggcaagtca gaccattagt agttatttaa attggtatca gcagaaacca   120
ggggaagccc ctaagctcct gatctatgct gcctccacct tgcaaagtgg ggtcccttca   180
aggttcggtg gcagtggatc tgggacagat ttcactctca ccatcagcag tctgcaacct   240
gaagattctg caacttacta ctgtcaacag aattacgata ctttgtggac gttcggccaa   300
gggaccaagg tggaaatcaa acgtacggtg gccgctccca gcgtgttcat cttcccccc    360
agcgacgagc agctgaagag cggcaccgcc agcgtggtgt gcctgctgaa caacttctac   420
ccccgggagg ccaaggtgca gtggaaggtg acaacgccc tgcagagcgg caacagccag   480
gagagcgtca ccgagcagga cagcaaggac tccacctaca gcctgagcag cacctgacc   540
ctgagcaagg ccgactacga aagcataag gtgtacgcct gcgaggtgac ccaccagggc    600
ctgtccagcc ccgtgaccaa gagcttcaac aggggcgagt gc                     642
```

<210> SEQ ID NO 198
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Gly Phe Thr Phe Asp Arg Tyr Gly Met His
1               5                   10

<210> SEQ ID NO 199
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 199

Gly Ile Trp His Glu Gly Ser His Lys Tyr Tyr Ala Asp Ser Leu Arg
1               5                   10                  15
Gly

<210> SEQ ID NO 200
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Gln Thr Asn Arg Gly Arg Leu Asp Asp Ala Phe Asp Ile
1               5                   10

<210> SEQ ID NO 201
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

```
              Synthetic peptide"

<400> SEQUENCE: 201

Arg Tyr Gly Met His
1               5

<210> SEQ ID NO 202
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Gly Ile Trp His Glu Gly Ser His Lys Tyr Tyr Ala Asp Ser Leu Arg
1               5                   10                  15

Gly

<210> SEQ ID NO 203
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Gln Thr Asn Arg Gly Arg Leu Asp Asp Ala Phe Asp Ile
1               5                   10

<210> SEQ ID NO 204
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Gly Phe Thr Phe Asp Arg Tyr
1               5

<210> SEQ ID NO 205
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Trp His Glu Gly Ser His
1               5

<210> SEQ ID NO 206
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 206

Gln Thr Asn Arg Gly Arg Leu Asp Asp Ala Phe Asp Ile
1               5                   10

<210> SEQ ID NO 207
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Gly Phe Thr Phe Asp Arg Tyr Gly
1               5

<210> SEQ ID NO 208
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ile Trp His Glu Gly Ser His Lys
1               5

<210> SEQ ID NO 209
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Val Arg Gln Thr Asn Arg Gly Arg Leu Asp Asp Ala Phe Asp Ile
1               5                   10                  15

<210> SEQ ID NO 210
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Arg Tyr
            20                  25                  30

Gly Met His Trp Val Arg Gln Ala Pro Gly Lys Gly Leu Glu Trp Val
        35                  40                  45

Ala Gly Ile Trp His Glu Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95
```

Val Arg Gln Thr Asn Arg Gly Arg Leu Asp Asp Ala Phe Asp Ile Trp
            100                 105                 110

Gly Gln Gly Thr Met Val Thr Val Ser Ser
            115                 120

<210> SEQ ID NO 211
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211
caggtgcagc tggttgaatc tggtggcgga gtggtgcagc ctggcagatc tctgagactg     60
tcttgtgccg ccagcggctt caccttcgac agatatggca tgcactgggt ccgacaggcc    120
cctggaaaag gacttgaatg ggtggccgga atctggcacg aaggcagcca caagtactac    180
gccgatagcc tgagaggccg gttcaccatc agcagagaca cgccaagaa caccctggac    240 ctccagctga acagactgag agccgaggat accagcgtgt actactgcgt gcggcagacc    300
aacagaggca gactggacga tgccttcgat atctggggcc aagggacaat ggtcaccgtt    360
agctca                                                              366

<210> SEQ ID NO 212
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Arg Tyr
            20                  25                  30

Gly Met His Trp Val Arg Gln Ala Pro Gly Lys Gly Leu Glu Trp Val
        35                  40                  45

Ala Gly Ile Trp His Glu Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95

Val Arg Gln Thr Asn Arg Gly Arg Leu Asp Asp Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr

```
                180               185                190
Val Pro Ser Ser Leu Gly Thr Gln Thr Tyr Ile Cys Asn Val Asn
                195               200              205

His Lys Pro Ser Asn Thr Lys Val Asp Lys Arg Val Glu Pro Lys Ser
    210               215              220

Cys Asp Lys Thr His Thr Cys Pro Pro Cys Pro Ala Pro Glu Leu Leu
225               230              235              240

Gly Gly Pro Ser Val Phe Leu Phe Pro Pro Lys Pro Lys Asp Thr Leu
                245              250              255

Met Ile Ser Arg Thr Pro Glu Val Thr Cys Val Val Val Asp Val Ser
            260              265              270

His Glu Asp Pro Glu Val Lys Phe Asn Trp Tyr Val Asp Gly Val Glu
        275              280              285

Val His Asn Ala Lys Thr Lys Pro Arg Glu Glu Gln Tyr Asn Ser Thr
    290              295              300

Tyr Arg Val Val Ser Val Leu Thr Val Leu His Gln Asp Trp Leu Asn
305              310              315              320

Gly Lys Glu Tyr Lys Cys Lys Val Ser Asn Lys Ala Leu Pro Ala Pro
                325              330              335

Ile Glu Lys Thr Ile Ser Lys Ala Lys Gly Gln Pro Arg Glu Pro Gln
            340              345              350

Val Tyr Thr Leu Pro Pro Ser Arg Glu Glu Met Thr Lys Asn Gln Val
        355              360              365

Ser Leu Thr Cys Leu Val Lys Gly Phe Tyr Pro Ser Asp Ile Ala Val
    370              375              380

Glu Trp Glu Ser Asn Gly Gln Pro Glu Asn Asn Tyr Lys Thr Thr Pro
385              390              395              400

Pro Val Leu Asp Ser Asp Gly Ser Phe Phe Leu Tyr Ser Lys Leu Thr
                405              410              415

Val Asp Lys Ser Arg Trp Gln Gln Gly Asn Val Phe Ser Cys Ser Val
            420              425              430

Met His Glu Ala Leu His Asn His Tyr Thr Gln Lys Ser Leu Ser Leu
        435              440              445

Ser Pro Gly Lys
    450

<210> SEQ ID NO 213
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
caggtgcagc tggttgaatc tggtggcgga gtggtgcagc ctggcagatc tctgagactg      60
tcttgtgccg ccagcggctt caccttcgac agatatggca tgcactgggt ccgacaggcc     120
cctggaaaag gacttgaatg ggtggccgga atctggcacg aaggcagcca caagtactac     180
gccgatagcc tgagaggccg gttcaccatc agcagagaca cgccaagaa caccctggac     240 ctccagctga acagactgag agccgaggat accagcgtgt actactgcgt gcggcagacc     300
aacagaggca gactggacga tgccttcgat atctggggcc aagggacaat ggtcaccgtt     360
agctcagcta gcaccaaggg ccccagcgtg ttccccctgg cccccagcag caagagcacc     420
```

```
agcggcggca cagccgccct gggctgcctg gtgaaggact acttccccga gcccgtgacc    480
gtgtcctgga acagcggagc cctgacctcc ggcgtgcaca ccttccccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgcccccccc gcccagcccc agagctgctg    720
ggcggaccct ccgtgttcct gttccccccc aagcccaagg acaccctgat gatcagcagg    780
acccccgagg tgacctgcgt ggtggtggac gtgagccacg aggacccaga ggtgaagttc    840
aactggtacg tggacggcgt ggaggtgcac aacgccaaga ccaagccag agaggagcag    900 tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc    1020
atcagcaagg ccaagggcca gccacgggag ccccaggtgt acaccctgcc ccctcccgg    1080 gaggagatga ccaagaacca ggtgtccctg acctgtctgg tgaagggctt ctacccagc    1140 gacatcgccg tggagtggga gagcaacggc cagcccgaga caactacaa gaccaccccc    1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gagcctgag cctgtccccc ggcaag                              1356
```

<210> SEQ ID NO 214
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Arg Ala Ser Gln Thr Ile Ser Ser Tyr Leu Asn
1               5                   10

<210> SEQ ID NO 215
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Ala Ala Ser Thr Leu Gln Ser
1               5

<210> SEQ ID NO 216
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Gln Gln Asn Tyr Asp Thr Leu Trp Thr
1               5

<210> SEQ ID NO 217

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Arg Ala Ser Gln Thr Ile Ser Ser Tyr Leu Asn
1               5                   10

<210> SEQ ID NO 218
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Ala Ala Ser Thr Leu Gln Ser
1               5

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Gln Gln Asn Tyr Asp Thr Leu Trp Thr
1               5

<210> SEQ ID NO 220
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Ser Gln Thr Ile Ser Ser Tyr
1               5

<210> SEQ ID NO 221
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Ala Ala Ser
1

<210> SEQ ID NO 222
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 222

Asn Tyr Asp Thr Leu Trp
1               5

<210> SEQ ID NO 223
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gln Thr Ile Ser Ser Tyr
1               5

<210> SEQ ID NO 224
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Ala Ala Ser
1

<210> SEQ ID NO 225
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Gln Gln Asn Tyr Asp Thr Leu Trp Thr
1               5

<210> SEQ ID NO 226
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
```

```
                65                  70                  75                  80
Glu Asp Ser Ala Thr Tyr Tyr Cys Gln Gln Asn Tyr Asp Thr Leu Trp
                    85                  90                  95

Thr Phe Gly Gln Gly Thr Lys Val Glu Ile Lys
            100                 105

<210> SEQ ID NO 227
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 227
gatatccaga tgacccagtc tccatcctcc ctgtctgcag ctgtaggaga cagagtcacc      60
atctcttgcc gggcaagtca gaccattagt agttatttaa attggtatca gcagaaacca    120
ggggaagccc ctaagctcct gatctatgct gcctccacct tgcaaagtgg ggtcccttca    180
aggttcggtg cagtggatc tgggacagat tcactctca ccatcagcag tctgcaacct     240
gaagattctg caacttacta ctgtcaacag aattacgata ctttgtggac gttcggccaa    300
gggaccaagg tggaaatcaa a                                              321

<210> SEQ ID NO 228
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 228

Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Asn Tyr Asp Thr Leu Trp
                    85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 229
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 229
gatatccaga tgacccagtc tccatcctcc ctgtctgcag ctgtaggaga cagagtcacc        60
atctcttgcc gggcaagtca gaccattagt agttatttaa attggtatca gcagaaacca       120
ggggaagccc ctaagctcct gatctatgct gcctccacct tgcaaagtgg ggtcccttca       180
aggttcggtg gcagtggatc tgggacagat ttcactctca ccatcagcag tctgcaacct       240
gaagattctg caacttacta ctgtcaacag aattacgata cttttgtgga cgttcggcca       300
gggaccaagg tggaaatcaa acgtacggtg gccgctccca gcgtgttcat cttccccccc       360
agcgacgagc agctgaagag cggcaccgcc agcgtggtgt gcctgctgaa caacttctac       420
ccccgggagg ccaaggtgca gtggaaggtg gacaacgccc tgcagagcgg caacagccag       480
gagagcgtca ccgagcagga cagcaaggac tccacctaca gcctgagcag caccctgacc       540
ctgagcaagg ccgactacga aagcataag gtgtacgcct gcgaggtgac ccaccagggc       600
ctgtccagcc ccgtgaccaa gagcttcaac aggggcgagt gc                         642

<210> SEQ ID NO 230
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 230

Gly Phe Thr Phe Glu Arg Tyr Gly Met His
1               5                   10

<210> SEQ ID NO 231
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Gly Ile Trp His Glu Gly Ser His Lys Tyr Tyr Ala Asp Ser Leu Arg
1               5                   10                  15

Gly

<210> SEQ ID NO 232
<211> LENGTH: 13
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 232

Gln Thr Asn Arg Gly Arg Leu Asp Asp Ala Phe Asp Ile
1               5                   10

<210> SEQ ID NO 233
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Arg Tyr Gly Met His
1               5

<210> SEQ ID NO 234
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Gly Ile Trp His Glu Gly Ser His Lys Tyr Tyr Ala Asp Ser Leu Arg
1               5                   10                  15

Gly

<210> SEQ ID NO 235
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Gln Thr Asn Arg Gly Arg Leu Asp Asp Ala Phe Asp Ile
1               5                   10

<210> SEQ ID NO 236
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Gly Phe Thr Phe Glu Arg Tyr
1               5

<210> SEQ ID NO 237
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 237

Trp His Glu Gly Ser His
1               5

<210> SEQ ID NO 238
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Gln Thr Asn Arg Gly Arg Leu Asp Asp Ala Phe Asp Ile
1               5                   10

<210> SEQ ID NO 239
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Phe Thr Phe Glu Arg Tyr Gly
1               5

<210> SEQ ID NO 240
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ile Trp His Glu Gly Ser His Lys
1               5

<210> SEQ ID NO 241
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Val Arg Gln Thr Asn Arg Gly Arg Leu Asp Asp Ala Phe Asp Ile
1               5                   10                  15

<210> SEQ ID NO 242
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Glu Arg Tyr
            20                  25                  30

Gly Met His Trp Val Arg Gln Ala Pro Gly Lys Gly Leu Glu Trp Val
        35                  40                  45

Ala Gly Ile Trp His Glu Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95

Val Arg Gln Thr Asn Arg Gly Arg Leu Asp Asp Ala Phe Asp Ile Trp
            100                 105                 110

Gly Gln Gly Thr Met Val Thr Val Ser Ser
            115                 120

<210> SEQ ID NO 243
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 243
caggtgcagc tggttgaatc tggtggcgga gtggtgcagc ctggcagatc tctgagactg      60
tcttgtgccg ccagcggctt caccttcgag agatatggca tgcactgggt ccgacaggcc     120
cctggaaaag gacttgaatg gtggccgga atctggcacg aaggcagcca caagtactac     180
gccgatagcc tgagaggccg gttcaccatc agcagagaca cgccaagaa caccctggac     240 ctccagctga acagactgag agccgaggat accagcgtgt actactgcgt gcggcagacc     300
aacagaggca gactggacga tgccttcgat atctggggcc aagggacaat ggtcaccgtt     360
agctca                                                               366

<210> SEQ ID NO 244
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Glu Arg Tyr
            20                  25                  30

Gly Met His Trp Val Arg Gln Ala Pro Gly Lys Gly Leu Glu Trp Val
        35                  40                  45

Ala Gly Ile Trp His Glu Gly Ser His Lys Tyr Tyr Ala Asp Ser Leu
    50                  55                  60

Arg Gly Arg Phe Thr Ile Ser Arg Asp Asn Ala Lys Asn Thr Leu Asp
65                  70                  75                  80

Leu Gln Leu Asn Arg Leu Arg Ala Glu Asp Thr Ser Val Tyr Tyr Cys
                85                  90                  95

Val Arg Gln Thr Asn Arg Gly Arg Leu Asp Asp Ala Phe Asp Ile Trp
            100                 105                 110

Gly Gln Gly Thr Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 245
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 245

```
caggtgcagc tggttgaatc tggtggcgga gtggtgcagc tggcagatc tctgagactg      60
tcttgtgccg ccagcggctt caccttcgag agatatggca tgcactgggt ccgacaggcc    120
cctggaaaag gacttgaatg ggtggccgga atctggcacg aaggcagcca caagtactac    180
gccgatagcc tgagaggccg gttcaccatc agcagagaca cgccaagaa caccctggac     240
ctccagctga acagactgag agccgaggat accagcgtgt actactgcgt gcggcagacc    300
aacagaggca gactggacga tgccttcgat atctggggcc aagggacaat ggtcaccgtt    360
agctcagcta gcaccaaggg ccccagcgtg ttccccctgg ccccagcag caagagcacc     420
agcggcggca gccgccct gggctgcctg gtgaaggact acttccccga gccgtgacc       480
gtgtcctgga caccggagc cctgacctcc ggcgtgcaca ccttcccgc cgtgctgcag      540
agcagcggcc tgtacagcct gtccagcgtg gtgacagtgc ccagcagcag cctgggcacc   600
cagacctaca tctgcaacgt gaaccacaag cccagcaaca ccaaggtgga caagagagtg   660
gagcccaaga gctgcgacaa gacccacacc tgccccccct gcccagcccc agagctgctg   720
ggcggaccct ccgtgttcct gttccccccc aagcccaagg acaccctgat gatcagcagg  780
accccgagg tgacctgcgt ggtggtggac gtgagccacg aggacccaga ggtgaagttc     840
aactggtacg tggacggcgt ggaggtgcac aacgccaaga ccaagcccag agaggagcag   900
tacaacagca cctacagggt ggtgtccgtg ctgaccgtgc tgcaccagga ctggctgaac  960
ggcaaggaat acaagtgcaa ggtctccaac aaggccctgc cagcccccat cgaaaagacc 1020
atcagcaagg ccaagggcca gccacgggag ccccaggtgt acaccctgcc ccctcccgg  1080
gaggagatga ccaagaacca ggtgtccctg acctgtctgg tgaagggctt ctaccccagc  1140
gacatcgccg tggagtggga gagcaacggc cagcccgaga caactacaa gaccacccc   1200
ccagtgctgg acagcgacgg cagcttcttc ctgtacagca agctgaccgt ggacaagtcc  1260
aggtggcagc agggcaacgt gttcagctgc agcgtgatgc acgaggccct gcacaaccac  1320
tacacccaga gagcctgag cctgtccccc ggcaag                             1356
```

<210> SEQ ID NO 246
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 246

Arg Ala Ser Gln Thr Ile Ser Ser Tyr Leu Asn
1               5                   10

<210> SEQ ID NO 247
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 247

Ala Ala Ser Thr Leu Gln Ser
1               5

<210> SEQ ID NO 248
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 248

Gln Gln Asn Tyr Asp Thr Leu Trp Thr
1               5

<210> SEQ ID NO 249
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Arg Ala Ser Gln Thr Ile Ser Ser Tyr Leu Asn
1               5                   10

<210> SEQ ID NO 250
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Ala Ala Ser Thr Leu Gln Ser
1               5

<210> SEQ ID NO 251
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gln Gln Asn Tyr Asp Thr Leu Trp Thr
1               5

<210> SEQ ID NO 252
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ser Gln Thr Ile Ser Ser Tyr
1               5

<210> SEQ ID NO 253
<211> LENGTH: 3
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Ala Ala Ser
1

<210> SEQ ID NO 254
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Asn Tyr Asp Thr Leu Trp
1               5

<210> SEQ ID NO 255
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Gln Thr Ile Ser Ser Tyr
1               5

<210> SEQ ID NO 256
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Ala Ala Ser
1

<210> SEQ ID NO 257
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Gln Gln Asn Tyr Asp Thr Leu Trp Thr
1               5

<210> SEQ ID NO 258
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 258

Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Asn Tyr Asp Thr Leu Trp
                85                  90                  95

Thr Phe Gly Gln Gly Thr Lys Val Glu Ile Lys
            100                 105

<210> SEQ ID NO 259
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 259
gatatccaga tgacccagtc tccatcctcc ctgtctgcag ctgtaggaga cagagtcacc       60
atctcttgcc gggcaagtca gaccattagt agttatttaa attggtatca gcagaaacca      120
ggggaagccc ctaagctcct gatctatgct gcctccacct tgcaaagtgg ggtcccttca      180
aggttcggtg cagtggatc tgggacagat ttcactctca ccatcagcag tctgcaacct       240
gaagattctg caacttacta ctgtcaacag aattacgata cttttgtggac gttcggccaa     300 gggaccaagg tggaaatcaa a                                                321

<210> SEQ ID NO 260
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 260

Asp Ile Gln Met Thr Gln Ser Pro Ser Ser Leu Ser Ala Ala Val Gly
1               5                   10                  15

Asp Arg Val Thr Ile Ser Cys Arg Ala Ser Gln Thr Ile Ser Ser Tyr
            20                  25                  30

Leu Asn Trp Tyr Gln Gln Lys Pro Gly Glu Ala Pro Lys Leu Leu Ile
        35                  40                  45

Tyr Ala Ala Ser Thr Leu Gln Ser Gly Val Pro Ser Arg Phe Gly Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Asn Tyr Asp Thr Leu Trp
                85                  90                  95

```
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 261
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 261

| | | | | | |
|---|---|---|---|---|---|
| gatatccaga | tgacccagtc | tccatcctcc | ctgtctgcag | ctgtaggaga | cagagtcacc | 60 |
| atctcttgcc | gggcaagtca | gaccattagt | agttatttaa | attggtatca | gcagaaacca | 120 |
| ggggaagccc | ctaagctcct | gatctatgct | gcctccacct | tgcaaagtgg | ggtcccttca | 180 |
| aggttcggtg | gcagtggatc | tgggacagat | ttcactctca | ccatcagcag | tctgcaacct | 240 |
| gaagattctg | caacttacta | ctgtcaacag | aattacgata | cttttgtgga | cgttcggcca | 300 |
| gggaccaagg | tggaaatcaa | acgtacggtg | gccgctccca | gcgtgttcat | cttccccccc | 360 |
| agcgacgagc | agctgaagag | cggcaccgcc | agcgtggtgt | gcctgctgaa | caacttctac | 420 |
| ccccggagg  | ccaaggtgca | gtggaaggtg | gacaacgccc | tgcagagcgg | caacagccag | 480 |
| gagagcgtca | ccgagcagga | cagcaaggac | tccacctaca | gcctgagcag | caccctgacc | 540 |
| ctgagcaagg | ccgactacga | gaagcataag | gtgtacgcct | gcgaggtgac | ccaccagggc | 600 |
| ctgtccagcc | ccgtgaccaa | gagcttcaac | aggggcgagt | gc | | 642 |

<210> SEQ ID NO 262
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

```
Gly Phe Ile Phe Thr Asp Tyr Tyr Met Thr
1               5                   10
```

<210> SEQ ID NO 263
<211> LENGTH: 17
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 263

Phe Ile Thr Ser Gly Gly Glu Thr Thr Tyr Tyr Ala Asp Ser Val Lys
1               5                   10                  15

Gly

<210> SEQ ID NO 264
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Ala His Phe Asp Gly Tyr Gln Tyr Asp Thr Arg Gly Asp Phe Thr Tyr
1               5                   10                  15

Tyr Phe Asp Asn
            20

<210> SEQ ID NO 265
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Asp Tyr Tyr Met Thr
1               5

<210> SEQ ID NO 266
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Phe Ile Thr Ser Gly Gly Glu Thr Thr Tyr Tyr Ala Asp Ser Val Lys
1               5                   10                  15

Gly

<210> SEQ ID NO 267
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Ala His Phe Asp Gly Tyr Gln Tyr Asp Thr Arg Gly Asp Phe Thr Tyr
1               5                   10                  15

Tyr Phe Asp Asn
            20

```
<210> SEQ ID NO 268
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Gly Phe Ile Phe Thr Asp Tyr
1               5

<210> SEQ ID NO 269
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Thr Ser Gly Gly Glu Thr
1               5

<210> SEQ ID NO 270
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 270

Ala His Phe Asp Gly Tyr Gln Tyr Asp Thr Arg Gly Asp Phe Thr Tyr
1               5                   10                  15

Tyr Phe Asp Asn
            20

<210> SEQ ID NO 271
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 271

Gly Phe Ile Phe Thr Asp Tyr Tyr
1               5

<210> SEQ ID NO 272
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Ile Thr Ser Gly Gly Glu Thr Thr
1               5
```

<210> SEQ ID NO 273
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Val Arg Ala His Phe Asp Gly Tyr Gln Tyr Asp Thr Arg Gly Asp Phe
1               5                   10                  15

Thr Tyr Tyr Phe Asp Asn
            20

<210> SEQ ID NO 274
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 274

Gln Val Gln Leu Gln Glu Ser Gly Gly Arg Leu Val Arg Pro Gly Gly
1               5                   10                  15

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Gly Tyr Gln Tyr Asp Thr Arg Gly Asp Phe
            100                 105                 110

Thr Tyr Tyr Phe Asp Asn Trp Gly Leu Gly Thr Leu Val Ser Val Ser
        115                 120                 125

Ser

<210> SEQ ID NO 275
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 275
caggtgcagc tgcaggagtc ggggggacgc ttggtcaggc ctggagggtc cctgagactc      60
tcctgtgcag cctccggatt catcttcact gactactaca tgacctggat ccgccaggct     120
ccagggaagg ggccggagtg gattgcattt atcacaagtg ggggcgagac cacatactac     180
gcagactctg tgaagggccg cttcaccatt tccagggaca acgccaagaa gtcactcttt     240
ctgcaaatgt acagcctgag agccgacgac acggccgtgt attattgtgt gagagcccac     300
tttgatggtt atcagtatga tactcgtggt gacttcactt attactttga caactggggc     360
ctgggaaccc tggtcagcgt ctcctca                                          387

<210> SEQ ID NO 276
<211> LENGTH: 459
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 276

```
Gln Val Gln Leu Gln Glu Ser Gly Gly Arg Leu Val Arg Pro Gly Gly
1               5                   10                  15

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Gly Tyr Gln Tyr Asp Thr Arg Gly Asp Phe
            100                 105                 110

Thr Tyr Tyr Phe Asp Asn Trp Gly Leu Gly Thr Leu Val Ser Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350
```

Gly Gln Pro Arg Glu Pro Gln Val Tyr Thr Leu Pro Pro Ser Arg Glu
            355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455

<210> SEQ ID NO 277
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 277

```
caggtgcagc tgcaggagtc ggggggacgc ttggtcaggc ctggagggtc cctgagactc      60
tcctgtgcag cctccggatt catcttcact gactactaca tgacctggat ccgccaggct     120
ccagggaagg ggccggagtg gattgcattt atcacaagtg ggggcgagac cacatactac     180
gcagactctg tgaagggccg cttcaccatt tccaggaca acgccaagaa gtcactcttt      240
ctgcaaatgt acagcctgag agccgacgac acggccgtgt attattgtgt gagagcccac     300
tttgatggtt atcagtatga tactcgtggt gacttcactt attactttga caactggggc     360
ctgggaaccc tggtcagcgt ctcctcagct agcaccaagg gcccagcgt gttccccctg      420
gcccccagca gcaagagcac cagcggcggc acagccgccc tgggctgcct ggtgaaggac     480
tacttccccg agcccgtgac cgtgtcctgg aacagcggag ccctgacctc cggcgtgcac     540
accttccccg ccgtgctgca gagcagcggc ctgtacagcc tgtccagcgt ggtgacagtg     600
cccagcagca gcctgggcac ccagacctac atctgcaacg tgaaccacaa gcccagcaac     660
accaaggtgg acaagagagt ggagcccaag agctgcgaca gacccacac ctgcccccc       720
tgcccagccc cagagctgct gggcggaccc tccgtgttcc tgttcccccc caagcccaag     780
gacaccctga tgatcagcag gacccccgag gtgacctgcg tggtggtgga cgtgagccac     840
gaggacccag aggtgaagtt caactggtac gtggacggcg tggaggtgca aacgccaag      900
accaagccca gagaggagca gtacaacagc acctacaggg tggtgtccgt gctgaccgtg     960
ctgcaccagg actggctgaa cggcaaggaa tacaagtgca aggtctccaa caaggccctg    1020
ccagccccca tcgaaaagac catcagcaag gccaagggcc agccacggga gccccaggtg    1080
tacaccctgc ccccctcccg ggaggagatg accaagaacc aggtgtccct gacctgtctg    1140
gtgaagggct tctaccccag cgacatcgcc gtggagtggg agagcaacgg ccagcccgag    1200
aacaactaca agaccacccc cccagtgctg gacagcgacg gcagcttctt cctgtacagc    1260
aagctgaccg tggacaagtc caggtggcag caggcaacg tgttcagctg cagcgtgatg    1320
cacgaggccc tgcacaacca ctacacccag aagagcctga gcctgtcccc cggcaag       1377
```

```
<210> SEQ ID NO 278
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Arg Ala Ser Gln Ser Val Ser Ser Ser Leu Ala
1               5                   10

<210> SEQ ID NO 279
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Gly Ala Ser Thr Arg Ala Thr
1               5

<210> SEQ ID NO 280
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

His Gln Tyr Ile Asn Trp Pro Pro Gly Asp Thr
1               5                   10

<210> SEQ ID NO 281
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Arg Ala Ser Gln Ser Val Ser Ser Ser Leu Ala
1               5                   10

<210> SEQ ID NO 282
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gly Ala Ser Thr Arg Ala Thr
1               5

<210> SEQ ID NO 283
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

His Gln Tyr Ile Asn Trp Pro Pro Gly Asp Thr
1               5                   10

<210> SEQ ID NO 284
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Ser Gln Ser Val Ser Ser Ser
1               5

<210> SEQ ID NO 285
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 285

Gly Ala Ser
1

<210> SEQ ID NO 286
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Tyr Ile Asn Trp Pro Pro Gly Asp
1               5

<210> SEQ ID NO 287
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Gln Ser Val Ser Ser Ser
1               5

<210> SEQ ID NO 288
<211> LENGTH: 3
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 288

Gly Ala Ser
1

<210> SEQ ID NO 289
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

His Gln Tyr Ile Asn Trp Pro Pro Gly Asp Thr
1               5                   10

<210> SEQ ID NO 290
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 290

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser
            20                  25                  30

Leu Ala Trp Tyr Gln Gln Lys Pro Gly Arg Ala Pro Arg Leu Leu Ile
        35                  40                  45

Tyr Gly Ala Ser Thr Arg Ala Thr Gly Val Pro Ala Arg Phe Ser Gly
    50                  55                  60

Gly Gly Ser Gly Thr Asp Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                85                  90                  95

Gly Asp Thr Phe Gly Gln Gly Thr Arg Leu Asp Ile Lys
            100                 105

<210> SEQ ID NO 291
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 291
gaaatagtga tgactcagtc tccagccacc ctgtctgtgt ctccagggga aagagtcacc      60
ctctcctgca gggccagtca gagtgttagt agcagcttag cctggtacca gcagaaacct     120
ggccgggctc ccaggctcct catttatgga gcatccacca gggccactgg tgtcccagcc     180
aggttcagtg gcggtgggtc tgggacagac ttcactctca ccatcagcag cctgcagtct     240
gaagattttg cagtttatta ctgtcaccag tatattaatt ggcctccggg ggacactttt     300
ggccagggga cgaggctgga tatcaaa                                         327

<210> SEQ ID NO 292
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 292

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser
            20                  25                  30

Leu Ala Trp Tyr Gln Gln Lys Pro Gly Arg Ala Pro Arg Leu Leu Ile
        35                  40                  45

Tyr Gly Ala Ser Thr Arg Ala Thr Gly Val Pro Ala Arg Phe Ser Gly
    50                  55                  60

Gly Gly Ser Gly Thr Asp Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                85                  90                  95

Gly Asp Thr Phe Gly Gln Gly Thr Arg Leu Asp Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 293
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 293
gaaatagtga tgactcagtc tccagccacc ctgtctgtgt ctccagggga aagagtcacc      60
ctctcctgca gggccagtca gagtgttagt agcagcttag cctggtacca gcagaaacct     120
ggccgggctc ccaggctcct catttatgga gcatccacca gggccactgg tgtcccagcc     180
aggttcagtg gcggtgggtc tgggacagac ttcactctca ccatcagcag cctgcagtct     240
gaagattttg cagtttatta ctgtcaccag tatattaatt ggcctccggg ggacactttt     300
ggccagggga cgaggctgga tatcaaacgt acggtggccg ctcccagcgt gttcatcttc     360

```
cccccagcg acgagcagct gaagagcggc accgccagcg tgtgtgcct gctgaacaac      420 ttctaccccc gggaggccaa ggtgcagtgg aaggtggaca acgccctgca gagcggcaac      480
agccaggaga gcgtcaccga gcaggacagc aaggactcca cctacagcct gagcagcacc      540
ctgaccctga gcaaggccga ctacgagaag cataaggtgt acgcctgcga ggtgacccac      600
cagggcctgt ccagccccgt gaccaagagc ttcaacaggg gcgagtgc                   648
```

```
<210> SEQ ID NO 294
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Gly Phe Ile Phe Thr Asp Tyr Tyr Met Thr
1               5                   10

<210> SEQ ID NO 295
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Phe Ile Thr Ser Gly Gly Glu Thr Thr Tyr Tyr Ala Asp Ser Val Lys
1               5                   10                  15
Gly

<210> SEQ ID NO 296
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Ala His Phe Asp Leu Tyr Gln Tyr Asp Thr Arg Gly Asp Phe Thr Tyr
1               5                   10                  15
Tyr Phe Asp Asn
            20

<210> SEQ ID NO 297
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Asp Tyr Tyr Met Thr
1               5

<210> SEQ ID NO 298
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Phe Ile Thr Ser Gly Gly Glu Thr Thr Tyr Tyr Ala Asp Ser Val Lys
1               5                   10                  15

Gly

<210> SEQ ID NO 299
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ala His Phe Asp Leu Tyr Gln Tyr Asp Thr Arg Gly Asp Phe Thr Tyr
1               5                   10                  15

Tyr Phe Asp Asn
            20

<210> SEQ ID NO 300
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Gly Phe Ile Phe Thr Asp Tyr
1               5

<210> SEQ ID NO 301
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Thr Ser Gly Gly Glu Thr
1               5

<210> SEQ ID NO 302
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Ala His Phe Asp Leu Tyr Gln Tyr Asp Thr Arg Gly Asp Phe Thr Tyr
1               5                   10                  15

Tyr Phe Asp Asn
            20
```

```
<210> SEQ ID NO 303
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Gly Phe Ile Phe Thr Asp Tyr Tyr
1               5

<210> SEQ ID NO 304
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ile Thr Ser Gly Gly Glu Thr Thr
1               5

<210> SEQ ID NO 305
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Val Arg Ala His Phe Asp Leu Tyr Gln Tyr Asp Thr Arg Gly Asp Phe
1               5                   10                  15

Thr Tyr Tyr Phe Asp Asn
            20

<210> SEQ ID NO 306
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 306

Gln Val Gln Leu Gln Glu Ser Gly Gly Arg Leu Val Arg Pro Gly Gly
1               5                   10                  15

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Leu Tyr Gln Tyr Asp Thr Arg Gly Asp Phe
```

```
              100                 105                 110
Thr Tyr Tyr Phe Asp Asn Trp Gly Leu Gly Thr Leu Val Ser Val Ser
            115                 120                 125

Ser

<210> SEQ ID NO 307
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 307
caggttcagc tgcaagaatc tggcggcaga ctcgttagac ctggcggctc tctgagactg      60
tcttgtgccg ccagcggctt catcttcacc gactactaca tgacctggat cagacaggcc     120
cctggcaagg gacctgagtg gatcgccttt atcacaagcg gcggagagac aacctactac     180
gccgatagcg tgaagggcag attcaccatc agccgggaca cgccaagaa gtccctgttc     240 ctccagatgt acagcctgag agccgacgat accgccgtgt attattgcgt gcgggcccac     300
tttgacctgt accagtacga taccagaggc gatttcacct actacttcga caactggggc     360
ctgggaaccc tggtgtctgt ctcttct                                          387

<210> SEQ ID NO 308
<211> LENGTH: 459
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 308

Gln Val Gln Leu Gln Glu Ser Gly Gly Arg Leu Val Arg Pro Gly Gly
1               5                   10                  15

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Leu Tyr Gln Tyr Asp Thr Arg Gly Asp Phe
            100                 105                 110

Thr Tyr Tyr Phe Asp Asn Trp Gly Leu Gly Thr Leu Val Ser Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
```

```
            180                 185                 190
Ser Leu Ser Ser Val Val Thr Val Pro Ser Ser Leu Gly Thr Gln
        195                 200                 205

Thr Tyr Ile Cys Asn Val Asn His Lys Pro Ser Asn Thr Lys Val Asp
        210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Glu
                355                 360                 365

Glu Met Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455

<210> SEQ ID NO 309
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 309
caggttcagc tgcaagaatc tggcggcaga ctcgttagac ctggcggctc tctgagactg      60
tcttgtgccg ccagcggctt catcttcacc gactactaca tgacctggat cagacaggcc     120
cctggcaagg gacctgagtg gatcgccttt atcacaagcg gcggagagac aacctactac     180
gccgatagcg tgaagggcag attcaccatc agccgggaca cgccaagaa gtccctgttc      240 ctccagatgt acagcctgag agccgacgat accgccgtgt attattgcgt gcgggcccac     300 tttgaccctgt accagtacga taccagaggc gatttcacct actacttcga caactggggc     360
ctgggaaccc tggtgtctgt ctcttctgct agcaccaagg gcccagcgt gttccccctg      420
```

```
gcccccagca gcaagagcac cagcggcggc acagccgccc tgggctgcct ggtgaaggac      480
tacttccccg agcccgtgac cgtgtcctgg aacagcggag ccctgacctc cggcgtgcac      540
accttccccg ccgtgctgca gagcagcggc ctgtacagcc tgtccagcgt ggtgacagtg      600
cccagcagca gcctgggcac ccagacctac atctgcaacg tgaaccacaa gcccagcaac      660
accaaggtgg acaagagagt ggagcccaag agctgcgaca gacccacac atgccccccc      720 tgcccggcgc cagagctgct gggcggaccc tccgtgttcc tgttcccccc caagcccaag      780
gacaccctga tgatcagcag gaccccggag gtgacctgcg tggtggtgga cgtgagccac      840
gaggacccag aggtgaagtt caactggtac gtggacggcg tggaggtgca aacgccaag       900 accaagccca gagaggagca gtacaacagc acctacaggg tggtgtccgt gctgaccgtg      960
ctgcaccagg actggctgaa cggcaaggaa tacaagtgca aggtctccaa caaggccctg     1020
ccagccccca tcgaaaagac catcagcaag gccaagggcc agccacggga gccccaggtg     1080
tacaccctgc cccctcccg ggaggagatg accaagaacc aggtgtccct gacctgtctg     1140
gtgaagggct tctaccccag cgacatcgcc gtggagtggg agagcaacgg ccagcccgag     1200
aacaactaca agaccacccc cccagtgctg gacagcgacg gcagcttctt cctgtacagc     1260
aagctgaccg tggacaagtc caggtggcag cagggcaacg tgttcagctg cagcgtgatg     1320
cacgaggccc tgcacaacca ctacacccag aagagcctga gcttaagccc cggcaag       1377
```

<210> SEQ ID NO 310
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Arg Ala Ser Gln Ser Val Ser Ser Ser Leu Ala
1               5                   10

<210> SEQ ID NO 311
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Gly Ala Ser Thr Arg Ala Thr
1               5

<210> SEQ ID NO 312
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

His Gln Tyr Ile Asn Trp Pro Pro Gly Asp Thr
1               5                   10

<210> SEQ ID NO 313

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Arg Ala Ser Gln Ser Val Ser Ser Ser Leu Ala
1               5                   10

<210> SEQ ID NO 314
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Gly Ala Ser Thr Arg Ala Thr
1               5

<210> SEQ ID NO 315
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

His Gln Tyr Ile Asn Trp Pro Pro Gly Asp Thr
1               5                   10

<210> SEQ ID NO 316
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Ser Gln Ser Val Ser Ser Ser
1               5

<210> SEQ ID NO 317
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Gly Ala Ser
1

<210> SEQ ID NO 318
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 318

Tyr Ile Asn Trp Pro Pro Gly Asp
1               5

<210> SEQ ID NO 319
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Gln Ser Val Ser Ser Ser
1               5

<210> SEQ ID NO 320
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Gly Ala Ser
1

<210> SEQ ID NO 321
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

His Gln Tyr Ile Asn Trp Pro Pro Gly Asp Thr
1               5                   10

<210> SEQ ID NO 322
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 322

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser
            20                  25                  30

Leu Ala Trp Tyr Gln Gln Lys Pro Gly Arg Ala Pro Arg Leu Leu Ile
        35                  40                  45

Tyr Gly Ala Ser Thr Arg Ala Thr Gly Val Pro Ala Arg Phe Ser Gly
    50                  55                  60

Gly Gly Ser Gly Thr Asp Phe Thr Leu Thr Ile Ser Ser Leu Gln Ser
```

```
                    65                  70                  75                  80
Glu Asp Phe Ala Val Tyr Tyr Cys His Gln Tyr Ile Asn Trp Pro Pro
                    85                  90                  95

Gly Asp Thr Phe Gly Gln Gly Thr Arg Leu Asp Ile Lys
                100                 105
```

<210> SEQ ID NO 323
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 323

```
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaa                                       327
```

<210> SEQ ID NO 324
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser
                20                  25                  30

Leu Ala Trp Tyr Gln Gln Lys Pro Gly Arg Ala Pro Arg Leu Leu Ile
            35                  40                  45

Tyr Gly Ala Ser Thr Arg Ala Thr Gly Val Pro Ala Arg Phe Ser Gly
        50                  55                  60

Gly Gly Ser Gly Thr Asp Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                    85                  90                  95

Gly Asp Thr Phe Gly Gln Gly Thr Arg Leu Asp Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 325
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 325
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaacgt acggtggccg ctcccagcgt gttcatcttc   360
ccccccagcg acgagcagct gaagagcggc accgccagcg tggtgtgcct gctgaacaac   420 ttctacccc ggaggccaa ggtgcagtgg aaggtggaca acgccctgca gagcggcaac   480
agccaggaga gcgtcaccga gcaggacagc aaggactcca cctacagcct gagcagcacc   540
ctgaccctga gcaaggccga ctacgagaag cataaggtgt acgcctgcga ggtgacccac   600
cagggcctgt ccagccccgt gaccaagagc ttcaacaggg gcgagtgc              648

<210> SEQ ID NO 326
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Gly Phe Ile Phe Thr Asp Tyr Tyr Met Thr
1               5                   10

<210> SEQ ID NO 327
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Phe Ile Thr Ser Gly Gly Glu Thr Thr Tyr Tyr Ala Asp Ser Val Lys
1               5                   10                  15

Gly

<210> SEQ ID NO 328
<211> LENGTH: 20
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 328

Ala His Phe Asp Ile Tyr Gln Tyr Asp Thr Arg Gly Asp Phe Thr Tyr
1               5                   10                  15

Tyr Phe Asp Asn
            20

<210> SEQ ID NO 329
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Asp Tyr Tyr Met Thr
1               5

<210> SEQ ID NO 330
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Phe Ile Thr Ser Gly Gly Glu Thr Thr Tyr Tyr Ala Asp Ser Val Lys
1               5                   10                  15

Gly

<210> SEQ ID NO 331
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Ala His Phe Asp Ile Tyr Gln Tyr Asp Thr Arg Gly Asp Phe Thr Tyr
1               5                   10                  15

Tyr Phe Asp Asn
            20

<210> SEQ ID NO 332
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Gly Phe Ile Phe Thr Asp Tyr
1               5

<210> SEQ ID NO 333
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Thr Ser Gly Gly Glu Thr
1               5

<210> SEQ ID NO 334
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Ala His Phe Asp Ile Tyr Gln Tyr Asp Thr Arg Gly Asp Phe Thr Tyr
1               5                   10                  15

Tyr Phe Asp Asn
            20

<210> SEQ ID NO 335
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Gly Phe Ile Phe Thr Asp Tyr Tyr
1               5

<210> SEQ ID NO 336
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Ile Thr Ser Gly Gly Glu Thr Thr
1               5

<210> SEQ ID NO 337
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Val Arg Ala His Phe Asp Ile Tyr Gln Tyr Asp Thr Arg Gly Asp Phe
1               5                   10                  15

Thr Tyr Tyr Phe Asp Asn
            20
```

<210> SEQ ID NO 338
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 338

```
Gln Val Gln Leu Gln Glu Ser Gly Gly Arg Leu Val Arg Pro Gly Gly
1               5                   10                  15

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Ile Tyr Gln Tyr Asp Thr Arg Gly Asp Phe
            100                 105                 110

Thr Tyr Tyr Phe Asp Asn Trp Gly Leu Gly Thr Leu Val Ser Val Ser
        115                 120                 125

Ser
```

<210> SEQ ID NO 339
<211> LENGTH: 387
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 339

```
caggttcagc tgcaagaatc tggcggcaga ctcgttagac ctggcggctc tctgagactg     60
tcttgtgccg ccagcggctt catcttcacc gactactaca tgacctggat cagacaggcc    120
cctggcaagg gacctgagtg gatcgccttt atcacaagcg gcggagagac aacctactac    180
gccgatagcg tgaagggcag attcaccatc agcggaaca cgccaagaa gtccctgttc      240
ctccagatgt acagcctgag agccgacgat accgccgtgt attattgcgt gcgggcccac    300
tttgacatct accagtacga taccagaggc gatttcacct actacttcga caactggggc    360
ctgggaaccc tggtgtctgt ctcttct                                        387
```

<210> SEQ ID NO 340
<211> LENGTH: 459
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 340

```
Gln Val Gln Leu Gln Glu Ser Gly Gly Arg Leu Val Arg Pro Gly Gly
1               5                   10                  15
```

Ser Leu Arg Leu Ser Cys Ala Ala Ser Gly Phe Ile Phe Thr Asp Tyr
            20                  25                  30

Tyr Met Thr Trp Ile Arg Gln Ala Pro Gly Lys Gly Pro Glu Trp Ile
        35                  40                  45

Ala Phe Ile Thr Ser Gly Gly Glu Thr Thr Tyr Tyr Ala Asp Ser Val
    50                  55                  60

Lys Gly Arg Phe Thr Ile Ser Arg Asp Asn Ala Lys Lys Ser Leu Phe
65                  70                  75                  80

Leu Gln Met Tyr Ser Leu Arg Ala Asp Asp Thr Ala Val Tyr Tyr Cys
                85                  90                  95

Val Arg Ala His Phe Asp Ile Tyr Gln Tyr Asp Thr Arg Gly Asp Phe
            100                 105                 110

Thr Tyr Tyr Phe Asp Asn Trp Gly Leu Gly Thr Leu Val Ser Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr

```
                435                 440                 445
Thr Gln Lys Ser Leu Ser Leu Ser Pro Gly Lys
    450                 455

<210> SEQ ID NO 341
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 341
caggttcagc tgcaagaatc tggcggcaga ctcgttagac ctggcggctc tctgagactg      60
tcttgtgccg ccagcggctt catcttcacc gactactaca tgacctggat cagacaggcc    120
cctggcaagg gacctgagtg gatcgccttt atcacaagcg gcggagagac aacctactac    180
gccgatagcg tgaagggcag attcaccatc agccgggaca cgccaagaa gtccctgttc    240 ctccagatgt acagcctgag agccgacgat accgccgtgt attattgcgt gcgggcccac    300
tttgacatct accagtacga taccagaggc gatttcacct actacttcga caactggggc    360
ctgggaaccc tggtgtctgt ctcttctgct agcaccaagg gcccagcgt gttcccctg      420 gccccagca gcaagagcac cagcggcggc acagccgccc tgggctgcct ggtgaaggac    480
tacttccccg agcccgtgac cgtgtcctgg aacagcggag ccctgacctc cggcgtgcac    540
accttccccg ccgtgctgca gagcagcggc ctgtacagcc tgtccagcgt ggtgacagtg    600
cccagcagca gcctgggcac ccagacctac atctgcaacg tgaaccacaa gcccagcaac    660
accaaggtgg acaagagagt ggagcccaag agctgcgaca gaccacac atgcccccc       720 tgcccggcgc cagagctgct gggcggaccc tccgtgttcc tgttcccccc caagcccaag    780
gacaccctga tgatcagcag gaccccgag gtgacctgcg tggtggtgga cgtgagccac    840
gaggacccag aggtgaagtt caactggtac gtggacggcg tggaggtgca aacgccaag    900 accaagccca gagaggagca gtacaacagc acctacaggg tggtgtccgt gctgaccgtg    960
ctgcaccagg actggctgaa cggcaaggaa tacaagtgca aggtctccaa caaggccctg   1020
ccagccccca tcgaaaagac catcagcaag gccaagggcc agccacggga gccccaggtg   1080
tacaccctgc ccccctcccg ggaggagatg accaagaacc aggtgtccct gacctgtctg   1140
gtgaagggct tctaccccag cgacatcgcc gtggagtggg agagcaacgg ccagcccgag   1200
aacaactaca agaccacccc cccagtgctg gacagcgacg gcagcttctt cctgtacagc   1260
aagctgaccg tggacaagtc caggtggcag cagggcaacg tgttcagctg cagcgtgatg   1320
cacgaggccc tgcacaacca ctacacccag aagagcctga gcttaagccc cggcaag      1377

<210> SEQ ID NO 342
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Arg Ala Ser Gln Ser Val Ser Ser Ser Leu Ala
1               5                   10
```

```
<210> SEQ ID NO 343
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 343

Gly Ala Ser Thr Arg Ala Thr
1               5

<210> SEQ ID NO 344
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

His Gln Tyr Ile Asn Trp Pro Pro Gly Asp Thr
1               5                   10

<210> SEQ ID NO 345
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Arg Ala Ser Gln Ser Val Ser Ser Ser Leu Ala
1               5                   10

<210> SEQ ID NO 346
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Gly Ala Ser Thr Arg Ala Thr
1               5

<210> SEQ ID NO 347
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

His Gln Tyr Ile Asn Trp Pro Pro Gly Asp Thr
1               5                   10

<210> SEQ ID NO 348
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 348

Ser Gln Ser Val Ser Ser Ser
1               5

<210> SEQ ID NO 349
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Gly Ala Ser
1

<210> SEQ ID NO 350
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Tyr Ile Asn Trp Pro Pro Gly Asp
1               5

<210> SEQ ID NO 351
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Gln Ser Val Ser Ser Ser
1               5

<210> SEQ ID NO 352
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Gly Ala Ser
1

<210> SEQ ID NO 353
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 353

His Gln Tyr Ile Asn Trp Pro Pro Gly Asp Thr
1               5                   10

<210> SEQ ID NO 354
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 354

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser
                20                  25                  30

Leu Ala Trp Tyr Gln Gln Lys Pro Gly Arg Ala Pro Arg Leu Leu Ile
            35                  40                  45

Tyr Gly Ala Ser Thr Arg Ala Thr Gly Val Pro Ala Arg Phe Ser Gly
        50                  55                  60

Gly Gly Ser Gly Thr Asp Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                85                  90                  95

Gly Asp Thr Phe Gly Gln Gly Thr Arg Leu Asp Ile Lys
            100                 105

<210> SEQ ID NO 355
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 355
gaaatagtga tgactcagtc tccagccacc ctgtctgtgt ctccagggga aagagtcacc      60
ctctcctgca gggccagtca gagtgttagt agcagcttag cctggtacca gcagaaacct     120
ggccgggctc ccaggctcct catttatgga gcatccacca gggccactgg tgtcccagcc     180
aggttcagtg gcggtgggtc tgggacagac ttcactctca ccatcagcag cctgcagtct     240
gaagattttg cagtttatta ctgtcaccag tatattaatt ggcctccggg ggacactttt     300
ggccagggga cgaggctgga tatcaaa                                        327

<210> SEQ ID NO 356
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 356

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Ser

```
                 20                  25                  30
Leu Ala Trp Tyr Gln Gln Lys Pro Gly Arg Ala Pro Arg Leu Leu Ile
             35                  40                  45

Tyr Gly Ala Ser Thr Arg Ala Thr Gly Val Pro Ala Arg Phe Ser Gly
         50                  55                  60

Gly Gly Ser Gly Thr Asp Phe Thr Leu Thr Ile Ser Ser Leu Gln Ser
65                  70                  75                  80

Glu Asp Phe Ala Val Tyr Tyr Cys His Gln Tyr Ile Asn Trp Pro Pro
                 85                  90                  95

Gly Asp Thr Phe Gly Gln Gly Thr Arg Leu Asp Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 357
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 357

```
gaaatagtga tgactcagtc tccagccacc ctgtctgtgt ctccagggga aagagtcacc    60
ctctcctgca gggccagtca gagtgttagt agcagcttag cctggtacca gcagaaacct   120
ggccgggctc ccaggctcct catttatgga gcatccacca gggccactgg tgtcccagcc   180
aggttcagtg gcggtgggtc tgggacagac ttcactctca ccatcagcag cctgcagtct   240
gaagattttg cagtttatta ctgtcaccag tatattaatt ggcctccggg ggacactttt   300
ggccagggga cgaggctgga tatcaaacgt acggtggccg ctcccagcgt gttcatcttc   360
ccccccagcg acgagcagct gaagagcggc accgccagcg tggtgtgcct gctgaacaac   420
ttctaccccc gggaggccaa ggtgcagtgg aaggtggaca acgccctgca gagcggcaac   480
agccaggaga gcgtcaccga gcaggacagc aaggactcca cctacagcct gagcagcacc   540
ctgaccctga gcaaggccga ctacgagaag cataaggtgt acgcctgcga ggtgacccac   600
cagggcctgt ccagccccgt gaccaagagc ttcaacaggg gcgagtgc                648
```

<210> SEQ ID NO 358
<211> LENGTH: 10
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 358

Gly Phe Thr Phe Ser Tyr Tyr Gly Met Asn
1               5                   10

<210> SEQ ID NO 359
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 359

Gly Ile Thr Asn Ser Gly Ser Ile Thr Tyr Tyr Ala Asp Ser Val Lys
1               5                   10                  15

Gly

<210> SEQ ID NO 360
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Val Gly Val Arg Ser Ser Ser Gly Met Trp Asp Leu Asp Tyr
1               5                   10

<210> SEQ ID NO 361
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Tyr Tyr Gly Met Asn
1               5

<210> SEQ ID NO 362
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Gly Ile Thr Asn Ser Gly Ser Ile Thr Tyr Tyr Ala Asp Ser Val Lys
1               5                   10                  15

Gly

<210> SEQ ID NO 363
<211> LENGTH: 14
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 363

Val Gly Val Arg Ser Ser Ser Gly Met Trp Asp Leu Asp Tyr
1               5                   10

<210> SEQ ID NO 364
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Gly Phe Thr Phe Ser Tyr Tyr
1               5

<210> SEQ ID NO 365
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Thr Asn Ser Gly Ser Ile
1               5

<210> SEQ ID NO 366
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Val Gly Val Arg Ser Ser Ser Gly Met Trp Asp Leu Asp Tyr
1               5                   10

<210> SEQ ID NO 367
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Gly Phe Thr Phe Ser Tyr Tyr Gly
1               5

<210> SEQ ID NO 368
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368
```

Ile Thr Asn Ser Gly Ser Ile Thr
1               5

<210> SEQ ID NO 369
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ala Lys Val Gly Val Arg Ser Ser Ser Gly Met Trp Asp Leu Asp Tyr
1               5                   10                  15

<210> SEQ ID NO 370
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 370

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Asn Ser Gly Ser Ile Thr Tyr Tyr Ala Asp Ser Val
    50                  55                  60

Lys Gly Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Val Gly Val Arg Ser Ser Ser Gly Met Trp Asp Leu Asp Tyr
            100                 105                 110

Trp Gly Gln Gly Thr Leu Val Thr Val Ser Ser
        115                 120

<210> SEQ ID NO 371
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 371
gaggttcaat tgttggagtc tgggggaggc ctggtacagc cggggggtc ccggagactg      60 tcctgtgcag cctctggatt cacctttagc tactatggca tgaactgggt ccgccaggct     120
ccagggaagg gactggaatg ggtctcaggt attactaata gtggtagtat cacatactac    180
gcagactccg tgaagggccg gttcagcatc tccagagaca attccaagaa cacgttgttt    240
ctgcaaatga acagcctgag agccgaggac acggccgtat attactgtgc gaaggtggga    300
gtgcgcagtt cgtccgggat gtgggacctt gactactggg gccagggaac cctggtcacc    360
gtcagctca                                                                 369

<210> SEQ ID NO 372
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 372

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Asn Ser Gly Ser Ile Thr Tyr Tyr Ala Asp Ser Val
    50                  55                  60

Lys Gly Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Val Gly Val Arg Ser Ser Gly Met Trp Asp Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 373
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 373

```
gaggttcaat tgttggagtc tgggggaggc tggtacagc cggggggtc ccggagactg      60
tcctgtgcag cctctggatt caccttagc tactatggca tgaactgggt ccgccaggct    120
ccagggaagg gactggaatg ggtctcaggt attactaata gtggtagtat cacatactac   180
gcagactccg tgaagggccg gttcagcatc tccagagaca attccaagaa cacgttgttt   240
ctgcaaatga acagcctgag agccgaggac acggccgtat attactgtgc gaaggtggga   300
gtgcgcagtt cgtccgggat gtgggacctt gactactggg gccagggaac cctggtcacc   360
gtcagctcag ctagcaccaa gggcccagc gtgttccccc tggccccag cagcaagagc    420
accagcggcg gcacagccgc cctgggctgc ctggtgaagg actacttccc cgagcccgtg   480
accgtgtcct ggaacagcgg agccctgacc tccggcgtgc acaccttccc cgccgtgctg   540
cagagcagcg gcctgtacag cctgtccagc gtggtgacag tgcccagcag cagcctgggc   600
acccagacct acatctgcaa cgtgaaccac aagcccagca caccaaggt ggacaagaga    660
gtggagccca gagctgcga caagacccac acctgccccc cctgcccagc ccagagctg    720
ctgggcggac cctccgtgtt cctgttcccc ccaagccca aggacaccct gatgatcagc   780
aggaccccg aggtgacctg cgtggtggtg gacgtgagcc acgaggaccc agaggtgaag   840
ttcaactggt acgtggacgg cgtggaggtg cacaacgcca agaccaagcc agagaggag    900
cagtacaaca gcacctacag ggtggtgtcc gtgctgaccg tgctgcacca ggactggctg   960
aacggcaagg aatacaagtg caaggtctcc aacaaggccc tgccagcccc catcgaaaag  1020
accatcagca aggccaaggg ccagccacgg gagccccagg tgtacaccct gcccccctcc  1080
cgggaggaga tgaccaagaa ccaggtgtcc ctgacctgtc tggtgaaggg cttctacccc  1140
agcgacatcg ccgtggagtg ggagagcaac ggccagcccg agaacaacta caagaccacc  1200
cccccagtgc tggacagcga cggcagcttc ttcctgtaca gcaagctgac cgtggacaag  1260
tccaggtggc agcagggcaa cgtgttcagc tgcagcgtga tgcacgaggc cctgcacaac  1320
cactacaccc agaagagcct gagcctgtcc cccggcaag                         1359
```

```
<210> SEQ ID NO 374
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Gly Gly Asn Asn Ile Gly Ser Lys Ser Leu Gln
1               5                   10

<210> SEQ ID NO 375
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Asp Asp Ser Asp Arg Pro Ser
1               5

<210> SEQ ID NO 376
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Gln Val Trp Asp Thr Ser Ser Asp His Val Val
1               5                   10

<210> SEQ ID NO 377
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Gly Gly Asn Asn Ile Gly Ser Lys Ser Leu Gln
1               5                   10

<210> SEQ ID NO 378
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Asp Asp Ser Asp Arg Pro Ser
1               5

<210> SEQ ID NO 379
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Gln Val Trp Asp Thr Ser Ser Asp His Val Val
1               5                   10

<210> SEQ ID NO 380
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 380

Asn Asn Ile Gly Ser Lys Ser
1               5

<210> SEQ ID NO 381
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Asp Asp Ser
1

<210> SEQ ID NO 382
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Trp Asp Thr Ser Ser Asp His Val
1               5

<210> SEQ ID NO 383
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Asn Ile Gly Ser Lys Ser
1               5

<210> SEQ ID NO 384
<211> LENGTH: 3
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 384

Asp Asp Ser
1

<210> SEQ ID NO 385
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385

Gln Val Trp Asp Thr Ser Ser Asp His Val Val
1               5                   10

<210> SEQ ID NO 386
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 386

Ser Tyr Val Leu Thr Gln Pro Pro Ser Val Ser Val Ala Pro Gly Gln
1               5                   10                  15

Thr Ala Arg Leu Ser Cys Gly Gly Asn Asn Ile Gly Ser Lys Ser Leu
            20                  25                  30

Gln Trp Tyr Gln Gln Lys Pro Gly Gln Ala Pro Val Leu Val Val Asn
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Val Val Phe Gly Gly Gly Thr Lys Leu Thr Val Leu
            100                 105

<210> SEQ ID NO 387
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 387
tcctatgtgc tgactcagcc accctcggtg tcagtggccc caggacagac ggccagactt      60
tcctgtgggg gaaacaacat tggaagtaaa agtctgcagt ggtaccagca gaagccaggc     120
caggcccctg tgctggtcgt caatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatactagta gtgatcatgt ggtcttcggc     300
ggagggacca agctgaccgt ccta                                            324
```

<210> SEQ ID NO 388
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 388

```
Ser Tyr Val Leu Thr Gln Pro Pro Ser Val Ser Val Ala Pro Gly Gln
1               5                   10                  15

Thr Ala Arg Leu Ser Cys Gly Gly Asn Asn Ile Gly Ser Lys Ser Leu
            20                  25                  30

Gln Trp Tyr Gln Gln Lys Pro Gly Gln Ala Pro Val Leu Val Val Asn
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 389
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 389

```
tcctatgtgc tgactcagcc accctcggtg tcagtggccc caggacagac ggccagactt      60
tcctgtgggg gaaacaacat tggaagtaaa agtctgcagt ggtaccagca gaagccaggc     120
caggcccctg tgctggtcgt caatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatactagta gtgatcatgt ggtcttcggc     300
ggagggacca agctgaccgt cctaggccag cctaaggccg ctcccctccg tgaccctgttc     360
```

```
cccccccagct ccgaggaact gcaggccaac aaggccaccc tggtgtgcct gatcagcgac    420
ttctaccctg gcgccgtgac cgtggcctgg aaggccgaca gcagccccgt gaaggccggc    480
gtggagacaa ccaccccag caagcagagc aacaacaagt acgccgccag cagctacctg     540
agcctgaccc ccgagcagtg gaagagccac agaagctaca gctgccaggt cacccacgag    600
ggcagcaccg tggagaaaac cgtggccccc accgagtgca gc                        642
```

<210> SEQ ID NO 390
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 390

```
Gly Phe Thr Phe Ser Tyr Tyr Gly Met Asn
1               5                   10
```

<210> SEQ ID NO 391
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 391

```
Gly Ile Thr Gln Ser Gly Ser Ile Thr Tyr Tyr Ala Asp Thr Val Lys
1               5                   10                  15
Gly
```

<210> SEQ ID NO 392
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 392

```
Val Gly Val Arg Ser Ser Ser Gly Met Trp Asp Leu Asp Tyr
1               5                   10
```

<210> SEQ ID NO 393
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 393

```
Tyr Tyr Gly Met Asn
1               5
```

<210> SEQ ID NO 394
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Gly Ile Thr Gln Ser Gly Ser Ile Thr Tyr Tyr Ala Asp Thr Val Lys
1               5                   10                  15

Gly

<210> SEQ ID NO 395
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Val Gly Val Arg Ser Ser Ser Gly Met Trp Asp Leu Asp Tyr
1               5                   10

<210> SEQ ID NO 396
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

Gly Phe Thr Phe Ser Tyr Tyr
1               5

<210> SEQ ID NO 397
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Thr Gln Ser Gly Ser Ile
1               5

<210> SEQ ID NO 398
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Val Gly Val Arg Ser Ser Ser Gly Met Trp Asp Leu Asp Tyr
1               5                   10

<210> SEQ ID NO 399
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 399

Gly Phe Thr Phe Ser Tyr Tyr Gly
1               5

<210> SEQ ID NO 400
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Ile Thr Gln Ser Gly Ser Ile Thr
1               5

<210> SEQ ID NO 401
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 401

Ala Lys Val Gly Val Arg Ser Ser Ser Gly Met Trp Asp Leu Asp Tyr
1               5                   10                  15

<210> SEQ ID NO 402
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 402

Glu Val Gln Leu Leu Glu Ser Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Gln Ser Gly Ser Ile Thr Tyr Tyr Ala Asp Thr Val
    50                  55                  60

Lys Gly Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Val Gly Val Arg Ser Ser Ser Gly Met Trp Asp Leu Asp Tyr
            100                 105                 110

Trp Gly Gln Gly Thr Leu Val Thr Val Ser Ser
        115                 120

<210> SEQ ID NO 403
<211> LENGTH: 369
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic polynucleotide"

<400> SEQUENCE: 403

```
gaggttcaat tgttggagtc tgggggaggc ctggtacagc cggggggtc ccggagactg      60
tcctgtgcag cctctggatt cacctttagc tactatggca tgaactgggt ccgccaggct     120
ccagggaagg gactggaatg ggtctcaggt attactcaga gtggtagtat cacatactac     180
gcagacaccg tgaagggccg gttcagcatc tccagagaca attccaagaa cacgttgttt     240
ctgcaaatga acagcctgag agccgaggac acggccgtat attactgtgc gaaggtggga     300
gtgcgcagtt cgtccgggat gtgggacctt gactactggg gccagggaac cctggtcacc     360
gtcagctca                                                             369
```

<210> SEQ ID NO 404
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 404

```
Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Gln Ser Gly Ser Ile Thr Tyr Tyr Ala Asp Thr Val
    50                  55                  60

Lys Gly Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Val Gly Val Arg Ser Ser Gly Met Trp Asp Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 405
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 405

```
gaggttcaat tgttggagtc tggggggaggc ctggtacagc cggggggggtc ccggagactg      60
tcctgtgcag cctctggatt cacctttagc tactatggca tgaactgggt ccgccaggct     120
ccagggaagg gactggaatg ggtctcaggt attactcaga gtggtagtat cacatactac     180
gcagacaccg tgaagggccg gttcagcatc tccagagaca attccaagaa cacgttgttt     240
ctgcaaatga acagcctgag agccgaggac acggccgtat attactgtgc gaaggtggga     300
gtgcgcagtt cgtccgggat gtgggacctt gactactggg gccagggaac cctggtcacc     360
gtcagctcag ctagcaccaa gggcccccagc gtgttccccc tggcccccag cagcaagagc     420
accagcggcg gcacagccgc cctgggctgc ctggtgaagg actacttccc cgagcccgtg     480
accgtgtcct ggaacagcgg agccctgacc tccggcgtgc acaccttccc cgccgtgctg     540
cagagcagcg gcctgtacag cctgtccagc gtggtgacag tgcccagcag cagcctgggc     600
acccagacct acatctgcaa cgtgaaccac aagcccagca caccaaggt ggacaagaga     660
gtggagccca gagctgcga caagacccac acctgccccc cctgcccagc cccagagctg     720
ctgggcggac cctccgtgtt cctgttcccc cccaagccca aggacaccct gatgatcagc     780
aggacccccg aggtgacctg cgtggtggtg gacgtgagcc acgaggaccc agaggtgaag     840
```

```
ttcaactggt acgtggacgg cgtggaggtg cacaacgcca agaccaagcc cagagaggag    900
cagtacaaca gcacctacag ggtggtgtcc gtgctgaccg tgctgcacca ggactggctg    960
aacggcaagg aatacaagtg caaggtctcc aacaaggccc tgccagcccc catcgaaaag   1020
accatcagca aggccaaggg ccagccacgg gagccccagg tgtacaccct gcccccctcc   1080
cgggaggaga tgaccaagaa ccaggtgtcc ctgacctgtc tggtgaaggg cttctacccc   1140
agcgacatcg ccgtggagtg ggagagcaac ggccagcccg agaacaacta caagaccacc   1200
cccccagtgc tggacagcga cggcagcttc ttcctgtaca gcaagctgac cgtggacaag   1260
tccaggtggc agcagggcaa cgtgttcagc tgcagcgtga tgcacgaggc cctgcacaac   1320
cactacaccc agaagagcct gagcctgtcc cccggcaag                          1359
```

<210> SEQ ID NO 406
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Gly Gly Asn Asn Ile Gly Ser Lys Ser Leu Gln
1               5                   10

<210> SEQ ID NO 407
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Asp Glu Ser Asp Arg Pro Ser
1               5

<210> SEQ ID NO 408
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 408

Gln Val Trp Asp Thr Ser Ser Asp His Val Val
1               5                   10

<210> SEQ ID NO 409
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 409

Gly Gly Asn Asn Ile Gly Ser Lys Ser Leu Gln
1               5                   10

```
<210> SEQ ID NO 410
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 410

Asp Glu Ser Asp Arg Pro Ser
1               5

<210> SEQ ID NO 411
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 411

Gln Val Trp Asp Thr Ser Ser Asp His Val Val
1               5                   10

<210> SEQ ID NO 412
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 412

Asn Asn Ile Gly Ser Lys Ser
1               5

<210> SEQ ID NO 413
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 413

Asp Glu Ser
1

<210> SEQ ID NO 414
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 414

Trp Asp Thr Ser Ser Asp His Val
1               5

<210> SEQ ID NO 415
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 415

Asn Ile Gly Ser Lys Ser
1               5

<210> SEQ ID NO 416
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 416

Asp Glu Ser
1

<210> SEQ ID NO 417
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 417

Gln Val Trp Asp Thr Ser Ser Asp His Val Val
1               5                   10

<210> SEQ ID NO 418
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 418

Ser Tyr Val Leu Thr Gln Pro Pro Ser Val Ser Val Ala Pro Gly Gln
1               5                   10                  15

Thr Ala Arg Leu Ser Cys Gly Gly Asn Asn Ile Gly Ser Lys Ser Leu
            20                  25                  30

Gln Trp Tyr Gln Gln Lys Pro Gly Gln Ala Pro Val Leu Val Val Asn
        35                  40                  45

Asp Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Val Val Phe Gly Gly Gly Thr Lys Leu Thr Val Leu
            100                 105

<210> SEQ ID NO 419
<211> LENGTH: 324
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic polynucleotide"

<400> SEQUENCE: 419

```
tcctatgtgc tgactcagcc accctcggtg tcagtggccc caggacagac ggccagactt      60
tcctgtgggg gaaacaacat tggaagtaaa agtctgcagt ggtaccagca gaagccaggc     120
caggcccctg tgctggtcgt caatgatgag agcgaccggc cctcagggat ccctgagcga     180
ttctctggct ccaactctgg gaacacggcc accctgacca tcagcagggt cgaagccggg     240
gatgaggccg actattactg tcaggtgtgg gatactagta gtgatcatgt ggtcttcggc     300
ggagggacca agctgaccgt ccta                                            324
```

<210> SEQ ID NO 420
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 420

Ser Tyr Val Leu Thr Gln Pro Pro Ser Val Ser Val Ala Pro Gly Gln
1               5                   10                  15

Thr Ala Arg Leu Ser Cys Gly Gly Asn Asn Ile Gly Ser Lys Ser Leu
            20                  25                  30

Gln Trp Tyr Gln Gln Lys Pro Gly Gln Ala Pro Val Leu Val Val Asn
        35                  40                  45

Asp Glu Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 421
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 421

```
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt cctaggccag cctaaggccg ctccctccgt gaccctgttc   360
ccccccagct ccgaggaact gcaggccaac aaggccaccc tggtgtgcct gatcagcgac   420
ttctaccctg cgccgtgac cgtggcctgg aaggccgaca gcagcccgt gaaggccggc   480
gtggagacaa ccaccccag caagcagagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                     642
```

<210> SEQ ID NO 422
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 422

Gly Phe Thr Phe Ser Tyr Tyr Gly Met Asn
1               5                   10

<210> SEQ ID NO 423
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 423

Gly Ile Thr Asn Val Gly Ser Ile Thr Tyr Tyr Ala Asp Thr Val Lys
1               5                   10                  15
Gly

<210> SEQ ID NO 424
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 424

Val Gly Val Arg Ser Ser Ser Gly Met Trp Asp Leu Asp Tyr
1               5                   10

<210> SEQ ID NO 425
<211> LENGTH: 5
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 425

Tyr Tyr Gly Met Asn
1               5

<210> SEQ ID NO 426
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 426

Gly Ile Thr Asn Val Gly Ser Ile Thr Tyr Tyr Ala Asp Thr Val Lys
1               5                   10                  15

Gly

<210> SEQ ID NO 427
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 427

Val Gly Val Arg Ser Ser Ser Gly Met Trp Asp Leu Asp Tyr
1               5                   10

<210> SEQ ID NO 428
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 428

Gly Phe Thr Phe Ser Tyr Tyr
1               5

<210> SEQ ID NO 429
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 429

Thr Asn Val Gly Ser Ile
1               5

<210> SEQ ID NO 430
<211> LENGTH: 14
<212> TYPE: PRT
<213> ORGANISM: Artificial Sequence
<220> FEATURE:
<221> NAME/KEY: source
```

```
-continued

<223> OTHER INFORMATION: /note="Description of Artificial Sequence:
      Synthetic peptide"

<400> SEQUENCE: 430

Val Gly Val Arg Ser Ser Ser Gly Met Trp Asp Leu Asp Tyr
1               5                   10

<210> SEQ ID NO 431
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 431

Gly Phe Thr Phe Ser Tyr Tyr Gly
1               5

<210> SEQ ID NO 432
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 432

Ile Thr Asn Val Gly Ser Ile Thr
1               5

<210> SEQ ID NO 433
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 433

Ala Lys Val Gly Val Arg Ser Ser Ser Gly Met Trp Asp Leu Asp Tyr
1               5                   10                  15

<210> SEQ ID NO 434
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 434

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Asn Val Gly Ser Ile Thr Tyr Tyr Ala Asp Thr Val
    50                  55                  60

Lys Gly Arg Phe Ser Ile Ser Arg Asp Asn Ser Lys Asn Thr Leu Phe
65                  70                  75                  80
```

-continued

```
Leu Gln Met Asn Ser Leu Arg Ala Glu Asp Thr Ala Val Tyr Tyr Cys
                85                  90                  95

Ala Lys Val Gly Val Arg Ser Ser Gly Met Trp Asp Leu Asp Tyr
            100                 105                 110

Trp Gly Gln Gly Thr Leu Val Thr Val Ser Ser
        115                 120

<210> SEQ ID NO 435
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 435
gaggttcaat tgttggagtc tgggggaggc ctggtacagc cggggggtc ccggagactg      60 tcctgtgcag cctctggatt caccttagc tactatggca tgaactgggt ccgccaggct     120
ccagggaagg gactggaatg ggtctcaggt attactaatg tgggtagtat cacatactac    180
gcagacaccg tgaagggccg gttcagcatc tccagagaca attccaagaa cacgttgttt    240
ctgcaaatga acagcctgag agccgaggac acggccgtat attactgtgc gaaggtggga    300
gtgcgcagtt cgtccgggat gtgggacctt gactactggg gccagggaac cctggtcacc    360
gtcagctca                                                             369

<210> SEQ ID NO 436
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 436

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Phe Ser Tyr Tyr
            20                  25                  30

Gly Met Asn Trp Val Arg Gln Ala Pro Gly Lys Gly Leu Glu Trp Val
        35                  40                  45

Ser Gly Ile Thr Asn Val Gly Ser Ile Thr Tyr Tyr Ala Asp Thr Val
    50                  55                  60

Lys Gly Arg Phe Ser Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Val Gly Val Arg Ser Ser Gly Met Trp Asp Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175
Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly Lys
    450

<210> SEQ ID NO 437
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 437
gaggttcaat tgttggagtc tgggggaggc ctggtacagc cggggggggtc ccggagactg      60 tcctgtgcag cctctggatt cacctttagc tactatggca tgaactgggt ccgccaggct     120
ccagggaagg gactggaatg ggtctcaggt attactaatg tgggtagtat cacatactac     180
gcagacaccg tgaagggccg gttcagcatc tccagagaca attccaagaa cacgttgttt     240
ctgcaaatga acagcctgag agccgaggac acggccgtat attactgtgc gaaggtggga     300
gtgcgcagtt cgtccgggat gtgggacctt gactactggg gccagggaac cctggtcacc     360
```

-continued

```
gtcagctcag ctagcaccaa gggccccagc gtgttccccc tggcccccag cagcaagagc      420
accagcggcg gcacagccgc cctgggctgc ctggtgaagg actacttccc cgagcccgtg      480
accgtgtcct ggaacagcgg agccctgacc tccggcgtgc acaccttccc cgccgtgctg      540
cagagcagcg gcctgtacag cctgtccagc gtggtgacag tgcccagcag cagcctgggc      600
acccagacct acatctgcaa cgtgaaccac aagcccagca acaccaaggt ggacaagaga      660
gtggagccca gagctgcga caagacccac acctgccccc cctgcccagc ccagagctg       720 ctgggcggac cctccgtgtt cctgttcccc ccaagcccca aggacaccct gatgatcagc      780
aggacccccg aggtgacctg cgtggtggtg gacgtgagcc acgaggaccc agaggtgaag      840
ttcaactggt acgtggacgg cgtggaggtg cacaacgcca agaccaagcc cagagaggag      900
cagtacaaca gcacctacag ggtggtgtcc gtgctgaccg tgctgcacca ggactggctg      960
aacggcaagg aatacaagtg caaggtctcc aacaaggccc tgccagcccc catcgaaaag     1020
accatcagca aggccaaggg ccagccacgg gagcccagg tgtacaccct gccccctcc       1080 cgggaggaga tgaccaagaa ccaggtgtcc ctgacctgtc tggtgaaggg cttctacccc     1140
agcgacatcg ccgtggagtg ggagagcaac ggccagcccg agaacaacta caagaccacc     1200
cccccagtgc tggacagcga cggcagcttc ttcctgtaca gcaagctgac cgtggacaag     1260
tccaggtggc agcagggcaa cgtgttcagc tgcagcgtga tgcacgaggc cctgcacaac     1320
cactacaccc agaagagcct gagcctgtcc cccggcaag                            1359
```

<210> SEQ ID NO 438
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 438

Gly Gly Asn Asn Ile Gly Ser Lys Ser Leu Gln
1               5                   10

<210> SEQ ID NO 439
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 439

Asp Glu Ser Asp Arg Pro Ser
1               5

<210> SEQ ID NO 440
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 440

Gln Val Trp Asp Thr Ser Ser Asp His Val Val
1               5                   10

```
<210> SEQ ID NO 441
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 441

Gly Gly Asn Asn Ile Gly Ser Lys Ser Leu Gln
1               5                   10

<210> SEQ ID NO 442
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 442

Asp Glu Ser Asp Arg Pro Ser
1               5

<210> SEQ ID NO 443
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 443

Gln Val Trp Asp Thr Ser Ser Asp His Val Val
1               5                   10

<210> SEQ ID NO 444
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 444

Asn Asn Ile Gly Ser Lys Ser
1               5

<210> SEQ ID NO 445
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 445

Asp Glu Ser
1

<210> SEQ ID NO 446
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 446

Trp Asp Thr Ser Ser Asp His Val
1               5

<210> SEQ ID NO 447
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 447

Asn Ile Gly Ser Lys Ser
1               5

<210> SEQ ID NO 448
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 448

Asp Glu Ser
1

<210> SEQ ID NO 449
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 449

Gln Val Trp Asp Thr Ser Ser Asp His Val Val
1               5                   10

<210> SEQ ID NO 450
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 450

Ser Tyr Val Leu Thr Gln Pro Pro Ser Val Ser Val Ala Pro Gly Gln
1               5                   10                  15

Thr Ala Arg Leu Ser Cys Gly Gly Asn Asn Ile Gly Ser Lys Ser Leu
            20                  25                  30

Gln Trp Tyr Gln Gln Lys Pro Gly Gln Ala Pro Val Leu Val Val Asn
        35                  40                  45

Asp Glu Ser Asp Arg Pro Ser Gly Ile Pro Glu Arg Phe Ser Gly Ser
```

```
                50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Ser Ser Asp His
                 85                  90                  95

Val Val Phe Gly Gly Gly Thr Lys Leu Thr Val Leu
                100                 105

<210> SEQ ID NO 451
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 451
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcaggat cc ctgagcga   180 ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca agctgaccgt ccta                                          324

<210> SEQ ID NO 452
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 452

Ser Tyr Val Leu Thr Gln Pro Pro Ser Val Ser Val Ala Pro Gly Gln
 1               5                  10                  15

Thr Ala Arg Leu Ser Cys Gly Gly Asn Asn Ile Gly Ser Lys Ser Leu
                20                  25                  30

Gln Trp Tyr Gln Gln Lys Pro Gly Gln Ala Pro Val Leu Val Val Asn
             35                  40                  45

Asp Glu Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Ser Ser Asp His
                 85                  90                  95

Val Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 453
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 453

```
tcctatgtgc tgactcagcc accctcggtg tcagtggccc caggacagac ggccagactt    60
tcctgtgggg gaaacaacat tggaagtaaa agtctgcagt ggtaccagca gaagccaggc   120
caggcccctg tgctggtcgt caatgatgag agcgaccggc cctcagggat ccctgagcga   180
ttctctggct ccaactctgg gaacacggcc accctgacca tcagcagggt cgaagccggg   240
gatgaggccg actattactg tcaggtgtgg gatactagta gtgatcatgt ggtcttcggc   300
ggagggacca gctgaccgt cctaggccag cctaaggccg ctccctccgt gaccctgttc   360 cccccccagct ccgaggaact gcaggccaac aaggccaccc tggtgtgcct gatcagcgac   420
ttctaccctg gcgccgtgac cgtggcctgg aaggccgaca gcagcccgt gaaggccggc   480 gtggagacaa ccacccccag caagcagagc aacaacaagt acgccgccag cagctacctg   540
agcctgaccc ccgagcagtg gaagagccac agaagctaca gctgccaggt cacccacgag   600
ggcagcaccg tggagaaaac cgtggccccc accgagtgca gc                      642
```

<210> SEQ ID NO 454
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 454

```
Gly Tyr Thr Phe Thr Ser Tyr Tyr Met His
1               5                   10
```

<210> SEQ ID NO 455
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 455

```
Ile Ile Ser Pro Ser Gly Gly Ser Thr Ser Tyr Ala Gln Lys Phe Gln
1               5                   10                  15

Gly
```

<210> SEQ ID NO 456
<211> LENGTH: 16

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 456

Asp Trp Glu Gly Gly Asp Pro Tyr Gly Tyr Tyr Tyr Ala Phe Asp Tyr
1               5                   10                  15

<210> SEQ ID NO 457
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 457

Ser Tyr Tyr Met His
1               5

<210> SEQ ID NO 458
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 458

Ile Ile Ser Pro Ser Gly Gly Ser Thr Ser Tyr Ala Gln Lys Phe Gln
1               5                   10                  15

Gly

<210> SEQ ID NO 459
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 459

Asp Trp Glu Gly Gly Asp Pro Tyr Gly Tyr Tyr Tyr Ala Phe Asp Tyr
1               5                   10                  15

<210> SEQ ID NO 460
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 460

Gly Tyr Thr Phe Thr Ser Tyr
1               5

<210> SEQ ID NO 461
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 461

Ser Pro Ser Gly Gly Ser
1               5

<210> SEQ ID NO 462
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 462

Asp Trp Glu Gly Gly Asp Pro Tyr Gly Tyr Tyr Tyr Ala Phe Asp Tyr
1               5                   10                  15

<210> SEQ ID NO 463
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 463

Gly Tyr Thr Phe Thr Ser Tyr Tyr
1               5

<210> SEQ ID NO 464
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 464

Ile Ser Pro Ser Gly Gly Ser Thr
1               5

<210> SEQ ID NO 465
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Ala Arg Asp Trp Glu Gly Gly Asp Pro Tyr Gly Tyr Tyr Tyr Ala Phe
1               5                   10                  15

Asp Tyr

<210> SEQ ID NO 466
<211> LENGTH: 125
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 466

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Glu Gly Gly Asp Pro Tyr Gly Tyr Tyr Tyr Ala Phe
            100                 105                 110

Asp Tyr Trp Gly Gln Gly Thr Leu Val Thr Val Ser Ser
        115                 120                 125

<210> SEQ ID NO 467
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 467
caggtgcaat tggtgcagag cggagccgaa gtgaaaaaac ctggggccag cgtgaaagtg      60
tcctgcaaag cctccggata caccttcacc agctactaca tgcactgggt ccgccaggcc     120
ccaggccagg gactcgagtg gatgggcatc atcagcccta gcggcggcag caccagctac     180
gcccagaaat tccagggccg ggtgaccatg acccgcgaca ccagcaccag caccgtgtac     240
atggaactga gcagcctgcg cagcgaggac accgccgtgt attattgcgc gcgtgactgg     300
gaaggtggtg acccgtacgg ttactactac gctttcgact actggggtca aggcaccctg     360
gttacagtca gctca                                                      375

<210> SEQ ID NO 468
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 468

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Gly Ser Thr Ser Tyr Ala Gln Lys Phe
    50                  55                  60

Gln Gly Arg Val Thr Met Thr Arg Asp Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Glu Gly Gly Asp Pro Tyr Gly Tyr Tyr Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Arg Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
450                 455

<210> SEQ ID NO 469
<211> LENGTH: 1365
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 469

```
caggtgcaat tggtgcagag cggagccgaa gtgaaaaaac ctggggccag cgtgaaagtg      60
tcctgcaaag cctccggata caccttcacc agctactaca tgcactgggt ccgccaggcc     120
ccaggccagg gactcgagtg gatgggcatc atcagcccta gcggcggcag caccagctac     180
gcccagaaat tccagggccg ggtgaccatg acccgcgaca ccagcaccag caccgtgtac     240
atggaactga gcagcctgcg cagcgaggac accgccgtgt attattgcgc gcgtgactgg     300
gaaggtggtg acccgtacgg ttactactac gctttcgact actggggtca aggcaccctg     360
gttacagtca gctcagctag caccaagggc cccagcgtgt tccccctggc ccccagcagc     420
aagagcacca gcggcggcac agccgccctg ggctgcctgg tgaaggacta cttccccgag     480
cccgtgaccg tgtcctggaa cagcggagcc ctgacctccg gcgtgcacac cttccccgcc     540
gtgctgcaga gcagcggcct gtacagcctg tccagcgtgg tgacagtgcc cagcagcagc     600
ctgggcaccc agacctacat ctgcaacgtg aaccacaagc ccagcaacac caaggtggac     660
aagagagtgg agcccaagag ctgcgacaag acccacacct gccccccctg cccagcccca     720
gagctgctgg gcggacccte cgtgttcctg ttccccccca gcccaaagga caccctgatg     780
atcagcagga cccccgaggt gacctgcgtg gtggtggacg tgagccacga ggacccagag     840
gtgaagttca actggtacgt ggacggcgtg gaggtgcaca cgccaagac caagcccaga     900
gaggagcagt acaacagcac ctacagggtg gtgtccgtgc tgaccgtgct gcaccaggac     960
tggctgaacg gcaaggaata caagtgcaag gtctccaaca aggccctgcc agcccccatc    1020
gaaaagacca tcagcaaggc caagggccag ccacgggagc cccaggtgta caccctgccc    1080
ccctcccggg aggagatgac caagaaccag gtgtccctga cctgtctggt gaagggcttc    1140
taccccagcg acatcgccgt ggagtgggag agcaacggcc agcccgagaa caactacaag    1200
accaccccc cagtgctgga cagcgacggc agcttcttcc tgtacagcaa gctgaccgtg    1260
gacaagtcca ggtggcagca gggcaacgtg ttcagctgca gcgtgatgca cgaggccctg    1320
cacaaccact acacccagaa gagcctgagc ctgtccccg gcaag                    1365
```

<210> SEQ ID NO 470
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 470

Arg Ala Ser Gln Ser Ile Ser Ser Tyr Leu Asn
1               5                   10

<210> SEQ ID NO 471
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 471

Ala Ala Ser Ser Leu Gln Ser
1               5

<210> SEQ ID NO 472
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Gln Gln Ser Tyr Ser Thr Pro Leu Thr
1               5

<210> SEQ ID NO 473
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 473

Arg Ala Ser Gln Ser Ile Ser Ser Tyr Leu Asn
1               5                   10

<210> SEQ ID NO 474
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 474

Ala Ala Ser Ser Leu Gln Ser
1               5

<210> SEQ ID NO 475
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 475

Gln Gln Ser Tyr Ser Thr Pro Leu Thr
1               5

<210> SEQ ID NO 476
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 476

Ser Gln Ser Ile Ser Ser Tyr
1               5
```

```
<210> SEQ ID NO 477
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 477

Ala Ala Ser
1

<210> SEQ ID NO 478
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 478

Ser Tyr Ser Thr Pro Leu
1               5

<210> SEQ ID NO 479
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 479

Gln Ser Ile Ser Ser Tyr
1               5

<210> SEQ ID NO 480
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 480

Ala Ala Ser
1

<210> SEQ ID NO 481
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 481

Gln Gln Ser Tyr Ser Thr Pro Leu Thr
1               5

<210> SEQ ID NO 482
<211> LENGTH: 107
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 482

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 483
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 483
gatatccaga tgacccagag ccctagcagc ctgagcgcca gcgtgggcga ccgcgtgacc      60
attacctgca gagccagcca gagcatcagc agctacctga actggtacca gcagaaacct     120
ggcaaggcgc ccaaactatt aatctacgcc gccagcagcc ttcagagcgg cgtgccaagc     180
cgctttagcg gatccggcag cggcaccgac ttcaccctga ccatcagctc ccttcagcct     240
gaagacttcg ccacctacta ctgccagcag agctacagca cccctctgac ctttggccag     300
ggcaccaaag tggaaatcaa a                                               321

<210> SEQ ID NO 484
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 484

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Pro Leu
                    85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 485
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 485

```
gatatccaga tgacccagag ccctagcagc ctgagcgcca gcgtgggcga ccgcgtgacc      60
attacctgca gagccagcca gagcatcagc agctacctga actggtacca gcagaaacct     120
ggcaaggcgc ccaaactatt aatctacgcc gccagcagcc ttcagagcgg cgtgccaagc     180
cgctttagcg gatccggcag cggcaccgac ttcaccctga ccatcagctc ccttcagcct     240
gaagacttcg ccacctacta ctgccagcag agctacagca cccctctgac ctttggccag     300
ggcaccaaag tggaaatcaa acgtacggtg gccgctccca gcgtgttcat cttcccccc      360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag cacactgacc     540
ctgagcaagg ccgactacga gaagcataag gtgtacgcct gcgaggtgac ccaccagggc     600
ctgtccagcc ccgtgaccaa gagcttcaac agggcgagt gc                         642
```

<210> SEQ ID NO 486
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 486

```
Gly Tyr Thr Phe Thr Ser Leu Glu Met His
1               5                   10
```

-continued

```
<210> SEQ ID NO 487
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 487

Ile Ile Glu Pro Ser Gly Gly Ser Thr Ser Tyr Ala Gln Lys Phe Gln
1               5                   10                  15

Gly

<210> SEQ ID NO 488
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 488

Asp Trp Glu Gly Gly Asp Pro Tyr Gly Tyr Tyr Tyr Ala Phe Asp Tyr
1               5                   10                  15

<210> SEQ ID NO 489
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 489

Ser Leu Glu Met His
1               5

<210> SEQ ID NO 490
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 490

Ile Ile Glu Pro Ser Gly Gly Ser Thr Ser Tyr Ala Gln Lys Phe Gln
1               5                   10                  15

Gly

<210> SEQ ID NO 491
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 491

Asp Trp Glu Gly Gly Asp Pro Tyr Gly Tyr Tyr Tyr Ala Phe Asp Tyr
1               5                   10                  15
```

```
<210> SEQ ID NO 492
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 492

Gly Tyr Thr Phe Thr Ser Leu
1               5

<210> SEQ ID NO 493
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 493

Glu Pro Ser Gly Gly Ser
1               5

<210> SEQ ID NO 494
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 494

Asp Trp Glu Gly Gly Asp Pro Tyr Gly Tyr Tyr Ala Phe Asp Tyr
1               5                   10                  15

<210> SEQ ID NO 495
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 495

Gly Tyr Thr Phe Thr Ser Leu Glu
1               5

<210> SEQ ID NO 496
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 496

Ile Glu Pro Ser Gly Gly Ser Thr
1               5

<210> SEQ ID NO 497
<211> LENGTH: 18
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 497

Ala Arg Asp Trp Glu Gly Gly Asp Pro Tyr Gly Tyr Tyr Tyr Ala Phe
1               5                   10                  15

Asp Tyr

<210> SEQ ID NO 498
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 498

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Leu
            20                  25                  30

Glu Met His Trp Val Arg Gln Ala Pro Gly Gln Gly Leu Glu Trp Met
        35                  40                  45

Gly Ile Ile Glu Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Glu Gly Gly Asp Pro Tyr Gly Tyr Tyr Tyr Ala Phe
            100                 105                 110

Asp Tyr Trp Gly Gln Gly Thr Leu Val Thr Val Ser Ser
        115                 120                 125

<210> SEQ ID NO 499
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 499
caggtccaat tggtgcagtc tggcgccgaa gtgaagaaac caggcgccag cgtgaaggtg      60
tcctgtaaag ccagcggcta cacctttacc agcctggaaa tgcattgggt ccgacaggct     120
ccaggacagg gactcgagtg gatgggaatt atcgagccta gcggcggcag cacaagctac     180
gcccagaaat tccagggcag agtgaccatg accagagaca ccagcacctc caccgtgtac     240
atggaactga gcagcctgag aagcgaggac accgccgtgt attattgcgc gcgtgattgg     300
gaaggcggcg accttatgg ctactactac gcctttgatt actggggcca gggcaccctg      360
gtcacagtta gctca                                                      375

<210> SEQ ID NO 500
<211> LENGTH: 455
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 500

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Leu
            20                  25                  30

Glu Met His Trp Val Arg Gln Ala Pro Gly Gln Gly Leu Glu Trp Met
        35                  40                  45

Gly Ile Ile Glu Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Glu Gly Gly Asp Pro Tyr Gly Tyr Tyr Tyr Ala Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380
```

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 501
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 501
caggtccaat tggtgcagtc tggcgccgaa gtgaagaaac caggcgccag cgtgaaggtg      60
tcctgtaaag ccagcggcta cacctttacc agcctggaaa tgcattgggt ccgacaggct     120
ccaggacagg gactcgagtg gatgggaatt atcgagccta cggcggcag cacaagctac      180 gcccagaaat tccagggcag agtgaccatg accagagaca ccagcacctc caccgtgtac     240
atggaactga gcagcctgag aagcgaggac accgccgtgt attattgcgc cgtgattgg     300 gaaggcggcg acccttatgg ctactactac gcctttgatt actggggcca gggcaccctg     360
gtcacagtta gctcagctag caccaagggc ccagcgtgt tccccctggc ccccagcagc     420
aagagcacca gcggcggcac agccgccctg ggctgcctgg tgaaggacta cttccccgag     480
cccgtgaccg tgtcctggaa cagcggagcc ctgacctccg gcgtgcacac cttccccgcc     540
gtgctgcaga gcagcggcct gtacagcctg tccagcgtgg tgacagtgcc agcagcagc     600 ctgggcaccc agacctacat ctgcaacgtg aaccacaagc ccagcaacac caaggtggac     660
aagagagtgg agcccaagag ctgcgacaag acccacacat gcccccctg cccggcgcca     720 gagctgctgg gcggaccctc cgtgttcctg ttccccccca gcccaagga caccctgatg     780 atcagcagga cccccgaggt gacctgcgtg gtggtggacg tgagccacga ggacccagag     840
gtgaagttca actggtacgt ggacggcgtg gaggtgcaca acgccaagac caagcccaga     900
gaggagcagt acaacagcac ctacagggtg gtgtccgtgc tgaccgtgct gcaccaggac     960
tggctgaacg gcaaggaata caagtgcaag gtctccaaca aggccctgcc agcccccatc    1020
gaaaagacca tcagcaaggc caagggccag ccacgggagc ccaggtgta caccctgccc    1080 ccctcccggg aggagatgac caagaaccag gtgtccctga cctgtctggt gaagggcttc    1140 tacccagcg acatcgccgt ggagtgggag agcaacggcc agcccgagaa caactacaag    1200
accacccccc cagtgctgga cagcgacggc agcttcttcc tgtacagcaa gctgaccgtg    1260
gacaagtcca ggtggcagca gggcaacgtg ttcagctgca gcgtgatgca cgaggccctg    1320
cacaaccact acacccagaa gagcctgagc ttaagccccg gcaag                   1365

<210> SEQ ID NO 502
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 502

Arg Ala Ser Gln Ser Ile Ser Ser Tyr Leu Asn
1               5                   10

<210> SEQ ID NO 503
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 503

Ala Ala Ser Ser Leu Gln Ser
1               5

<210> SEQ ID NO 504
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 504

Gln Gln Ser Tyr Ser Thr Pro Leu Thr
1               5

<210> SEQ ID NO 505
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 505

Arg Ala Ser Gln Ser Ile Ser Ser Tyr Leu Asn
1               5                   10

<210> SEQ ID NO 506
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 506

Ala Ala Ser Ser Leu Gln Ser
1               5

<210> SEQ ID NO 507
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 507

Gln Gln Ser Tyr Ser Thr Pro Leu Thr
1               5

<210> SEQ ID NO 508
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 508

Ser Gln Ser Ile Ser Ser Tyr
1               5

<210> SEQ ID NO 509
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 509

Ala Ala Ser
1

<210> SEQ ID NO 510
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 510

Ser Tyr Ser Thr Pro Leu
1               5

<210> SEQ ID NO 511
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 511

Gln Ser Ile Ser Ser Tyr
1               5

<210> SEQ ID NO 512
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 512

Ala Ala Ser
1
```

<210> SEQ ID NO 513
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 513

Gln Gln Ser Tyr Ser Thr Pro Leu Thr
1               5

<210> SEQ ID NO 514
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 514

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 515
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 515
gatatccaga tgacccagag ccctagcagc ctgagcgcca gcgtgggcga ccgcgtgacc      60
attacctgca gagccagcca gagcatcagc agctacctga actggtacca gcagaaacct     120
ggcaaggcgc ccaaactatt aatctacgcc gccagcagcc ttcagagcgg cgtgccaagc     180
cgctttagcg gatccggcag cggcaccgac ttcaccctga ccatcagctc ccttcagcct     240
gaagacttcg ccacctacta ctgccagcag agctacagca cccctctgac ctttggccag     300
ggcaccaaag tggaaatcaa a                                               321

<210> SEQ ID NO 516
<211> LENGTH: 214
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 516

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 517
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 517
gatatccaga tgacccagag ccctagcagc ctgagcgcca gcgtgggcga ccgcgtgacc      60
attacctgca gagccagcca gagcatcagc agctacctga actggtacca gcagaaacct    120
ggcaaggcgc ccaaactatt aatctacgcc gccagcagcc ttcagagcgg cgtgccaagc    180
cgctttagcg gatccggcag cggcaccgac ttcaccctga ccatcagctc ccttcagcct    240
gaagacttcg ccacctacta ctgccagcag agctacagca cccctctgac ctttggccag    300
ggcaccaaag tggaaatcaa acgtacggtg gccgctccca gcgtgttcat cttcccccca    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480

```
gagagcgtca ccgagcagga cagcaaggac tccacctaca gcctgagcag caccctgacc      540
ctgagcaagg ccgactacga gaagcataag gtgtacgcct gcgaggtgac ccaccagggc      600
ctgtccagcc ccgtgaccaa gagcttcaac aggggcgagt gc                        642
```